(12) United States Patent
Wamhoff et al.

(10) Patent No.: US 10,221,394 B2
(45) Date of Patent: Mar. 5, 2019

(54) IN VITRO MODEL FOR A TUMOR MICROENVIRONMENT

(71) Applicant: HemoShear, LLC, Charlottesville, VA (US)

(72) Inventors: Brian R. Wamhoff, Charlottesville, VA (US); Brett R. Blackman, Charlottesville, VA (US); Robert A. Figler, Earlysville, VA (US); Daniel G. Gioeli, Charlottesville, VA (US); Michael B. Simmers, Charlottesville, VA (US)

(73) Assignee: HemoShear, LLC, Charlottesville, VA (US)

( * ) Notice: Subject to any disclaimer, the term of this patent is extended or adjusted under 35 U.S.C. 154(b) by 0 days.

(21) Appl. No.: 15/483,010

(22) Filed: Apr. 10, 2017

(65) Prior Publication Data
US 2018/0016557 A1    Jan. 18, 2018

Related U.S. Application Data

(62) Division of application No. 14/520,303, filed on Oct. 21, 2014, now Pat. No. 9,617,521.

(60) Provisional application No. 61/893,402, filed on Oct. 21, 2013.

(51) Int. Cl.
| | | |
|---|---|---|
| *C12Q 1/02* | (2006.01) | |
| *C12N 5/09* | (2010.01) | |
| *C12N 5/071* | (2010.01) | |

(52) U.S. Cl.
CPC ........... *C12N 5/0693* (2013.01); *C12N 5/067* (2013.01); *C12N 5/0697* (2013.01); *C12N 2502/1323* (2013.01); *C12N 2502/28* (2013.01); *C12N 2502/30* (2013.01); *C12N 2503/04* (2013.01); *C12N 2521/00* (2013.01); *C12N 2533/54* (2013.01)

(58) Field of Classification Search
CPC ...................................................... C12Q 1/025
See application file for complete search history.

(56) References Cited

U.S. PATENT DOCUMENTS

| | | | |
|---|---|---|---|
| 7,534,601 | B2 | 5/2009 | Wikswo et al. |
| 7,811,782 | B2 | 10/2010 | Blackman et al. |
| 8,871,461 | B2 | 10/2014 | Blackman et al. |

(Continued)

FOREIGN PATENT DOCUMENTS

| | | |
|---|---|---|
| JP | H05-211893 A | 8/1993 |
| JP | 2009-027928 A | 2/2009 |

(Continued)

OTHER PUBLICATIONS

Salas, S., et al., "Therapeutic Drug Monitoring for Dose Individualization of Cisplatin in Testicular Cancer Patients Based Upon Total Platinum Measurement in Plasma," Therapeutic Drug Monitoring, Aug. 2006, pp. 532-539, vol. 28, No. 4.

(Continued)

*Primary Examiner* — Rosanne Kosson
(74) *Attorney, Agent, or Firm* — Stinson Leonard Street LLP

(57) ABSTRACT

Methods for mimicking a tumor microenvironment in vitro are provided. The methods comprise indirectly applying a shear stress upon at least one tumor cell type plated on a surface within a cell culture container. Methods for mimicking tumor metastasis and methods for testing drugs or compounds in such systems are also provided.

48 Claims, 53 Drawing Sheets

Specification includes a Sequence Listing.

(56) References Cited

U.S. PATENT DOCUMENTS

| | | | |
|---|---|---|---|
| 9,500,642 | B2 | 11/2016 | Blackman et al. |
| 9,617,521 | B2 | 4/2017 | Wamhoff et al. |
| 9,658,211 | B2 | 5/2017 | Blackman et al. |
| 2001/0055804 | A1 | 12/2001 | Shekhar et al. |
| 2002/0119441 | A1 | 8/2002 | Elias |
| 2005/0130254 | A1 | 6/2005 | Park |
| 2006/0234207 | A1 | 10/2006 | Khaldoyanidi |
| 2007/0077265 | A1 | 4/2007 | Klueh et al. |
| 2010/0304355 | A1 | 12/2010 | Shuler et al. |
| 2011/0081664 | A1 | 4/2011 | Forbes et al. |
| 2011/0294154 | A1 | 12/2011 | Jaron et al. |
| 2012/0052524 | A1 | 3/2012 | Kinooka et al. |

FOREIGN PATENT DOCUMENTS

| | | |
|---|---|---|
| WO | 98/03634 A1 | 1/1998 |
| WO | 02/39949 A2 | 5/2002 |
| WO | 2004/038368 A2 | 5/2004 |
| WO | 2008/066525 A2 | 6/2008 |
| WO | 2010/128464 A1 | 11/2010 |
| WO | 2013/056217 A1 | 4/2013 |

OTHER PUBLICATIONS

Schwachtgen, J.-L., et al., "Fluid Shear Stress Activation of egr-1 Transcription in Cultured Human Endothelial and Epithelial Cells is Mediated via the Extracellular signal-Related Kinase 1/2 Mitogen-Activated Protein Kinase Pathway," The Journal of Clinical Investigation, Jun. 1, 1998, pp. 2540-2549, vol. 101, No. 11.

Seebach, J., et al., "Endothelial Barrier Function Under Laminar Fluid Shear Stress," Laboratory Investigation, 2000, p. 1819, vol. 80, No. 12.

Shiwa, T., et al., "Co-Culture Microdevice with Oxygen Gradient for Tumor Microenvironment Model and Metastasis Imaging," American Journal of Biomedical Engineering, 2012, pp. 175-180, vol. 2, No. 4.

Shyy, Y.-J., et al., "Fluid Shear Stress Induces a Biphasic Response of Human Monocyte Chemotactic Protein I Gene Expression in Vascular Endothelium," Proceedings of the National Academy of Sciences of the United States of America, May 24, 1994, pp. 4678-4682, vol. 91, No. 11.

Siolas, D., et al., "Patient Derived Tumor Xenografts: Transforming Clinical Samples Into Mouse Models," Cancer Research, Sep. 2013, pp. 5315-5319, vol. 73, No. 17.

Smalley, K. S., et al., "In vitro Three-Dimensional Tumor Microenvironment Models for Anticancer Drug Discovery," Expert Opinion on Drug Discovery, Jan. 2008, pp. 1-10, vol. 3, No. 1.

Starmans-Kool, et al., "Measurement of Hemodynamics in Human Carotid Artery Using Ultrasound and Computational Fluid Dynamics," Journal of Applied Physiology, Mar. 2002, pp. 957-961, vol. 92, No. 3.

Tannock, I. F., et al., "Limited Penetration of Anticancer Drugs Through Tumor Tissue: A Potential Cause of Resistance of Solid Tumors to Chemotherapy," Clinical Cancer Research, Mar. 2002, pp. 878-884, vol. 8, No. 3.

Tapuria, N., et al., "Effect of Remote Ischemic Preconditioning on Hepatic Microcirculation and Function in a Rat Model of Hepatic Ischemia Reperfusion Injury," HPB: The Official Journal of the Hepato Pancreato Biliary Association, Mar. 2009, pp. 108-117, vol. 11, No. 2.

Tilghman, R. W., et al., "Matrix Rigidity Regulates Cancer Cell Growth and Cellular Phenotype," PLoS one, 2010, pp. 1-10, vol. 5, No. 9.

Toh, Y.-C., et al, "A Novel 3D Mammalian Cell Perfusion-Culture System in Microfluidic Channels," Lab on a Chip, 2007, pp. 302-309, vol. 7, No. 3.

Toley, B. J., et al., "Microfluidic Device for Recreating a Tumor Microenvironment in Vitro," Journal of Visualized Experiments, Nov. 2011, pp. 1-5, vol. 57, Article e2425.

Tveit, K. M., et al., "The Usefulness of Human Tumor Cell Lines in the Study of Chemosensitivity. A Study of Malignant Melanomas," International Journal of Cancer, Oct. 15, 1981, pp. 403-408, vol. 28, No. 4.

Urien, S., et al., "Pharmacokinetics of Platinum After Oral or Intravenous Cisplatin: A Phase 1 Study in 32 Adult Patients," Cancer Chemotherapy and Pharmacology, Jan. 2005, pp. 55-60, vol. 55, No. 1.

Walsh, C. L., et al., "A Multipurpose Microfluidic Device Designed to Mimic Microenvironment Gradients and Develop Targeted Cancer Therapeutics," Lab on a Chip, Feb. 2009, pp. 545-554, vol. 9, No. 4.

Wamhoff, B. R., et al., "Hemodynamic Flow and Heterotypic Cell Communication are Necessary for Predicting Human Vascular Drug Response in Preclinical Vascular in Vitro Systems," Abstract #1169, The Toxicologist, Supplement to Toxicological Sciences, 51st Annual Meeting and ToxExpo, Mar. 11-15, 2012, p. 251, vol. 126, Issue 1.

Wang, H. Q., et al., "Shear Stress Protects Against Endothelial Regulation of Vascular Smooth Muscle Cell Migration in a Coculture System," Endothelium, May-Jun. 2006, pp. 171-180, vol. 13, No. 3.

Wilczek, K., et al., "Comparison of Self-Expanding Polyethylene Terephthalate and Metallic Stents Implanted in Porcine Iliac Arteries," CardioVascular and Interventional Radiology, 1996, pp. 176-180, vol. 19.

Wilding, J. L., et al., "Cancer cell lines for drug discovery and development," Cancer Research, 2014, pp. 2377-2384, vol. 74, No. 9.

Wirz, W., et al., "Hepatic Stellate Cells Display a Functional Vascular Smooth Muscle Cell Phenotype in a Three-Dimensional Co-Culture Model With Endothelial Cells," Differentiation, 2008, pp. 784-794, vol. 76, No. 7.

Xia, L., et al., "Laminar-Flow Immediate-Overlay Hepatocyte Sandwich Perfusion System for Drug Hepatotoxicity Testing," Biomaterials, 2009, pp. 5927-5936, vol. 30.

Yamamoto, K., et al., "Fluid Shear Stress Induces Differentiation of Flk-1-Positive Embryonic Stem Cells Into Vascular Endothelial Cells in vitro," American Journal of Physiology, Heart and Circulatory Physiology, Apr. 2005, pp. H1915-H1924, vol. 288, No. 4.

Yap, T. A., et al., "First-in-Man Clinical Trial of the Oral Pan-AKT Inhibitor MK-2206 in Patients with Advanced Solid Tumors," Journal of Clinical Oncology, Dec. 2011, pp. 4688-4695, vol. 29, No. 35.

Yeh, T. C., et al., "Biological Characterization of ARRY-142886 (AZD6244), a Potent, Highly Selective Mitogen-Activated Protein Kinase Kinase 1/2 Inhibitor," Clinical Cancer Research, Mar. 2007, pp. 1576-1583, vol. 13, No. 5.

Zervantonakis, I.K., et al., "Three-Dinensional Microfluidic Model for Tumor Cell Intravasation and Endothelial Barrier Function," PNAS, Aug. 21, 2012, pp. 13515-13520, vol. 109, No. 34.

Zhang, C., et al., "Towards A Human-on-Chip: Culturing Multiple Cell Types on a Chip With Compartmentalized Microenvironments," Lab on a Chip, 2009, pp. 3185-3192, vol. 9, No. 22.

Zhang, P., et al., "Gleevec (STI-571) Inhibits Lung Cancer Cell Growth (A549) and Potentiates the Cisplatin Effect in Vitro," Molecular Cancer, Jan. 2003, 9 pages, vol. 2, No. 1.

Zhang, Y.-X., et al., "Cisplatin Upregulates MSHZ Expression by Reducing miR-21 to Inhibit A549 Cell Growth," Biomedicine and Pharmacotherapy, Mar. 2013, pp. 97-102, vol. 67, No. 2.

Albini, A., et al., "A Rapid in Vitro Assay for Quantitating the Invasive Potential of Tumor Cells," Cancer Research, Jun. 15, 1987, pp. 3239-3245, vol. 47, No. 12.

Andriani, F., et al., "Increased Sensitivity to Cisplatin in Non-Small Cell Lung Cancer Cell Lines After FHIT Gene Transfer," Nepolasia, Jan. 2006, pp. 9-17, vol. 8, No. 1.

Arnold, J. T., et al., "Endometrial Stromal Cells Regulate Epithelial Cell Growth in Vitro: A New Co-Culture Model," Human Reproduction, 2001, pp. 836-845, vol. 16, No. 5.

Bader, A., et al., "3-D Coculture of Hepatic Sinusoidal Cells with Primary Hepatocytes-Design of an Organotypical Model," Experimental Cell Research, 1996, pp. 223-233, vol. 226, Article No. 0222.

(56) References Cited

OTHER PUBLICATIONS

Bain, J., et al., "The Selectivity of Protein Kinase Inhibitors: A Further Update," The Biochemical Journal, Dec. 2007, pp. 297-315, vol. 408, No. 3.

Bancroft, G. N., et al., "Fluid Flow Increases Mineralized Matrix Deposition in 3D Perfusion Culture of Marrow Stomal Osteoblasts in a Dose-Dependent Manner," Proceedings of the National Academy of Sciences of the United States of America, Oct. 1, 2002, pp. 12600-12605, vol. 99, No. 22.

Barr, M. P., et al., "Generation and Characterisation of Cisplatin-Resistant Non-Small Cell Lung Cancer Cell Lines Displaying a Stem-Like Signature," PLoS one, Jan. 2013, pp. 1-19, vol. 8, No. 1.

Basu, I., et al., "Growth and Metastases of Human Lung Cancer Are Inhibited in Mouse Xenografts by a Transition State Analogue of 5'-Methylthioadenosine Phosphorylase," The Journal of Biological Chemistry, Feb. 11, 2011, pp. 4902-4911, vol. 286, No. 6.

Definition of "Bathe," accessed at http://www.thefreedictionary.com/bathe on May 14, 2014, 4 pages.

Blackman, B. R., et al., "A New in Vitro Model to Evaluate Differential Responses of Endothelial Cells to Simulated Arterial Shear Stress Wafeforms," Journal of Biomechanical Engineering, Aug. 2002, pp. 397-407, vol. 124, No. 4.

Blackman, B. R., et al., "In Vitro Cell Shearing Device to Investigate the Dynamic Response of Cells in a Controlled Hydrodynamic Environment," Annals of Biomedical Engineering, Apr. 2000, pp. 363-372, vol. 28, No. 4.

Boyden, S., "The Chemotactic Effect of Mixtures of Antibody and Antigen on Polymorphonuclear Leucocytes," The Journal of Experimental Medicine, Mar. 1, 1962, pp. 453-466, vol. 115.

Bradford, J. R., et aL, "RNA-Seq Differentiates Tumour and Hose mRNA Expression Changes Induced by Treatment of Human Tumour Xenografts with the VEGFR Tyrosine Kinase Inhibitor Cediranib," PLoS one, Jun. 2013, pp. 1-12, vol. 8, No. 6.

Braet, F., et al., "Liver Sinusoidal Endothelial Cell Modulation Upon Resection and Shear Stress in vitro," Comparative Hepatology, 2004, pp. 1-11, vol. 3, No. 7.

Bronneberg, D., et al., "MMP-2 and MMP-9 Regulation of a Vascular Coculture System under Shear Stress," Eindhoven University of Technology, Apr. 2003, pp. 1-34, Downloaded from <http://www.mate.tue.nl/mate/pdfs/2893.pdf>.

Brooks, A. R., et al., "Gene Expression Profiling of Vascular Endothelial Cells Exposed to Fluid Mechanical Forces: Relevance for Focal Susceptibility to Atherosclerosis," Endothelium, Jan.-Feb. 2004, pp. 45-57, vol. 11, No. 1.

Carraro, A., et al., "In vitro Analysis of a Hepatic Device With Intrinsic Microvascular-Based Channels," Biomedical Microdevices, 2008, pp. 795-805, vol. 10, No. 6.

Cartmell, S. H., et al., "Effects of Medium Perfusion Rate on Cell-Seeded Three-Dimensional Bone Constructs in vitro," Tissue Engineering, 2003, pp. 1197-1203, vol. 9, No. 6.

Cattaruzza, M., et al., "Shear Stress Insensitivity of Endothelial Nitric Oxide Synthase Expression as a Genetic Risk Factor for Coronary Heart Disease," Circulation Research, 2004, pp. 841-847, vol. 95, No. 8.

Chiu, J.-J., et al., "A Model for Studying the Effect of Shear Stress on Interactions Between Vascular Endothelial Cells and Smooth Muscle Cells," Journal of Biomechanics, Apr. 2004, pp. 531-539, vol. 37, No. 4.

Chiu J.-J., et al., "Shear Stress Inhibits Adhesion Molecule Expression in Vascular Endothelial Cells Induced by Coculture with Smooth Muscle Cells," Blood, Apr. 2003, pp. 2667-2674, vol. 101, No. 7.

Chou, T.-C., et al., "Therapeutic Effect Against Human Xenograft Tumors in Nude Mice by the Third Generation Microtubule Stabilizing Epothilones," Proceedings of the National Academy of Sciences of the United State of America, Sep. 2, 2008, pp. 13157-13162, vol. 105, No. 35.

Chung, E. J., et al., "In vitro and in vivo Radiosensitization with AZD6244 (ARRY-142886), an Inhibitor of Mitogen Activated Protein Kinase/Extracellular Signal-regulated Kinsase 1/2 Kinase," Clinical Cancer Research, May 2009, pp. 3050-3057, vol. 15, No. 9.

Cifone, M. A., "In vitro Growth Characteristics Associated with Benign and Metastatic Variants of Tumor Cells," Cancer Metastasis Reviews, 1982, pp. 335-347, vol. 1, No. 4.

Corning Incorporated, "Transwell(R) Permeable Supports Selection and Use Guide," Life Sciences, 2006, pp. 1-11.

Creighton, C. J., et al., "Analysis of Tumor-Host Interactions by Gene Expression Profiling of Lung Adenocarcinoma Xenografts Identifies Genes Involved in Tumor Formation," Molecular Cancer Research, Mar. 2005, pp. 119-129, vol. 3, No. 3.

Cunningham, K. S., et al., "The Role of Shear Stress in the Pathogenesis of Atherosclerosis," Laboratory Investigation, 2005, pp. 9-23, vol. 85, No. 1.

Dai, G., et al., "Distinct Endothelial Phenotypes Evoked by Arterial Waveforms Derived from Atherosclerosis-Susceptible and -Resistant Regions of Human Vasculature," Proceedings of the National Academy of Sciences of the United States of America, Oct. 12, 2004, pp. 14871-14876, vol. 101, No. 41.

Dai, G., et al., "Distinct Endothelial Phenotypes Evoked by Arterial Waveforms Derived from Atherosclerosis-Susceptible and -Resistant Regions of Human Vasculature—Supporting Materials and Methods," Proceedings of the National Academy of Sciences of the United States of America, Oct. 12, 2004, 2 pages.

Dardik, A., et al., "Shear Stress-Stimulated Endothelial Cells Induce Smooth Muscle Cell Chemotaxis via Platelet-Derived Growth Factor-BB and Interleukin-1alpha," Journal of Vascular Surgery, Feb. 2005, pp. 321-331, vol. 41, No. 2.

Dash, A., "Control of Flow and Oxygen in a 3-D Perfused Micro-Environment Fosters Balanced Survival of Hepatocyte-Non-Parenchymal Cell Co-Cultures," A Thesis presented to the Biological Engineering Division of the Massachusetts Institute of Technology, Jun. 2007, 146 pages.

Dash, A., et al., "Hemodynamic Flow Improves Rat Hepatocyte Morphology, Function, and Metabolic Activity in vitro," American Journal of Physiology-Cell Physiology, 2013, pp. C1053-C1063, vol. 304, No. 11.

Dash, A., et al., "Liver Tissue Engineering in the Evaluation of Drug Safety," Expert Opinion on Drug Metabolism & Toxicology, 2009, pp. 1159-1174, vol. 5, No. 10.

Dash, A., et al., "Physiological Hemodynamic Flow and Transport are Necessary for Retention of Primary Hepatocyte Drug Metabolism and Toxicity Indices," Abstract #504, The Toxicologist, Supplement to Toxicological Sciences, 51st Annual Meeting and ToxExpo, Mar. 11-15, 2012, p. 109, vol. 126, Issue 1.

De Bleser, P. J., et al., "Insulinlike Growth Factor—II/Mannose 6-Phosphate Receptor is Expressed on CCI4-Exposed Rat Fat-Storing Cells and Facilitates Activation of Latent Transforming Growth Factor-beta in Cocultures with Sinusoidal Endothelial Cells," Hepatology, May 1995, pp. 1429-1437, vol. 21, No. 5.

DeMeuse, P., et al., "Compartmentalized Coculture of Rat Brain Endothelial Cells and Astrocytes: A Syngenic Model to Study the Blood-Brain Barrier," Journal of Neuroscience Methods, Nov. 15, 2002, pp. 21-31, vol. 121, No. 1.

Denton, C. L., et al., "Pharmacokinetics and Pharmacodynamics of AZD6244 (ARRY-142886) in Tumor-Bearing Nude Mice," Cancer Chemother Pharmacol, Feb. 2011, pp. 349-360, vol. 67, No. 2.

DePaolo N. et al., "Electrical Impedance of Cultured Endothelium Under Fluid Flow," Annals of Biomedical Engineenng, 2001, pp. 648-656, vol. 29.

Domansky, K., et al., "Perfused Multiwell Plate for 3D Liver Tissue Engineering," Lab on a Chip, 2010, pp. 51-58, vol. 10, No. 1.

Fukushima, S., et al., "Microscopic Velocimetry With a Scaled-Up Model for Evaluating a Flow Field Over Cultured Endothelial Cells," Journal of Biomechanical Enginering, Apr. 2002, pp. 176-179, vol. 124, No. 2.

Garcia-Cardena, G., et al., "Biomechanical Activation of Vascular Endothelium as a Determinant of its Functional Phenotype," Proceedings of the National Academy of Sciences of the United States of America, Apr. 10, 2001, pp. 4478-4485, vol. 98, No. 8.

(56) References Cited

OTHER PUBLICATIONS

Gerthoffer, W. T., et al., "Secretory Functions of Smooth Muscle: Cytokines and Growth Factors," Molecular Interventions, Nov. 2002, pp. 447-456, vol. 2, No. 7.

Giaever, I., et al., "Monitoring Fibroblast Behavior in Tissue Culture with an Applied Electric Field," Proceedings of the National Academy of Sciences of the United States of America, Jun. 1984, pp. 3761-3764, vol. 81, No. 12.

Gomes, M. E., et al., "Effect of Flow Perfusion on the Osteogenic Differentiation of Bone Marrow Stromal Cells Cultured on Starch-Based Three-Dimensional Scaffolds," Journal of Biomedical Materials Research, Part A, Oct. 2003, pp. 87-95, vol. 67, No. 1.

Gorg, C., et al., "Color Doppler Sonographic Mapping of Pulmonary Lesions: Evidence of Dual Arterial Supply by Spectral Analysis," Journal of Ultrasound in Medicine, Oct. 2003, pp. 1033-1039, vol. 22, No. 10.

Grierson, J. P., et al., "Shear Stress-Induced [Ca2+]i Transients and Oscillations in Mouse Fibroblasts are Mediated by Endogenously Released ATP," The Journal of Biological Chemistry, Mar. 3, 1995, pp. 4451-4456, vol. 270, No. 9.

Harris, S. G., et al., "Development of a Physiologically Based in Vitro Model of the Blood-Brain Barrier," Bioengineering Conference, Proceedings of the IEEE 28th, 2002, pp. 1-2.

Hastings, N. E., "Atherosclerosis-Prone Hemodynamics Differentially Regulates Endothelial and Smooth Muscle Cell Phenotypes and Promotes Pro-Inflammatory Priming," American Journal of Physiology, Cell Physiology, 2007, pp. C1824-C1833, vol. 293, No. 6.

Hsu, W. H., et al., "Color Doppler Ultrasound Signals of Thoracic Lesions. Correlation with Resected Histologic Specimens," American Journal of Respiratory and Critical Care Medicine, Jun. 1996, pp. 1938-1951, vol. 153, No. 6 (Part 1).

Hsu, W. H., et al., "Color Doppler US Pulmonary Artery Vessel Signal: A Sign for Predicting the Benign Lesions," Ultrasound in Medicine & Biology, Mar. 2007, pp. 379-388, vol. 33, No. 3.

Hudis, C., et al., "A Phase 1 Study Evaluating the Combination of an Allosteric AKT Inhibitor (MK-2206) and Trastuzumab in Patients With HER2-Positive Solid Tumors," Breast Cancer Research, 2013, 10 pages, vol. 15, No. R110.

Hui, E. E., et al., "Micromechanical Control of Cell-Cell Interactions," Proceedings of the National Academy of Sciences of the United States of America, 2007, pp. 5722-5726, vol. 104, No. 14.

Iadecola, C., "Neurovascular Regulation in the Normal Brain and in Alzheimer's Disease," Nature Reviews, Neuroscience, May 2004, pp. 347-360, vol. 5, No. 5.

International Search Report and Written Opinion issued for PCT/US2014/061653, dated Feb. 4, 2015, 22 pages.

Ji, J. Y., et al., "Shear Stress Causes Nuclear Localization of Endothelial Glucocorticoid Receptor and Expression from the GRE Promoter," Circulation Research, Journal of the American Heart Association, Feb. 21, 2003, pp. 279-285, vol. 92, No. 3.

Johnsson, A., et al., "Pharmacokinetics and Tissue Distribution of Cisplatin in Nude Mice: Platinum Levels and Cisplatin—DNA Adducts," Cancer Chemotherapy and Pharmacology, 1995, pp. 23-31, vol. 37, Nos. 1-2.

Jung, M.-Y., et al., "Stabilin-2 is Involved in Lymphocyte Adesion to the Hepatic Sinusoidal Endothelium via the Interaction with alphaMbeta2 Integrin," Journal of Leukocyte Biology, Nov. 2007, pp. 1156-1165, vol. 82, No. 5.

Khetani, S. R., et al., "Microscale Culture of Human Liver Cells for Drug Development," Nature Biotechnology, Jan. 2008, pp. 120-126, vol. 26, No. 1.

Lalor, P. F., et al., "Vascular Adhesion Protein-1 Mediates Adhesion and Transmigration of Lymphocytes on Human Hepatic Endothelial Cells," The Journal of Immunology, 2002, pp. 983-992, vol. 169.

Langmead, B., et al., "Ultrafast and Memory-Efficient Alignment of Short DNA Sequences to the Human Genome," Genome Biology, 2009, pp. R25-R25.10, vol. 10.

Laurens, N., et al., "Isolation, Purification and Culture of Human Micro- and Macrovascular Endothelial Cells," Chapter 1, Springer Lab Manual, Methods in Endothelial Cell Biology, 2004, pp. 3-8.

Lee, P. J., et al., "An Artificial Liver Sinusoid With a Microfluidic Endothelial-Like Barrier for Primary Hepatocyte Culture," Biotechnology and Bioengineering, 2007, pp. 1340-1346, vol. 97, No. 5.

Lee, J. S. H., et al., "Cdc42 Mediates Nucleus Movement and MTOC Polarization in Swiss 3T3 Fibroblasts Under Mechanical Shear Stress," Molecular Biology of the Cell, Feb. 2005, pp. 871-880, vol. 16, No. 2.

Leijen, S., et al., "A Phase I, Open-Label, Randomized Crossover Study to Access the Effect of Dosing of the MEK 1/2 Inhibitor Selumetinib (AZD6244; ARRY-142866) in the Presence and Absence of Food in Patients with Advanced Solid Tumors," Cancer Chemotherapy and Pharmacology, 2011, pp. 1619-1628, vol. 68, No. 6.

Li, K. et al., "Reversal of Multidrug Resistance by Cisplatin-Loaded Magnetic Fe3O4 Nanoparticles in A549/DDP Lung Cancer Cells in Vitro and in Vivo," International Journal of Nanomedicine, 2013, pp. 1867-1877, vol. 8.

Ma, S. H., et al., "An Endothelial and Astrocyte Co-Culture Model of the Blood-Brain Barrier Utilizing an Ultra-Thin, Nanofabricated Silicon Nitride Membrane," Lab on a Chip, Jan. 2005, pp. 74-85, vol. 5, No. 1.

Malek, A. M., et al., "A Cone-Plate Apparatus for the in Vitro Biochemical and Molecular Analysis of the Effect of Shear Stress on Adherent Cells," Methods in Cell Science, 1995, pp. 165-176, vol. 17.

March, S., et al., "Microenvironmental Regulation of the Sinusoidal Endothelial Cell Phenotype in Vitro," Hepatology, Sep. 2009, pp. 920-928, vol. 50, No. 3.

Meng, J., et al., "Combination Treatment with MEK and AKT Inhibitors Is More Effective Than Each Drug Alone in Human Non-Small Cell Lung Cancer in Vitro and in Vivo," PLos One, Nov. 2010, pp. 1-10, vol. 5, Issue 11.

Millipore Corporation, "Millicell Technical Guide," A Publication of Technical Services, Literature No. TN2004EN00, Apr. 2004, pp. 1-25.

Moro, M., et al., "Patient-Derived Xenografts of Non Small Cell Lung Cancer: Resurgence of an Old Model for Investigation of Modern Concepts of Tailored Therapy and Cancer Stem Cells," Journal of Biomedicine and Biotechnology, 2012, 11 pages, vol. 2012, Article ID 568567.

Mukaida, N., et al., "Chemokines in Tumor Development and Progression," Experimental Cell Research, 2012, pp. 95-102, vol. 318, No. 2.

National Cancer Institute, "MK2206 and Erlotinib Hydrochloride in Treating Patients With Advanced Non-Small Cell Lung Cancer Who Have Progressed After Previous Response to Erlotinib Hydrochloride Therapy," Accessed from http://clinicaltrials.gov/show/NCT01294306> on Sep. 9, 2014, 5 pages.

National Cancer Institute, "Non-Small Cell Lung Cancer Treatment (PDQ(R))," Accessed from <http://www.cancergov/cancertopics/pdq/treatment/non-smal-celllung/healthprofessional/page11> on Jul. 2, 2014, 14 pages.

National Cancer Institute, "Randomized Phase II Study of AZD6244 (Mitogen-Activated Protein Kinase Inhibitor) MEK-Inhibitor With Erlotinib in KRAS Wild Type Advanced Non-Small Cell Lung Cancer (NSCLC) and a Randomized Phase II Study of AZD6244 With Erlotinib in Mutant KRAS Advanced Non-Small Cell Lung Cancer," Accessed from <http://clinicaltrials.gov/ct2/show/study/NCT01229150> on Sep. 9, 2014, 6 pages.

Navab, M., et al., "Monocyte Migration into the Subendothelial Space of a Coculture of Adult Human Aortic Endothelial and Smooth Muscle Cells," Journal of Clinical Investigation, Dec. 1988, pp. 1853-1863, vol. 82.

Nayak, L., et al., ""Go With the Flow": How Kruppel-Like Factor 2 Regulates the Vasoprotective Effects of Shear Stress," Antioxidants & Redox Signaling, 2011, pp. 1449-1461, vol. 15, No. 5.

Novik, E., et al., "A Microfluidic Hepatic Coculture Platform for Cell-Based Drug Metabolism Studies," Biochemical Pharmacology, Apr. 1, 2010, pp. 1036-1044, vol. 79, No. 7.

(56) References Cited

OTHER PUBLICATIONS

Ogata, H., et al., "KEGG: Kyoto Encyclopedia of Genes and Genomes," Nucleic Acids Research, 1999, pp. 29-34, vol. 27, No. 1.
O'Neil, B. H., et al., "Phase II Study of the Mitogen-Activated Protein Kinase 1/2 Inhibitor Selumetinib in Patients With Advanced Hepatocellular Carcinoma," Journal of Clinical Oncology, Jun. 10, 2011, pp. 2350-2356, vol. 29, No. 17.
Orr, A. W., et al., "Mechanisms of Mechanotransduction," Developmental Cell, Jan. 2006, pp. 11-20, vol. 10, No. 1.
Papadimitriou, M. N. B., et al., "Integrin alpha4beta1/VCAM-1 Pathway Mediates Primary Adhesion of RAW117 Lymphoma Cells to Hepatic Sinusoidal Endothelial Cells Under Flow," Clincal & Experimental Metastasis, 1999, pp. 669-676, vol. 17, No. 8.
Papaioannou, T. G., et al., "Vascular Wall Shear Stress: Basic Principles and Methods," Hellenic Journal of Cardiology, 2005, pp. 9-15, vol. 46, No. 1.
Pazzano, D., et al., "Comparison of Chondrogensis in Static and Perfused Bioreactor Culture," Biotechnology Progress, Sep.-Oct. 2000, pp. 893-896, vol. 16, No. 5.
Definition of "Perfusion," accessed at http://www.medical-dictionary.thefreedictionary.com/perfusion on Feb. 25, 2014, 3 pages.
Piovan, E., et al., "Direct Reversal of Glucocorticoid Resistance by AKT Inhibition in Acute Lymphoblastic Leukemia," Cancer Cell, Dec. 2013, 24 pages, vol. 24, No. 6.
Polyak, K., et al., "Co-Evolution of Tumor Cells and Their Microenvironment," Trends in Genetics, Jan. 2009, pp. 30-38, vol. 25, No. 1.
Powers, M. J. et al., "A Microfabricated Array Bioreactor for Perfused 3D Liver Culture," Biotechnology and Bioengineenng, May 2002, pp. 257-269, vol. 78, No. 3.
Price, D. T., et al., "Design Rule for Optimization of Microelectrodes Used in Electric Cell-Subtrate Impedance Sensing (ECIS)," Biosensors and Bioelectronics, 2009, pp. 2071-2076, vol. 24, No. 7.
Qazi, H., et al., "Fluid Shear Stress Regulates the Invasive Potential of Glioma Cells via Modulation of Migratory Activity and Matrix Metalloproteinase Expression," PLoS One, 2011, pp. 1-13, vol. 6, No. 5.
Rainger, G. E, et al., "A Novel System for Investigating the Ability of Smooth Muscle Cells and Fibroblasts to Regulate Adhesion of Flowing Leukocytes to Endothelial Cells," Journal of Immunological Methods, Sep. 1, 2001, pp. 73-82, vol. 255, No. 1-2.
Rasanen, K., et al., "Activation of Fibroblasts in Cancer Stroma," Experimental Cell Research, Oct. 2010, pp. 2713-2722, vol. 316, No. 17.
Raskatov, J. A., et al., "Gene Expression Changes in a Tumor Xenograft by a Pyrrole-Imidazole Polyamide," Proceedings of the National Academy of Sciences of the United States of America, 2012, pp. 16041-16045, vol. 109, No. 40.
Roberts, A., et al., "Streaming Fragment Assignment for Real-Time Analysis of Sequencing Experiments," Nature Methods, Jan. 2013, pp. 71-73, vol. 10, No. 1.
Robinson, M. D., et al., "A Scaling Normalization Method for Differential Expression Analysis of RNA-Seq Data," Genome Biology, 2010, 9 pages, vol. 11, No. R25.
Rossi, A., et al., "Carboplatin- or Cisplatin-Based Chemotherapy in First-Line Treatment of Small-Cell Lung Cancer: The COCIS Meta-Analysis of Individual Patient Data," Journal of Clinical Oncology, May 2012, pp. 1692-1698, vol. 30, No. 14.
Saggar, J. K., et al., "The Tumor Microenvironment and Strategies to Improve Drug Distribution," Frontiers in Oncology, Jun. 2013, pp. 1-6, vol. 3, Article 154.
Saidi, H., et al., "IFN-Gamma-Activated Monocytes Weakly Produce HIV-1 but Induce the Recruitment of HIV-Sensitive T Cells and Enhance the Viral Production by These Recruited T Cells," Journal of Leukocyte Biology, Mar. 2007, pp. 642-653, vol. 81, No. 3.
Saito, M., et al., "Reconstruction of Liver Organoid Using a Bioreactor," World Journal of Gastroenterology, Mar. 2006, pp. 1881-1888, vol. 12, No. 12.
Saito, M., et al., "The Functional Interrelationship Between Gap Junctions and Fenestrae in Endothelial Cells of the Liver Organoid," The Journal of Membrane Biology, Jun. 2007, pp. 115-121, vol. 217, Nos. 3.

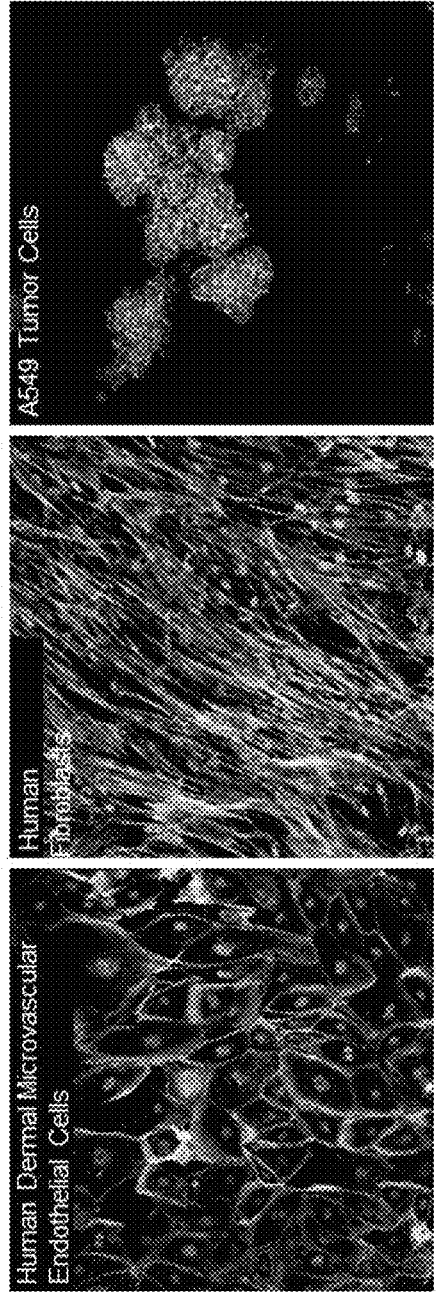
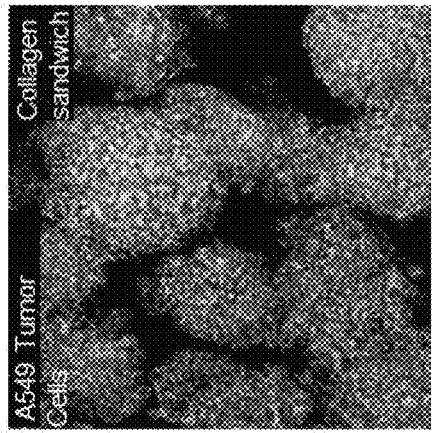
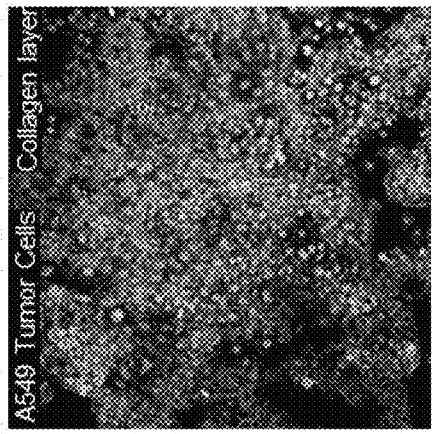
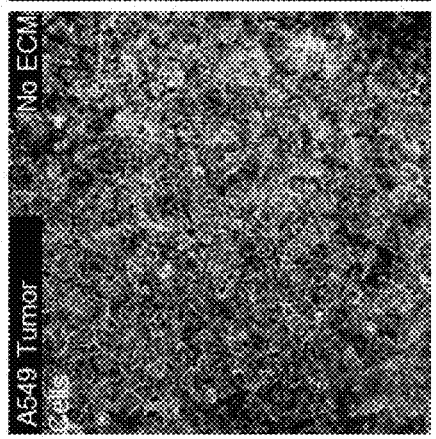
FIG. 13A  FIG. 13B  FIG. 13C
FIG. 13D  FIG. 13E  FIG. 13F Day 7 Static Sandwich Culture E-cadherin

FIG. 20B
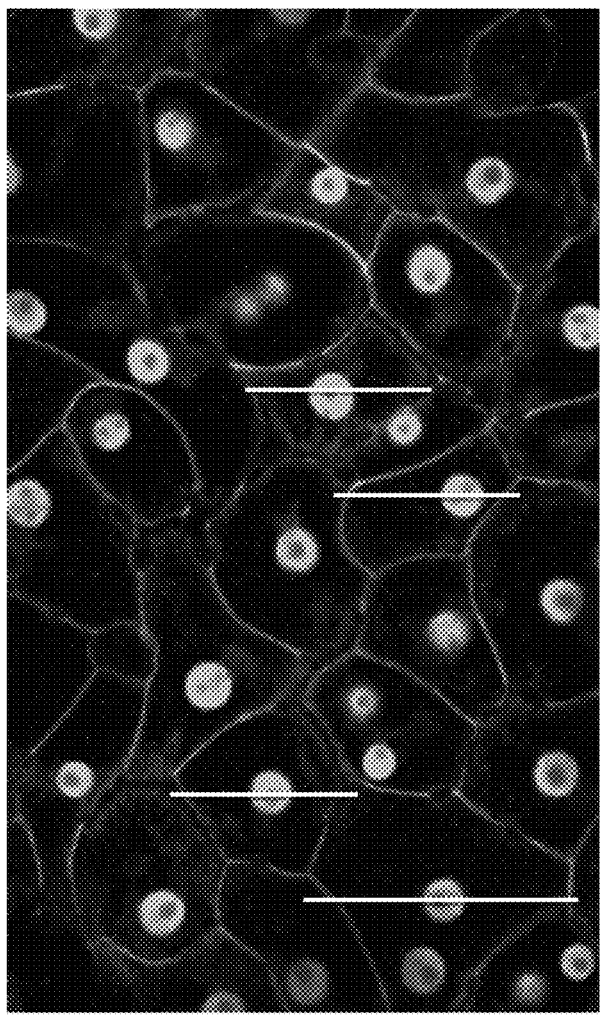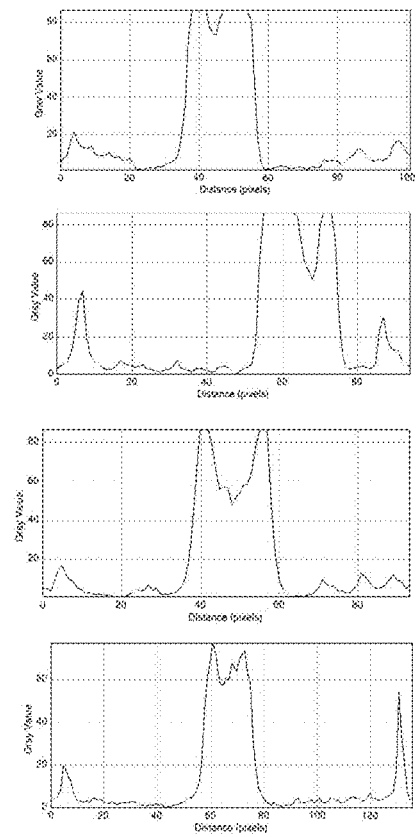
E-cadherin

Day 14 Controlled Hemodynamics

MRP - 2

Day 14 Static Sandwich Culture

MRP - 2

FIG. 21A
Day 14 Controlled Hemodynamics:
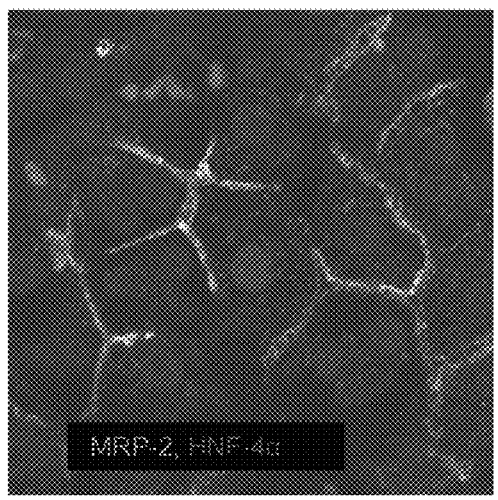
FIG. 21B
In vivo liver:
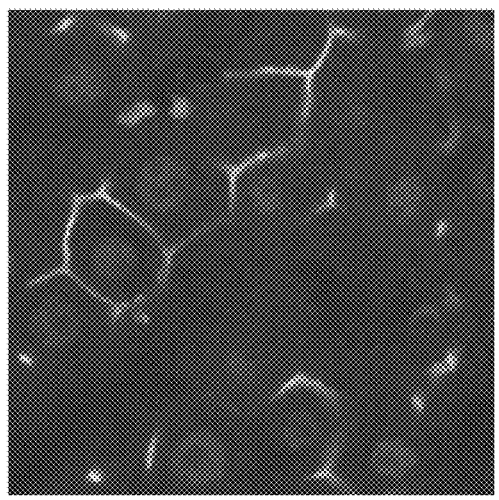
FIG. 21C
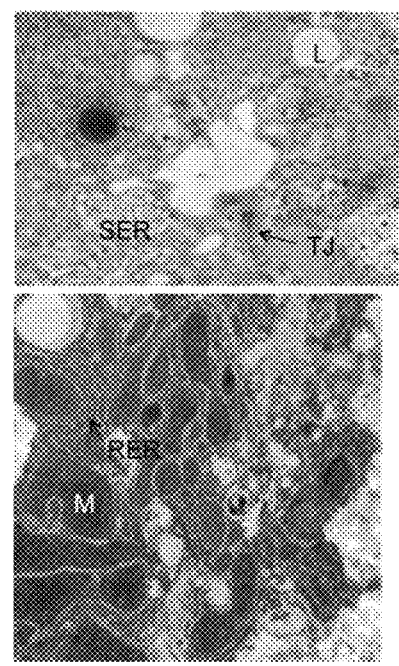
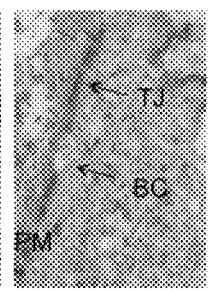
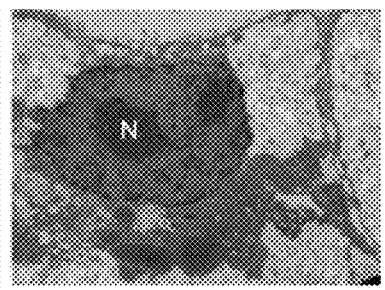
L – Lipid Droplet
BC – Bile Canaliculi
SER – Smooth Endoplasmic Reticulum
RER – Rough Endoplasmic Reticulum
M – Mitochondria
TJ – Tight Junctions
PM – Plasma Membrane
N – Nucleolus
Day 7 Controlled Hemodynamics:

FIG. 23A
FIG. 23B
Gene Expression of Controlled Hemodynamics Relative to Static at Day 7
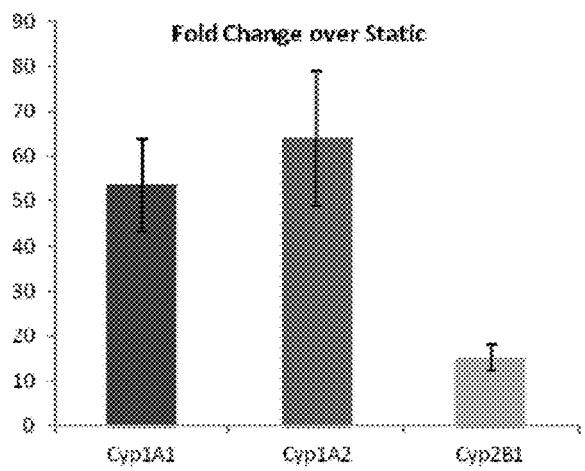
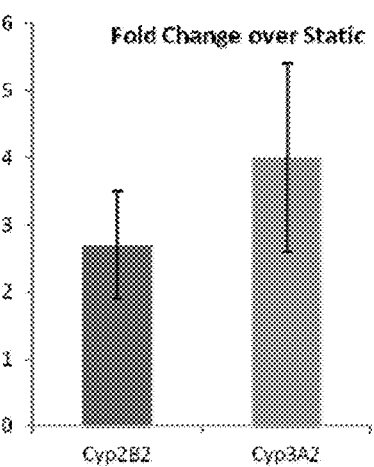
FIG. 23C
FIG. 23D
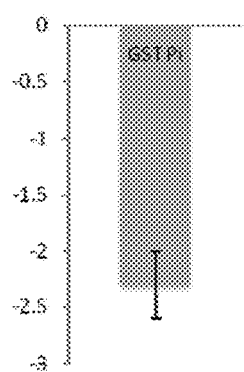
UGT1
β-actin
Day 4 Static | Day 4 Device | Day 7 Static | Day 7 Device | Day 14 Static | Day 14 Device
Effect of Controlled Hemodynamics in Device on UGT1 Protein Expression Over 2 Weeks Day 7 Controlled Hemodynamics:
Biliary Efflux Activity: CDFDA → CDF Healthy Phalloidin  Nile Red  Draq5

Disease

Phalloidin  Nile Red  Draq5

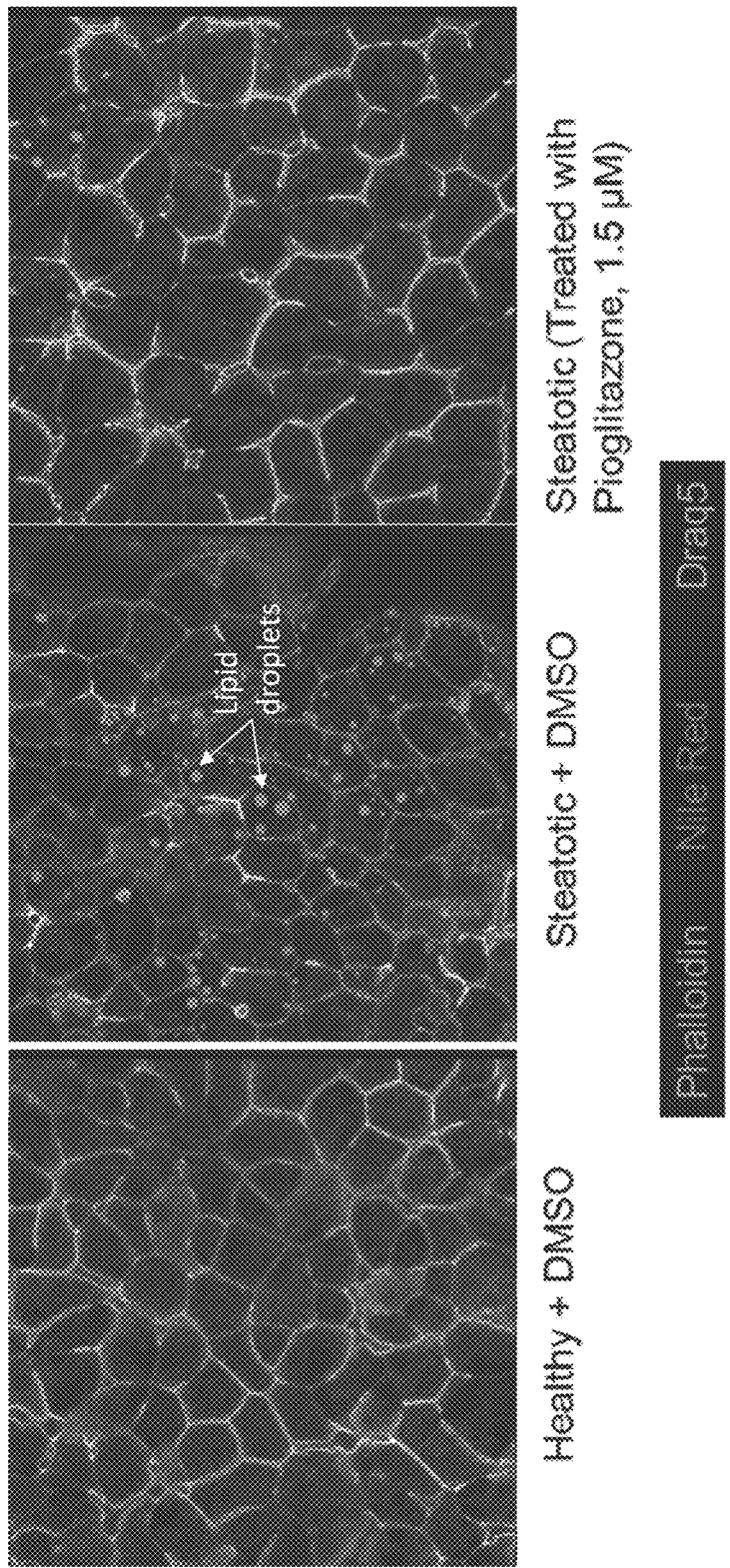

KalyCell Donor # N1309VT

IN VITRO MODEL FOR A TUMOR MICROENVIRONMENT

CROSS-REFERENCE TO RELATED APPLICATIONS

This application is a divisional of U.S. Non-Provisional patent application Ser. No. 14/520,303, filed Oct. 21, 2014, which claims the benefit of U.S. Provisional Patent Application Ser. No. 61/893,402, filed Oct. 21, 2013. Each of the above-cited applications is incorporated herein by reference in its entirety.

GOVERNMENT LICENSE RIGHTS

This invention was made with Government support under Contract Number HSN261201300024C awarded by the National Cancer Institute at the National Institutes of Health. The Government has certain rights in the invention.

FIELD OF THE INVENTION

The present invention generally relates to methods for mimicking a tumor microenvironment in vitro. The present invention also relates to methods for testing drugs or compounds in such systems and identifying potential cancer drug targets.

BACKGROUND OF THE INVENTION

In vivo, the tumor microenvironment is a complex milieu containing multiple cell types including tumor cells, vascular cells such as endothelial cells, and stromal cells, such as fibroblasts. In addition, in vivo, these cells are exposed to blood flow and various biological transport conditions. In vivo, microvascular cells in a tumor are affected by blood flow and communicate with tumor and non-tumor cells, both physically and through diffusible factors. In addition, the tumor vasculature is abnormal, characterized by chaotic branching, a low flow rate, and leaky vessels, and thus serves as a major transport barrier to anticancer therapies that target tumor cells. The interplay between tumor cells, endothelial cells, and stromal cells affects each cell type, leading to increased angiogenesis and tumor cell proliferation, and this crosstalk may be an important factor in determining the responsiveness of tumor cells to anticancer drugs.

Conventional in vitro tumor models using static monocultures of tumor cells fail to adequately model in vivo tumor biology. Current in vitro tumor models also do not accurately predict efficacy and safety of anticancer therapies in vivo. Traditional in vitro studies performed under static conditions are generally poor predictors of drug sensitivity, due to the lack of representation of components of the tumor microenvironment. Furthermore, the conventional models often do not exhibit responses to drugs or compounds at concentrations that produce the response in vivo, instead requiring much higher concentrations of the drug or compound to induce the same response. Thus, there exists a need in the art for methods for accurately mimicking the in vivo tumor microenvironment in vitro. Such methods would improve the accuracy of preclinical screening of anticancer agents for efficacy and safety.

SUMMARY OF THE INVENTION

A method for mimicking a tumor microenvironment in vitro is provided. The method comprises adding a culture medium to a cell culture container and plating at least one tumor cell type on a surface within the cell culture container. A shear stress is indirectly applied upon the at least one tumor cell type, the shear stress resulting from flow of the culture medium induced by a flow device, the flow mimicking flow to which the tumor cells are indirectly exposed in vivo in the tumor microenvironment. The flow is time-variant.

Another method for mimicking a tumor microenvironment in vitro is also provided. The method comprising adding a culture medium to a cell culture container and plating at least one tumor cell type on a first surface of a porous membrane within the cell culture container. A shear stress is indirectly applied upon the at least one tumor cell type by applying a shear stress upon a second surface of the porous membrane, the shear stress resulting from flow of the culture medium induced by a flow device, the flow mimicking flow to which the tumor cells are indirectly exposed in vivo in the tumor microenvironment.

Yet another method for mimicking a tumor microenvironment in vitro is also provided. The method comprises adding a culture medium to a cell culture container and plating at least one tumor cell type or stromal cell type on a first surface of a porous membrane within the cell culture container. When the stromal cell type is plated on the first surface of the porous membrane, at least one tumor cell type is present on a surface within the cell culture container. A shear stress is indirectly applied upon the at least one tumor cell type by applying a shear stress upon a second surface of the porous membrane, the shear stress resulting from flow of the culture medium induced by a flow device, the flow mimicking flow to which the tumor cells are indirectly exposed in vivo in the tumor microenvironment.

A further method for mimicking a tumor microenvironment in vitro is also provided. The method comprises adding a culture medium to a cell culture container and plating at least one stromal cell type on a first surface of a first porous membrane within the cell culture container. A second porous membrane is placed on the plated stromal cell type, such that a first surface of the second porous membrane contacts the plated stromal cells. At least one tumor cell type is plated on a second surface of the second porous membrane. A shear stress is indirectly applied upon the at least one tumor cell type by applying a shear stress upon the second surface of the first porous membrane, the shear stress resulting from flow of the culture medium induced by a flow device, the flow mimicking flow to which the tumor cells are indirectly exposed in vivo in the tumor microenvironment.

An in vitro method of testing a drug or a compound for an effect on a tumor is provided. The method comprises mimicking the tumor microenvironment and adding a drug or a compound to the culture medium. A shear stress is indirectly applied upon the at least one tumor cell type directly or indirectly exposed to the drug or the compound. A change in the at least one tumor cell type, in the presence of the drug or the compound, indicates that the drug or the compound has an effect on the tumor.

A method for mimicking tumor metastasis in vitro is also provided. The method comprises introducing cells of the at least one tumor cell type cultured according to any of the methods described above into an in vitro system that models an organ or tissue.

Another method for mimicking tumor metastasis is also provided. The method comprises introducing cells of the at least one tumor cell type cultured according to any of the methods described above into an animal.

Yet another method for mimicking tumor metastasis in vitro is provided. The method comprises adding a culture medium to a cell culture container and plating at least one cell type on a first surface of a porous membrane within the cell culture container, wherein the porous membrane is suspended in the cell culture container such that the first surface is proximal and in spaced relation to a bottom surface of the cell culture container, thereby defining within the cell culture container a lower volume comprising the at least one cell type and an upper volume comprising a second surface of the porous membrane. A shear stress is indirectly applied upon the at least one cell type, the shear stress resulting from flow of the culture medium induced by a flow device, the flow mimicking flow to which the cells are indirectly exposed in vivo. Tumor cells derived from a human or a humanized animal are introduced into the upper volume or the lower volume.

An in vitro method of testing a drug or a compound for an effect on tumor metastasis is provided. The method comprises mimicking tumor metastasis in vitro and adding a drug or a compound to the culture medium. A change in the cells of the at least one tumor cell type in the in vitro system that models the organ or tissue, in the presence of the drug or the compound, indicates that the drug or the compound has an effect on tumor metastasis.

A method for selecting a chemotherapy regimen to be administered to a subject having a tumor is provided. The method comprises testing a drug or a compound in vitro for an effect on the tumor or testing a drug or a compound for an in vitro effect on tumor metastasis, wherein the at least one tumor cell type comprises tumor cells derived from the subject's tumor. The method further comprises determining whether to administer the drug or the compound to the subject based on the results of the in vitro testing.

Other objects and features will be in part apparent and in part pointed out hereinafter.

BRIEF DESCRIPTION OF THE DRAWINGS

FIGS. 13A-C provide fluorescent microscopy images for human dermal microvascular endothelial cells (FIG. 13A), human fibroblasts (FIG. 13B), and A549 human non-small cell lung carcinoma (NSCLC) tumor cells (FIG. 13C) cultured using the method depicted in FIG. 9 under hemodynamic shear stress. FIGS. 13D-F provide fluorescent microscopy images for A549 tumor cells cultured using the method depicted in FIG. 9 under hemodynamic shear stress in the substantial absence of exogenously added extracellular matrix (ECM) (FIG. 13D), where the A549 tumor cells were plated on a layer of collagen (FIG. 13E), or where the A549 tumor cells were plated on a layer of collagen and another layer of collagen was deposited on top of the plated A549 tumor cells such that the collagen substantially surrounded the tumor cells (FIG. 13F, "collagen sandwich").

FIGS. 20A-F are fluorescent microscopy images of hepatocytes cultured under static conditions or in the presence of controlled hemodynamics.

FIG. 21A is a fluorescent microscopy image of hepatocytes cultured under controlled hemodynamics.

FIG. 21B is a fluorescent microscopy image of in vivo liver.

FIG. 21C shows transmission electron microscopy images of hepatocytes cultured under controlled hemodynamics.

FIGS. 23A-D provide metabolic gene expression data for hepatocytes cultured under static conditions or controlled hemodynamics.

FIGS. 32A-3C show fluorescent microscopy images from hepatocytes cultured under healthy conditions or under conditions that mimic fatty liver disease, in the presence or absence of pioglitazone.

Corresponding reference characters indicate corresponding parts throughout the drawings.

DETAILED DESCRIPTION OF THE INVENTION

Figure 1:
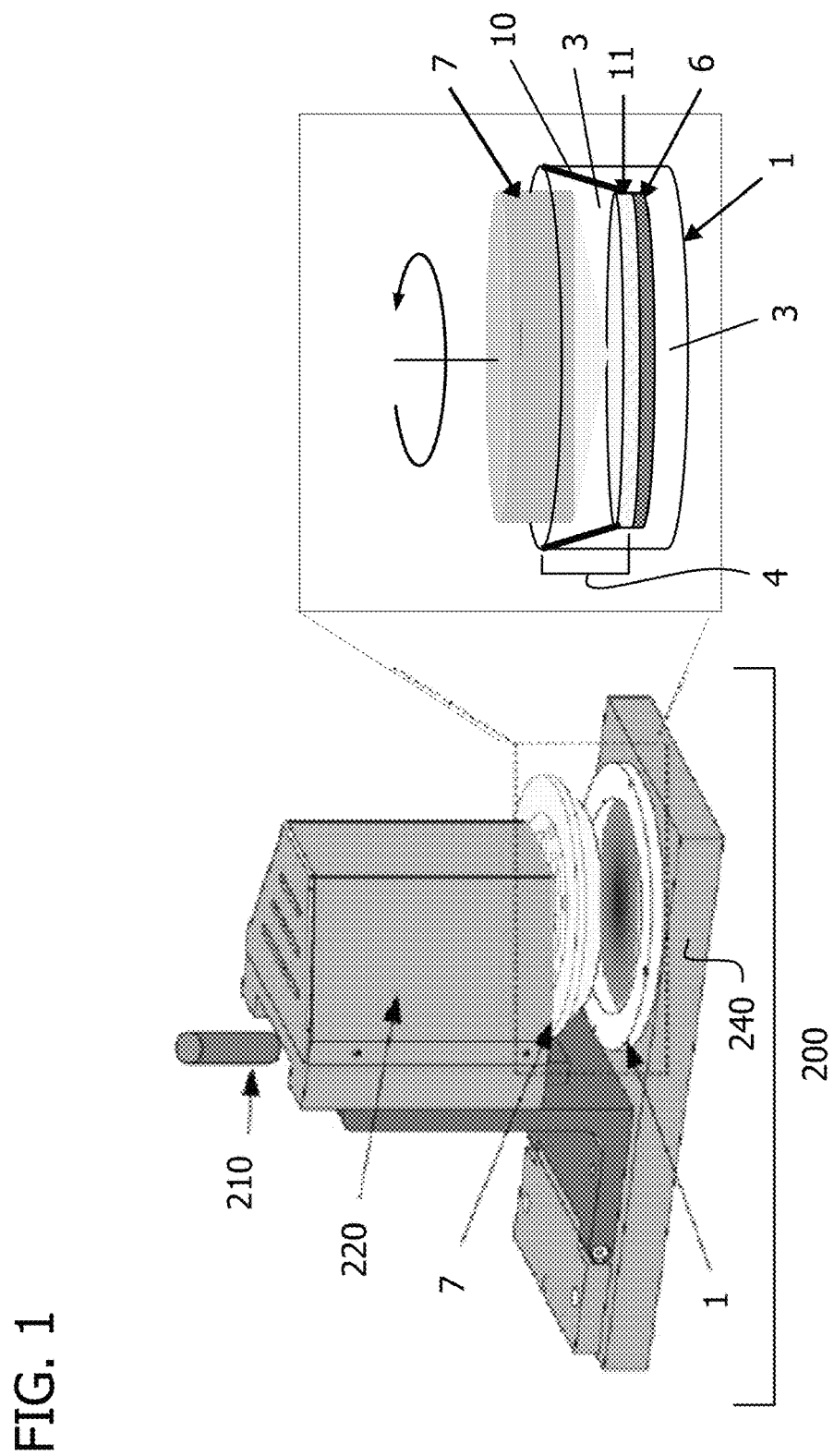
FIG. 1 depicts a cone-and-plate device and indirect application of a shear stress to tumor cells.

The present invention provides methods for mimicking a tumor microenvironment in vitro. In contrast to the static monoculture models currently used as the standard in vitro models of tumor biology by the pharmaceutical and biopharmaceutical industries, the methods of the present invention recreate the tumor microenvironment and can be used to assess multiple aspects of cancer, including endothelial cell barrier function, tumor growth, cell proliferation, cell migration, cell invasion, and alterations in responsiveness of tumor cells to anticancer therapies.

A method for mimicking a tumor microenvironment in vitro is provided. The method comprises adding a culture medium to a cell culture container, plating at least one tumor cell type on a surface within the cell culture container, and indirectly applying a shear stress upon the at least one tumor cell type. The shear stress results from flow of the culture medium induced by a flow device. The flow mimics flow to which the tumor cells are indirectly exposed in vivo in the tumor microenvironment. The flow is time-variant.

At least one extracellular matrix component can be deposited on the surface within the cell culture container, and the at least one tumor cell type can be plated on the at least one extracellular matrix component. Alternatively, the at least one tumor cell type can be suspended in a solution comprising at least one extracellular matrix component to create a suspension comprising the at least one tumor cell type and the at least one extracellular matrix component. The suspension can then be deposited on the surface within the cell culture container. The shear stress can be indirectly applied upon the at least one extracellular matrix component and the at least one tumor cell type.

The method can further comprise plating the at least one tumor cell type on a first surface of a porous membrane and indirectly applying the shear stress upon the at least one tumor cell type by applying the shear stress upon a second surface of the porous membrane.

Another method for mimicking a tumor microenvironment in vitro is also provided. The method comprises adding a culture medium to a cell culture container, plating at least one tumor cell type on a first surface of a porous membrane within the cell culture container, and indirectly applying a shear stress upon the at least one tumor cell type by applying a shear stress upon a second surface of the porous membrane. The shear stress results from flow of the culture medium induced by a flow device. The flow mimics flow to which the tumor cells are indirectly exposed in vivo in the tumor microenvironment.

Yet another method for mimicking a tumor microenvironment in vitro is provided. The method comprises adding a culture medium to a cell culture container and plating at least one tumor cell type or stromal cell type on a first surface of a porous membrane within the cell culture container. When the stromal cell type is plated on the first surface of the porous membrane, at least one tumor cell type is present on a surface within the cell culture container. Shear stress is indirectly applied upon the at least one tumor cell type by applying a shear stress upon a second surface of the porous membrane, the shear stress resulting from flow of the culture medium induced by a flow device, the flow mimicking flow to which the tumor cells are indirectly exposed in vivo in the tumor microenvironment.

In any of the methods wherein the at least one tumor cell type is plated on a first surface of a porous membrane, the porous membrane can be suspended in the cell culture container such that the first surface is proximal and in spaced relation to a bottom surface of the cell culture container, thereby defining within the cell culture container a lower volume comprising the at least one tumor cell type and an upper volume comprising a second surface of the porous membrane. The shear stress is applied upon the second surface of the porous membrane in the upper volume of the container.

In addition, in any of the methods wherein the at least one tumor cell type is plated on a first surface of a porous membrane, the method can further comprise depositing at least one extracellular matrix component on the first surface of the porous membrane and plating the at least one tumor cell type on the at least one extracellular matrix component. Alternatively, the at least one tumor cell type can be suspended in a solution comprising at least one extracellular matrix component to create a suspension comprising the at least one tumor cell type and the at least one extracellular matrix component, and the suspension can be deposited on the first surface of the porous membrane. The porous membrane is suspended in the cell culture container such that the first surface is proximal and in spaced relation to a bottom surface of the cell culture container, thereby defining within the cell culture container a lower volume comprising the at least one extracellular matrix component and the at least one tumor cell type, and an upper volume comprising a second surface of the porous membrane. The shear stress is applied upon the second surface of the porous membrane in the upper volume of the container.

The method can further comprise plating endothelial cells on the second surface of the porous membrane, and applying the shear stress upon the plated endothelial cells. The at least one tumor cell type is plated on a first surface of the porous membrane.

The method can further comprise plating at least one stromal cell type on the second surface of the porous membrane and applying the shear stress upon the plated stromal cell type.

In methods where the at least one stromal cell type is plated on the second surface of the porous membrane, the method can further comprise plating endothelial cells on the second surface of the porous membrane. The at least one stromal cell type can be mixed with the endothelial cells prior to plating, and the method can comprise applying the shear stress upon the plated mixture of the at least one stromal cell type and the endothelial cells. Alternatively, the at least one stromal cell type and the endothelial cells can be sequentially plated on the second surface of the porous membrane. For example, the method can comprise plating the at least one stromal cell type on the second surface of the porous membrane, subsequently plating the endothelial cells on the plated stromal cell type, and applying the shear stress on the plated endothelial cells. Alternatively, the method can comprise plating the endothelial cells on the second surface of the porous membrane, subsequently plating the at least one stromal cell type on the plated endothelial cells, and applying the shear stress on the plated stromal cell type.

In the methods wherein the at least one tumor cell type is plated on a first surface of a porous membrane, the porous membrane can be a first porous membrane and the method can comprise plating the at least one tumor cell type on a first surface of the first porous membrane. At least one stromal cell type is plated on a second surface of the first porous membrane. A second porous membrane is placed on the plated stromal cell type such that a first surface of the second porous membrane contacts the plated stromal cells. The shear force is applied upon a second surface of the second porous membrane.

In the methods comprising depositing at least one extracellular matrix component or a suspension comprising the at least one tumor cell type and at least one extracellular matrix component on the first surface of a porous membrane the porous membrane can be a first porous membrane and the method can further comprise depositing the at least one extracellular matrix component on the first surface of the first porous membrane and plating the at least one tumor cell type on the at least one extracellular matrix component. Alternatively, the method can further comprise depositing the suspension comprising the at least one tumor cell type and the at least one extracellular matrix component on the first surface of the first porous membrane. Either method further comprises plating at least one stromal cell type on a second surface of the first porous membrane, placing a second porous membrane on the plated stromal cell type such that a first surface of the second porous membrane contacts the plated stromal cells, and applying the shear force upon a second surface of the second porous membrane.

In the methods wherein the porous membrane is a first porous membrane described above, the method can further comprise plating endothelial cells on the second surface of the second porous membrane and applying the shear force upon the plated endothelial cells.

In the methods that comprise plating at least one tumor cell type or stromal cell type on a first surface of a porous membrane, the porous membrane can be a first porous membrane and the method can further comprise plating the at least one stromal cell type on a first surface of a first porous membrane. A second porous membrane is placed on the plated stromal cell type, such that a first surface of the second porous membrane contacts the plated stromal cells. At least one tumor cell type is plated on a second surface of the second porous membrane. The shear force is indirectly applied upon the at least one tumor cell type by applying the shear stress upon the second surface of the first porous membrane.

The present invention is also directed to another method for mimicking a tumor microenvironment in vitro. The method comprises adding a culture medium to a cell culture container and plating at least one stromal cell type on a first surface of a first porous membrane within the cell culture container. A second porous membrane is placed on the plated stromal cell type, such that a first surface of the second porous membrane contacts the plated stromal cells. At least one tumor cell type is plated on a second surface of the second porous membrane. Shear stress is indirectly applied upon the at least one tumor cell type by applying a shear stress upon the second surface of the first porous membrane, the shear stress resulting from flow of the culture medium induced by a flow device, the flow mimicking flow to which the tumor cells are indirectly exposed in vivo in the tumor microenvironment.

In the methods comprising plating at least one stromal cell type on a first surface of a first porous membrane, the first porous membrane can be suspended in the cell culture container such that the first surface of the first porous membrane is proximal and in spaced relation to a bottom surface of the cell culture container, thereby defining within the cell culture container a lower volume comprising the at least one tumor cell type, the second porous membrane, and the at least one stromal cell type, and an upper volume comprising a second surface of the first porous membrane. The shear stress is applied upon the second surface of the first porous membrane in the upper volume of the container.

In the methods comprising plating at least one stromal cell type on a first surface of a first porous membrane, the method can further comprise depositing at least one extracellular matrix component on the second surface of the second porous membrane and plating the at least one tumor cell type on the at least one extracellular matrix component. Alternatively, the method can further comprise suspending the at least one tumor cell type in a solution comprising at least one extracellular matrix component to create a suspension comprising the at least one tumor cell type and the at least one extracellular matrix component, and depositing the suspension on the second surface of the second porous membrane.

In the methods comprising plating at least one stromal cell type on a first surface of a first porous membrane, the method can further comprise plating endothelial cells on the second surface of the first porous membrane and applying the shear stress upon the plated endothelial cells.

In the methods comprising the use of a second porous membrane, the method can further comprise immersing the second porous membrane in a solution comprising at least one extracellular matrix component prior to placing the second porous membrane on the plated stromal cell type.

In any of the methods comprising plating endothelial cells, the method can further comprises coplating at least one tumor cell type with the endothelial cells. The coplating can comprise mixing the at least one tumor cell type with the endothelial cells prior to plating. Alternatively, the coplating can comprise sequentially plating the at least one tumor cell type and the endothelial cells. For example, the coplating can comprise plating the at least one tumor cell type and subsequently plating the endothelial cells. Alternatively, the coplating can comprise plating the endothelial cells and subsequently plating the at least one tumor cell type.

In any of the methods comprising coplating at least one tumor cell type with the endothelial cells, the coplating can comprise plating the endothelial cells and the at least one tumor cell type at a ratio of about 100:1 to about 3:1. For example, the coplating can comprise plating the endothelial cells and the at least one tumor cell type at a ratio of about 50:1 to about 10:1.

In any of the methods comprising coplating at least one tumor cell type with the endothelial cells, the at least one tumor cell type can be any of the tumor cell types described herein. In these methods, the at least one tumor cell type preferably comprises cells derived from a glioblastoma.

In any of the methods wherein cells are plated on a porous membrane, the porous membrane, the first porous membrane, or the second porous membrane can adapted to permit fluid communication of the culture medium and physical interaction and communication between cells plated on opposing sides of the porous membrane.

The present invention also relates to an in vitro method of testing a drug or a compound for an effect on a tumor. The method comprises mimicking the tumor microenvironment, adding a drug or a compound to the culture medium, and indirectly applying the shear stress upon the at least one tumor cell type directly or indirectly exposed to the drug or the compound. A change in the at least one tumor cell type, in the presence of the drug or the compound, indicates that the drug or the compound has an effect on the tumor. The tumor microenvironment can be mimicked by the in vitro methods of mimicking a tumor microenvironment described above.

To confirm that the in vivo tumor microenvironment is mimicked, a change in the level or localization of a marker of the tumor microenvironment can be compared between a method of the invention and the same method in the absence of the application of the shear stress. The level or localization of the marker in the at least one tumor cell type, the at least one stromal cell type, or the endothelial cells upon application of the shear stress is compared to the level or localization of the marker in the at least one tumor cell type, the at least one stromal cell type, or the endothelial cells in the absence of the application of shear stress. Alternatively, the level of a marker in the culture medium upon application of the shear stress is compared to the level of the marker in the culture medium in the absence of the application of the shear stress. For example, if a marker is known to be associated with the presence of a tumor and its concentration is known to increase in the serum when a tumor is present in vivo, an increase in the level of the marker in the culture medium of the method of the invention with application of the shear stress as compared to the level of the marker in the culture medium in the absence of the application of the shear stress confirms that the tumor microenvironment is mimicked by the in vitro method of the invention.

In any of the above methods, the cell culture container can comprise inlets and outlets. The inlets and outlets can be used for perfusing cell culture medium, drugs, compounds, and other components into and out of the cell culture container.

The inlets and outlets can be within the portions of the cell culture container defining the upper and lower volumes.

Any of the methods can comprise perfusing culture medium into and out of the cell culture container. For example, the methods can comprise perfusing culture medium into and out of the upper volume and/or perfusing culture medium into and out of the lower volume.

Any of the methods for mimicking a tumor microenvironment in vitro can comprise mimicking the tumor microenvironment in vitro in a first cell culture container according to any of the methods described herein, mimicking the tumor microenvironment in vitro in a second cell culture container according to any of the methods described herein, and transferring cells of the at least one tumor cell type cultured in the first cell culture container into the second cell culture container. The transferring can comprise manually transferring the cells of the at least one tumor cell type cultured in the first cell culture container into the second cell culture container. Alternatively, an outlet in the first cell culture container can be connected to an inlet in the second cell culture container, and the method can further comprise pumping culture medium comprising the at least one tumor cell type out of the first cell culture container and into the second cell culture container.

In any of the methods for mimicking a tumor microenvironment in vitro described herein, the method can further comprise introducing cells cultured in an in vitro system that models an organ or tissue into the cell culture container.

Cell Types

Any of the methods described above can further comprise plating at least one stromal cell type on the surface within the cell culture container, on the at least one extracellular matrix component, or on the first surface of the porous membrane. Alternatively, at least one stromal cell type can be suspended with the tumor cell type in the solution comprising the at least one extracellular matrix component to create a suspension comprising the at least one stromal cell type, the at least one tumor cell type, and the at least one extracellular matrix component, and the suspension can be deposited on the surface within the cell culture container or on the first surface of the porous membrane.

For methods wherein the at least one tumor cell type is plated on a first surface of a first porous membrane, the methods can further comprise plating at least one stromal cell type on the first surface of the first porous membrane. Alternatively, the methods can further comprise suspending at least one stromal cell type with the tumor cell type in the solution comprising the at least one extracellular matrix component to create a suspension comprising the at least one stromal cell type, the at least one tumor cell type, and the at least one extracellular matrix component, and depositing the suspension on the first surface of the first porous membrane.

For methods wherein the at least one tumor cell type is plated on a second surface of a second porous membrane, the methods can further comprise plating at least one stromal cell type on the second surface of the second porous membrane. Alternatively, the methods can further comprise suspending at least one stromal cell type with the tumor cell type in the solution comprising the at least one extracellular matrix component to create a suspension comprising the at least one stromal cell type, the at least one tumor cell type, and the at least one extracellular matrix component, and depositing the suspension on the second surface of the second porous membrane.

Any of the methods described above can also further comprise plating one or more additional cell types on a surface of the cell culture container, on the at least one extracellular matrix component, on the first or second surface of the porous membrane, on the first or second surface of the first porous membrane, or on the first or second surface of the second porous membrane; or suspending one or more additional cell types in the culture medium within the upper volume or in the culture medium within the lower volume.

In any of the methods that comprise suspending the at least one tumor cell type in a solution comprising at least one extracellular matrix component, the method can further comprise suspending one or more additional cell types with the at least one tumor cell type in the solution comprising the at least on extracellular matrix component to create a suspension comprising the one or more additional cell types, the at least one tumor cell type, and the at least one extracellular matrix component, and depositing the suspension on the surface within the cell culture container, on the first surface of the porous membrane, on the first surface of the first porous membrane, or on the second surface of the second porous membrane.

Cell types for use in the methods of the invention include primary cells and immortalized cells. The at least one tumor cell type, the endothelial cells, the at least one stromal cell type, or the one or more additional cell types can comprise immortalized cells. The at least one tumor cell type, the endothelial cells, the at least one stromal cell type, or the one or more additional cell types can comprise primary cells.

Any of the cell types can comprise cells derived from an animal, e.g., from a genetically modified animal or a human.

In any of the methods of the invention, the method can further comprise the step of culturing the cell type or cell types.

The at least one tumor cell type, the endothelial cells, the at least one stromal cell type, and additional cell types that can be used in the methods are further described below.

Tumor Cells

The at least one tumor cell type can comprise cells derived from a carcinoma, a sarcoma, a lymphoma, an adenosquamous carcinoma, a mixed mesodermal tumor, carcinosarcoma, a teratocarcinoma, or a combination thereof.

The cells derived from a carcinoma can comprise cells derived from an adenocarcinoma, cells derived from a squamous cell carcinoma, or a combination thereof.

The cells derived from a sarcoma can comprise cells derived from an osteosarcoma, a chondrosarcoma, a leiomyosarcoma, a rhabdomyosarcoma, a mesothelial sarcoma (mesothelioma), a fibrosarcoma, an angiosarcoma (e.g., from a hemangioendothelioma, a lymphangiosarcoma, or a combination thereof), a liposarcoma, a glioma, an astrocytoma, a myxosarcoma, a mesenchymous tumor, a mixed mesodermal tumor, or a combination thereof.

The cells derived from a lymphoma can comprise cells derived from a Hodgkin lymphoma, a non-Hodgkin lymphoma, or a combination thereof.

The at least one tumor cell type can be derived from a tumor of connective tissue, a tumor of endothelium or mesothelium, a tumor of lymphoid tissue, a tumor of muscle, a tumor of an epithelial tissue, a tumor of a neural tissue, a tumor of the amine precursor uptake and decarboxylation (APUD) system, a tumor of a neural crest-derived cell, a gonadal tumor, or a combination thereof.

Where the at least one tumor cell type is derived from a tumor of connective tissue, the tumor can comprise a tumor of adult fibrous tissue (e.g., a firboma or a fibrosarcoma), embryonic (myxomatous) fibrous tissue (e.g., a myxoma or a myxosarcoma), adipose tissue (e.g., a lipoma or a liposarcoma), cartilage tissue (e.g., a chondroma or a chondrosarcoma), bone (e.g., osteoma or a osteosarcoma), notochord (e.g., a chordoma), a fibrous histiocytoma (e.g., a malignant fibrous histiocytoma), or a combination thereof.

Where the at least one tumor cell type is derived from a tumor of endothelium or mesothelium, the tumor can comprise a blood vessel tumor (e.g., a hemangioma, a hemangiopericytoma, a hemangiosarcoma, or an angiosarcoma), a lymph vessel tumor (e.g., a lymphangioma or a lymphangiosarcoma), a mesothelium tumor (e.g., a mesothelioma), or a combination thereof.

Where the at least one tumor cell type is derived from a tumor of lymphoid tissue, the tumor can comprises a plasmacytoma, a Hodgkin lymphoma, a non-Hodgkin lymphoma, or a combination thereof.

Where the at least one tumor cell type is derived from a tumor of muscle, the tumor can comprise a smooth muscle tumor (e.g., a leiomyoma or a leiomyosarcoma), a striated muscle tumor (e.g., a rhabdomyoma or a rhabdomyosarcoma), or a combination thereof.

Where the at least one tumor cell type is derived from a tumor of an epithelial tissue, the tumor can comprise a tumor of a stratified squamous tissue (e.g., a papilloma, a seborrheic keratosis, a skin adnexal tumor, a squamous cell carcinoma, or an epidermoid carcinoma), a tumor of a glandular epithelium (e.g., a tumor of the glandular epithelium or a liver, kidney or bile duct), a tumor of transitional epithelium (e.g., a transitional cell papilloma or a transitional cell carcinoma), a placental tumor (e.g., a hydatidiform mole or a choriocarcinoma), a testicular tumor (e.g., a seminoma or an embryonal cell carcinoma), or a combination thereof. Where the tumor of the glandular epithelium is a tumor of the glandular epithelium of the liver, the tumor can comprise a hepatic adenoma or a hepatocellular carcinoma. Where the tumor of the glandular epithelium is a tumor of the glandular epithelium of the kidney, the tumor can comprise a renal tubular adenoma, a renal cell carcinoma, or a hypernephroma. Where the tumor of the glandular epithelium is a tumor of the glandular epithelium of the bile duct, the tumor can comprise a bile duct adenoma or a cholangiocarcinoma.

Where the at least one tumor cell type is derived from a tumor of a neural tissue, the tumor can comprise a glial cell tumor (e.g., a glioma or a glioblastoma), a nerve cell tumor (e.g., a ganglioneuroma, a nueroblastoma, or a medulloblastoma), a tumor of the meninges (e.g., a meningioma), a nerve sheath tumor (e.g., a Schwannoma, a neurilemmoma, a neurofibroma, a minigioma, or a neurofibrosarcoma), or a combination thereof.

Where the at least one tumor cell type is derived from a tumor of the amine precursor uptake and decarboxylation (APUD) system, the tumor can comprise a pituitary tumor (e.g., a basophilic adenoma, a eosinophilic adenoma, or a chromophobe adenoma), a parathyroid tumor (e.g., a parathyroid adenoma or a parathyroid carcinoma), a thyroid tumor (e.g., a C cell hyperplasia or a medullary carcinoma of the thyroid), a bronchial lining tumor (e.g., a bronchial carcinoid or an oat cell carcinoma), an adrenal medulla tumor (e.g., a pheochromocytoma), a pancreatic tumor (e.g., an islet celladenoma, an insulinoma, a gastrinoma, or an islet cell carcinoma), a tumor of the stomach or intestines (e.g., a carcinoid), a tumor of the carotid body tumor or chemoreceptor system (e.g., a chemodectoma, a paraganglioma, or a carcinoid), or a combination thereof.

Where the at least one tumor cell type is derived from a tumor of a neural crest-derived cell, the tumor can comprise a tumor of a pigment producing cell (e.g., a nevus or a melanoma), a tumor of a Schwann cell of the peripheral nervous system (e.g., a Schwannoma or a neurilemmoma), a tumor of a Merkel cell (e.g., a Merkel cell neoplasm), or a combination thereof.

Where the at least one tumor cell type is derived from a gonadal tumor, the gonadal tumor can comprises a tumor of the ovary, a tumor of the testis, a seminoma, a dysgerminoma, a choriocarcinoma, an embryonal carcinoma, an endodermal sinus tumor, a teratocarcinoma, a Sertoli-Leydig cell tumor, an arrhenoblastoma, a granulosa-theca cell tumor, a hilar cell tumor, a lipid cell tumor, or a combination thereof.

The at least one tumor cell type can be derived from a tumor of the lung, breast, colon, rectum, prostate, bladder, bone, pancreas, liver, bile duct, ovary, testis, uterus, placenta, brain, cartilage, smooth muscle, striated muscle, membranous lining of a body cavity, fibrous tissue, blood vessel, lymph vessel, lymph node, adipose tissue, neurogenic connective tissue of the brain, kidney, pituitary gland, parathyroid, thyroid, bronchial lining, adrenalmedulla, stomach, large intestine, small intestine, carotid body, chemoreceptor system, skin, gall bladder, or a combination thereof.

The at least one tumor cell type can comprise immortalized cells. For example, the at least one tumor cell type can comprise an immortalized cell line comprising non-small cell lung adenocarcinoma cells, breast carcinoma cells, pancreas carcinoma cells, prostate cancer cells, ovarian carcinoma cells, colon cancer cells, or a combination thereof. For example, the immortalized cell line can comprise human non-small cell lung adenocarcinoma cell line A549, human breast carcinoma cell line MDA-MB-231, human pancreas carcinoma cell line BxPC-3, human prostate cancer cell line DU145, human prostate cancer cell line LNCaP, human ovarian carcinoma cell line SKOV-3, human colon cancer cell line COLO-205, or a combination thereof.

The at least one tumor cell type can comprise primary cells. For example, the tumor cell type can comprise primary tumor cells obtained from a subject by biopsy, tumor resection, blood draw, or a combination thereof. A blood draw can be used to obtain cancer cells that have been shed from the primary tumor and that are present in the circulatory system. The primary tumor cells can be obtained from a stage I tumor, a stage II tumor, a stage III tumor, or a stage IV tumor.

The at least one tumor cell type can comprise tumor cells derived from a humanized animal bearing a tumor derived from a human subject, such as a humanized mouse. For example, the humanized mouse can be a non-obese diabetic severe combined immunodeficiency (NOD SCID) mouse, a NOD/Shi-scid/IL-2Rγnull (NOG) mouse, or a NOD SCID IL-2Rγ knockout (NSG) mouse.

Endothelial Cells

The endothelial cells can comprise microvascular endothelial cells, macrovascular endothelial cells, endothelial progenitor cells, or a combination thereof.

The endothelial cells can be derived from a tumor. For example, where the at least one tumor cell type comprises cells derived from a tumor of an animal, the endothelial cells can be derived from the same tumor.

The endothelial cells can also be derived from an organ or tissue in which a tumor resides. For example, where the at least one tumor cell type comprises cells derived from a tumor of an animal, the endothelial cells can be derived from the organ or tissue in which that tumor resides. Thus, for instance, if the at least one tumor cell type comprises cells derived from a tumor of the lung, the endothelial cells can comprise endothelial cells derived from lung tissue of that animal or lung tissue of a different animal.

The endothelial cells can comprise endothelial cells derived from lung, breast, colon, rectum, prostate, bladder, bone, pancreas, liver, bile duct, ovary, testis, uterus, placenta, brain, cartilage, smooth muscle, striated muscle, a membranous lining of a body cavity, fibrous tissue, blood vessel, lymph vessel, lymph node, adipose tissue, neurogenic connective tissue of the brain, kidney, pituitary gland, parathyroid, thyroid, bronchial lining, adrenalmedulla, stomach, large intestine, small intestine, carotid body, chemoreceptor system, skin, gall bladder, or a combination thereof.

For example, the endothelial cells can comprise lung microvascular endothelial cells, breast microvascular endothelial cells, pancreatic microvascular endothelial cells, prostate microvascular endothelial cells, ovarian microvascular endothelial cells, colon microvascular endothelial cells, or a combination thereof.

The endothelial cells can comprise cells derived from inducible pluripotent stem cells (iPSC).

Stromal Cells

The at least one stromal cell type can comprise fibroblasts, immune cells, pericytes, inflammatory cells, or a combination thereof.

Where the at least one stromal cell type comprises fibroblasts, the fibroblasts can comprise fetal stromal fibroblasts, for example, human fetal stromal fibroblast cell line IMR-90. Alternatively, the fibroblasts can comprise human lung fibroblast cell line Hs888Lu.

Where the at least one stromal cell type comprises immune cells, the immune cells can comprise macrophages, lymphocytes, dendritic cells, or a combination thereof.

Where the at least one stromal cell type comprises inflammatory cells, the inflammatory cells can comprise B cells, T cells, or a combination thereof.

The at least one stromal cell type can comprise cells derived from inducible pluripotent stem cells (iPSC).

The at least one stromal cell type can be mixed with the at least one tumor cell type prior to plating. For example, the at least one stromal cell type can be mixed with the at least one tumor cell type at a ratio of about 0.1:1 to about 3:1, a ratio of about 0.2:1 to about 2:1, a ratio of about 0.25:1, or a ratio of about 1:1.

Alternatively, the method can comprise sequentially plating the at least one tumor cell type and the at least one stromal cell type. For example, the method can comprise plating the at least one tumor cell type and subsequently plating the at least one stromal cell type on the plated tumor cell type. Alternatively, the method can comprise plating the at least one stromal cell type and subsequently plating the at least one tumor cell type on the plated stromal cell type.

Additional Cell Types

The methods described herein can also further comprise plating one or more additional cell types on a surface of the cell culture container, on the at least one extracellular matrix component, on the first or second surface of the porous membrane, on the first or second surface of the first porous membrane, or on the first or second surface of the second porous membrane; or suspending one or more additional cell types in the culture medium within the upper volume or in the culture medium within the lower volume. For example, the one or more additional cell types can comprise a cell type adhered to the bottom surface of the cell culture container.

In any of the methods that comprise suspending the at least one tumor cell type in a solution comprising at least one extracellular matrix component, the method can further comprise suspending one or more additional cell types with the at least one tumor cell type in the solution comprising the at least on extracellular matrix component to create a suspension comprising the one or more additional cell types, the at least one tumor cell type, and the at least one extracellular matrix component, and depositing the suspension on the surface within the cell culture container, on the first surface of the porous membrane, on the first surface of the first porous membrane, or on the second surface of the second porous membrane.

The one or more additional cell types can comprise fibroblasts, immune cells, pericytes, inflammatory cells, or a combination thereof.

Where the one or more additional cell types comprise fibroblasts, the fibroblasts can comprise fetal stromal fibroblasts, for example, human fetal stromal fibroblast cell line IMR-90. Alternatively, the fibroblasts can comprise human lung fibroblast cell line Hs888Lu.

Where the one or more additional cell types comprises immune cells the immune cells can comprise macrophages, lymphocytes, dendritic cells, or a combination thereof. For example, the immune cells can comprise the lymphocytes and the lymphocytes can be suspended in the culture medium within the upper volume.

Where the one or more additional cell types comprises inflammatory cells, the inflammatory cells can comprise B cells, T cells, or a combination thereof.

Extracellular Matrix Components

The one or more extracellular matrix components can be produced by a cell type plated on a surface within the cell culture container (e.g., by the at least one tumor cell type). When the extracellular matrix is produced by a cell type or cell types plated on a surface within the cell culture container, the extracellular matrix is referred to herein as "endogenous" extracellular matrix.

By contrast, when one or more extracellular matrix components are deposited on a surface within the cell culture container during the methods described herein, the extracellular matrix is referred to as "exogenous" or "exogenously added" extracellular matrix.

The methods described herein can comprise culturing the cell type or cell types in the substantial absence of exogenously added extracellular matrix. The "substantial absence of exogenously added extracellular matrix" means that the method does not comprise depositing an extracellular matrix component on a surface within the cell culture container, or suspending one or more cell types in a solution comprising an extracellular matrix component to create a suspension comprising the cell type and the at least one extracellular matrix component and depositing the suspension on a surface within the cell culture container. However, where the methods comprise the use of first and second porous membranes, the method can comprise immersing the second porous membrane in a solution comprising at least one extracellular matrix component prior to placing the second porous membrane on the plated stromal cell type. Without being bound to any particular theory, it is thought that when this immersion step is performed, the extracellular matrix component is absorbed by the porous membrane and aids in the attachment of cells to the membrane, but only results in the addition of a very small amount of extracellular matrix to the cell culture container. Thus, cells can be cultured in the "substantial absence of exogenously added extracellular matrix" even where this immersion step has been performed. Culturing cells in the "substantial absence of exogenously added extracellular matrix" also includes methods that do not comprise adding any exogenous extracellular matrix whatsoever to the cell culture container.

Extracellular matrix components for use in the methods of the invention can comprise a collagen, heparan sulfate, chondroitin sulfate, keratan sulfate, hyaluronic acid, an elastin, a fibronectin, a laminin, a vitronectin, or a combination thereof. The extracellular matrix component is preferably a type of extracellular matrix component that is present in the in vivo environment of the tumor cells, endothelial cells, stromal cells, and/or one or more additional cell types.

For example, where the extracellular matrix component comprises a collagen, the collagen can comprise collagen type I, collagen type II, collagen type III, collagen type IV, collagen type V, collagen type VI, collagen type VII, collagen type VIII, collagen type IX, collagen type X, collagen type XI, collagen type XII, collagen type XIII, collagen type XIV, collagen type XV, collagen type XVI, collagen type XVII, collagen type XVIII, collagen type XIX, collagen type XX, collagen type XXI, collagen type XXII, collagen type XXIII, collagen type XXIV, collagen type XXV, collagen type XXVI, collagen type XXVII, collagen type XXVIII, or a combination thereof. Where the extracellular matrix component comprises a collagen, the concentration of the collagen is preferably about 1 mg/ml to about 10 mg/ml, about 2 mg/ml to about 5 mg/ml, or at least about 2 mg/ml.

The extracellular matrix component can comprise decellularized extracellular matrix purified from a biological source (e.g., human placenta).

The extracellular matrix component can be secreted by a cell type or cell types within the cell culture container (e.g., by the at least one tumor cell type).

The extracellular matrix component can be secreted by fibroblasts, chondrocytes, or osteoblasts plated on a surface within the cell culture container.

The extracellular matrix component suitably mimics the stiffness of the in vivo tumor microenvironment. For example, the at least one extracellular matrix component can have a Young's modulus of about 0.1 kPa to about 25 kPa, about 0.15 kPa to about 15 kPa, or about 3 kPa to about 12 kPa.

The at least one extracellular matrix component can have a non-uniform Young's modulus. For example, two or more different types of an extracellular matrix component or two or more concentrations of a single extracellular matrix component can be deposited on the surface within the cell culture container or the surface of the porous membrane to create a layer of extracellular matrix that has a non-uniform Young's modulus. The Young's modulus of the extracellular matrix can vary in a linear gradient across the surface within the cell culture container or across the surface of the porous membrane. Alternatively the Young's modulus of the extracellular matrix can vary in a concentric gradient on the surface within the cell culture container or the surface of the porous membrane.

The methods of the invention can also comprise depositing an additional layer of at least one extracellular matrix component on top of the at least one tumor cell type, such that the at least one extracellular matrix component substantially surrounds the at least one tumor cell type. The additional layer of at least one extracellular matrix component can have a Young's modulus that is different from the Young's modulus of the at least one extracellular matrix component deposited on the surface within the cell culture container, on the first surface of the porous membrane, on the first surface of the first porous membrane, or on the second surface of the second porous membrane. Alternatively, the additional layer of at least one extracellular matrix component can have a Young's modulus that is substantially the same as the Young's modulus of the at least one extracellular matrix component deposited on the surface within the cell culture container, on the first surface of the porous membrane, on the first surface of the first porous membrane, or on the second surface of the second porous membrane. The Young's modulus of the additional layer of at least one extracellular matrix component can also be non-uniform.

In any of the methods that comprise the addition of one or more exogenous extracellular matrix components, the method can comprise the addition of single or multiple layers of ECM.

In any of the methods that comprise the addition of one or more exogenous extracellular matrix components, the exogenous extracellular matrix can comprise a single ECM protein or a mixture of multiple ECM proteins. For example, the exogenous extracellular matrix can comprise a mixture of collagen, fibronectin, and/or laminin.

Cell Culture Medium

Standard culture medium can be used in the methods of the invention. The composition of the culture medium will vary depending on the particular cell type(s) being cultured.

Additional components can also be included in the culture medium. For example, factors that are known to influence adipogenesis, such as GM-CSF and TGF-β, can be added to the culture medium. In vivo, these factors are secreted by macrophages.

The culture medium can comprise sera, blood, blood cells, a blood component, immune cells, conditioned culture medium, or a combination thereof.

The sera, blood, blood cells, blood component, or immune cells can be derived from a human or an animal (e.g., a mouse, rat, guinea pig, hamster, rabbit, cat, dog, monkey, cow, pig, horse, goat, sheep, bird, or fish).

The immune cells can comprise B cells, dendritic cells, granulocytes, innate lymphoid cells, megakaryocytes, monocytes, macrophages, natural killer cells, T cells, thymocytes, or a combination thereof.

The blood cells can comprise platelets, red blood cells, or a combination thereof.

The blood component can comprises a clotting factor, a lipoprotein, a triglyceride, or a combination thereof.

The conditioned culture medium can comprises conditioned culture medium from a culture comprising tumor cells, a culture comprising endothelial cells, a culture comprising a stromal cell type, or a combination thereof.

Flow Devices

The shear stress can be applied using any suitable flow device which is capable of inducing flow of the culture media, wherein the flow mimics flow to which the cell type or cell types being cultured are exposed in vivo in the tumor microenvironment. For example, the flow device can be a cone-and-plate device or a parallel plate flow device.

The flow device can be a cone-and-plate device substantially as described in U.S. Pat. No. 7,811,782 and in Hastings, et al., *Atherosclerosis prone hemodynamics differentially regulates endothelial and smooth muscle cell phenotypes and promotes pro-inflammatory priming*, AMERICAN J. PHYSIOLOGY & CELL PHYSIOLOGY 293:1824-33 (2007), the contents of each of which are hereby incorporated by reference with respect to their teachings regarding cone-and-plate flow devices. An example of such a device is depicted in FIG. 1. The device 200 comprises an electronic controller for receiving a set of electronic instructions, a motor 220 operated by the electronic controller, and a shear stress applicator operatively connected to the motor for being driven by the motor. The shear stress applicator can comprise a cone 7, which is attached to the motor, and the cone can be directly driven by the motor. The motor causes the cone to rotate in either direction (clockwise or counterclockwise). The device further comprises a Z-axis micrometer 210 that allows the cone 7 of the device to be raised and lowered.

The cone-and-plate device accommodates a cell culture container 1, for example a Petri dish (e.g., a 75-mm diameter Petri dish). The cone 7 can be adapted to fit inside the cell culture container. Thus, for example, in a device adapted for use with 75-mm diameter Petri dishes, the cone has a diameter of about 71.4 mm. The cone generally has a shallow cone angle. For example, the angle between the surface of the cone and the surface within the Petri dish is approximately 0.5°-2° (e.g., 1°).

When the cone 7 of the device 200 is submerged in culture media 3 in the cell culture container 1 and rotated by the motor 220, the cone exerts a rotational stress upon the culture media, and this in turn applies shear stress to cells plated within the cell culture container or to a surface of a porous membrane 11 suspended in the cell culture container. For example, cells 6 can be plated on a first surface of a porous membrane, the cone can be used to apply a shear stress to the opposing surface of the membrane as depicted in the inset in FIG. 1.

A porous membrane can be suspended in the cell culture container using a cell culture insert 4 that includes a porous membrane 11 and a support 10. The cell culture insert is adapted to fit inside the cell culture container. The cell culture insert suitably has a height that is shorter than the height of the cell culture container, such that when the cell culture insert is placed into the cell culture container, the support portion of the cell culture insert contacts the perimeter of the cell culture container and holds the porous membrane in a suspended position within the cell culture container. For example, the insert can have a rim that extends around the perimeter of the insert, wherein the rim of the insert then contacts the perimeter of the cell culture container to suspend the insert in the cell culture container. Cell culture inserts in a variety of sizes are commercially available from a number of manufacturers (e.g., Corning, which manufactures TRANSWELL inserts; Millicell; and ThinCert). The porous membranes can be made of any suitable porous material (e.g., polyester, polycarbonate, collagen-coated polytetrafluoroethylene (PTFE), or polyethylene terephthalate (PET)) and can have a variety of thicknesses and pore sizes.

The cone-and-plate device can also include a base 240 for securely holding the cell culture container. The device can also include clips that mount on the cell culture container dish and secure inflow and outflow tubing, which is used to perfuse the upper and lower volumes, as described further below.

The flow can be derived from a previously measured hemodynamic pattern, and can be modeled into a set of electronic instructions. The shear stress is based on the set of electronic instructions.

The flow device can comprise a body adapted for being positioned in the culture medium in the upper volume of the cell culture container and a motor adapted to rotate the body. The body can have a conical surface or a flat surface.

The flow device can be adapted for positioning the conical or flat surface of the body in the cell culture container and in contact with the culture medium.

The flow device can comprise an electronic controller for receiving the set of electronic instructions. The motor is operated by the electronic controller. A shear stress applicator operatively connected to the motor is driven by the motor. Preferably, the shear stress applicator comprises a cone or a disc attached to the motor.

The flow device is used in conjunction with a cell culture container. The cell culture container can include inlets and outlets for perfusing cell culture medium, drugs, compounds, and other components into and out of the cell culture container.

Figure 2:
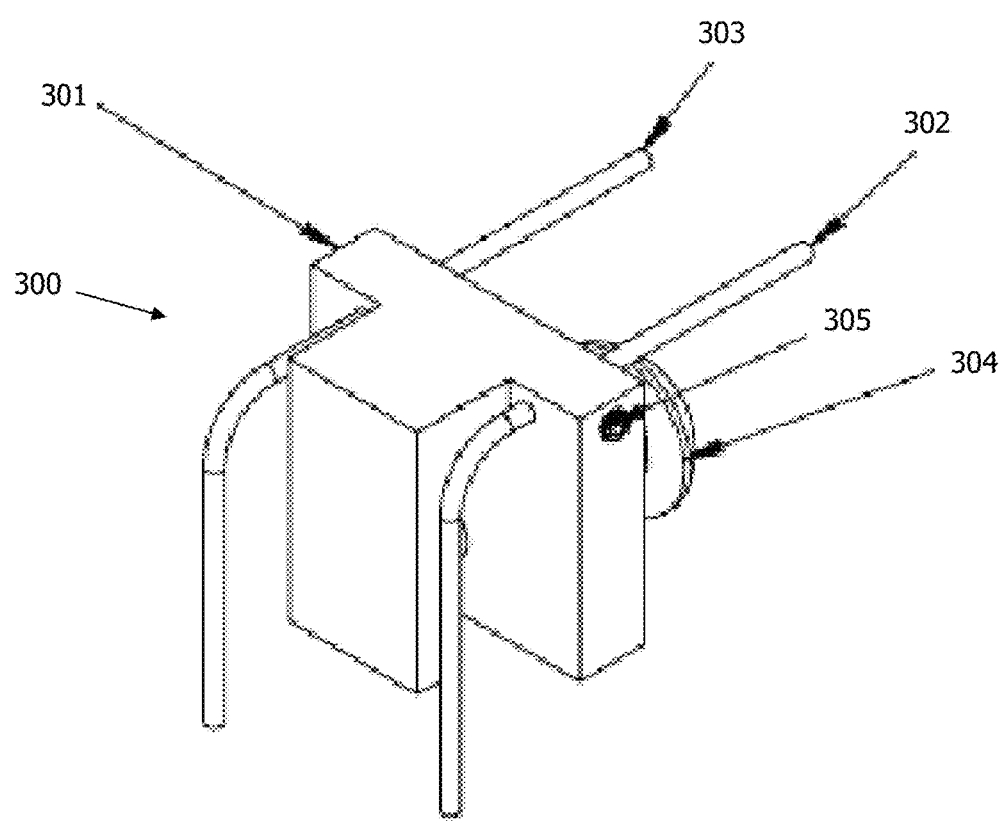
FIG. 2 is a perspective of the clip that mounts on the cell culture container and secures inflow and outflow tubing to perfuse the upper and lower volumes.

The inlets and outlets can be secured to the cell culture container by clips. FIG. 2 depicts a clip. Each clip 300 is made up of three parts: the main body 301 and two pieces of thin metal tubing 302 and 303 as shown in FIG. 2. The clip 300 can be secured to the side of a cell culture container from the outside by a screw 304. For example, two clips can be attached and tightened to the side of the container from the outside by a screw 304. The main body 301 is made of treated stainless steel metal and angles around the edge of the dish for attachment and access purposes. Two pieces of thin metal tubing (302 and 303) per clip are bent to provide access to the dish for supplying and drawing off media efficiently, without obstructing the cone rotation. A set screw 305 on either side of the main body 301 secures the metal tubing 302, 303 to the main body and holds the metal tubing in place such that it extends to the correct depth within the culture media. Flexible tubing then slides over the metal tubing, which is used to perfuse media into and out of the cell culture container (e.g., from a source bottle to the container via mechanical peristaltic pump).

Figure 3:
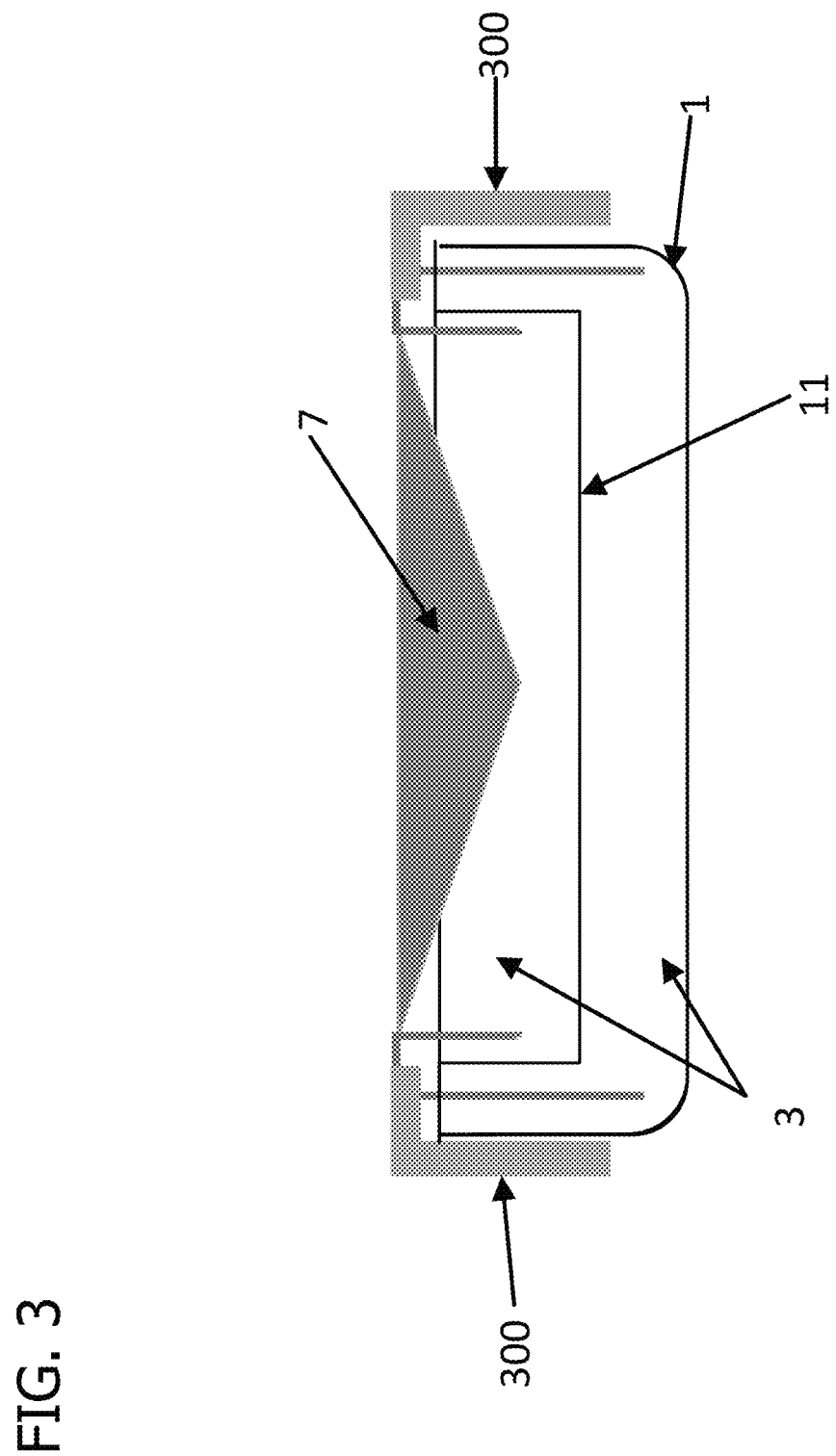
FIG. 3 shows the positioning of two clips in a cell culture container.

FIG. 3 shows two clips 300 positioned in a cell culture container 1. In the configuration shown in FIG. 3, a porous membrane 11 is suspended in the cell culture container. FIG. 3 also depicts the cone 7 of a cone-and-plate flow device and the culture medium 3.

As the cone of the cone-and-plate device rotates, fluid is transported in a concentric manner within the upper volume of the cell culture container. In addition, the rotation of the cone causes a downward flow of cell culture medium through the porous membrane and through any cells plated on the porous membrane and/or extracellular matrix components deposited on the porous membrane.

Hemodynamic Patterns

The flow can be derived from a previously measured hemodynamic pattern.

The hemodynamic pattern can be derived from the vasculature of a tumor.

The hemodynamic pattern can be derived from at least a portion of a capillary, an arteriole, an artery, a venule, or a vein.

The hemodynamic pattern can be derived from at least a portion of an organ. For example, the hemodynamic pattern can be derived from a liver, a kidney, a lung, a brain, a pancreas, a spleen, a large intestine, a small intestine, a heart, a skeletal muscle, an eye, a tongue, a reproductive organ, or an umbilical cord.

The hemodynamic pattern can be derived from analysis of ultrasound data.

The hemodynamic pattern can be derived from analysis of magnetic resonance imaging (MRI) data.

The flow or the hemodynamic pattern can be time-variant.

The flow or the hemodynamic pattern can be derived from an animal, such as a genetically modified animal or a human. Preferably, the hemodynamic pattern is derived from a human.

Figure 4:
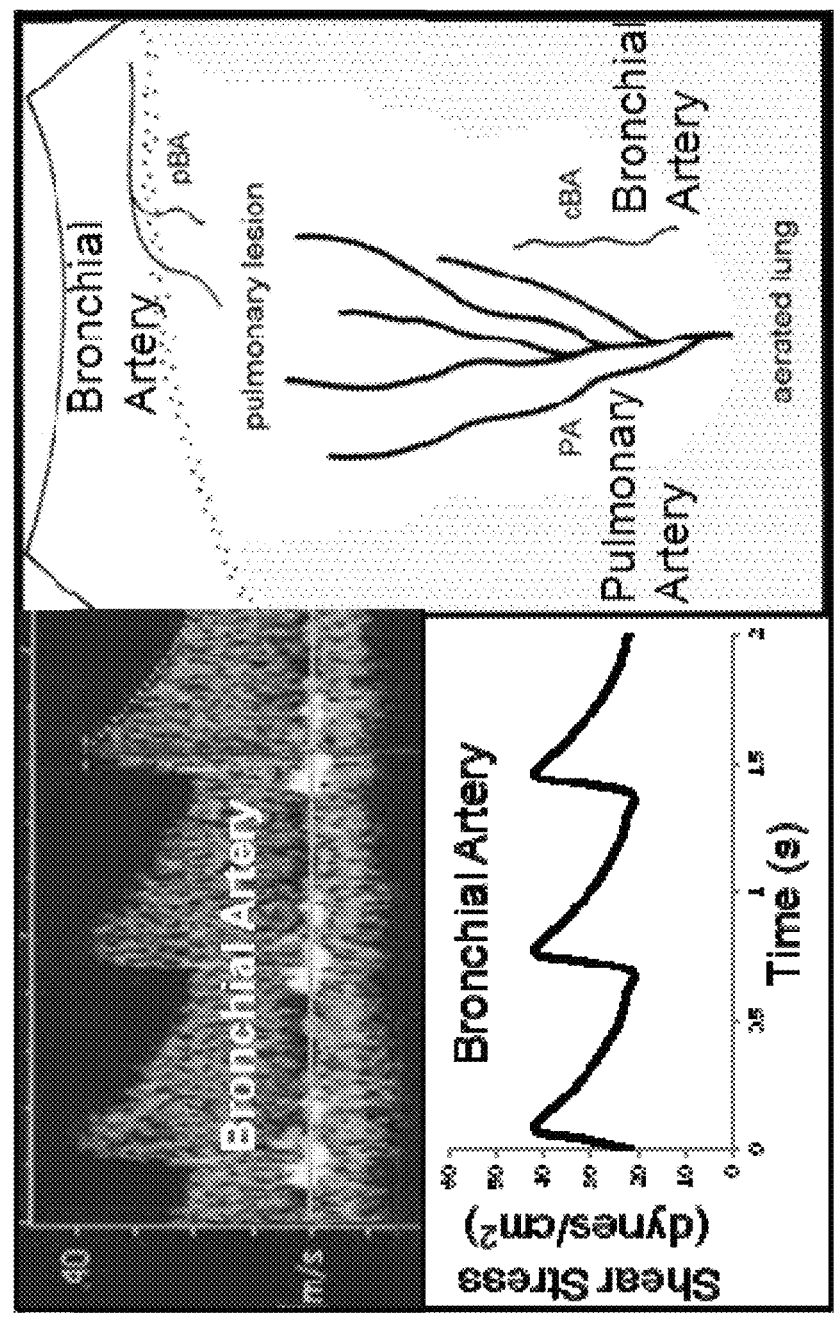
FIG. 4A shows a Doppler sonography image of the central bronchial artery in a patient diagnosed with a pulmonary lesion.
FIG. 4B depicts wall shear stress calculations (dynes/cm$^2$) of the Doppler flow signal of a human pulmonary lesion.
FIG. 4C is a schematic illustration of an exemplary arterial blood supply in a pulmonary lesion. "PA" stands for pulmonary artery, "cBA" stands for central bronchial artery, and "pBA" stands for peripheral bronchial artery.
Figure 5:
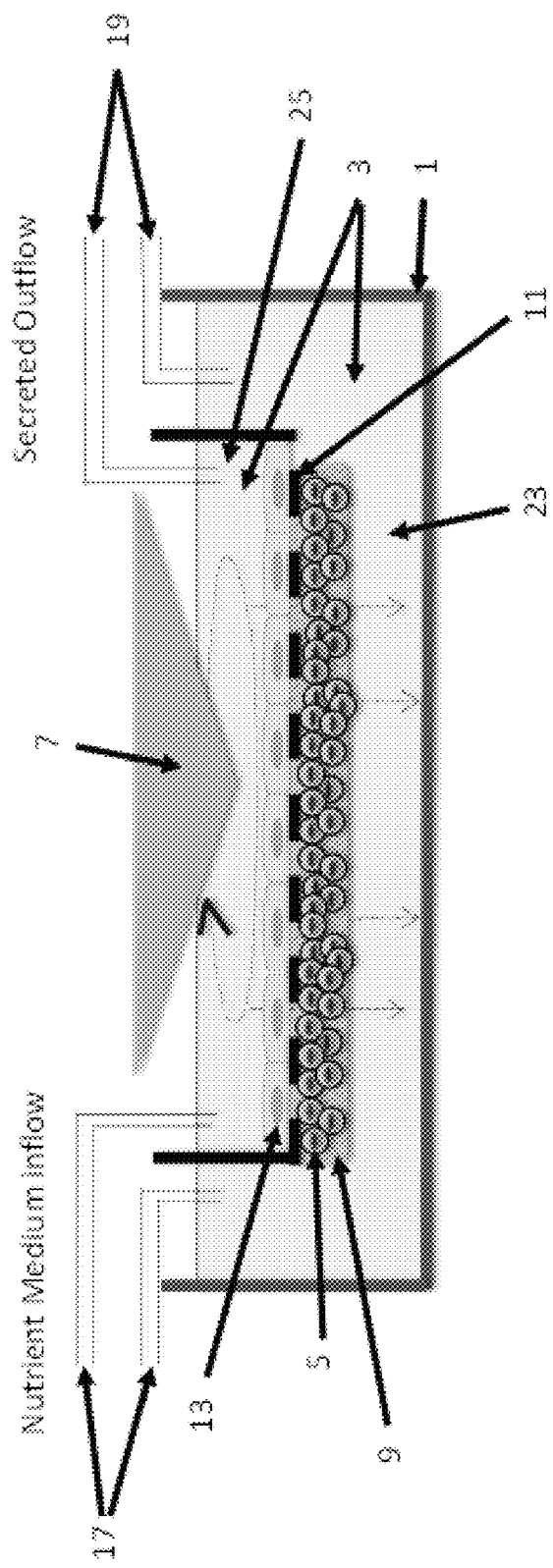
FIGS. 5-10 are schematic diagrams illustrating methods for mimicking a tumor microenvironment in vitro.

For example, FIG. 4A shows a Doppler sonography image of the central bronchial artery in a patient diagnosed with a pulmonary lesion. The mono-phasic low-impedance flow signal is indicative of a malignant lesion. FIG. 4B depicts wall shear stress calculations (dynes/cm²) of the Doppler flow signal of a human pulmonary lesion. FIG. 4C provides a schematic illustration of an exemplary arterial blood supply in a pulmonary lesion.

The shear stress applied upon the at least one tumor cell type can be about 0.1 dynes/cm² to about 200 dynes/cm². For example, the shear stress applied upon the at least one tumor cell type can be about 0.1 dynes/cm² to about 100 dynes/cm².

The shear stress can be applied at a rate of about 1 sec$^{-1}$ to about 1000 sec$^{-1}$.

Exemplary Methods for Mimicking a Tumor Microenvironment In Vitro

FIGS. 5 through 10 are schematic diagrams illustrating exemplary methods for mimicking a tumor microenvironment in vitro. In each of FIGS. 5-10, a cell culture container 1 contains a culture medium 3.

In FIGS. 5-8, the cell culture container also contains a porous membrane 11. The porous membrane is suspended in the cell culture container such that a first surface of the porous membrane is proximal and in spaced relation to the bottom surface of the cell culture container, thereby defining within the cell culture container a lower volume 23 comprising the tumor cells 5 and an upper volume 25 comprising a second surface of the porous membrane. The porous membrane shown in FIGS. 5-8 can be a porous membrane of a cell culture insert adapted to fit inside the cell culture container.

In FIGS. 5-8, at least one extracellular matrix component (ECM) 9 is present on the first surface of the porous membrane. The extracellular matrix component can be endogenously produced by cells plated within the cell culture container. Alternatively, exogenous extracellular matrix can be deposited on the first surface of the porous membrane by any of the methods described herein. The extracellular matrix can include both endogenous extracellular matrix produced by cells plated within the cell culture container and exogenously added extracellular matrix.

Figure 6:
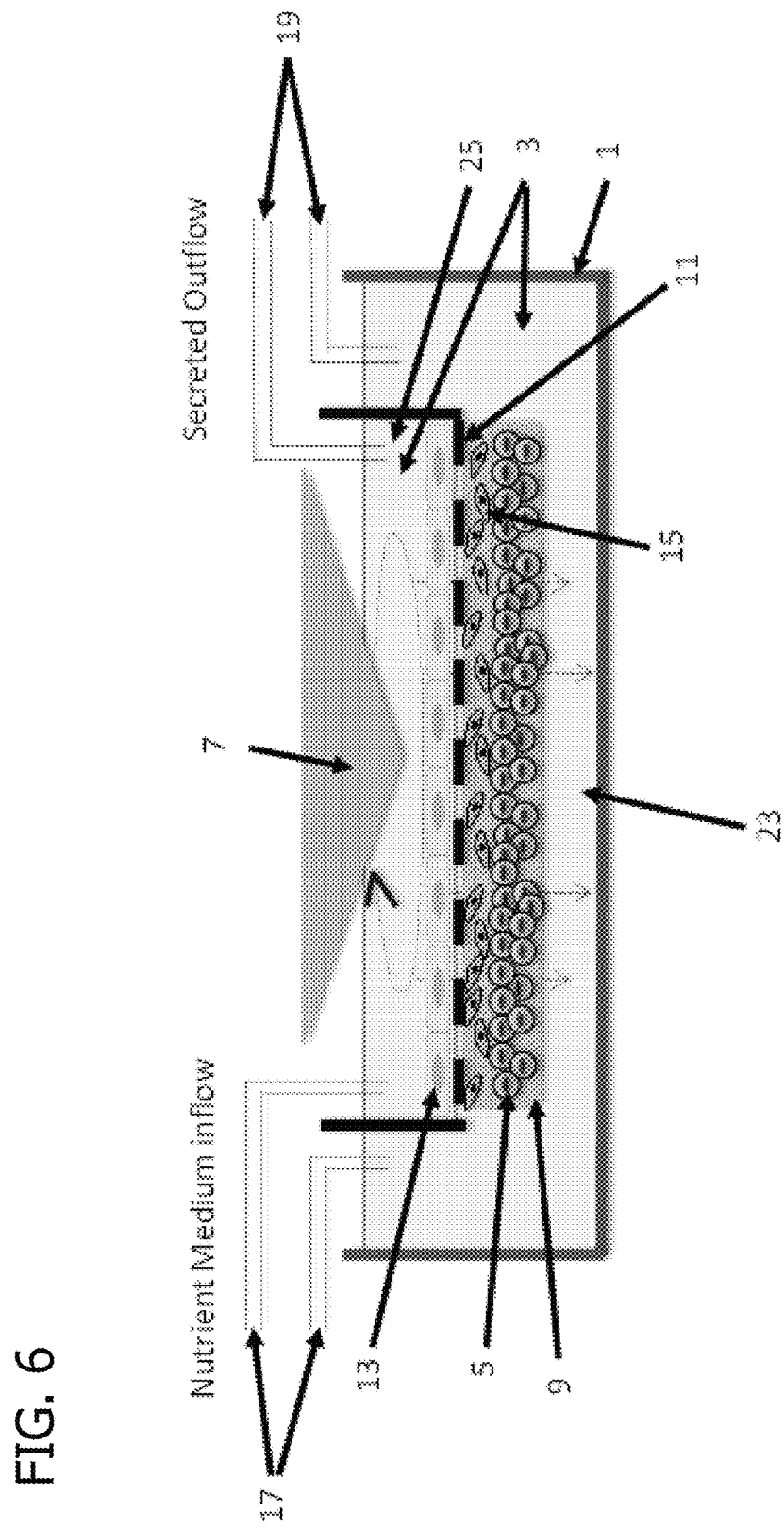
Figure 7:
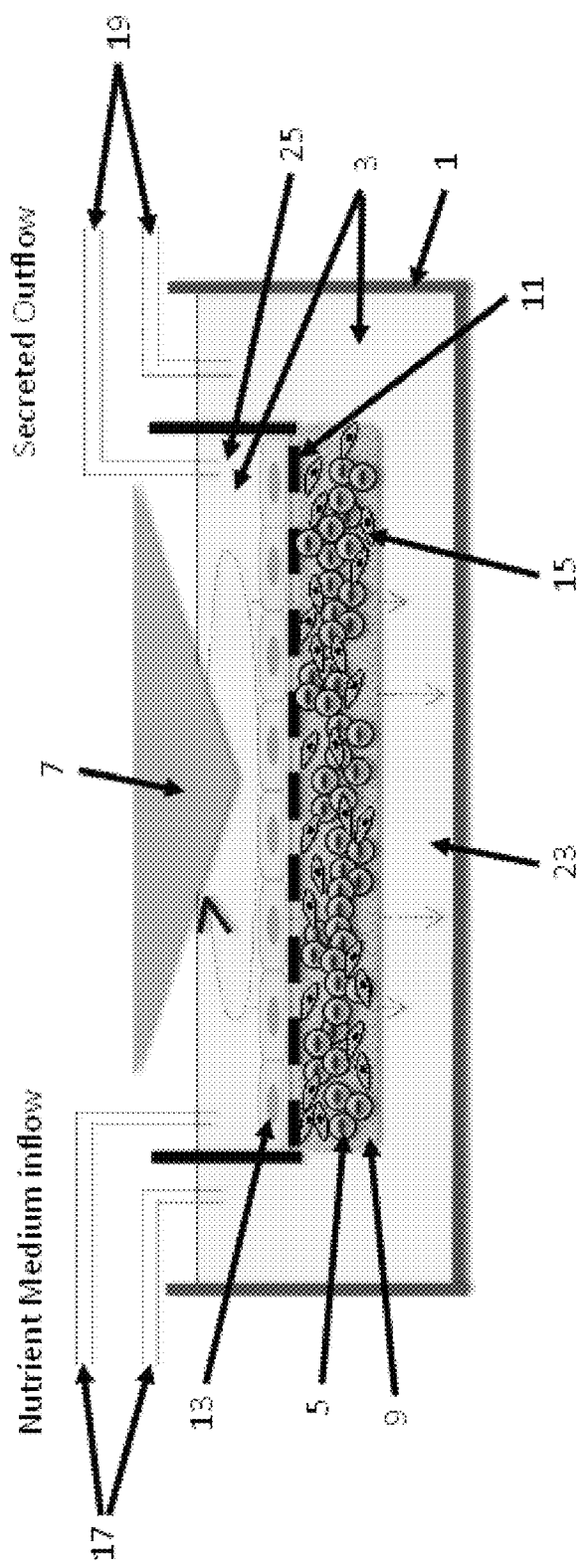

In FIGS. 5-8, tumor cells 5 are also present on the first surface of the porous membrane and are substantially surrounded by the ECM. In FIGS. 6 and 7, both tumor cells 5 and stromal fibroblasts 15 are also present on the first surface of the porous membrane and are substantially surrounded by the ECM. In FIG. 6, the stromal fibroblasts and tumor cells are plated sequentially, with the stromal fibroblasts being plated first, and the tumor cells being plated on the plated stromal fibroblasts. In FIG. 7, the stromal fibroblasts and tumor cells are mixed together with one another prior to plating.

Figure 8:
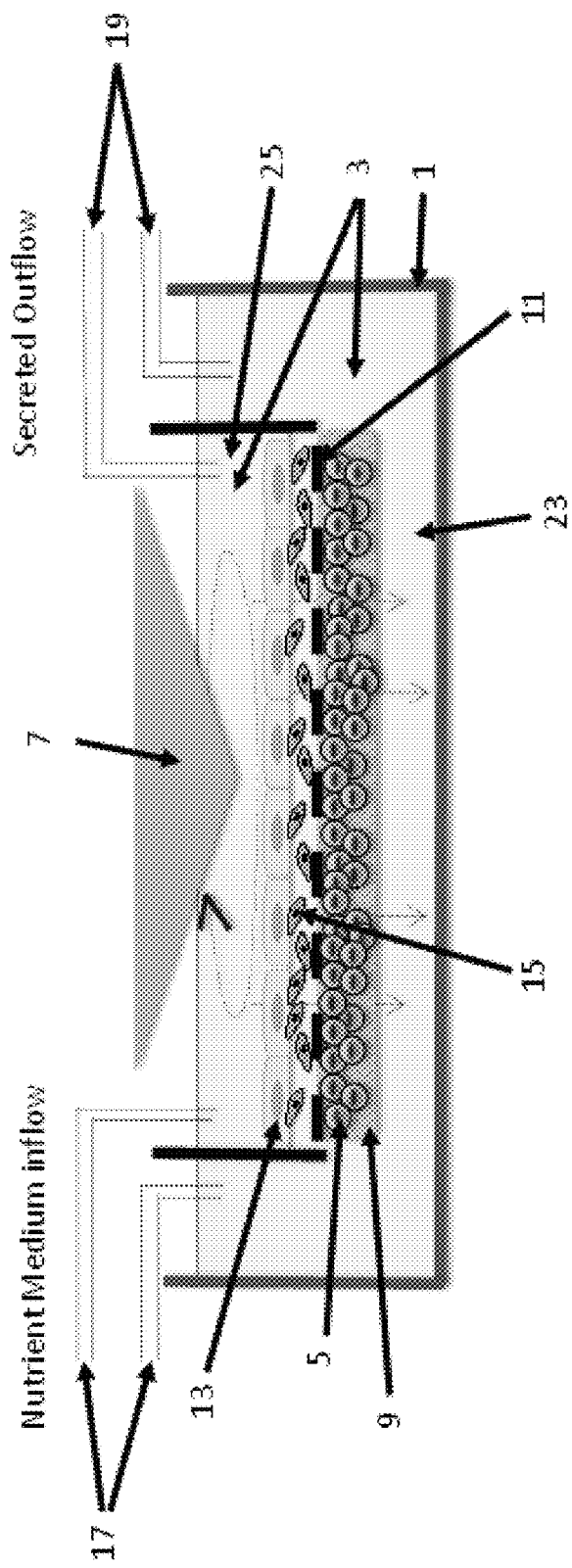

In each of FIGS. 5-8, endothelial cells 13 are plated on the second surface of the porous membrane. In FIG. 8, stromal fibroblasts 15 are also plated on the second surface of the porous membrane. In FIG. 8, the stromal fibroblasts and endothelial cells are plated sequentially, with the stromal fibroblasts being plated first on the second surface of the porous membrane, and the endothelial cells being plated on the plated stromal fibroblasts. Alternatively, although not depicted, the stromal fibroblasts and endothelial cells can be mixed together with one another prior to plating.

Figure 9:
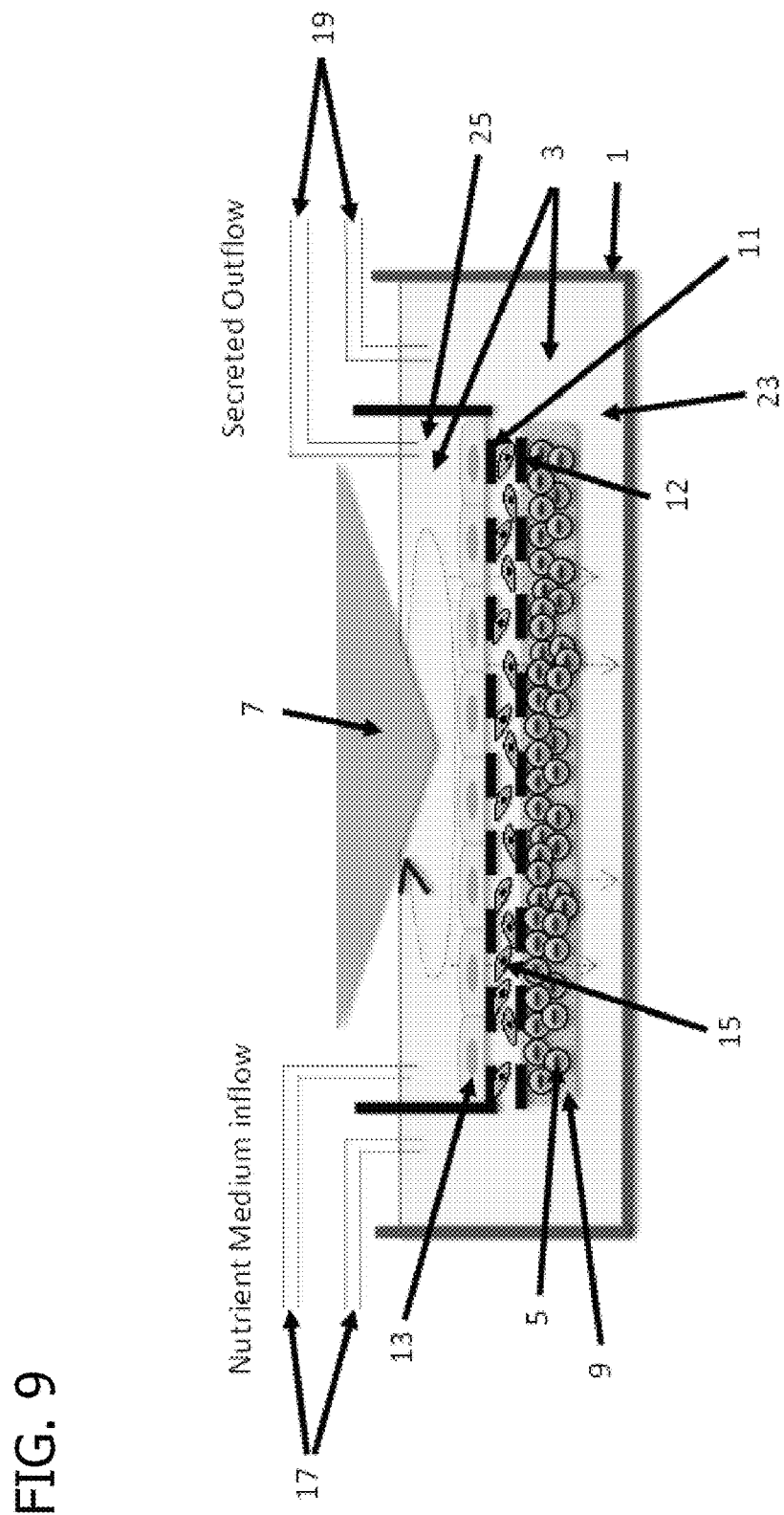
Figure 10:
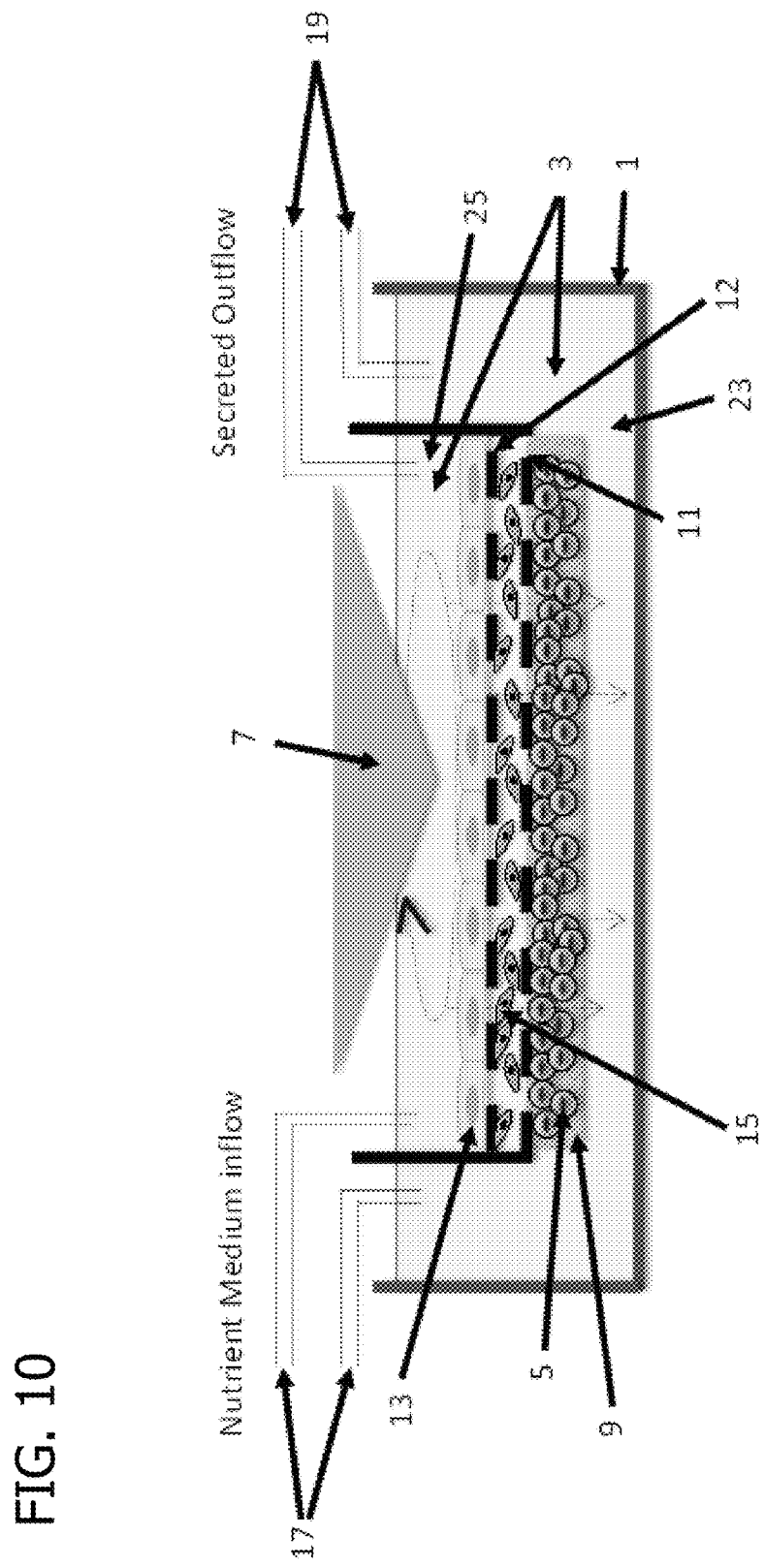

FIGS. 9 and 10 depict methods that use two porous membranes, a first porous membrane and a second porous membrane. In FIG. 9, stromal fibroblasts 15 are plated on a first surface of a first porous membrane 11. The porous membrane is suspended in the cell culture container such that a first surface of the first porous membrane is proximal and in spaced relation to the bottom surface of the cell culture container, thereby defining within the cell culture container a lower volume 23 comprising the tumor cells 5 and an upper volume 25 comprising a second surface of the porous membrane. The first porous membrane 11 can be a porous membrane of a cell culture insert adapted to fit inside the cell culture container. A second porous membrane 12 is placed on the plated stromal cell type, such that a first surface of the second porous membrane contacts the plated stromal fibroblasts. ECM 9 is present on the second surface of the second porous membrane. The ECM can be endogenously produced by cells plated within the cell culture container. Alternatively, ECM can be deposited on the second surface of the second porous membrane by any of the methods described herein. The ECM can include both endogenous ECM produced by cells plated within the cell culture container and exogenously added ECM. Tumor cells 5 are also present on the second surface of the second porous membrane and are substantially surrounded by the ECM. Endothelial cells 13 are plated on the second surface of the first porous membrane.

In FIG. 10, ECM 9 is present on the first surface of a first porous membrane 11. The porous membrane is suspended in the cell culture container such that a first surface of the porous membrane is proximal and in spaced relation to the bottom surface of the cell culture container, thereby defining within the cell culture container a lower volume 23 comprising the tumor cells 5 and an upper volume 25 comprising a second surface of the porous membrane. The first porous membrane can be a porous membrane of a cell culture insert adapted to fit inside the cell culture container. The ECM can be endogenously produced by cells plated within the cell culture container. Alternatively, ECM can be deposited on the first surface of the first porous membrane by any of the methods described herein. The ECM can include both endogenous ECM produced by cells plated within the cell culture container and exogenously added ECM. Tumor cells 5 are also present on the first surface of the first porous membrane and are substantially surrounded by the ECM. Stromal fibroblasts 15 are plated on a second surface of the first porous membrane. A second porous membrane 12 is placed on the plated stromal fibroblasts such that a first surface of the second porous membrane contacts the plated stromal fibroblasts. Endothelial cells 13 are plated on the second surface of the second porous membrane.

FIGS. 5-10 also show inlets 17 and outlets 19 that can be used for perfusing cell culture medium, drugs, compounds, and other components into and out of the cell culture container.

The cone 7 of a cone-and-plate flow device is also shown in FIGS. 5-10. The cone induces concentric flow of the culture medium within the upper volume of the cell culture container, as represented by the dotted circular arrow. The flow of the medium in turn applies a shear stress upon the endothelial cells. The dotted arrows pointing downwards towards the bottom of the cell culture container represent the downward transport of medium, drugs, and other components through the porous membrane that occurs upon application of the shear stress and perfusion of culture medium into and out of the cell culture container.

Methods for Mimicking Tumor Metastasis

The present invention further relates to methods for mimicking tumor metastasis. The methods for mimicking tumor metastasis include methods for mimicking tumor metastasis in vitro, and methods for mimicking tumor metastasis in an animal.

Methods for Mimicking Tumor Metastasis In Vitro

A method for mimicking tumor metastasis in vitro is provided. The method comprises introducing cells of at least one tumor cell type cultured according to any one of the methods described above into an in vitro system that models an organ or tissue. For example, the in vitro system that models the organ or tissue can be an in vitro system that models the liver, pancreas, bone, lung, blood vessels, the lymphatic system, brain, muscle, bladder, kidney, intestine, colon, gall bladder, skin, or bone.

In vitro systems that model the liver are described in U.S. Patent Application Publication No. US 2013/0309677 and PCT Publication No. 2013/0158939, the contents of both of which are hereby incorporated by reference in their entirety and which are described herein in the section entitled "In vitro systems that model the liver," Examples12-14, and FIGS. 20-43. An in vitro system that models the liver described in U.S. Patent Application Publication No. US 2013/0309677 comprises a cell culture container containing a culture medium and a porous membrane, wherein hepatocytes are plated on a first surface of the porous membrane and the porous membrane is suspended in the another cell culture container such that the first surface is proximal and in spaced relation to a bottom surface of the container, thereby defining within the container a lower volume comprising the hepatocytes and an upper volume comprising a second surface of the porous membrane. A shear stress is applied upon the second surface of the porous membrane in the upper volume, the shear stress mimicking flow to which the hepatocytes are exposed in vivo. The cell culture container further comprises inlets within the portions of the cell culture container defining the upper and lower volumes. The cell culture container can also comprise outlets within the portions of the cell culture container defining the upper and lower volumes.

Thus, in the method for mimicking tumor metastasis in vitro, the in vitro system that models the liver can comprise another cell culture container comprising a culture medium and a porous membrane. Hepatocytes are plated on a first surface of the porous membrane, and the porous membrane is suspended in the another cell culture container such that the first surface is proximal and in spaced relation to a bottom surface of the container, thereby defining within the container a lower volume comprising the hepatocytes and an upper volume comprising a second surface of the porous membrane. A shear stress is applied upon the second surface of the porous membrane in the upper volume, the shear stress mimicking flow to which the hepatocytes are exposed in vivo. The another cell culture container further comprises inlets within the portions of the cell culture container defining the upper and lower volumes.

In the in vitro system that models the liver described in U.S. Patent Application Publication No. US 2013/0309677 and PCT Publication No. 2013/0158939, at least one extracellular matrix component (e.g., a collagen) can be plated on the first surface of the porous membrane, and the hepatocytes can be plated on the at least one extracellular matrix component. An additional layer of at least one extracellular matrix component can be deposited on top of the hepatocytes, such that the at least one extracellular matrix component substantially surrounds the hepatocytes.

In the in vitro system that models the liver described in U.S. Patent Application Publication No. US 2013/0309677 and PCT Publication No. 2013/0158939, sinusoidal endothelial cells can be plated on the second surface of the porous membrane. Additional non-parenchymal cell types, such as hepatic stellate cells, Kupffer cells, or a combination thereof, can also be plated on the first or second surface of the porous membrane.

Figure 11:
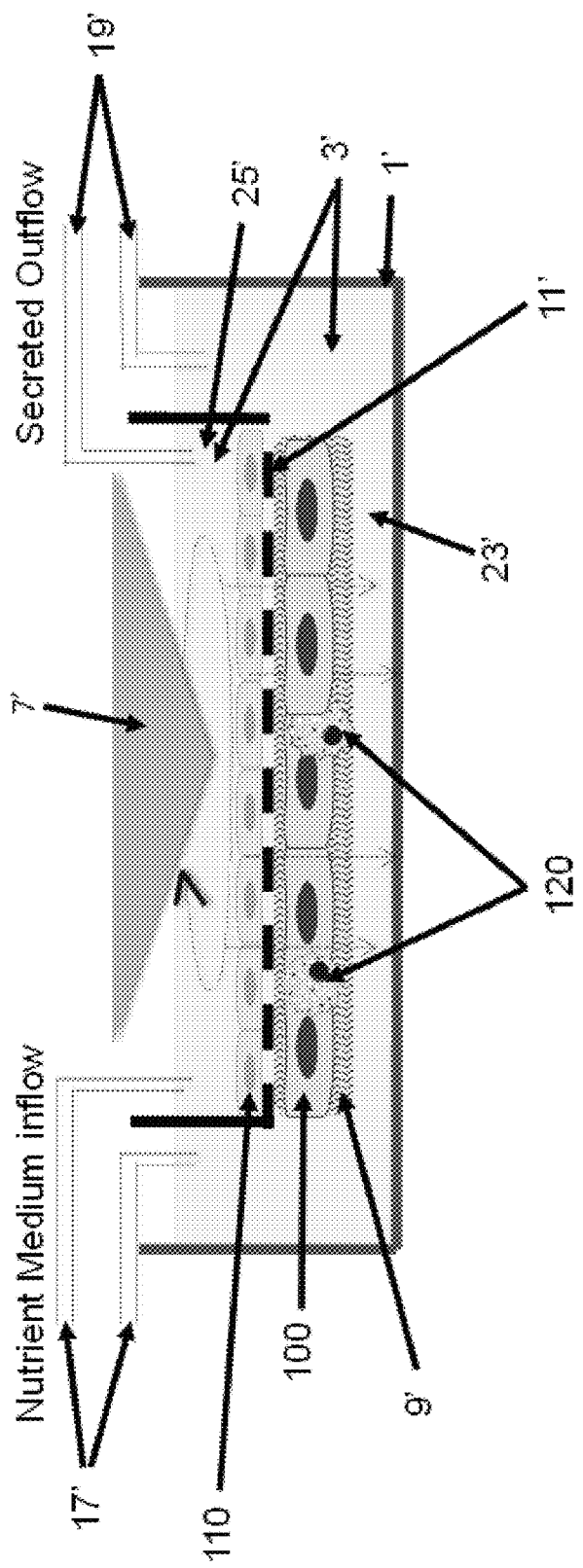
FIG. 11 shows an exemplary system that models the liver, which can be used to mimic tumor metastasis in vitro.

FIG. 11 provides a schematic diagram illustrating an exemplary in vitro system that models the liver. A cell culture container 1' contains a culture medium 3'. The cell culture container also contains a porous membrane 11'. The porous membrane is suspended in the cell culture container such that a first surface of the porous membrane is proximal and in spaced relation to the bottom surface of the cell culture container, thereby defining within the cell culture container a lower volume 23' comprising hepatocytes and an upper volume 25' comprising a second surface of the porous membrane. The porous membrane can be a porous membrane of a cell culture insert adapted to fit inside the cell culture container. An extracellular matrix component (ECM) 9' is present on the first surface of the porous membrane. Hepatocytes 100 and Kupffer cells 120 are also present on the first surface of the porous membrane and are substantially surrounded by the ECM. The ECM can be endogenously produced by cells plated within the cell culture container. Alternatively, exogenous ECM can be deposited on the first surface of the porous membrane by any of the methods described herein. The ECM can include both endogenous ECM produced by cells plated within the cell culture container and exogenously added ECM. Sinusoidal endothelial cells 110 are plated on the second surface of the porous membrane.

FIG. 11 also shows inlets 17' and outlets 19' that can be used for perfusing culture medium, drugs, compounds, cells, and other components into and out of the cell culture container.

FIG. 11 also depicts the cone 7' of a cone-and-plate flow device. The cone induces flow of the culture medium, as represented by the dotted circular arrow in the upper volume. The flow of the medium in turn applies a shear stress upon the endothelial cells. The dotted arrows pointing downwards towards the bottom of the cell culture container represent the transport of medium, drugs, and other components that occurs upon application of the shear stress and perfusion of culture medium into and out of the cell culture container.

In the method for mimicking tumor metastasis in vitro, the cells of the at least one tumor cell type can be introduced into the in vitro system that models the liver by transferring the cells of the at least one tumor cell type into the lower volume or the upper volume of the in vitro system that models the liver. When the cells of the at least one tumor cell type are introduced into the upper volume of the in vitro system that models the liver, the method can further comprise assessing migration of the cells of the at least one tumor cell type into the lower volume of the in vitro system that models the liver. Assessing migration of the tumor cells from the upper volume to the lower volume can be achieved by fixing the cells in the upper and lower chamber and performing microscopic imaging of the cells in the upper and lower volumes, and/or by sorting the cells in the upper or lower volumes where the tumor cells are labeled with a molecular tracer (e.g., a radiolabelled probe, a fluorescent protein, or colorometric tracer).

The transferring can comprise manually transferring the cells of the at least one tumor cell type into the lower volume or the upper volume of the in vitro system that models the liver. For example, the cells of the least one tumor cell type can be removed from the surface within the cell culture container or the porous membrane by trypsinization or by enzymatic digestion of the ECM, if present. The cells of the at least one tumor cell type can then be transferred to the upper or lower volume of the in vitro system that models the liver using a pipette. Alternatively, culture medium from the upper or lower volume of the cell culture container containing the at least one tumor cell type can be pipetted into the upper or lower volume of the in vitro system that models the liver.

Figure 12A:
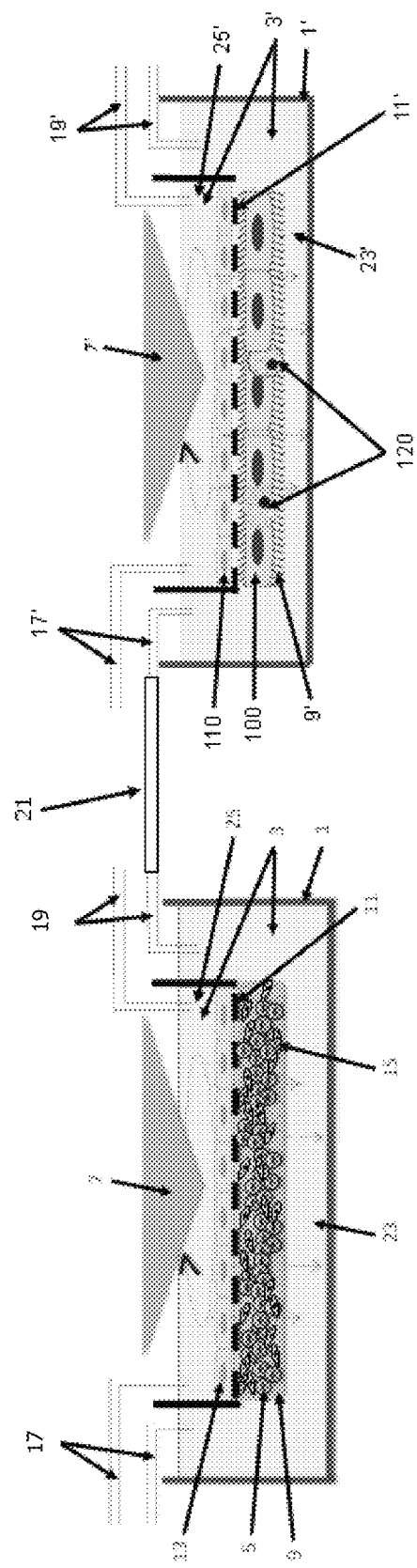
FIGS. 12A-D depict exemplary configurations for modeling tumor metastasis in vitro by pumping culture medium out of a cell culture container comprising at least one tumor cell type and into an in vitro system that models the liver.
Figure 12B:
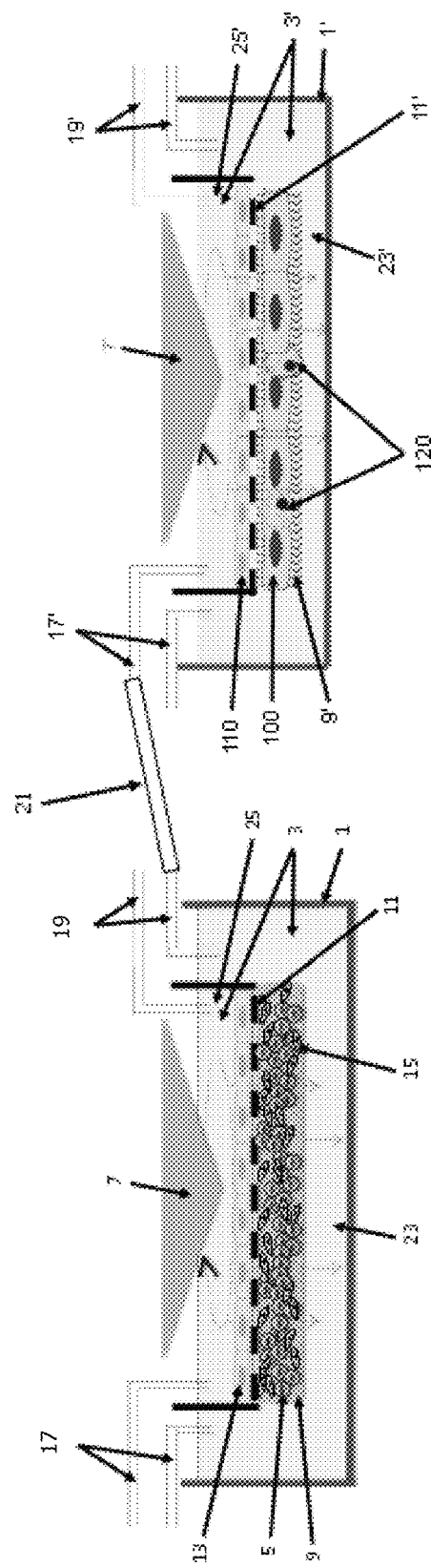
Figure 12C:
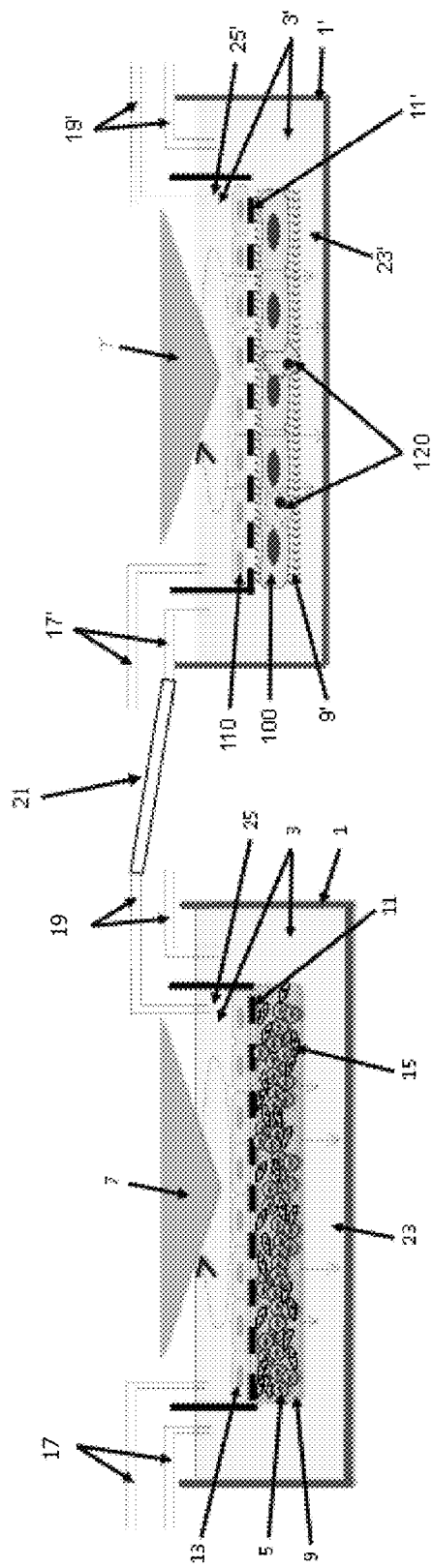
Figure 12D:
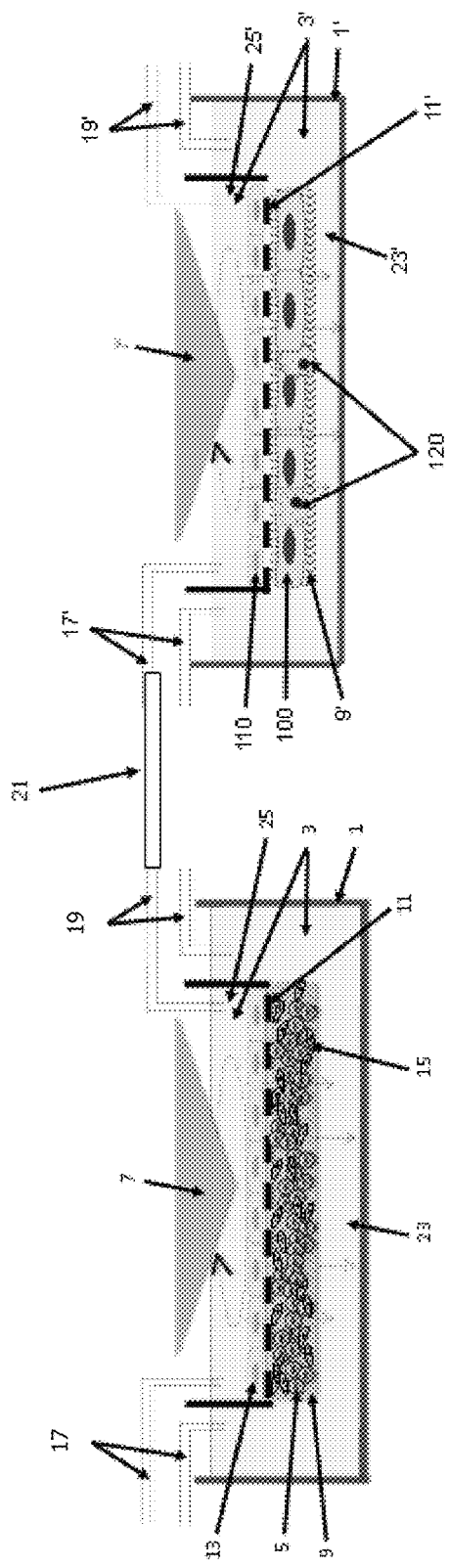

Alternatively, the transferring can comprise pumping cell culture medium out of the upper or lower volume of the cell culture container containing the at least one tumor cell type and into the upper or lower volume of the cell culture container of the in vitro system that models the liver. This mimics the seeding of distal organs by tumor cells in vitro. Such methods are illustrated in FIGS. 12A-D. In FIG. 12A, for example, tubing 21 is used to connect to an outlet 19 within the lower volume 23 of the cell culture container 1 comprising the at least one tumor cell type 5 to an inlet 17' in the lower volume 23' of the cell culture container 1' of the in vitro system that models the liver. The culture medium can be pumped through the tubing to transfer the cells of the at least one tumor cell type into the lower volume of the in vitro system that models the liver. The methods depicted in FIGS. 12B, C, and D are similar, but involve pumping culture medium from the lower volume 23 of the cell culture container 1 that contains the at least one tumor cell type 5 into the upper volume 25' of the cell culture container 1' of the in vitro system that models the liver (FIG. 12B), pumping culture medium from the upper volume 25 of the cell culture container 1 that contains the at least one tumor cell type 5 into the lower volume 23' of the cell culture container 1' of the in vitro system that models the liver (FIG. 12C), or pumping culture medium from the upper volume 25 of the cell culture container 1 that contains the at least one tumor cell type 5 into the upper volume 25' of the cell culture container 1' of the in vitro system that models the liver (FIG. 12D).

Thus, the cell culture container comprising the at least one tumor cell type can further comprise an outlet within the portion of the cell culture container defining the lower volume and containing the at least one tumor cell type. The outlet is connected to an inlet in the another cell culture container of the in vitro system that models the liver. The transferring comprises pumping the culture medium out of the lower volume of the cell culture container comprising the at least one tumor cell type and into the upper or lower volume of the another cell culture container of the in vitro system that models the liver.

Alternatively, the cell culture container comprising the at least one tumor cell type can further comprise an outlet within the portion of the cell culture container defining the upper volume. The outlet is connected to an inlet in the another cell culture container of the in vitro system that models the liver. The transferring comprises pumping the culture medium out of the upper volume of the cell culture container and into the upper or lower volume of the another cell culture container of the in vitro system that models the liver.

The present invention further relates to another method for mimicking tumor metastasis in vitro. The method comprises adding a culture medium to a cell culture container and plating at least one cell type on a first surface of a porous membrane within the cell culture container, wherein the porous membrane is suspended in the cell culture container such that the first surface is proximal and in spaced relation to a bottom surface of the cell culture container, thereby defining within the cell culture container a lower volume comprising the at least one cell type and an upper volume comprising a second surface of the porous membrane. A shear stress is indirectly applied upon the at least one cell type, the shear stress resulting from flow of the culture medium induced by a flow device, the flow mimicking flow to which the cells are indirectly exposed in vivo. Tumor cells derived from a human or a humanized animal are introduced into the upper volume or the lower volume.

The at least one cell type can comprise hepatocytes or smooth muscle cells.

The method can further comprise plating a second cell type on the second surface of the porous membrane. The second cell type can comprise endothelial cells.

Where the tumor cells are derived from a humanized animal, the humanized animal is suitably a humanized mouse, for example, a non-obese diabetic severe combined immunodeficiency (NOD SCID) mouse, a NOD/Shi-scid/IL-2Rγnull (NOG) mouse, or a NOD SCID IL-2Rγ knockout (NSG) mouse.

The present invention further relates to an in vitro method of testing a drug or a compound for an effect on tumor metastasis. The method comprises mimicking tumor metastasis in vitro by any of the methods described above, and adding a drug or a compound to the culture medium. A change in the cells of the at least one tumor cell type in the in vitro system that models the organ or tissue, in the presence of the drug or the compound, indicates that the drug or the compound has an effect on tumor metastasis.

To confirm in vitro mimicking of tumor metastasis, a change in the level or localization of a marker of tumor metastasis can be compared between the method of the invention and the same method in the absence of the application of the shear stress. The level or localization of the marker in the at least one tumor cell type upon application of the shear stress is compared to the level or localization of the marker in the at least one tumor cell type in the absence of the application of the shear stress. Alternatively, the level of marker in the culture medium upon application of the shear stress is compared to the level of the marker in the culture medium upon the absence of the application of shear stress. For example, if a marker is known to be associated with tumor metastasis, and its concentration is known to increase in the serum during metastasis in vivo, an increase in the level of the marker in the culture medium of the method of the invention with application of shear stress as compared to the level of the marker in the culture medium in the absence of the application of the shear stress confirms that tumor metastasis is mimicked by the in vitro method of the invention.

Methods for Mimicking Tumor Metastasis in an Animal

The present invention also provides a method for mimicking tumor metastasis. The method comprises introducing cells of the at least one tumor cell type cultured according to any of the methods described above into an animal. The animal can be a mammal, for example a mouse, rat, guinea pig, hamster rabbit, cat, dog, monkey, cow, pig, horse, goat, or sheep. Alternatively, the animal can be a bird or a fish.

Where the animal is a mouse, the mouse is suitably a humanized mouse, and the at least one tumor cell type comprises a human tumor cell type. The humanized mouse can be a non-obese diabetic severe combined immunodeficiency (NOD SCID) mouse, a NOD/Shi-scid/IL-2Rγnull (NOG) mouse, or a NOD SCID IL-2Rγ knockout (NSG) mouse.

Personalized Medicine

The present invention provides a method for selecting a chemotherapy regimen to be administered to a subject having a tumor. The method comprises testing a drug or a compound in vitro for an effect on a tumor or testing a drug or a compound for an in vitro effect on tumor metastasis according to any of the methods described herein. The at least one tumor cell type comprises tumor cells derived from the subject's tumor. The method further comprises determining whether to administer the drug or the compound to the subject based on the results of the in vitro testing.

The method can further comprise selecting a dose of the drug or the compound to be administered to the subject based on the results of the in vitro testing. The dose selected will be a dose that is predicted to be both therapeutic and safe in the subject based on the results of the in vitro testing.

The method can further comprise selecting a rate of administration of the drug or the compound to be administered to the subject based on the results of the in vitro testing. The rate selected will be a rate that is predicted to be both therapeutic and safe in the subject based on the results of the in vitro testing.

Drugs and Compounds

In any of the in vitro methods of testing a drug or a compound for an effect on a tumor or for an effect on tumor metastasis described herein, the at least one tumor cell type can be exposed to the drug or the compound directly or indirectly. The at least one tumor cell type can be directly exposed to the drug or compound by adding the drug or compound to cell culture medium containing or contacting the at least one tumor cell type. For example, where the at least one tumor cell type is plated on a first surface of a porous membrane, and the porous membrane is suspended in the cell culture container such that the first surface is proximal and in spaced relation to a bottom surface of the cell culture container, thereby defining within the cell culture container a lower volume comprising the at least one tumor cell type and an upper volume comprising a second surface of the porous membrane, the at least one tumor cell type can be directly exposed to the drug or compound by adding the drug or compound to the cell culture medium in the lower volume. Adding the drug or compound to the upper volume can also result in directly exposing the at least one tumor cell type to the drug or compound, for example where the drug or compound is small enough to diffuse through the pores of the membrane or where the tumor cells have migrated into the upper volume. Alternatively, the at least one tumor cell type can be indirectly exposed to the drug or compound. For example, the at least one tumor cell type would be indirectly exposed to the drug or the compound when the drug or the compound is added to the upper volume and the drug or compound does not diffuse through the pores of the membrane, but exerts an effect on endothelial cells plated on the second surface of the porous membrane which in turn causes the endothelial cells to exert an effect on the at least one tumor cell type (e.g., secretion of a factor by the endothelial cells that diffuses through the porous membrane and has an effect on the at least one tumor cell type, or physical interaction of the endothelial cells with the at least one tumor cell type through the pores of the porous membrane).

The concentration of the drug or compound in the culture medium can be within the concentration range of the drug or the compound that achieves the effect in vivo. For example, the concentration of the drug or the compound in the culture medium can be within the concentration range of the in vivo therapeutic $C_{max}$ for the drug or the compound (e.g., the in vivo therapeutic plasma $C_{max}$ for the drug or the compound). The concentration of the drug or the compound in the culture medium can be approximately the same as the in vivo therapeutic $C_{max}$ for the drug or the compound (e.g., the in vivo therapeutic plasma $C_{max}$ for the drug or the compound).

Alternatively, the concentration of the drug or the compound in the culture medium can be lower than the concentration range of the drug or the compound that achieves the effect in vivo. This mimics the lower degree of drug penetration that is observed in many solid tumors in vivo. For example, the concentration of the drug or the compound in the culture medium can be about 2-fold to about 20-fold lower, about 5-fold to about 15-fold lower, or about 10-fold lower than the concentration range of the in vivo therapeutic $C_{max}$ for the drug or the compound (e.g., the in vivo therapeutic plasma $C_{max}$ for the drug or the compound).

The effect of the drug or the compound can comprise a toxic effect, a protective effect, a pathologic effect, a disease-promoting effect, an inflammatory effect, an oxidative effect, an endoplasmic reticulum stress effect, a mitochondrial stress effect, an apoptotic effect, a necrotic effect, an autophagic effect, an immunogenic cell death effect, a ferroptotic effect, a remodeling effect, a proliferative effect, an effect on angiogenesis, an effect on the activity of a protein, or an effect on the expression of a gene. The term "proliferative effect" encompasses both stimulation of proliferation and inhibition of proliferation. Similarly, the effect on angiogenesis encompasses both stimulation of angiogenesis and inhibition of angiogenesis.

Where the effect comprises the effect on the activity of a protein, the effect can comprise inhibition of the protein or activation of the protein.

Where the effect comprises the effect on the expression of a gene, the effect can comprise an increase in the expression of the gene or a decrease in the expression of the gene.

The in vitro methods of testing a drug or a compound for an effect on a tumor or on tumor metastasis can be used to screen candidate molecules for anti-cancer activity.

The in vitro methods of testing a drug or a compound for an effect on a tumor or on tumor metastasis can also be used to test drugs or compounds known or suspected to have anti-cancer activity.

The drug or compound can be capable of inhibiting, activating, or altering the function of proteins or genes in the at least one cell type.

The drug can comprise an anti-cancer agent. Anti-cancer agents include, for example, alkylating agents, anti-metabolites, anti-tumor antibiotics, topoisomerase inhibitors, corticosteroids, anti-microtubule agents, kinase inhibitors, pathway inhibitors, differentiating agents, hormone therapies, immunotherapies, L-asparaginase, chelating agents, ATP mimetics, biologic medical products, and combinations thereof.

When the anti-cancer agent comprises the alkylating agent, the alkylating agent can comprise altretamine, bendamustine, busulfan, carboplatin, carmustine, chlorambucil, cisplatin, cyclophosphamide, dacarbazine, ifosfamide, lomustine, mechlorethamine, melphalan, oxalaplatin, palifosamide, streptozocin, temozolomide, thiotepa, or a combination thereof.

When the anti-cancer agent comprises the anti-metabolite, the antimetabolite can comprise azathioprine, capecitabine, cladribine, clofarabine, cytarabine, floxuridine, fludarabine, fluorouracil, gemcitabine, hydroxyurea, mercaptopurine, methotrexate, nelarabine, pemetrexed, pentostatin, pralatrexate, raltitrexed, thioguanine, or a combination thereof.

When the anti-cancer agent comprises the anti-tumor antibiotic, the anti-tumor antibiotic can comprise bleomycin, dactinomycin, mitomycin, plicamycin, rifampicin, or a combination thereof.

When the anti-cancer agent comprises the topoisomerase inhibitor, the topoisomerase inhibitor can comprise amsacrine, topotecan, irinotecan , etoposide, teniposide, mitoxantrone, etirinotecan, camptothecin, daunorubicin, doxorubicin, epirubicin, idarubicin, valrubicin, amonafide, or a combination thereof.

When the anti-cancer agent comprises the corticosteroid, the corticosteroid can comprise prednisone, methylprednisolone, dexamethasone, cortisol sodium succinate, or a combination thereof.

When the anti-cancer agent comprises the anti-microtubule agent, the anti-microtubule agent can comprise vinblastine, vincristine, vindesine, vinorelbine, paclitaxel, docetaxel, ixabepilone, eribulin mesylate, cabazitaxel, or a combination thereof.

When the anti-cancer agent comprises the kinase inhibitor, the kinase inhibitor can comprise a small molecule inhibitor of a receptor or non-receptor tyrosine kinase, a serine/threonine-specific kinase inhibitor, or a dual-specificity kinase inhibitor.

The kinase inhibitor can comprise an epidermal growth factor (EGF) receptor inhibitor, a fibroblast growth factor (FGF) receptor inhibitor, a platelet-derived growth factor (PDGF) receptor inhibitor, a vascular endothelial growth factor (VEGF) receptor inhibitor, or a rho kinase inhibitor.

When the kinase inhibitor comprises the small molecule inhibitor of a receptor or non-receptor tyrosine kinase, the small molecule inhibitor of a receptor or non-receptor tyrosine kinase can comprise afatinib, alectinib, alisertib, amuvatinib, apatinib, axitinib, bafetinib, barasertib, baricitinib, bosutinib, brivanib, buparlisib, cabozantinib, canertinib, cenisertib, cobimetinib, crenolanib, crizotinib, dabrafenib, dacomitinib, danusertib, desatinib, dovitinib, epitinib, erlotinib, foretinib, fostamatinib, galunisertib, gefitinib, ibrutinib, imatinib, lapatinib, lenvatinib, lestaurtinib, linifanib, linsitinib, masitinib, momelotinib, motesanib, mubritinib, neratinib, nilotinib, nintedanib, orantinib, pacritinib, pazopanib, pelitinib, pimasertib, ponatinib, poziotinib, quizartinib, refametinib, regorafenib, ruxolitinib, selumetanib, sorafenib, sulfatinib, sunitinib, tandutinib, telatinib, theliatinib, tivantinib, tofacitinib, trametinib, vandetanib, vatalinib, vemurafenib, volasertib, volitinib, or a combination thereof.

When the kinase inhibitor comprises the serine/threonine-specific kinase inhibitor, the serine/threonine-specific kinase inhibitor can comprise MK2206.

When the anti-cancer agent comprises the pathway inhibitor, the pathway inhibitor can comprise a B-cell lymphoma 2 (Bcl-2) family inhibitor (e.g., navitoclax, obatoclax, oblimerson, or cinacalcet), a heat shock protein 90 (HSP-90) inhibitor (e.g., tanespimycin, retaspimycin, or ganetespib), a proteasome inhibitor (e.g., bortezomib, carfilzomib, oprozomib, ixazomib, marozomib, or delanzomib), a cyclin-dependent kinase inhibitor (e.g., flavopiridol, alvocidib, dinaciclib, seliciclib, or palbociclib), an inhibitor of poly ADP-ribose polymerase (PARP) (e.g., iniparib, veliparib, olaparib, rucaparib, or niraparib), an inhibitor of the mammalian target of rapamycin (mTOR) (e.g., deforolimus, everolimus, sirolimus, or temsirolimus), an inhibitor of histone deacetylase (HDAC) (e.g., belinostat, entinostat, mocetinostat, panobinostat, romidepsin, or vorinostat), an inhibitor of the hedgehog pathway (e.g., varidegib or vismodegib), a rho kinase inhibitor (e.g., Y27632), or a combination thereof.

When the anti-cancer agent comprises the differentiating agent, the differentiating agent can comprise a retinoid, tretinoin, bexarotene, arsenic trioxide, or a combination thereof.

When the anti-cancer agent comprises the hormone therapy, the hormone therapy can comprise a selective androgen-receptor modulator (SARM) (e.g., enobosarm), an androgen receptor antagonist (e.g., bicalutamide, flutamide, nilutamide, or enzalutamide), a selective estrogen receptor modulator (SERM) (e.g., tamoxifen, toremifene, or raloxifene), an estrogen receptor antagonist (e.g., fulvestrant), a progestin (e.g., megestrol acetate), an estrogen (e.g., estramustine), an aromatase inhibitor (e.g., anastrozole, exemestane, or letrozole), a gonadotropin-releasing hormone (GnRH) agonist or analog (e.g., leuprolide, goserelin, abarelix, degarelix, or triptorelin), ketoconazole, abiraterone, or a combination thereof.

When the anti-cancer agent comprises the immunotherapy, the immunotherapy can comprise a monoclonal antibody (e.g., rituximab, alemtuzumab, bevacizumab, abagovomab, or etaracizumab), a non-specific immunotherapy or adjuvant (e.g., interleukin-2 (IL-2), interferon-α, interferon-α2b, peginterferon alfa-2b, abatacept, or aldesleukin), an immunomodulating drug (e.g., thalidomide or lenalidomide), a cancer vaccine (e.g., Sipuleucel-T or *Bacillus* Calmette-Guérin (BCG) vaccine), a targeted immunotherapy (e.g., brentuzimab, cetuximab, ibritumomab, ipilimumab, ofatumumab, panitumumab, pertuzumab, tositmuomab, trastuzumab, tremelimumab, siltuximab, tocilizumab, canakinumab, lirilumab, nivolumab, pidilizumab, or lambrolizumab), or a combination thereof.

When the anti-cancer agent comprises the chelating agent, the chelating agent can comprise penicillamine, triethylene tetramine dihydrochloride, EDTA, DMSA, deferoxamine mesylate, or batimastat.

When the anti-cancer agent comprises the biologic medical product, the biologic medical product can comprise a synthetic polysaccharide; a synthetic, partially synthetic or humanized immunoglobulin; or a recombinant therapeutic protein.

The drug or the compound can comprise a radiocontrast agent, a radio-isotope, a prodrug, an antibody fragment, an antibody, a live cell, a therapeutic drug delivery microsphere, microbead, nanoparticle, gel or cell-impregnated gel, or a combination thereof.

In any of the in vitro methods of testing a drug or a compound for an effect on a tumor or for an effect on tumor metastasis described herein, adding the drug or the compound to the culture medium can comprise adding an antibody-drug conjugate or a modified release dosage form comprising the drug or the compound to the culture medium.

The modified release dosage form can comprise an oral modified release dosage form.

The modified release dosage form can a modified release polymer (e.g., hydroxypropylcellulose, hydroxypropylmethylcellulose, hydroxyethylcellulose, ethylcellulose, methylcellulose, carboxymethylcellulose, alginic acid, carrageenan, chitosan, heparin, starch, xanthan gum, polyvinyl alcohol, polyacrylic acid, polyethylene oxide, poloxamers, pluronics, polymethacrylate, polysialic acid, or a combination thereof).

The method can comprise perfusing the drug or the compound into at least one of the upper volume and the lower volume.

Analysis of the Cell Types and Cell Culture Medium

In methods of the invention involving comparing a change in the level or localization of a marker of the tumor microenvironment or a marker of tumor metastasis between a method of the invention and the same method in the absence of the application of the shear stress, the marker can comprise a marker of cell proliferation, cell invasion, angiogenesis, tumorigenesis, cell monolayer integrity, endothelial cell barrier function, permeability, inflammation, cell death, apoptosis, necrosis, contraction, cell motility, or a combination thereof.

The change in the level of a marker can be an increase in the level of the marker in the at least one tumor cell type or the endothelial cells.

The change in the level of a marker can be a decrease in the level of the marker in the at least one tumor cell type or the endothelial cells.

The marker can comprise VE-cadherin, E-cadherin, actin, or a combination thereof.

When the marker comprises a marker of angiogenesis, the marker of angiogenesis can comprise vascular endothelial growth factor (VEGF)-A, VEGF-C, VEGF-D, angiopoietin-1 (ANG1), angiopoietin-2 (ANG2), fibroblast growth factor-2 (FGF-2), placental growth factor (PLGF), or a combination thereof.

When the marker comprises a marker of cell proliferation, the marker of cell proliferation can comprise epidermal growth factor (EGF), epidermal growth factor receptor (EGFR), MKI67, proliferating cell nuclear antigen (PCNA), or a combination thereof.

When the marker comprises a marker of cell invasion, the marker of cell invasion can comprise vimentin (VIM), cadherin 1 (CDH-1), cadherin 2 (CDH-2), or a combination thereof.

When the marker comprises a marker of inflammation, the marker of inflammation can comprises interleukin-6 (IL-6), interleukin-8 (IL-8), NF-κB, endothelial nitric oxide synthase (eNOS), Krupple-like factor 2 (KLF2), monocyte chemotactic protein-1 (MCP-1), or a combination thereof.

The methods described herein can further comprise analyzing the endothelial cells for cell density, monolayer integrity, permeability, or a combination thereof.

The methods described herein can also further comprise analyzing the morphology of the at least one tumor cell type, the endothelial cells, the at least one stromal cell type, or the one or more additional cell types.

The methods described herein can also further comprise analyzing the culture medium for cytokine secretion, chemokine secretion, humoral factor secretion, microparticle secretion, growth factor secretion, shedding of a protein from the cellular surface, a metabolite of a compound, an immune cell, nitric oxide secretion, a vasodilator protein, a vasoconstrictive protein, miRNA, a secreted protein, or a secreted biological substance. For example, the culture medium can be analyzed for shedding of a protein from the cellular surface, and the protein comprises a vascular cell adhesion molecule (VCAM), E-selectin, or an intracellular adhesion molecule (ICAM). Alternatively or in addition, the culture medium can be analyzed for nitric oxide secretion by measuring nitrate or nitrite concentration.

In any of the methods comprising adding a drug or a compound to the culture medium, the method can further comprise analyzing the at least one tumor cell type, the endothelial cells, the at least one stromal cell type for toxicity, or the one or more additional cell types for inflammation, permeability, compatibility, cellular adhesion, cellular remodeling, cellular migration, or phenotypic modulation resulting from the drug or the compound.

Also, in any of the methods comprising adding a drug or a compound to the culture medium, the method can further comprise comparing at least one of the cell types after applying the shear stress for a period of time wherein the medium includes the drug or the compound to the at least one of the cell types after applying the shear stress for the period of time wherein the medium does not include the drug or the compound, to determine the effect of the drug or compound on the at least one of the cell types.

Any of the methods described herein can further include identifying a drug target. For example, a drug target can be identified by isolating proteins or nucleic acids from the at least one tumor cell type directly or indirectly exposed to the drug or compound and performing an appropriate screen to identify potential drug targets. Screening methods include proteomic analysis or phosphorylation screening, mRNA analysis (e.g., next generation RNA sequencing or gene arrays), DNA analysis, DNA methylation screening, and intracellular or extracellular miRNA analysis (e.g., miRNA arrays). Modulation of a signal (e.g., increased or decreased expression of a gene) indicates identification of a candidate drug target.

Any of the methods described herein can further include identifying a surface protein of the at least one tumor cell type, the at least one stromal cell type, the endothelial cells, or the one or more additional cell types as a target for a drug delivery modality. The drug delivery modality can comprise an antibody-drug conjugate, a nanoparticle (e.g., a lipid nanoparticle), a chemical conjugate (e.g., N-Acetylgalactosamine (GalNAc)), or a combination thereof. A protein, antibody, peptide, or nucleic acid molecule (e.g., an RNAi molecule) can be conjugated to or incorporated in the nanoparticle or the chemical conjugate. Surface proteins that are targets for a drug delivery modality can be identified by isolating the cell membrane fraction from tumor cells, stromal cells, endothelial cells, or the one or more additional cell types cultured according to any of the methods for mimicking a tumor microenvironment described herein, screening the cell membrane faction to identify potential targets for a drug delivery modality. Screening methods include proteomic analysis or phosphorylation screening, mRNA analysis (e.g., next generation RNA sequencing or gene arrays), DNA analysis, DNA methylation screening, and intracellular or extracellular miRNA analysis (e.g., miRNA arrays). Modulation of a signal (e.g., increased or decreased expression of a gene) indicates identification of a candidate target for a drug delivery modality.

In Vitro Systems that Model the Liver

As noted above, in vitro systems that model the liver are described in U.S. Patent Application Publication No. 2013/0309677 and PCT Publication No. 2013/0158939. The in vitro systems that model the liver described in these publications can be used in method for mimicking an in vivo pathological or physiologic condition. Unlike static models currently used as the standard in vitro models by the pharmaceutical and biopharmaceutical industries, the methods described in U.S. Patent Application Publication No. 2013/0309677 and PCT Publication No. 2013/0158939 apply shear forces to cultured cells and replicate an in vivo pathological or physiological condition using in vivo pathological or physiologic concentrations of various factors. For example, an in vitro liver model is described in which hepatocytes can be maintained at in vivo physiologic concentrations of insulin and glucose that are significantly decreased as compared to the concentrations used in the standard static model. When higher concentrations of insulin and glucose are used in such a model, the hepatocytes exhibit numerous hallmarks of fatty liver disease.

U.S. Patent Application Publication No. 2013/0309677 and PCT Publication No. 2013/0158939 describe a method for mimicking a pathological condition in vitro (e.g., a pathological condition of the liver). The method comprises adding a culture media to a cell culture container, adding at least one factor to the culture media, plating at least one cell type on at least one surface within the cell culture container, and applying a shear force upon the at least one plated cell type. The shear force results from flow of the culture media induced by a flow device. The flow mimics flow to which the at least one cell type is exposed in vivo in the pathological condition.

The concentration of the factor in the culture media can be within the in vivo concentration range of the factor observed in the pathological condition. Alternatively, the concentration of the factor in the culture media can be within the concentration range of the factor that would result in vivo from administration of a drug or a compound.

To confirm that the in vivo pathological condition is mimicked, a change in a level of a marker of the pathological condition can be compared between the method and the same method in the absence of application of the shear force. The level of the marker in the at least one plated cell type or in the culture media upon application of the shear force is compared to the level of the marker in the at least one plated cell type or in the culture media in the absence of application of the shear force. For example, if a marker is known to be associated with a pathological condition and its concentration is known to increase in the serum when the condition is present in vivo, an increase in the level of the marker in the culture media of the method with application of the shear force as compared to the level of the marker in the culture media in the absence of application of the shear force confirms that the in vivo pathological condition is mimicked by the in vitro method.

U.S. Patent Application Publication No. 2013/0309677 and PCT Publication No. 2013/0158939 also describe an in vitro method of testing a drug or a compound for an effect on a pathological condition. The method comprises mimicking the pathological condition, adding a drug or a compound to the culture media, and applying the shear force upon the at least one plated cell type exposed to the drug or the compound. A change in the at least one plated cell type, in the presence of the drug or the compound, indicates that the drug or the compound has an effect on the pathological condition.

In this in vitro method of testing a drug or compound, the pathological condition can be mimicked by the in vitro method of mimicking a pathological condition as described above.

The pathological condition of the in vitro method of testing a drug or compound can also be mimicked by plating primary cells or immortalized cells from a subject or subjects having the pathological condition, and culturing the cells in cell culture media.

U.S. Patent Application Publication No. 2013/0309677 and PCT Publication No. 2013/0158939 also describe a method of mimicking a physiologic condition in vitro (e.g., a healthy liver). The method comprises adding a culture media to a cell culture container, adding at least one factor to the culture media, plating at least one cell type on at least one surface within the cell culture container, and applying a shear force upon the at least one plated cell type. The shear force results from flow of the culture media induced by a flow device. The flow mimics flow to which the at least one cell type is exposed in vivo in the physiologic condition.

The concentration of the factor in the culture media can be within the in vivo concentration range of the factor observed in the physiologic condition. Alternatively, the concentration of the factor in the culture media can be within the concentration range of the factor that would result in vivo from administration of a drug or a compound.

To confirm that the in vivo physiologic condition is mimicked, a change in a level of a marker of the physiologic condition can be compared between the method and the same method in the absence of application of the shear force. The level of the marker in the at least one plated cell type or in the culture media upon application of the shear force is compared to the level of the marker in the at least one plated cell type or in the culture media in the absence of application of the shear force. For example, if a marker is known to be associated with a physiologic condition and its concentration is known to increase in the serum when the condition is present in vivo, an increase in the level of the marker in the culture media of the method with application of the shear force as compared to the level of the marker in the culture media in the absence of application of the shear force confirms that the in vivo physiologic condition is mimicked by the in vitro method.

U.S. Patent Application Publication No. 2013/0309677 and PCT Publication No. 2013/0158939 also describe an in vitro method of testing a drug or a compound for an effect on a physiologic condition. The method comprises mimicking the physiologic condition, adding a drug or a compound to the culture media, and applying the shear force upon the at least one plated cell type exposed to the drug or the compound. A change in the at least one plated cell type, in the presence of the drug or the compound, indicates that the drug or the compound has an effect on the physiologic condition.

In this in vitro method of testing a drug or compound, the physiologic condition can be mimicked by the in vitro method of mimicking a physiologic condition as described above.

The physiologic condition of this in vitro method of testing a drug or compound can also be mimicked by plating primary cells or immortalized cells, and culturing the cells in cell culture media.

U.S. Patent Application Publication No. 2013/0309677 and PCT Publication No. 2013/0158939 also describe an in vitro method of testing a drug or a compound for an effect (e.g., an effect on a pathological condition of the liver or on a healthy liver). The method comprises adding a culture media to a cell culture container, plating at least one cell type on at least one surface within the cell culture container, adding a drug or a compound to the culture media, and applying a shear force upon the at least one plated cell type exposed to the drug or the compound. The concentration of the drug or the compound in the culture media is within the concentration range of the drug or the compound that achieves the effect in vivo. The shear force results from flow of the culture media induced by a flow device. The flow mimics flow to which the at least one cell type is exposed in vivo. A change in the at least one plated cell type, in the presence of the drug or the compound, indicates that the drug or the compound has the effect.

The effect can be an effect on a pathological condition (e.g., a pathological condition of the liver). Alternatively, the effect can be an effect on a physiologic condition (e.g., a healthy liver.

In any of the above methods described in U.S. Patent Application Publication No. 2013/0309677 and PCT Publication No. 2013/0158939, the method can further comprise analyzing the cell culture media for cytokine secretion, chemokine secretion, humoral factor secretion, microparticle secretion, growth factor secretion, shedding of a protein from the cellular surface, a metabolite of a compound, an immune cell, nitric oxide secretion, a vasodilator protein, a vasoconstrictive protein, miRNA, a secreted protein, or a secreted biological substance. The cell culture media can be analyzed for nitric oxide secretion by measuring nitrate or nitrite concentration.

In any of the above methods described in U.S. Patent Application Publication No. 2013/0309677 and PCT Publication No. 2013/0158939, the method can further comprise the step of culturing the cell type or cell types.

In any of the above methods described in U.S. Patent Application Publication No. 2013/0309677 and PCT Publication No. 2013/0158939 wherein a drug or compound has been added to the culture media, the method can further comprise the step of comparing at least one of the cell types after applying the shear force for a period of time wherein the media includes the drug or the compound to the at least one of the cell types after applying the shear force for the period of time wherein the media does not include the drug or the compound, to determine the effect of the drug or compound on the at least one of the cell types.

U.S. Patent Application Publication No. 2013/0309677 and PCT Publication No. 2013/0158939 describe methods wherein drugs or compounds are tested for an effect on a healthy liver. In such methods, the factors comprise insulin and glucose, hepatocytes are plated on the surface within the cell culture container, and the shear force is applied indirectly to the plated hepatocytes.

For example, the hepatocytes can be plated on a first surface of a porous membrane. The porous membrane is then suspended in the cell culture container such that the first surface is proximal and in spaced relation to a bottom surface of the cell culture container, thereby defining within the cell culture container a lower volume and an upper volume. The lower volume comprises the hepatocytes and the upper volume comprises a second surface of the porous membrane. The shear force is applied to the second surface of the porous membrane in the upper volume of the container.

In the methods described in U.S. Patent Application Publication No. 2013/0309677 and PCT Publication No. 2013/0158939, use of a porous membrane suspended in the cell culture container is preferred in plating the cells. When shear force is applied to plated cells or to the surface of the porous membrane (e.g., when the shear is applied on a surface of the membrane absent plated cells), the shear force can enable the cell culture media to perfuse from the upper volume to the lower volume. Such perfusion favorably impacts transport of factors from the upper volume to the lower volume, or vice versa.

U.S. Patent Application Publication No. 2013/0309677 and PCT Publication No. 2013/0158939 describe methods of mimicking a pathological or physiologic condition of the liver in vitro. The method comprises adding a culture media to a cell culture container, adding at least one factor to the culture media, plating at least one hepatic cell type on at least one surface within the cell culture container, and applying a shear force upon the at least one plated hepatic cell type. The shear force results from flow of the culture media induced by a flow device. The flow mimics flow to which the at least one hepatic cell type is exposed in vivo in the pathological or physiologic condition.

In this method, the concentration of the factor in the culture media for mimicking the pathological condition can be within the in vivo concentration range of the factor observed in the pathological condition. Alternatively, in this method, the concentration of the factor in the culture media for mimicking the pathological condition can be within the concentration range of the factor that would result in vivo from administration of a drug or a compound. As a further alternative, in this method, the concentration of the factor in the culture media for mimicking the pathological condition can be capable of maintaining the mimicked pathological condition in vitro for a period of time under the shear force, the same concentration of factor being incapable of maintaining the mimicked pathological condition in vitro for the period of time in the absence of the shear force.

In this method, the concentration of the factor in the culture media for mimicking the physiologic condition can be within the in vivo concentration range of the factor observed in the physiologic condition. Alternatively, in this method, the concentration of the factor in the culture media for mimicking the physiologic condition can be within the concentration range of the factor that would result in vivo from administration of a drug or a compound. As a further alternative, in this method, the concentration of the factor in the culture media for mimicking the physiologic condition can be capable of maintaining the mimicked physiologic condition in vitro for a period of time under the shear force, the same concentration of factor being incapable of maintaining the mimicked physiologic condition in vitro for the period of time in the absence of the shear force.

In this method, a change in a level of a marker of the pathological or physiologic condition in the at least one plated hepatic cell type or in the culture media upon application of the shear force, as compared to the level of the marker in the at least one plated hepatic cell type or in the culture media in the absence of application of the shear force confirms mimicking of the pathological or physiologic condition.

Alternatively, in this method, the at least one plated hepatic cell type can comprise hepatocytes, and responsiveness to glucagon, insulin, or a glucose substrate in the hepatocytes confirms mimicking of the physiologic condition. The glucose substrate can be, for example, glycerol, lactate, pyruvate, or combinations thereof (e.g., a combination of lactate and pyruvate).

U.S. Patent Application Publication No. 2013/0309677 and PCT Publication No. 2013/0158939 also describe an in vitro method of testing a drug or a compound for an effect on a pathological or physiological condition (e.g., a pathological or physiological condition of the liver). The method comprises mimicking the pathological or physiological condition, adding a drug or a compound to the culture media, and applying the shear force upon at least one plated hepatic cell type exposed to the drug or the compound. A change in the at least one plated hepatic cell type, in the presence of the drug or the compound, indicates that the drug or the compound has an effect on the pathological or physiological condition.

In this in vitro method of testing a drug or compound, the pathological condition can be mimicked by the in vitro method of mimicking a pathological or physiological condition as described directly above.

The pathological or physiological condition of the in vitro method of testing a drug or compound can also be mimicked by plating primary cells or immortalized cells from a subject or subjects having the pathological condition, and culturing the cells in cell culture media.

U.S. Patent Application Publication No. 2013/0309677 and PCT Publication No. 2013/0158939 also describe a method of mimicking a pathological or physiologic condition of the liver in vitro. The method comprises adding a culture media to a cell culture container, depositing at least one extracellular matrix component on a surface within the cell culture container, plating hepatocytes on the at least one extracellular matrix component, and indirectly applying a shear force upon the at least one extracellular matrix component and the hepatocytes. The shear force results from flow of the culture media induced by a flow device. The flow mimics flow to which the hepatocytes are exposed in vivo in the pathological or physiologic condition.

In methods in which hepatic cells are plated on a porous membrane, at least one extracellular matrix component can be plated on a first surface of the porous membrane and the hepatic cells can subsequently be plated on the at least one extracellular matrix component. Optionally, nonparenchymal hepatic cells (e.g., sinusoidal endothelial cells) can be plated on the second surface of the porous membrane, and the shear stress applied to the nonparenchymal hepatic cells.

In the methods involving the deposition of an extracellular matrix component, for example, the at least one extracellular matrix component can be deposited on a first surface of a porous membrane. The hepatic cell type (e.g., hepatocytes) is subsequently plated on the at least one extracellular matrix component. The porous membrane is suspended in the cell culture container such that the first surface is proximal and in spaced relation to a bottom surface of the cell culture container, thereby defining within the cell culture container a lower volume and an upper volume. The lower volume comprises at least one extracellular matrix component and the hepatic cell type (e.g., hepatocytes), and the upper volume comprises a second surface of the porous membrane. The shear force is applied to the second surface of the porous membrane in the upper volume of the container. Optionally, nonparenchymal hepatic cells (e.g., sinusoidal endothelial cells) can be plated on the second surface of the porous membrane, and the shear stress applied to the nonparenchymal hepatic cells.

U.S. Patent Application Publication No. 2013/0309677 and PCT Publication No. 2013/0158939 also describe another method of mimicking a pathological or physiologic condition of the liver in vitro. The method comprises adding a culture media to a cell culture container, and plating hepatocytes on a first surface of a porous membrane. The porous membrane is suspended in the cell culture container such that the first surface is proximal and in spaced relation to a bottom surface of the container, thereby defining within the container a lower volume comprising the hepatocytes and an upper volume comprising a second surface of the porous membrane. A shear force is applied upon the second surface of the porous membrane in the upper volume of the container, the shear force resulting from flow of the culture media induced by a flow device. The flow mimics flow to which the hepatocytes are exposed in vivo in the pathological or physiologic condition. The flow device comprises a body adapted for being positioned in the culture media in the upper volume of the container and a motor adapted to rotate the body. Preferably, the body has a conical surface. It is also preferred that the flow device is adapted for positioning the conical surface of the body in the container and in contact with the cell culture media.

This method can further comprise plating nonparenchymal hepatic cells on the second surface of the porous membrane, wherein the shear stress is applied to the nonparenchymal hepatic cells. The nonparenchymal hepatic cells can comprise sinusoidal endothelial cells, hepatic stellate cells, Kupffer cells, or combinations thereof.

In the in vitro methods for mimicking a pathological or physiologic condition of the liver, a change in a level of a marker of the pathological or physiologic condition can be compared in the method to the same method in the absence of application of the shear force. A change in the level of the marker in any of the hepatic cells or in the culture media upon application of the shear force as compared to the level of the marker in the hepatic cells or in the culture media in the absence of application of the shear force confirms mimicking of the pathological or physiologic condition. For example, a change in the level of the marker in the hepatocytes or nonparenchymal hepatic cells or in the culture media upon application of the shear force as compared to the level of the marker in the hepatocytes or nonparenchymal hepatic cells or in the culture media in the absence of application of the shear force confirms mimicking of the pathological or physiologic condition.

Alternatively, when the at least one plated hepatic cell type comprises hepatocytes, responsiveness to glucagon, insulin, or a glucose substrate in the hepatocytes confirms mimicking of the physiologic condition. The glucose substrate can be, for example, glycerol, lactate, pyruvate, or combinations thereof (e.g., a combination of lactate and pyruvate).

Pathological Conditions

The pathological conditions of the liver that can be mimicked using the methods described in U.S. Patent Application Publication No. 2013/0309677 and PCT Publication No. 2013/0158939 include, but are not limited to fatty liver disease, hepatitis C, hepatitis B, liver fibrosis, bacterial infection, viral infection, cirrhosis, and alcohol-induced liver disease.

When the pathological condition is fatty liver disease, the cell types can comprise hepatocytes, nonparenchymal hepatic cells, or combinations thereof. The nonparenchymal hepatic cells can include sinusoidal endothelial cells, hepatic stellate cells, Kupffer cells, or combinations thereof.

When the pathological condition is fatty liver disease, the flow or hemodynamic pattern can be from a normal subject, a subject having fatty liver disease, or an animal genetically modified to model fatty liver disease.

Where the pathological condition is fatty liver disease and a porous membrane is used, hepatocytes can be plated on a first surface of the porous membrane. The porous membrane is suspended in the cell culture container such that the first surface is proximal and in spaced relation to a bottom surface of the cell culture container, thereby defining within the cell culture container a lower volume comprising the hepatocytes and an upper volume comprising a second surface of the porous membrane. The shear force is applied to the second surface of the porous membrane in the upper volume. Optionally, nonparenchymal hepatic cells can be plated on the second surface of the porous membrane, and the shear force is applied to the nonparenchymal hepatic cells in the upper volume. Optionally, an extracellular matrix component can be deposited on the first surface of the porous membrane, and subsequently hepatoctyes can be plated on the extracellular matrix component.

Where the pathological condition is fatty liver disease and a porous membrane is used, nonparenchymal hepatic cells can be plated on a second surface of a porous membrane. The porous membrane is suspended in the cell culture container such that a first surface of the porous membrane is proximal and in spaced relation to a bottom surface of the cell culture container, thereby defining within the cell culture container a lower volume comprising the first surface of the porous membrane and an upper volume comprising the nonparenchymal hepatic cells. The shear force is applied to the nonparenchymal hepatic cells in the upper volume. Optionally, an extracellular matrix component can be deposited on the first surface of the porous membrane, and subsequently hepatoctyes can be plated on the extracellular matrix component.

When the vascular pathological condition is fatty liver disease, the factor can comprise insulin, glucose, or a combination thereof. For example, the factor(s) can comprise insulin; glucose; or insulin and glucose.

When the pathological condition is diabetes, the cell type can comprise pancreatic (3-cells, pancreatic a-cells, or a combination thereof; and the factor can comprise insulin, glucose, or insulin and glucose.

Physiologic Conditions

The physiologic conditions that can be mimicked using the methods described in U.S. Patent Application Publication No. 2013/0309677 and PCT Publication No. 2013/0158939 include the physiologic conditions corresponding to any pathological condition of interest. For example, a physiologic condition corresponding to fatty liver disease can be a healthy liver state, and a physiologic condition corresponding to atherosclerosis can be an atheroprotective state.

Flow Devices

The flow devices that can be used in the methods described in U.S. Patent Application Publication No. 2013/0309677 and PCT Publication No. 2013/0158939 are the same as described hereinabove in the section entitled "Flow Devices."

Hemodynamic Patterns

The hemodynamic patterns that can be used in the methods described in U.S. Patent Application Publication No. 2013/0309677 and PCT Publication No. 2013/0158939 can be derived from a subject or subjects having the pathological condition or a disease-promoting condition. The disease-promoting condition can comprise atrophy, calculi, choristoma, pathologic constriction, pathologic dilation, diverticulum, hypertrophy, polyps, prolapse, rupture, an arteriovenous fistula, or an appendage (e.g., a left atrial appendage).

The hemodynamic pattern can be derived from at least a portion of an artery, an arteriole, a vein, a venule, or an organ.

When a hemodynamic pattern is derived from at least a portion of an artery or an arteriole, the artery or arteriole can comprise a carotid artery, thoracic artery, abdominal artery, pulmonary artery, femoral artery, renal efferent artery, renal afferent artery, coronary artery, brachial artery, internal mammary artery, cerebral artery, aorta, pre-capillary arteriole, hepatic artery, anterior cerebral artery, middle cerebral artery, posterior cerebral artery, basilar artery, external carotid artery, internal carotid artery, vertebral artery, subclavian artery, aortic arch, axillary artery, internal thoracic artery, branchial artery, deep branchial artery, radial recurrent artery, superior epigastric artery, descending aorta, inferior epigastric artery, interosseous artery, radial artery, ulnar artery, palmar carpal arch, dorsal carpal arch, superficial or deep palmar arch, digital artery, descending branch of the femoral circumflex artery, descending genicular artery, superior genicular artery, inferior genicular artery, anterior tibial artery, posterior tibial artery, peroneal artery, deep plantar arch, arcuate artery, common carotid artery, intercostal arteries, left or right gastric artery, celiac trunk, splenic artery, common hepatic artery, superior mesenteric artery, renal artery, inferior mesenteric artery, testicularis artery, common iliac artery, internal iliac artery, external iliac artery, femoral circumflex artery, perforating branch, deep femoral artery, popliteal artery, dorsal metatarsal artery, or dorsal digital artery.

When a hemodynamic pattern is derived from at least a portion of an vein or venule, the vein or venule can comprise a post-capillary venule, saphenous vein, hepatic portal vein, superior vena cava, inferior vena cava, coronary vein, Thesbian vein, superficial vein, perforator vein, systemic vein, pulmonary vein, jugular vein, sigmoid sinus, external jugular vein, internal jugular vein, inferior thyroid vein, subclavian vein, internal thoracic vein, axillary vein, cephalic vein, branchial vein, intercostal vein, basilic vein, median cubital vein, thoracoepigastric vein, ulnar vein, median antebranchial vein, inferior epigastric vein, deep palmar arch, superficial palmar arch, palmar digital vein, cardiac vein, inferior vena cava, hepatic vein, renal vein, abdominal vena cava, testicularis vein, common iliac vein, perforating branch, external iliac vein, internal iliac vein, external pudendal vein, deep femoral vein, great saphenous vein, femoral vein, accessory saphenous vein, superior genicular vein, popliteal vein, inferior genicular vein, great saphenous vein, small saphenous vein, anterior or posterior tibial vein, deep plantar vein, dorsal venous arch, or dorsal digital vein.

When a hemodynamic pattern is derived from at least a portion of an organ, the organ can comprise a liver, a kidney, a lung, a brain, a pancreas, a spleen, a large intestine, a small intestine, a heart, a skeletal muscle, an eye, a tongue, a reproductive organ, or an umbilical cord. The hemodynamic pattern is preferably derived from a liver.

The hemodynamic pattern can be derived from analysis of ultrasound data.

The hemodynamic pattern can be derived from analysis of magnetic resonance imaging (MRI) data.

The flow or the hemodynamic pattern can be time-variant.

The flow or the hemodynamic pattern can result from a physical change resulting from a pathological condition.

The flow or hemodynamic pattern can be derived from a subject wherein blood flow or a hemodynamic pattern has been altered as a direct or indirect effect of administration of a drug to a subject as compared to the flow or the hemodynamic pattern for the subject absent administration of the drug.

The flow or the hemodynamic pattern can be derived from an animal, such as a genetically modified animal or a human. Preferably, the pattern is derived from a human.

Cell Types

The cell types that can be used in the methods described in U.S. Patent Application Publication No. 2013/0309677 and PCT Publication No. 2013/0158939 include primary cells and immortalized cells. The primary cells or immortalized cells can comprise cells isolated from at least one subject having the pathological or physiologic condition, cells isolated from at least one subject having a risk factor for the pathological condition, cells isolated from at least one subject with a single nucleotide polymorphism linked to a pathological condition, cells isolated from at least one subject with an identified genotype linked to drug toxicity, or cells isolated from at least one subject with a single nucleotide polymorphism linked to drug toxicity.

The primary cells or the immortalized cells used in in vitro methods involving a physiologic condition comprise cells isolated from at least one subject having the physiologic condition, cells isolated from at least one subject having a risk factor for a pathological condition, cells isolated from at least one subject with a single nucleotide polymorphism linked to a pathological condition, cells isolated from at least one subject with an identified genotype linked to drug toxicity, or cells isolated from at least one subject with a single nucleotide polymorphism linked to drug toxicity.

The primary cells or immortalized cells used in in vitro methods involving a pathological condition can comprise cells isolated from at least one subject having the pathological condition, cells isolated from at least one subject having a risk factor for the pathological condition, cells isolated from at least one subject with a single nucleotide polymorphism linked to the pathological condition, cells isolated from at least one subject with an identified genotype linked to drug toxicity, or cells isolated from at least one subject with a single nucleotide polymorphism linked to drug toxicity.

The primary cells or immortalized cells used in in vitro methods involving a pathological condition can comprise cells isolated from at least one subject not having the pathological condition, cells isolated from at least one subject not having a risk factor for the pathological condition, cells isolated from at least one subject without a single nucleotide polymorphism linked to the pathological condition, cells isolated from at least one subject without an identified genotype linked to drug toxicity, or cells isolated from at least one subject without a single nucleotide polymorphism linked to drug toxicity.

The primary cells or immortalized cells used in in vitro methods involving a pathological condition can comprise cells isolated from at least one subject having a different pathological condition, cells isolated from at least one subject having a risk factor for a different pathological condition, or cells isolated from at least one subject with a single nucleotide polymorphism linked to a different pathological condition.

When the cells are isolated from at least one subject having a risk factor for the pathological condition, the risk factor can include, but is not limited to, smoking, age, gender, race, epigenetic imprinting, an identified genotype linked to the pathological condition, an identified single nucleotide polymorphism linked to the pathological condition, diabetes, hypertension, atherosclerosis, atherosclerotic plaque rupture, atherosclerotic plaque erosion, thoracic aortic aneurysm, cerebral aneurysm, abdominal aortic aneurysm, cerebral aneurysm, heart failure, stroke, Marfan syndrome, carotid intima-medial thickening, atrial fibrillation, kidney disease, pulmonary fibrosis, chronic obstructive pulmonary disease, pulmonary artery disease, pulmonary hypertension, hyperlipidemia, familial hypercholesterolemia, peripheral artery disease, arterial thrombosis, venous thrombosis (e.g., deep vein thrombosis), vascular restenosis, vascular calcification, myocardial infarction, obesity, hypertriglyceridemia, hypoalphalipoproteinemia, fatty liver disease, hepatitis C, hepatitis B, liver fibrosis, bacterial infection, viral infection, cirrhosis, liver fibrosis, or alcohol-induced liver disease.

The primary cells can include a cell lineage derived from stem cells (e.g., adult stem cells, embryonic stem cells, inducible pluripotent stem cells, or bone marrow-derived stem cells) or stem-like cells. The cell lineage derived from stem cells or stem-like cells can comprise endothelial cells, smooth muscle cells, cardiac myocytes, hepatocytes, neuronal cells, endocrine cells, pancreatic β-cells, pancreactic α-cells, or skeletal muscle cells.

The primary cells can comprise inducible pluripotent stem cell (iPSC)-derived cells from a subject having a pathological condition. For example, the iPSC-derived cells from a subject having a pathological condition can comprise iPSC-derived hepatocytes from a subject having familial hpercholesterolemia, glycogen storage disease type I, Wilson's disease, A1 anti-trypsin deficiency, Crigler-Najjar syndrome, progressive familial hereditary cholestasis, or hereditary tyrosinemia Type 1. Alternatively, the iPSC-derived cells from a subject having a pathological condition can comprise iPSC-derived vascular cells (e.g., iPSC-derived smooth muscle cells, iPSC-derived endothelial cells, or iPSC-derived endocardial cells) from a subject having Hutchinson-Gilford progeria, Williams-Beuren syndrome, Fabry's disease, Susac's syndrome, systemic capillary leak syndrome, Gleich syndrome, intravascular papillary endothelial hyperplasia, sickle cell disease, or hepatic veno-occlusive disease.

Cell types for use in methods include vascular cells and hepatic cell.

Specific cell types for use in the methods include endothelial cells, hepatocytes, nonparenchymal hepatic cells, endothelial progenitor cells, stem cells, and circulating stem cells. The nonparenchymal hepatic cells include hepatic stellate cells, sinusoidal endothelial cells, and Kupffer cells. Preferably, the specific cell types can include endothelial cells, hepatocytes, sinusoidal endothelial cells, or a combination thereof.

The cell types for use in the methods can be animal cell types, such as cells from a genetically modified animal. The animal cell types are preferably human cell types. The human cell types can be selected on the basis of age, gender, race, epigenetics, disease, nationality, the presence or absence of one or more single nucleotide polymorphisms, a risk factor as described herein, or some other characteristic that is relevant to the pathological or physiologic condition.

The shear force applied in the methods can be applied indirectly to the at least one plated cell type.

The shear force applied in the methods can be applied directly to the at least one plated cell type.

The cell types, additional components such as extracellular matrix component, and the porous membrane are within the culture media (i.e., covered with culture media) in the methods.

The methods can further comprise analyzing at least one of the cell types for toxicity, inflammation, permeability, compatibility, cellular adhesion, cellular remodeling, cellular migration, or phenotypic modulation resulting from the drug or the compound.

Cell Culture Media

Standard cell culture media can be used in the methods described in U.S. Patent Application Publication No. 2013/0309677 and PCT Publication No. 2013/0158939.

In Vivo Factor Concentrations

The physiologic in vivo concentrations of the factors for use in the methods described in U.S. Patent Application Publication No. 2013/0309677 and PCT Publication No. 2013/0158939 are well known in the art, as are the methods of determining these in vivo concentrations. Methods for determining in vivo concentrations of factors are available in the United States Pharmacopeia and in other literature.

A reported in vivo concentration range for a factor can vary depending upon the method used for determining the range, the source from which the factor is obtained (e.g., whole blood or serum), the medical condition of the patient (i.e., whether the patient has a pathological condition or physiologic condition), and time of day relative to normal sleep and eating schedule. However, it would be known to one of ordinary skill in the art that a concentration outside an in vivo physiological concentration range reported in the literature would be an in vivo pathological concentration using the method reported for determining the concentration. Likewise, a concentration below the lower endpoint or above the upper endpoint of an in vivo pathological concentration range reported in the literature would be an in vivo physiologic concentration using the method reported for determining the concentration; whether the in vivo physiologic concentration is below the lower endpoint or above the upper endpoint will depend upon the factor.

Extracellular Matrix Components

Extracellular matrix components for use in the methods described in U.S. Patent Application Publication No. 2013/0309677 and PCT Publication No. 2013/0158939 can comprise heparan sulfate, chondroitin sulfate, keratan sulfate, hyaluronic acid, a collagen, an elastin, a fibronectin, a laminin, a vitronectin, or combinations thereof. Collagen is a preferred extracellular matrix component, and is preferably the type of collagen that is present in the in vivo environment of the cell type or cell type(s) that are plated for a particular pathological or physiologic condition.

The extracellular matrix component can be secreted by fibroblasts, chondrocytes, or osteoblasts plated on the surface within the cell culture container.

Drugs or Compounds

The drug or compound for use in the methods described in U.S. Patent Application Publication No. 2013/0309677 and PCT Publication No. 2013/0158939 involving testing of a drug or compound can comprise any drug or compound.

The concentration of the drug or the compound in the culture media is suitably within the concentration range of the drug or the compound that achieves the effect in vivo. For example, the concentration of the drug or the compound in the culture media is suitably within the concentration range of the in vivo therapeutic $C_{max}$ for the drug or the compound.

Sera

In any of the methods described in U.S. Patent Application Publication No. 2013/0309677 and PCT Publication No. 2013/0158939 that involve adding a factor to the culture media or adding a drug or compound to the culture media, the step of adding the factor to the culture media or the step of adding the drug or a compound to the culture media can comprise adding sera from a subject to the culture media, wherein the sera comprises the factor, the drug, or the compound.

The subject can be an animal, e.g., as a genetically modified animal or a human. Preferably, the sera is derived from a human subject.

The sera can be from a subject having a physiologic condition or a subject having a pathological condition. For example, where the sera is from a subject that has a pathological condition, the pathological condition can comprise advanced inflammation, atherosclerosis, diabetic nephropathy, diabetic neuropathy, diabetic retinopathy, hypertension, hypertensive encephalopathy, hypertensive retinopathy, fatty liver disease, hypertension, heart failure, stroke, Marfan syndrome, carotid intima-medial thickening, atrial fibrillation, kidney disease, pulmonary fibrosis, chronic obstructive pulmonary disease, hyperlipidemia, hypercholesterolemia, diabetes, atherosclerotic plaque rupture, atherosclerotic plaque erosion, thoracic aortic aneurysm, cerebral aneurysm, abdominal aortic aneurysm, cerebral aneurysm, pulmonary artery disease, pulmonary hypertension, peripheral artery disease, arterial thrombosis, venous thrombosis (e.g., deep vein thrombosis), vascular restenosis, vascular calcification, myocardial infarction, obesity, hypertriglyceridemia, hypoalphalipoproteinemia, hepatitis C, hepatitis B, liver fibrosis, bacterial infection, viral infection, cirrhosis, liver fibrosis, or alcohol-induced liver disease.

Effect on the Physiologic or Pathological Condition

In methods of testing a drug or a compound for an effect described in U.S. Patent Application Publication No. 2013/0309677 and PCT Publication No. 2013/0158939, the effect can comprise an effect on a physiologic condition or an effect on a pathological condition. For example, the effect on the physiologic condition or the pathological condition can be a toxic effect, a protective effect, a pathologic effect, a disease-promoting effect, an inflammatory effect, an oxidative effect, an endoplasmic reticulum stress effect, a mitochondrial stress effect, an apoptotic effect, a necrotic effect, a remodeling effect, a proliferative effect, an effect on the activity of a protein, such as inhibition of a protein or activation of a protein, or an effect on the expression of a gene, such as an increase in the expression of the gene or a decrease in the expression of the gene.

Multiple Cell Type Configurations for the Flow Device

The methods described in U.S. Patent Application Publication No. 2013/0309677 and PCT Publication No. 2013/0158939 can further comprise perfusing culture media, factors, drugs or compounds into and out of the cell container.

When the surface within the cell culture container comprises a porous membrane suspended in the cell culture container, the method can further include the step of plating at least one cell type on a surface within the cell culture container comprising plating a first cell type on a first surface of a porous membrane, and optionally plating a second cell type on a second surface of the porous membrane, wherein the porous membrane is suspended in the cell culture container such that the first surface is proximal and in spaced relation to a bottom surface of the cell culture container, thereby defining within the cell culture container a lower volume comprising the first cell type and an upper volume comprising the optional second cell type. The porous membrane can be adapted to permit fluid communication of the cell culture media and physical interaction and communication between cells of the first cell type and cells of the optional second cell type. The shear force is applied to the second cell type or the second surface of the porous membrane in the upper volume. The method can further comprise perfusing culture media into and out of the upper volume and perfusing culture media into and out of the lower volume. The method can further comprise perfusing a drug or the compound into at least one of the upper volume and the lower volume.

When the surface within the cell culture container comprises a porous membrane suspended in the cell culture container, the method can further include the step of plating at least one cell type on a surface within the cell culture container comprising optionally plating a first cell type on a first surface of a porous membrane, and plating a second cell type on a second surface of the porous membrane, wherein the porous membrane is suspended in the cell culture container such that the first surface is proximal and in spaced relation to a bottom surface of the cell culture container, thereby defining within the cell culture container a lower volume comprising the optional first cell type and an upper volume comprising the second cell type. The porous membrane can be adapted to permit fluid communication of the cell culture media and physical interaction and communication between cells of the optional first cell type and cells of the second cell type. The shear force is applied to the second cell type in the upper volume. The method can further comprise perfusing culture media into and out of the upper volume and perfusing culture media into and out of the lower volume. The method can further comprise perfusing a drug or the compound into at least one of the upper volume and the lower volume.

The inlets and outlets in the cell culture container can be within the portions of the cell culture container defining the upper and lower volumes.

The methods described in this section can further comprise analyzing at least one of the first cell type or the second cell type for toxicity, inflammation, permeability, compatibility, cellular adhesion, cellular remodeling, cellular migration, or phenotypic modulation resulting from the drug or the compound.

These methods can further comprise plating a third cell type on a surface of the container or the first surface or second surface of the porous membrane, suspending a third cell type in the culture media within the upper volume, or suspending a third cell type in the culture media within the lower volume.

These methods can further comprise plating a fourth cell type on a surface of the container or the first or second surface of the porous membrane, suspending a fourth cell type in the culture media within the upper volume, or suspending a fourth cell type in the culture media within the lower volume.

These methods can further comprise plating a fifth cell type on a surface of the container or the first or second surface of the porous membrane, suspending a fifth cell type in the culture media within the upper volume, or suspending a fifth cell type in the culture media within the lower volume.

The first, second, third, fourth and fifth cell types can be various primary or immortalized cell types as described in the section above regarding cell types.

In each of these combinations, the cells of the third cell type, the cells of the fourth cell type or the cells of the fifth cell type can be adhered to the bottom surface of the container.

Definitions

With respect to the methods described in U.S. Patent Application Publication No. 2013/0309677 and PCT Publication No. 2013/0158939, the term "factor" means a biological substance that contributes to the production of a pathological or physiologic condition. Preferably, the factor provides a change in a level of a marker of the pathological or physiologic condition in the at least one plated cell type or in the culture media upon application of the shear force, as compared to the level of the marker in the at least one plated cell type or in the culture media in the absence of application of the shear force.

The term "pathological condition" means an abnormal anatomical or physiological condition, which includes the objective or subjective manifestation of a disease.

The term "physiologic condition" means a normal medical state that is not pathologic, and can be a medical state characteristic of or conforming to the normal functioning or state of the body or a tissue or organ.

Physiologic Liver Model

The methods described in U.S. Patent Application Publication No. 2013/0309677 and PCT Publication No. 2013/0158939 can be used to create a physiologic in vitro model of the liver. In such methods, hepatocytes are plated on a surface within a cell culture container, and shear forces are applied indirectly to the plated hepatocytes. For example, the hepatocytes are suitably plated on a first surface of a porous membrane, where the porous membrane is suspended in a cell culture container such that the first surface is proximal and in spaced relation to a bottom surface of the cell culture container, thereby defining within the cell culture container a lower volume comprising the hepatocytes and an upper volume comprising a second surface of the porous membrane. The shear force is applied to the second surface of the porous membrane in the upper volume of the container. Thus, the configuration of cells in the device is based on in vivo microarchitecture of hepatic lobules.

In hepatic lobules in vivo, cords of hepatocytes are separated from sinusoidal blood flow by a filtering layer of sinusoidal endothelial cells and a layer of extracellular matrix. The layer of extracellular matrix provides for anchorage of the hepatocytes, is involved in signaling, and provides a reservoir of cytokines and growth factors. The hepatocytes have a polarized morphology and biliary canaliculi are present in the hepatocyte layer. Sinusoidal blood flow and interstitial blood flow provide for oxygen and nutrient transport.

FIG. 11 depicts an exemplary configuration used in the in vitro liver model and is described above. The porous membrane acts analogously to the filtering layer of sinusoidal endothelial cells which is present in the liver. The hepatocytes are shielded from direct effects of flow, as they would be in vivo. Inlets and outlets in the upper and lower volumes within the cell culture container allow for the continuous perfusion of culture media and for perfusion of drugs or compounds into and out of the cell culture media. Application of the shear force creates controlled hemodynamics that regulate interstitial flow and solute transfer through the porous membrane. In the in vitro models described in U.S. Patent Application Publication No. 2013/0309677 and PCT Publication No. 2013/0158939, the hepatocytes maintain their polarized morphology and bile canaliculi.

At least one layer of one or more extracellular matrix components (e.g., a collagen gel) can suitably be deposited on a first surface of the porous membrane. The hepatocytes are then plated on the extracellular matrix component(s). One or more additional layers of the extracellular matrix component(s) can then be deposited on top of the hepatocytes, such that the hepatocytes are substantially surrounded by the extracellular matrix component(s). The extracellular matrix component suitably comprises heparan sulfate, chondroitin sulfate, keratan sulfate, hyaluronic acid, a collagen, an elastin, a fibronectin, a laminin, a vitronectin, or combinations thereof. For example, the extracellular matrix component can comprise collagen.

One or more additional cell types can be plated on a surface within the cell culture container or suspended in the culture media. For example, nonparenchymal hepatic cells are suitably plated on the second surface of the porous membrane, and the shear force is applied to the plated non-parenchymal cells. The nonparenchymal cells may include hepatic stellate cells, sinusoidal endothelial cells, Kupffer cells, or combinations thereof. The hepatocytes and nonparenchymal hepatic cells are suitably primary cells isolated from the liver of an animal, for example from the liver of a human. Alternatively, the hepatocytes and/or the nonparenchymal hepatic cells are immortalized cells.

Media is suitably continuously perfused on both sides of the porous membrane, while shear forces, derived from a range of physiological blood flow values, are continuously applied to the second surface of the porous membrane or to the plated nonparenchymal hepatic cells. The shear forces applied to the second surface of the porous membrane mimic the flow through hepatic sinusoids which occurs in vivo. The shear rate is suitably about 0.1 dynes/cm$^2$ to about 3.0 dynes/cm$^2$, about 0.2 dynes/cm$^2$ to about 2.5 dynes/cm$^2$, about 0.3 dynes/cm$^2$ to about 1.0 dynes/cm$^2$ or about 0.4 dynes/cm$^2$ to about 0.8 dynes/cm$^2$. For example, the shear rate can be about 0.6 dynes/cm$^2$. Alternatively, the shear rate can be about 2.0 dynes/cm$^2$.

In the physiologic in vitro liver model, one or more factors are present in the culture media. These one or more factors can be added to the media at concentrations which are capable of maintaining the mimicking of the physiologic liver condition in vitro for a period of time under the shear force, where the same concentrations of these factors are incapable of maintaining the mimicking of the physiologic liver condition in vitro for the period of time in the absence of the shear force. For example, the factors may comprise insulin, glucose, or a combination of insulin and glucose. The glucose and insulin are suitably present in reduced concentrations as compared to the concentrations which are typically used in static cultures (about 17.5 mM glucose and about 2 μM insulin). For example, the glucose may be present in the culture media at a concentration of about 5 mM to about 10 mM, or at a concentration of about 5.5 to about 7 mM, e.g., at a concentration of about 5.5 mM. The insulin may be present in the culture media at a concentration of about 0.05 nM to about 5 nM, for example about 0.1 nM to about 3 nM, or about 0.5 to about 2.5 nM, e.g., at a concentration of about 2 nM. The one or more factors are suitably added to the culture media before or concurrently with application of the shear force.

The concentrations of the one or more factors are suitably capable of maintaining the mimicking of the physiologic liver condition in vitro for at least about 7 days, at least about 14, days, at least about 21 days, at least about 30 days, or longer.

Mimicking of the physiologic liver condition can be assessed by a number of methods. In general, a change in a level of a marker of the physiologic liver condition in the hepatocytes or nonparenchymal hepatic cells or in the culture media upon application of the shear force, as compared to the level of the marker in the hepatocytes or nonparenchymal hepatic cells or in the culture media in the absence of application of the shear force confirms mimicking of the physiologic liver condition. For example, mimicking of the physiologic liver condition can be assessed by examining the hepatocytes or nonparenchymal hepatic cells for the expression of genes or proteins involved in maintaining the liver in a physiologic state (e.g., in hepatocytes, metabolic and insulin/glucose/lipid pathway genes); examining the hepatocytes for lipid accumulation; examining the hepatocytes or nonparenchymal hepatic cells for changes in differentiated function (e.g., in hepatocytes, measuring urea and albumin secretion); examining the hepatocytes or nonparenchymal hepatic cells for changes in metabolic activity (e.g., in hepatocytes, using cytochrome p450 assays) or transporter activity; or by examining the hepatocytes or nonparenchymal hepatic cells for morphological changes. The physiologic condition of the liver can also be assessed by comparing the response of the hepatocytes or nonparenchymal hepatic cells to xenobiotics, nutrients, growth factors or cytokines to the in vivo liver response to the same xenobiotics, nutrients, growth factors or cytokines.

As described further in Example 12 below, unlike hepatocytes cultured under static conditions, hepatocytes cultured in the physiologic in vitro liver model described in U.S. Patent Application Publication No. 2013/0309677 and PCT Publication No. 2013/0158939 maintain their responsiveness to glucagon, insulin, and glucose substrates. Thus, responsiveness to glucagon, insulin, or one or more glucose substrates (e.g., using a gluconeogenesis assay) can also be used to assess mimicking of the physiologic liver condition. Suitable glucose substrates include glycerol, lactate, pyruvate, or combinations thereof (e.g., a combination of lactate and pyruvate). Moreover, because the hepatocytes maintain responsiveness to glucagon, the physiologic in vitro liver model can be used for in vitro testing of drugs that interact with the glucagon receptor (e.g., glucagon receptor antagonists).

In addition, hepatocytes cultured in the physiologic in vitro liver model described in U.S. Patent Application Publication No. 2013/0309677 and PCT Publication No. 2013/0158939 display induction and toxicity responses to drugs at concentrations much closer to in vivo and clinical $C_{max}$ levels than static culture systems. Thus, this model can be used for in vitro testing of drugs and compounds at concentrations within the concentration range of the drug or compound that achieves an effect in vivo.

Fatty Liver

The methods described in U.S. Patent Application Publication No. 2013/0309677 and PCT Publication No. 2013/0158939 can also be used to create an in vitro model of fatty liver disease. Lipid regulation within hepatocytes is a complex and dynamic process. Triglyceride buildup can occur as a consequence of increased fatty acid uptake from a high fat diet, increased peripheral lipolysis, or from increased de novo lipogenesis. Insulin and glucose are key regulators of de novo lipogenesis and contribute to increased triglyceride content within hepatocytes by stimulating triglyceride synthesis as well as inhibiting fatty acid metabolism by beta oxidation.

Non-alcoholic fatty liver disease (NAFLD) is correlated with obesity, type II diabetes, and metabolic syndrome in the presence of insulin resistance. NAFLD is characterized by hepatic steatosis (excessive lipid accumulation in the liver) that if left untreated progresses to inflammatory changes (steatohepatitis) and cirrhosis. Many animal models induce steatosis through a hyperglycemic-hyperinsulinemic environment (e.g., through use of a low fat/high carbohydrate diet to stimulate lipogenesis). However, current in vitro hepatocyte models lack an adequate insulin-glucose response to induce the same, probably on account of the superphysiological levels of insulin/glucose required to maintain hepatocytes in culture under static conditions. Such in vitro models fail to induce fatty changes in hepatocytes through insulin and glucose, perhaps due to impaired insulin responsiveness of hepatocytes under static culture conditions and rapid dedifferentiation of the hepatocytes in vitro.

By contrast, as described above with respect to the physiological liver model, hepatocytes cultured in the presence of controlled liver-derived hemodynamics and transport retain differentiated function, morphology, and response at physiological glucose and insulin levels. In this system, introducing high concentrations of insulin and glucose (a "disease milieu") induces fatty changes in the hepatocytes. Thus, controlled hemodynamics and transport produces a more physiological response to insulin and glucose in the hepatocytes, thereby inducing the fatty changes associated with steatosis in a hyperinsulemic, hyperglycemic environment as is typically seen initially under insulin resistant conditions of diabetes. In addition, hepatocytes cultured in the presence of controlled hemodynamics and transport display induction and toxicity responses to drugs at concentrations much closer to in vivo and clinical $C_{max}$ levels than static culture systems. This system therefore provides an in vitro model of fatty liver disease.

In this model, the hepatocytes are generally plated in the same manner as described above for the physiological liver model. Hepatocytes are plated on a surface within a cell culture container, and shear forces are applied indirectly to the plated hepatocytes. For example, the hepatocytes are suitably plated on a first surface of a porous membrane, where the porous membrane is suspended in a cell culture container such that the first surface is proximal and in spaced relation to a bottom surface of the cell culture container, thereby defining within the cell culture container a lower volume comprising the hepatocytes and an upper volume comprising a second surface of the porous membrane. The shear force is applied to the second surface of the porous membrane in the upper volume of the container.

At least one layer of one or more extracellular matrix components can suitably be deposited on the first surface of the porous membrane. The hepatocytes are then plated on the extracellular matrix component(s). One or more additional layers of the extracellular matrix component(s) can then be deposited on top of the hepatocytes, such that the hepatocytes are substantially surrounded by the extracellular matrix component(s). The extracellular matrix component suitably comprises heparan sulfate, chondroitin sulfate, keratan sulfate, hyaluronic acid, a collagen, an elastin, a fibronectin, a laminin, a vitronectin, or combinations thereof. For example, the extracellular matrix component can comprise collagen.

One or more additional cell types can be plated on a surface within the cell culture container or suspended in the culture media. For example, nonparenchymal hepatic cells are suitably plated on the second surface of the porous membrane, and the shear force is applied to the plated non-parenchymal cells. The nonparenchymal cells may include hepatic stellate cells, sinusoidal endothelial cells, Kupffer cells, or combinations thereof. The hepatocytes and nonparenchymal hepatic cells are suitably primary cells isolated from the liver of an animal, for example from the liver of a human. Alternatively, the hepatocytes and/or the nonparenchymal hepatic cells are immortalized cells.

Media is suitably continuously perfused on both sides of the porous membrane, while shear forces, derived from a range of physiological blood flow values, are continuously applied to the second surface of the porous membrane or to the plated nonparenchymal hepatic cells. The shear forces applied to the second surface of the porous membrane mimic the flow through hepatic sinusoids which occurs in vivo. The shear rate is suitably about 0.1 dynes/cm$^2$ to about 3.0 dynes/cm$^2$, about 0.2 dynes/cm$^2$ to about 2.5 dynes/cm$^2$, about 0.3 dynes/cm$^2$ to about 1.0 dynes/cm$^2$ or about 0.4 dynes/cm$^2$ to about 0.8 dynes/cm$^2$. For example, the shear rate can be about 0.6 dynes/cm$^2$. Alternatively, the shear rate can be about 2.0 dynes/cm$^2$.

In the in vitro fatty liver model, one or more factors are present in the culture media. These one or more factors are added to the media at concentrations which are capable of maintaining the mimicking of fatty liver disease in vitro for a period of time under the shear force, the same concentration of factor being incapable of maintaining the mimicking of fatty liver disease for the period of time in the absence of the shear force. The factors may comprise, for example, insulin, glucose, or a combination thereof. The glucose is suitably present in the culture media at a concentration of about 10 mM to about 25 mM, about 12 mM to about 20 mM, or about 14 mM to about 18 mM, e.g., about 17.5 mM. The insulin is suitably present in the culture medium at a concentration of about 1 µM to about 3 µM, about 1.5 µM to about 2.5 µM, or about 1.8 µM to about 2.2 µM, e.g., about 2 µM. The one or more factors are suitably added to the culture media before or concurrently with application of the shear force.

The concentrations of the one or more factors are suitably capable of maintaining the mimicking of fatty liver disease condition in vitro for at least about 7 days, at least about 14, days, at least about 21 days, at least about 30 days, or longer.

Mimicking of fatty liver disease can be assessed by a number of methods. In general, a change in a level of a marker of fatty liver disease in the hepatocytes or nonparenchymal hepatic cells or in the culture media upon application of the shear force, as compared to the level of the marker in the hepatocytes or nonparenchymal hepatic cells or in the culture media in the absence of application of the shear force confirms mimicking of fatty liver disease. For example, mimicking of fatty liver disease can be assessed by examining the hepatocytes or nonparenchymal hepatic cells for the expression of genes or proteins involved in the fatty liver disease state (e.g., in hepatocytes, metabolic and insulin/glucose/lipid pathway genes); examining the hepatocytes for lipid accumulation (e.g., in hepatocytes, measuring triglyceride levels or visualizing lipid droplets); examining the hepatocytes or nonparenchymal hepatic cells for changes in differentiated function (e.g., in hepatocytes, measuring urea and albumin secretion); examining the hepatocytes or nonparenchymal hepatic cells for changes in metabolic activity (e.g., in hepatocytes, using cytochrome p450 assays) or transporter activity; or by examining the hepatocytes or nonparenchymal hepatic cells for morphological changes. Sequelae to fatty liver changes can also be assessed by measuring the changes in oxidative state of the hepatocytes and the changes in surrounding extracellular matrix composition and amount.

The methods described in U.S. Patent Application Publication No. 2013/0309677 and PCT Publication No. 2013/0158939 are further illustrated by Examples 12-14 below.

Definitions

For purposes of the inventions described herein, the term "hemodynamic" means blood flow that mimics the blood flow in vivo in a tumor or tissue of interest. For example, when blood flow in the microvasculature of a tumor, the acceleration/deceleration rates, flow reversal, forward basal flow, etc. are some parameters characterizing arterial hemodynamic flow. In some tissues, such as the liver, a constant blood flow may be used to characterize in vivo hemodynamics.

The term "subject" means an animal (e.g., a genetically modified animal or a human). The animal can include a mouse, rat, rabbit, cat, dog, primate, guinea pig, hamster, monkey, cow, pig, horse, goat, sheep, bird or fish, or any animal typically used in medical research.

Having described the invention in detail, it will be apparent that modifications and variations are possible without departing from the scope of the invention defined in the appended claims.

EXAMPLES

The following non-limiting examples are provided to further illustrate the present invention.

Example 1

Plating and Culturing Methods

Porous membranes used for plating were porous membranes of TRANSWELL cell culture inserts (polycarbonate, 10 µm or 18 µm thickness and 0.4 µm pore diameter, 75 mm insert diameter, custom ordered from Corning). To prepare the inserts for cell plating, both surfaces of the porous membrane were coated with gelatin (0.14% solution in sterile water). The porous membranes separate the cell types in the cultures but allow for cell-cell interactions to occur through the pores of the membrane.

The following cell types were used: human fibroblasts (Hs888Lu lung fibroblasts, American Type Culture Collection (ATCC) CCL-211), dtumor cells (A549 human non-small cell carcinoma (NSCLC) tumor cells, ATCC CL-185), and human dermal microvascular endothelial cells (HM-VECad, Gibco, catalogue # C-011-5C). Each of these cell lines was maintained, passaged and plated in DMEM base (without phenol red) containing 10% Fetal Bovine Serum (FBS), 100 units/mL penicillin (P), 100 µg/mL streptomycin (S), 2 mM L-glutamine (L-glut), 1 mM sodium pyruvate (NaP), 1× non-essential amino acids (NEAA, HyClone SH30238.011), and 4.5 g/L D-glucose.

The human fibroblasts were plated on the lower surface of the porous membrane of a cell culture insert at a plating density of $3.0 \times 10^3$ cells/cm$^2$ and allowed to adhere for at least two hours in a humidified chamber at 37° C. with 5% $CO_2$.

To generate tri-cultures, a secondary porous membrane was cut from a 75 mm insert (TRANSWELL, polycarbonate, 10 µm or 18 µm thickness and 0.4 µm pore diameter, custom ordered from Corning) and prewet with a collagen solution (2.0 mg/mL rat tail collagen in 1× PBS, pH 7.4) by dipping the membrane into a 100 mm dish containing 1.0 mL of collagen solution, wetting both sides of the membrane and allowing any excess collagen solution to drip off the membrane. The secondary membrane was placed on top of the fibroblasts plated on the lower surface of the porous membrane of the cell culture insert and allowed to adhere and the collagen to solidify for one hour in a humidified chamber at 37° C. with 5% $CO_2$. The secondary membrane separating the stromal fibroblasts and the tumor cells was needed to perform the RNAseq transcriptomics described hereinbelow, but can be omitted as shown, for example, in the configurations depicted in FIGS. 5-8.

Three plating conditions were used: (1) a plating configuration that was substantially free of exogenously added ECM (referred to in the Examples and Figures herein as "no collagen," "NC," "no ECM," or "no matrix"); (2) a plating configuration wherein the tumor cells were plated on a layer of exogenously added collagen (referred to in the Examples and Figures herein as "collagen layer" or "CL"); and (3) a plating configuration wherein the tumor cells were plated on a layer of exogenously added collagen, and wherein an additional layer of collagen was then added on top of the plated tumor cells such that the collagen substantially surrounded the tumor cells (referred to in the Examples and Figures herein as a "collagen sandwich" or CS).

In experiments where the plating configuration was substantially free of exogenous ECM, tumor cells were plated directly onto the opposing surface secondary membrane (i.e., the surface not in contact with the fibroblasts). In this configuration, the only exogenous ECM added to the cell culture container was the collagen into which the secondary membrane was immersed.

In experiments where a collagen layer or collagen sandwich configuration was desired, 900 µL of collagen solution (2.0 mg/mL rat tail collagen in 1× PBS, pH 7.4) was applied evenly to the prewet opposing surface of the secondary membrane (i.e., the surface not in contact with the fibroblasts) and allowed to adhere and collagen to solidify for one hour in a humidified chamber at 37° C. with 5% $CO_2$. This generated an approximately 200 micron thick collagen layer. This concentration of collagen produces a gel with a rigidity that mimics the stiffness of the tumor microenvironment.

Human tumor cells were then plated on the collagen layer on the surface of the secondary membrane at a plating density $3.0 \times 10^3$ cells/cm$^2$ and allowed to adhere for at least two hours in a humidified chamber at 37° C. with 5% $CO_2$. After cells had adhered, the cell culture inserts were inverted and placed into a 100 mm culture dish containing 15 mL DMEM base (without phenol red) +10% FBS, P/S, L-glut, NaP, NEAA and D-glucose (9 mL of the culture medium was in the lower volume, and 6 mL of the culture medium was in the lower volume).

If a collagen sandwich was desired (i.e., a plating configuration wherein collagen substantially surrounds the cells plated on the lower surface of the porous membrane of the cell culture insert), an additional 900 µL of collagen solution (2.0 mg/mL rat tail collagen in 1× PBS, pH 7.4) was evenly applied on top of tumor cells and allowed to solidify for one hour in a humidified chamber at 37° C. with 5% $CO_2$. This generated an approximately 200 micron thick layer of collagen on top of the cells plated on the lower surface of the porous membrane of the cell culture insert). After this top layer of collagen had solidified, the cell culture inserts were inverted and placed into a 100 mm culture dish containing 15 mL DMEM base (without phenol red)+10% FBS, P/S, L-glut, NaP, NEAA and D-glucose (9 mL of the culture medium was in the lower volume, and 6 mL of the culture medium was in the lower volume).

In all configurations, following plating of the fibroblasts and tumor cells, cells were allowed to grow for 48 hours in a humidified chamber at 37° C. with 5% $CO_2$. Human endothelial cells were then plated on the upper surface of the porous membrane of the cell culture insert at a plating density of $5.0 \times 10^4$ cells/cm$^2$ and allowed to adhere for 24 hours in a humidified chamber at 37° C. with 5% $CO_2$ under static conditions The resulting tri-culture plating configuration is illustrated in FIG. 9.

After endothelial cells had adhered, the tri-cultures were prepared for experimental hemodynamics and transport. Tri-cultures of tumor cells, fibroblasts, and endothelial cells were either maintained under static conditions (for static controls) or placed into a cone-and-plate device, the cone was lowered into the upper volume, and the cone was rotated to apply a shear force upon the endothelial cells. In cultures subjected to shear, transport was controlled in the system by perfusing cell culture medium into and out of both the upper and lower volumes of the cell culture dish via inlets 17 and outlets 19 in the upper and lower volumes, as depicted in FIG. 9. In experiments wherein drugs were used, drug solutions were added to the upper volume, which represents the vascular compartment.

The correlation of color Doppler ultrasound with histologic specimens from both benign and malignant tumors suggests that constant flow is more representative of the true neovascularization of malignant lung cancers (Hsu et al., 2007; Hsu et al. 1996; Görg et al. 2003). A monophasic low-impedance waveform more characteristic of peripheral bronchial artery blood flow was selected for application to the tri-cultures. Blood flow in this region is slower and lacks a significant systolic/diastolic variation, as illustrated in FIG. 4A-C. For contrast, the shear stress pattern from a pulmonary lesion near the pulmonary artery is illustrated in FIG. 4A-C.

Example 2

Morphology of Cells Cultured in In Vitro Tumor Microenvironment Tri-Cultures

Tri-cultures prepared as described above and as illustrated in FIG. 9 were fixed after seven days of hemodynamic shear stress in 4% Paraformaldehyde (Electron Microscopy Sciences) for 20 minutes at room temperature (RT), washed in phosphate Buffer saline (PBS) with Calcium and Magnesium (Fisher Scientific) and stored at 4° C. until processed. Samples were permeabilized with 0.1% Triton for 20 min, and stained with ALEXA FLUOR 488 (a fluorescent dye)-labeled Phalloidin (1:100; Life Technologies) to stain for F-actin and TO-PRO-3 nuclear stain (1:2000; Life Technologies) for one hour at room temperature. After three washes with PBS, samples were mounted between coverslips using FLUOROMOUNT G (an aqueous mounting medium, Southern Biotech). Images were taken with a Nikon ECLIPSE Ti Confocal Microscope using 20× oil immersion objectives.

Confocal microscopy images are provided in FIG. 13. FIGS. 13A, 13B, and 13C the morphology of the human dermal microvascular endothelial cells (FIG. 13A), the human fibroblasts (FIG. 13B) and the human A549 NSCLC tumor cells (FIG. 13C) plated in the collagen sandwich plating condition. FIGS. 13D, 13D, and 13F show the morphology of the A549 tumor cells under the three different plating conditions: no ECM (FIG. 13D), collagen layer (FIG. 13E), and collagen sandwich (FIG. 13F). The phenotype of the A549 cells in the collagen sandwich was spheroidal whereas in the no ECM condition, the A549 cells pile up on one another but do not form spheres.

Example 3

Tumor Cell Growth in In Vitro Tumor Microenvironment Tri-Cultures

Figure 14A:
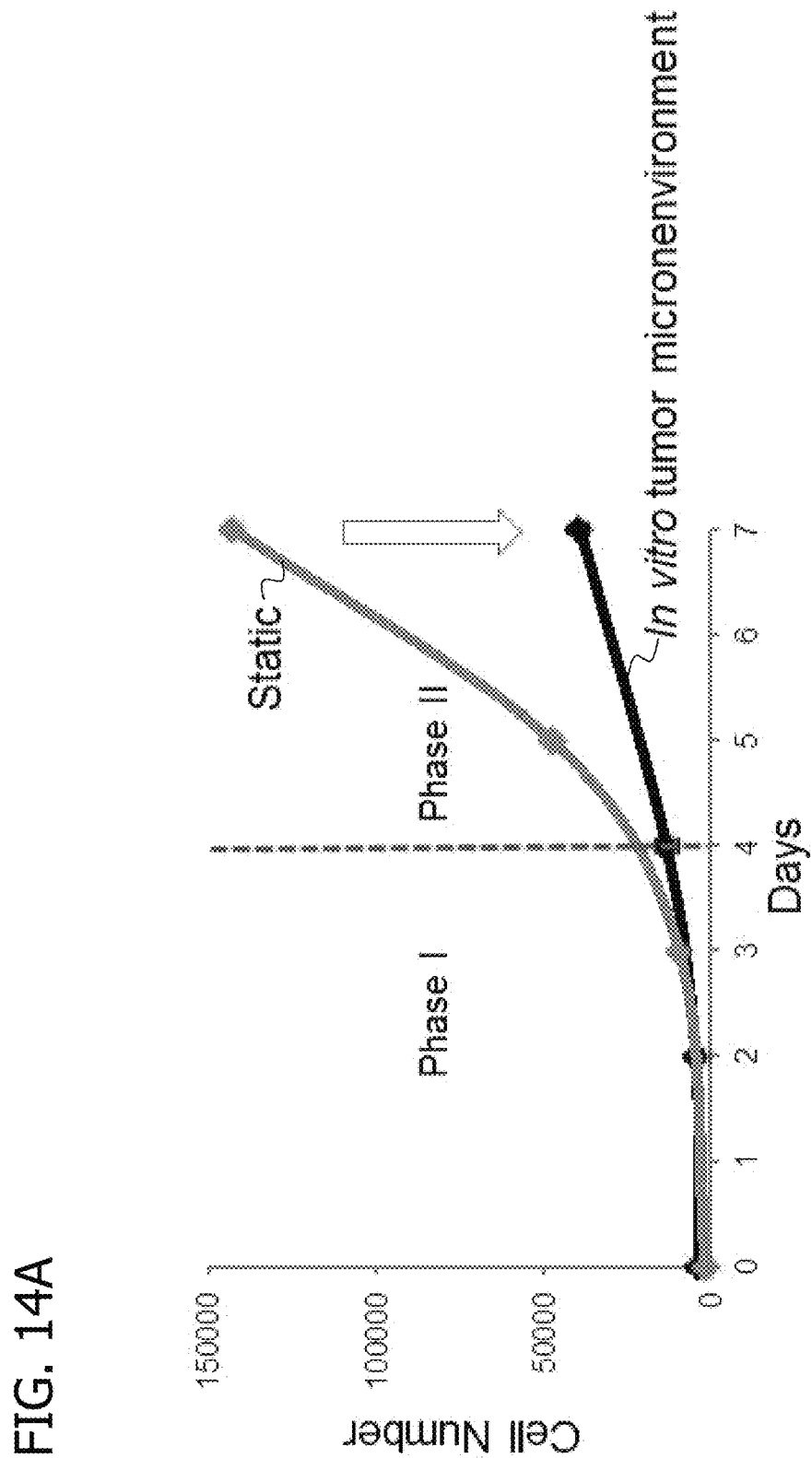
FIG. 14A provides results from an assay measuring cell growth of A549 tumor cells under two-dimensional static conditions or using the method depicted in FIG. 9.
Figure 14B:
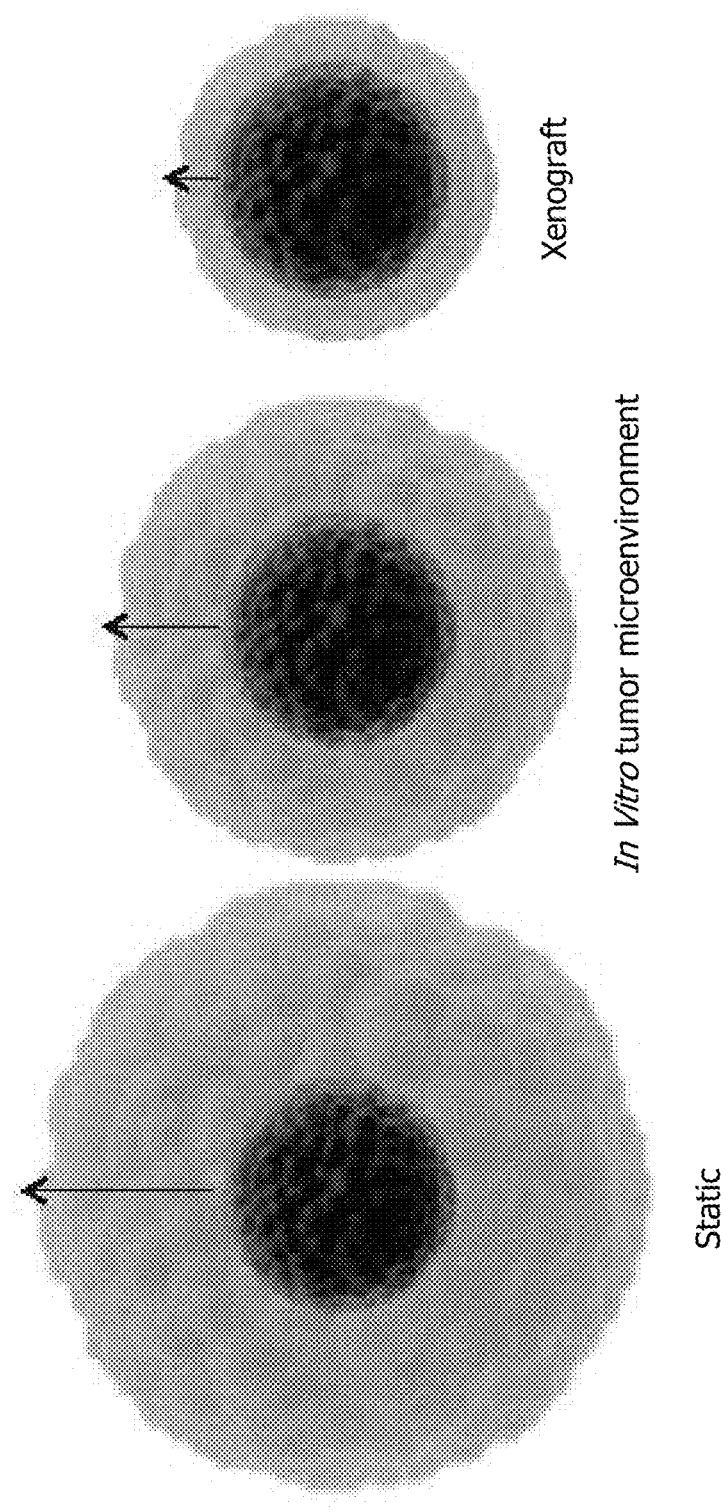
FIG. 14B provides a schematic illustration of the qualitative differences in the growth rate of tumor cells cultured in static two-dimensional cultures ("In Vitro"), in the in vitro tumor microenvironments described herein ("In vitro tumor microenvironment"), and in xenografts.
Figure 14C:
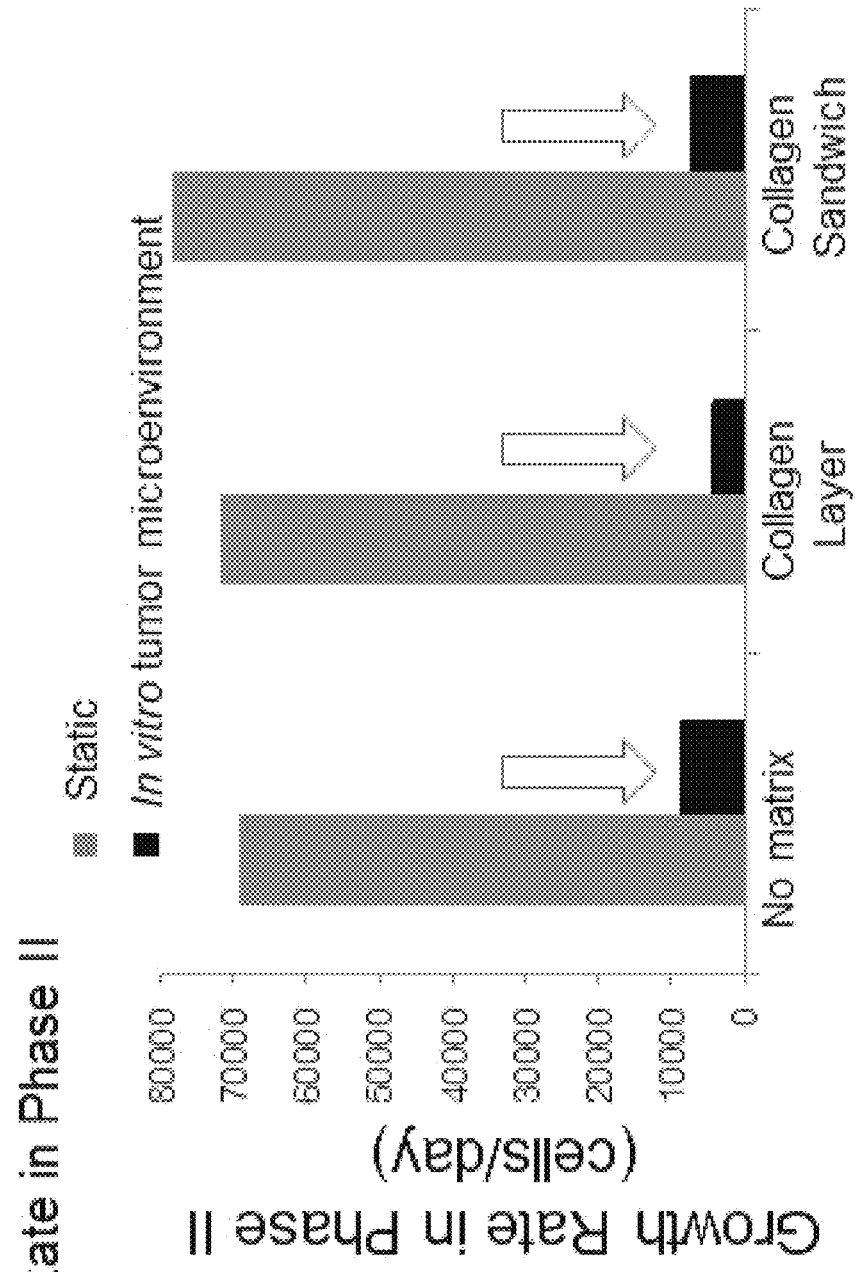
FIG. 14C provides results from an assay measuring the growth of A549 tumor cells cultured using the method depicted in FIG. 9 under hemodynamic shear stress in the substantial absence of exogenously added extracellular matrix ("no matrix"), where the A549 tumor cells were plated on a single layer of collagen ("collagen layer"), or where the A549 tumor cells were plated on a layer of collagen and another layer of collagen was deposited on top of the plated A549 tumor cells such that the collagen substantially surrounded the tumor cells ("collagen sandwich").

The growth rate of the human lung carcinoma cell line A549 (ATCC, Manassas, Va.) was determined in multiple matrix conditions when exposed to tumor capillary hemodynamics. Cells were plated as shown in FIG. 9. Hs888Lu human lung fibroblasts were plated onto the porous membrane of the cell culture insert at an initial plating density of $3 \times 10^3$ cells/cm$^2$. A secondary membrane was applied as described above in Example 1 and A549 tumor cells were then seeded at an initial density of $3 \times 10^3$ cells/cm$^2$ in each of the three matrix conditions as described above in Example 1: (1) cells plated directly onto the secondary membrane (no matrix); (2) cells plated onto single layer of collagen (collagen layer); or (3) cells plated in a collagen sandwich. After 48 hours of incubation in a static environment, dermal microvascular endothelial cells were plated on the upper surface of the porous membrane of the cell culture insert at an initial plating density of $5 \times 10^4$ cells/cm$^2$. Cultures were cultured for up to seven days under static conditions or subjected to hemodynamic flow and transport. For static cultures, cell number was determined at the time of seeding (Day 0) and days 2, 4 and 7 using the CYQUANT Cell Proliferation Assay Kit according to the manufacturer's instructions (Molecular Probes, Eugene, Oreg.). For cultures subjected to hemodynamic flow and transport, cell number was determined on the day cultures were subjected to hemodynamic flow and transport (Day 0) and on days 2, 4, and 7 of hemodynamic flow and transport. Data are shown in FIGS. 14A and 14C and are presented as the mean number of cells from duplicate cultures for each of the three matrix conditions. For each condition, the growth rates were compared to the growth rate of A549 cells grown in plastic two-dimensional (2D) tissue culture dishes without matrix and in the absence of hemodynamic flow and transport.

As shown in FIG. 14A, hemodynamic flow attenuated the growth rate of A549 tumor cells grown in the tri-cultures in collagen sandwiches as compared to static 2D culture. There has been a long standing disconnect between the doubling time of cells grown in static 2D cultures and the doubling time of in vivo tumors (Cifone, 1982), be that in xenograft tumors derived from cell lines or the rate of tumor growth in patients. When the growth rate of A549 NSCLC cells grown in static 2D cultures and the tri-cultures subjected to hemodynamic conditions were compared, the tumor cell growth in the tri-cultures subjected to hemodynamic conditions was diminished relative to growth in the static 2D system (FIG. 14A). The growth rate of A549 cells in static 2D conditions was 8-fold higher in phase II than in the tri-cultures subjected to hemodynamic conditions. While the growth rate of the A549 cells in the tri-cultures subjected to hemodynamic conditions still exceeds the rate of A549 xenografts (Basu et al., 2011; Chou et al., 2008; Li et al. 2013), the growth rate in the tri-cultures subjected to hemodynamic conditions was closer to the physiologic rate than that of static 2D cultures. 14B. FIG. 14B shows the qualitative differences in the growth rate between A549 cells grown in static 2-dimensional cultures ("static"), the tri-cultures subjected to hemodynamic conditions ("In vitro tumor microenvironment"), and xenografts. The darkly shaded spheres in FIG. 14B represent the starting tumor size, and the lightly shaded areas and arrows represent tumor growth over time.

FIG. 14C illustrates that the decrease in growth occurred in all three matrix conditions examined. Thus, hemodynamic flow and transport, not extracellular matrix, appear to be the driving contributors effecting growth rate.

Example 4

Assessment of Cell Density and Monolayer Integrity of Endothelial Cells

Endothelial cell density and monolayer integrity of endothelial cells cultured according to the methods described above in Example 1 can be evaluated by fixing and immunostaining the endothelial cells on the porous membrane for the endothelial junction protein VE-cadherin and examining the monolayer by confocal microscopy.

Example 5

Morphological Assessment of Tumor Cells

To assess the morphology of tumor cells cultured using the methods described above in Example 1, morphologies of the tumor cells can be determined by immunostaining the tumor cells on the porous membrane for E-cadherin and for actin using fluorescently labeled phalloidin. To quantitate the extension of invasive structures (invadopodia) through the pores of the porous membrane, the cultures can be fixed and immunostained for E-cadherin (for the tumor cells) and VE-cadherin (for endothelial cells), and a cross-section of the porous membrane can be analyzed by confocal microscopy.

Example 6

Endothelial Cell Monolayer Permeability

In in vivo tumor-vasculature regions, an increase in vessel permeability occurs due to the secretion of numerous growth factors from the tumor cells (Mukaida et al., 2012; Bradford et al., 2013). To demonstrate that tumor cells alter endothelial cell barrier function in the tri-culture systems described above in Examples 1, permeability assays were performed to measure increases in endothelial monolayer permeability. In this assay, horseradish peroxidase (HRP) was added to the upper volume and accumulation of HRP in the presence and absence of tumor cells was measured over time.

After establishing tumor cell/fibroblast/endothelial cell cocultures as described in Example 1 and as illustrated in FIG. 9, a known mass of low molecular weight HRP was added to the upper volume and allowed to diffuse. Following a 15-60 minute incubation period, media samples were removed from the lower volume. Application of shear stress upon the endothelial cells was continued during this process. HRP that diffused through the endothelial cells, porous membranes, fibroblasts, and A549 tumor cells was detected by guaiacol oxidation. Endothelial cell monocultures (grown on porous membranes without the tumor cells) that were subjected to the shear stress were assayed in parallel as a control.

Figure 15:
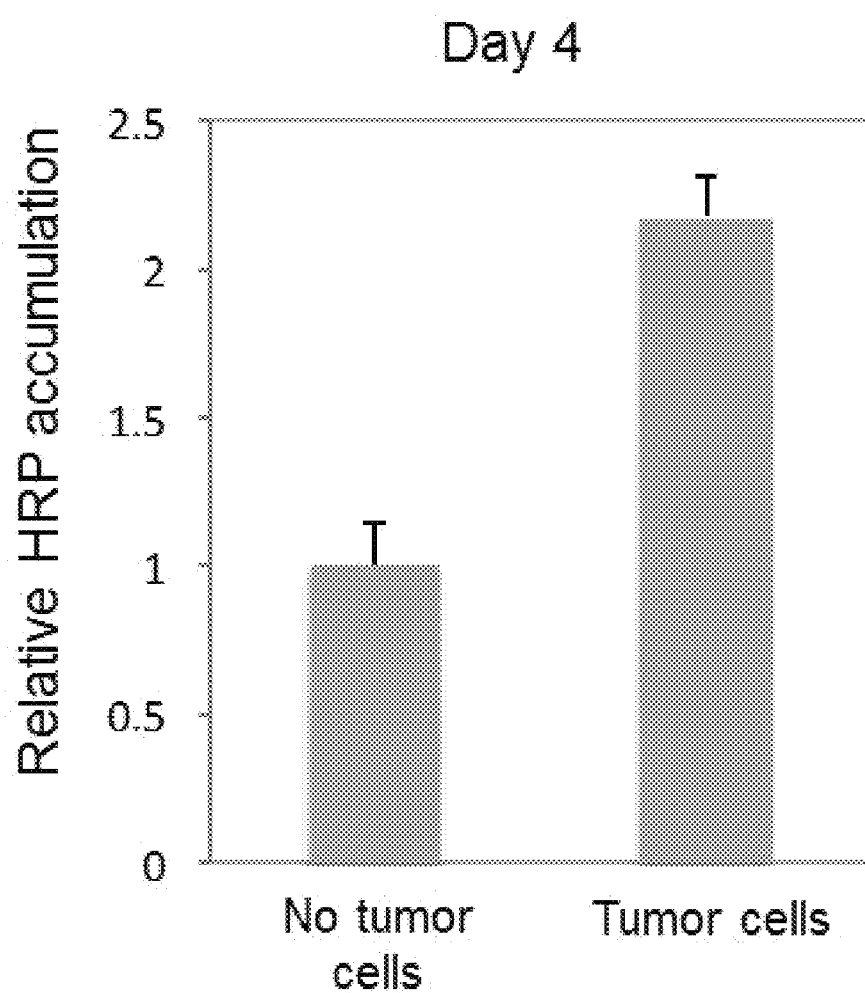
FIG. 15 provides results from a permeability assay assessing the permeability of endothelial cells cultured in the presence ("tumor cells") or absence ("no tumor cells") plated on the opposing side of a porous membrane and cultured under hemodynamic shear stress.

The results of this assay are provided in FIG. 15 and demonstrate that the NSCLC A549 cells increase endothelial cell permeability. Relative HRP accumulation in the absence and presence of NSCLC A549 cells is shown. In FIG. 15, "no tumor cells" indicates the endothelial cell monocultures, and "tumor cells" indicates the tumor cell/fibroblast/endothelial cell cocultures.

Example 7

Transcriptosomic Profile of Tumor Cells in In Vitro Tumor Microenvironment Tri-Cultures Next-generation RNA sequencing (RNA-seq) was used to compare the transcriptosome of A549 tumor cells grown under three different conditions: (1) in static two dimensional cultures; (2) in xenografts in propagated subcutaneously in athymic nude mice; and (3) in the tri-cultures generated as described above in Example 1 and subjected to hemodynamic conditions. RNA was isolated from tumors cells grown for 2, 4, and 7 days under hemodynamic conditions. This comparison indicated that transcriptosome of the tri-cultures subjected to hemodynamic conditions more closely resembled the in vivo xenografts than the in vitro static 2D cultures.

RNA-seq data were generated using a reverse strand library preparation from A549 NSCLC cells grown tri-cultures as described above in Example 1 and as illustrated i FIG. 9, under the three different matrix configurations. Approximately 20 million 50 bp paired-end reads were sequenced per sample. Raw sequence reads were aligned to the University of California Santa Cruz (UCSC) annotations of known isoforms in the hg19 assembly of the human genome using the Bowtie aligner (Langmead et al. 2009). Estimates of read counts per isoform were computed using the eXpress tool (Roberts and Pachter, 2012). Gene-wise counts were generated by summing the estimated counts across isoforms for each gene. Genes with low counts across the entire experiment were not considered in downstream analyses. Specifically, genes that were detected at a level of at least 2 counts per million in fewer than 5 samples were discarded. After filtering genes with low signal, library sizes were normalized using the Trimmed Mean of M-values (TMM) method (Robinson and Oshlack, 2010).

To distinguish human from mouse RNA in the xenograft samples, we used a strategy similar to that employed in Raskatov et al., 2012. Raw reads were aligned to the human hg19 and mouse mm10 transcriptomes simultaneously. The alignments were then quantified for each transcript (human and mouse) using eXpress. All eXpress estimates computed for mouse transcripts were discarded, and estimates for human transcripts were used in downstream analyses.

Gene-wise differential expression analysis was performed on the filtered and TMM-normalized abundance estimates using edgeR (Robinson et al., 2010). The NSCLC gene set is from the Kyoto Encyclopedia of Genes and Genomes (KEGG) database (Ogata et al., 1999). The gene set consists of: AKT3, CDK4, CDK6, RASSF1, E2F1, E2F2, E2F3, EGF, EGFR, ERBB2, AKT1, AKT2, EML4, GRB2, HRAS, ARAF, KRAS, NRAS, PDPK1, PIK3CA, PIK3CB, PIK3CD, PIK3R1, PIK3R2, PLCG1, PLCG2, PRKCA, PRKCG, MAPK1, MAPK3, MAP2K1, MAP2K2, RAF1, RARB, CCND1, RXRA, RXRB, SOS1, SOS2, BRAF, TGFA, RASSF5, PIK3R3, FOXO3, BAD, CASP9, RB1, STK4.

Figure 16A:
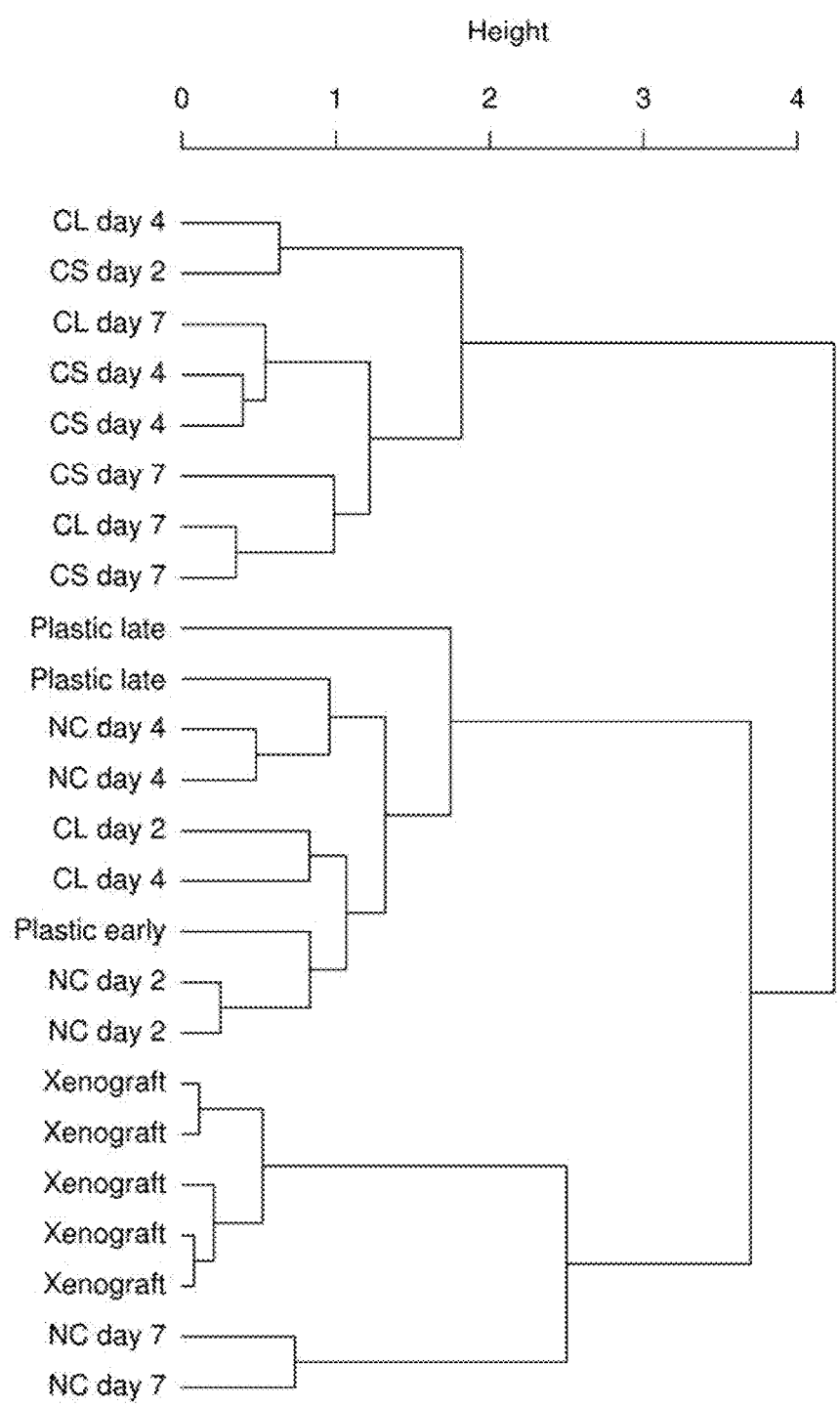
FIGS. 16A and 16B provide a dendogram (FIG. 16A) and a heatmap (FIG. 16B) showing the expression and clustering of 14,159 genes in A549 tumor cells grown under static two-dimensional conditions ("plastic"), in xenografts, or using the method shown in FIG. 9 under hemodynamic shear stress in the substantial absence of exogenously added extracellular matrix ("NC" or "no collagen"), where the A549 tumor cells were plated on a single layer of collagen ("CL" or "collagen layer") or where the A549 tumor cells were plated on a layer of collagen and another layer of collagen was deposited on top of the plated A549 tumor cells such that the collagen substantially surrounded the tumor cells ("CS" or "collagen sandwich").
Figure 16B:
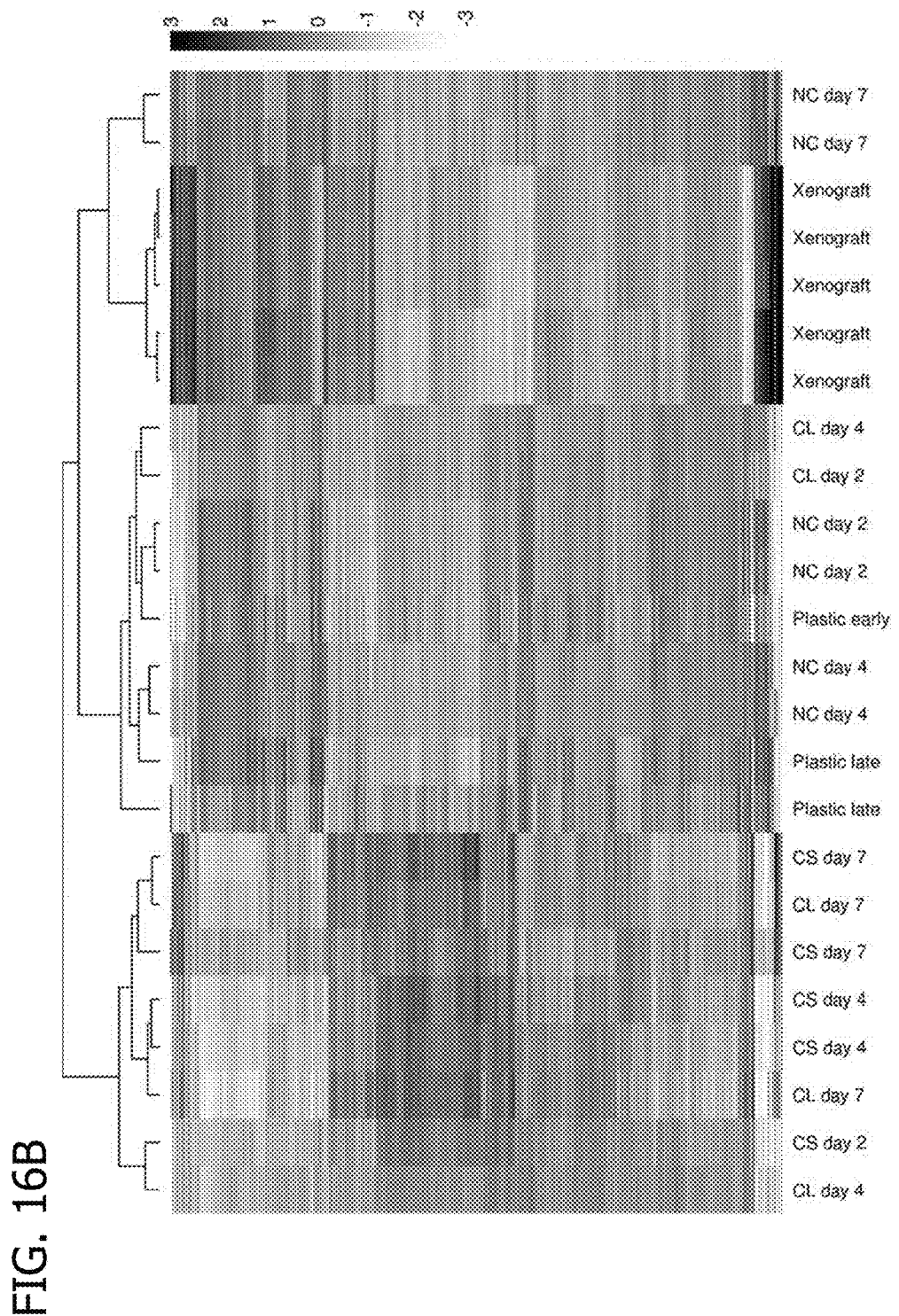

The results of RNA-seq transcriptosomal profiling are shown in FIGS. 16-18. FIG. 16 provides a dendogram (FIG. 16A) and a heatmap (FIG. 16B) showing the clustering of samples based on the gene-centered log2 expression values of all 14,159 genes that reach the signal threshold. A549 cells grown in the tri-cultures generated as described above and subjected to hemodynamic conditions clustered based on the matrix conditions. "CL"=collagen layer; "CS"=collagen sandwich; NC=no collagen. Xenograft samples clustered separately, with the exception of the no collagen condition on day 7, suggesting that increased time in the device in the absence of collagen more faithfully recapitulates the transcriptomic profile of xenograft tissue, relative to the other culture conditions. The hierarchical clustering was performed using an average linkage criteria, and Spearman rank correlation as the distance metric.

Figure 17A:
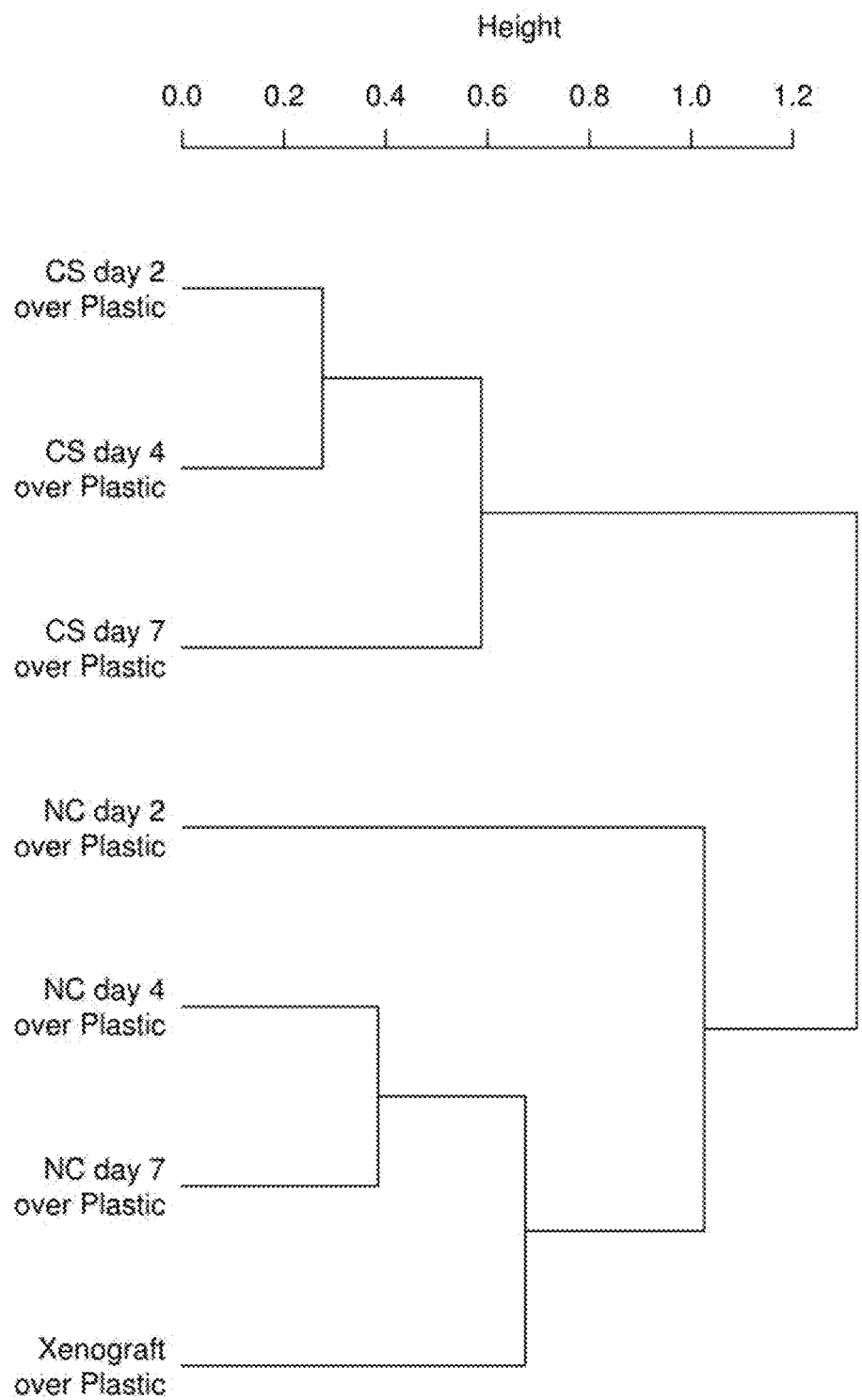
FIGS. 17A and 17B provide a dendogram (FIG. 17A) and a heatmap showing the expression and clustering of 7935 genes differentially expressed between xenografts and static two-dimensional cultures of A549 tumor cells in A549 tumor cells grown in xenografts or using the method depicted in FIG. 9 under hemodynamic shear stress in the substantial absence of exogenously added extracellular matrix (NC) or in a collagen sandwich (CS), as compared to static-two dimensional cultures ("plastic").
Figure 17B:
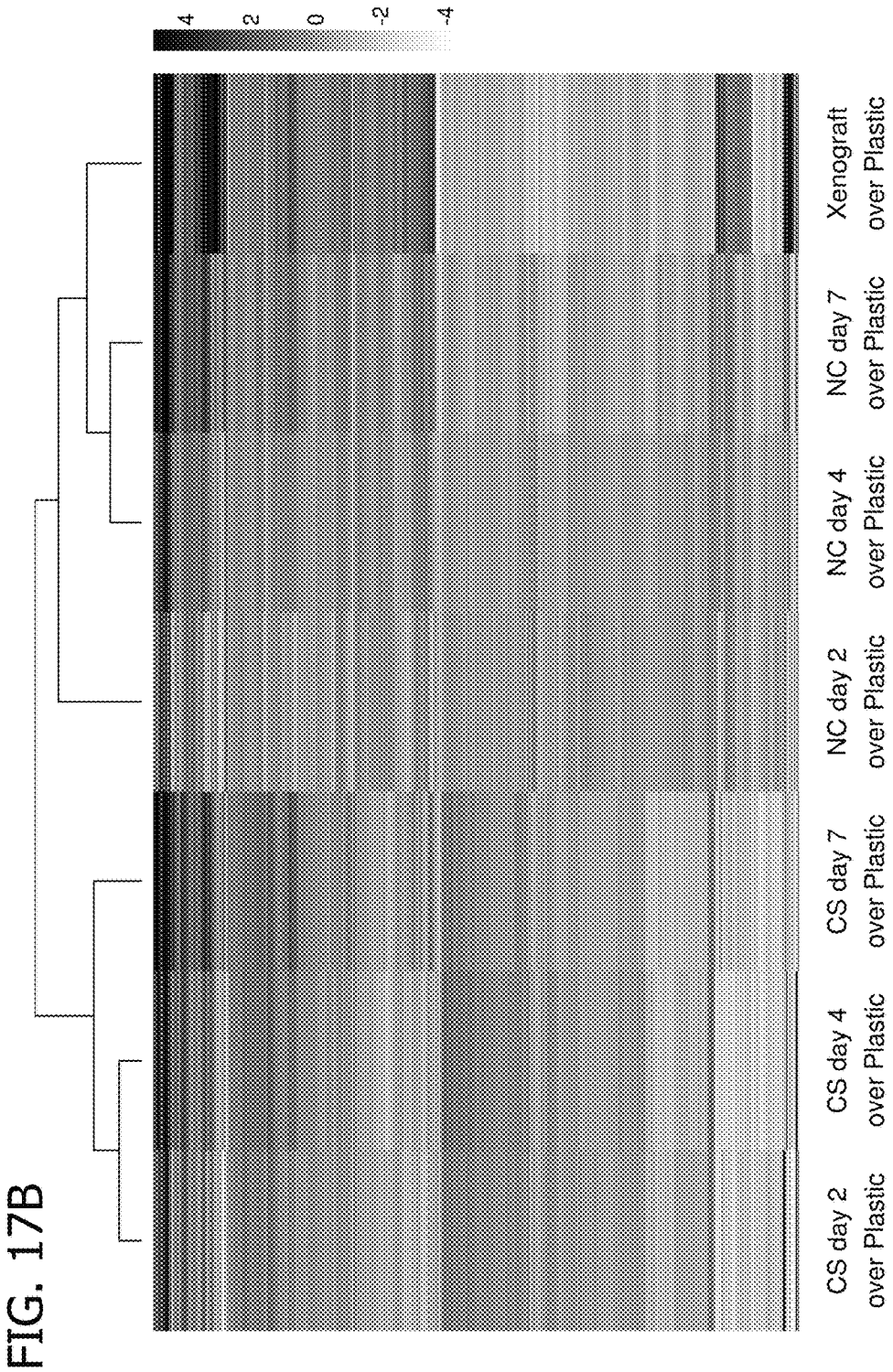

FIG. 17 provides a dendogram (FIG. 17A) and a heatmap (FIG. 17B) showing the clustering of samples based on the log2 fold changes of the 7935 genes differentially expressed between the xenograft and plastic conditions at a 5% false discovery rate (FDR). Xenograft samples cluster with the samples from tri-cultures subjected to hemodynamic conditions that do not contain exogenous collagen. This indicates that the transcriptomic differences between xenograft and static two-dimensional cultures are better reproduced in the absence of exogenous collagen. The hierarchical clustering was performed using an average linkage criteria, and Spearman rank correlation as the distance metric. "CS" =collagen sandwich; "NC"=no collagen; "plastic"=static 2D cultures.

Figure 18A:
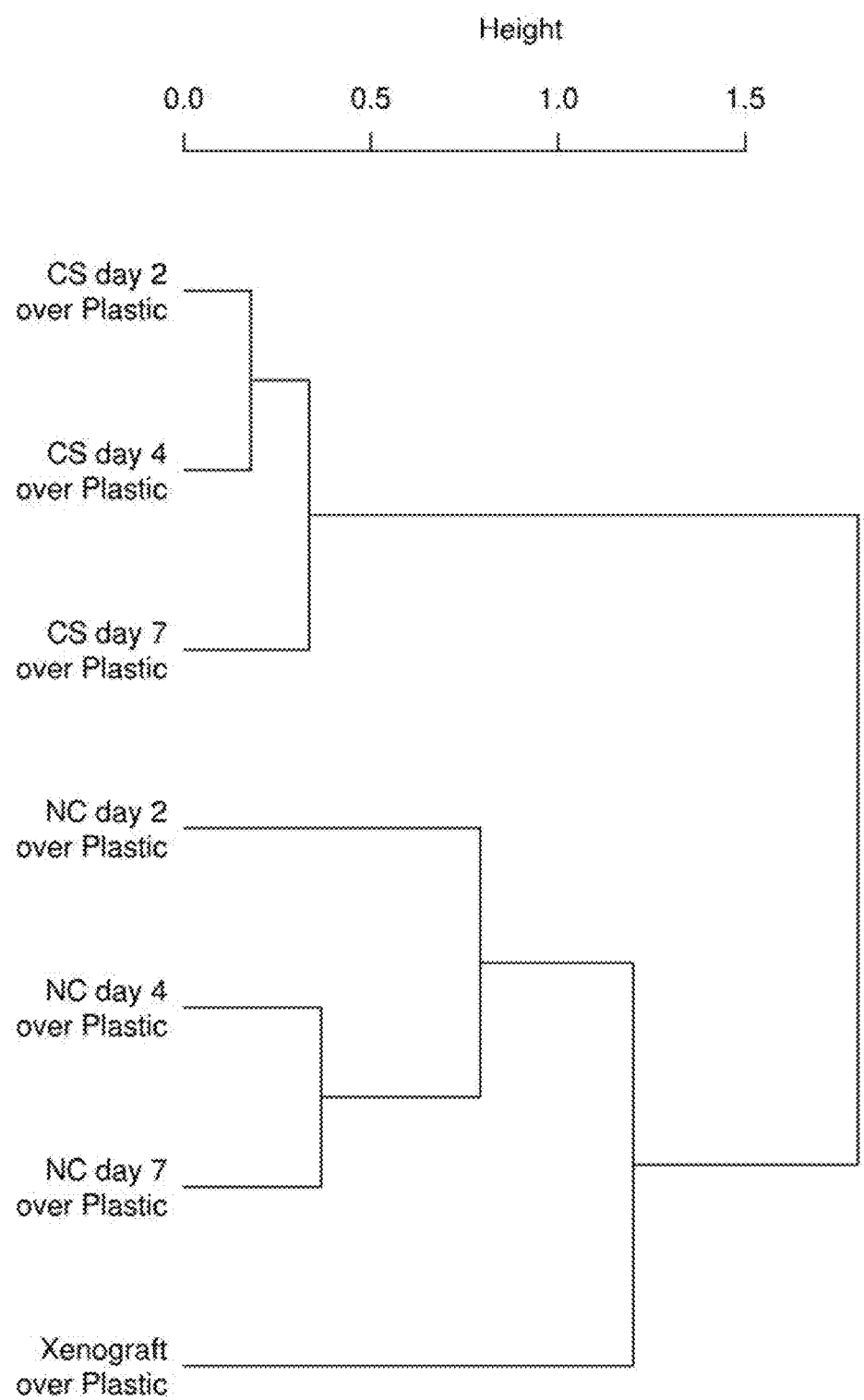
FIGS. 18A and 18B provide a dendogram (FIG. 18A) and a heatmap (FIG. 18B) showing the clustering of 48 genes annotated with "non-small cell lung cancer" in the Kyoto Encyclopedia of Genes and Genomes (KEGG) database in A549 tumor cells grown in xenografts or using the method depicted in FIG. 9 under hemodynamic shear stress in the substantial absence of exogenously added extracellular matrix (NC) or in a collagen sandwich (CS), as compared to static-two dimensional cultures ("plastic").
Figure 18B:
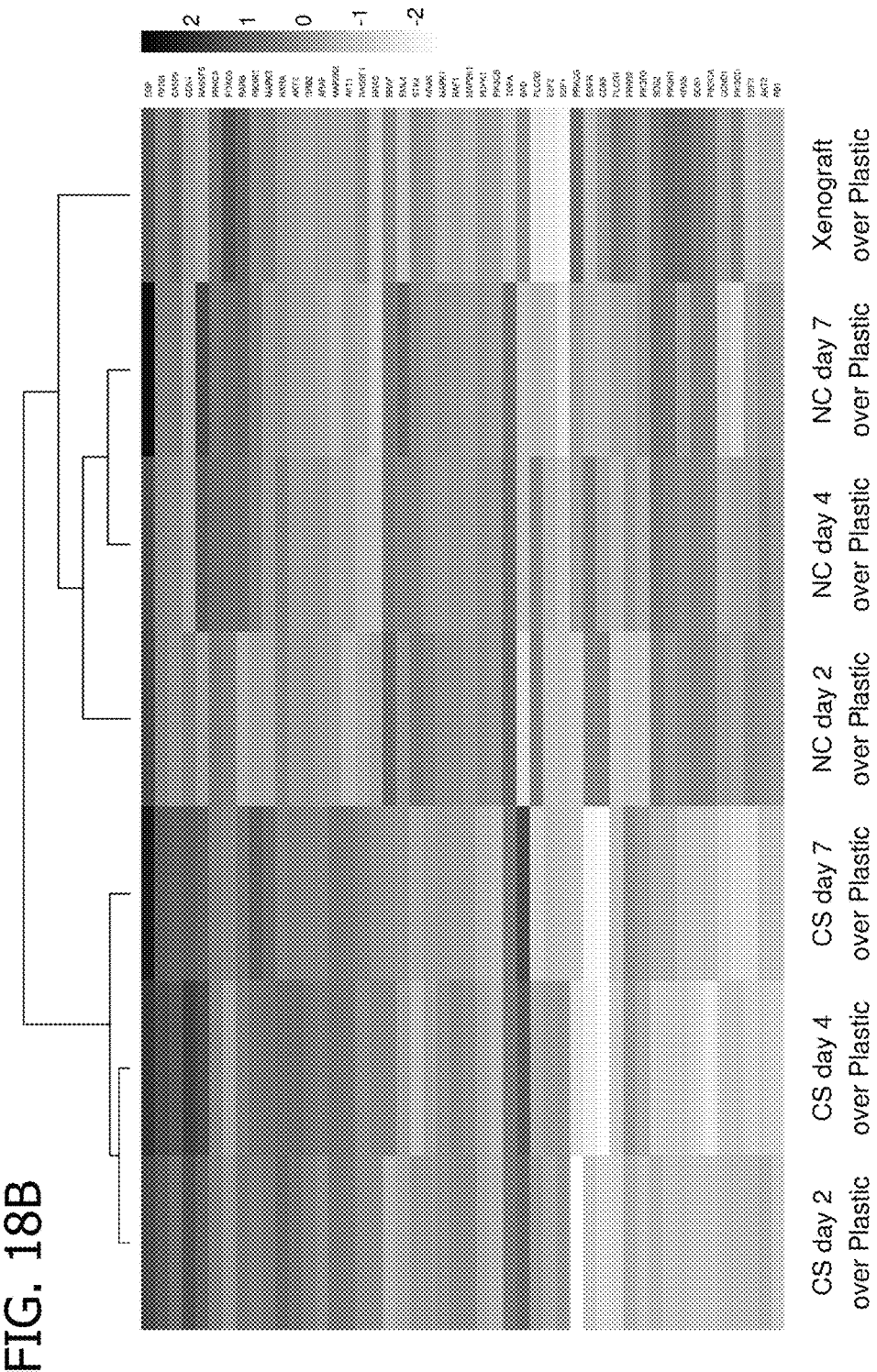

FIG. 18 provides a dendogram (FIG. 18A) and a heatmap (FIG. 18B) showing the clustering of samples based on the log2 fold changes (condition versus static 2D cultures ("plastic")) of the 48 genes in this dataset that are annotated with "Non-small cell lung cancer" in the KEGG database. Xenograft samples cluster with the samples from tri-cultures subjected to hemodynamic conditions that do not contain collagen. This indicates that the transcriptional responses of genes that are highly relevant to the disease phenotype are more similar to xenografts in the absence of collagen than in the presence of collagen. The hierarchical clustering was performed using an average linkage criteria, and Spearman rank correlation as the distance metric. CS=collagen sandwich; NC=no collagen; "plastic"=static 2D cultures. The 48 genes in the data set, the expression of which is indicated in the rows of the heatmap, from top the top row to the bottom row are: EGF, RXRB, CASP9, CDK4, RASSF5, PRKCA, FOXO3, RARB, PIK3R2, MAPK3, RXRA, AKT2, GRB2, ARAF, MAP2K2, AKT1, RASSF1, HRAS, BRAF, EML4, STK4, NRAS, MAPK1, RAF1, MAP2K1, PDPK1, PIK3CB, TGFA, BAD, PLCG2, E2F2, E2F1, PRKCG, EGFR, CDK6, PLCG1, ERBB2, PIK3R3, SOS2, PIK3R1, KRAS, SOS1, PIK3CA, CCND1, PIK3CD, E2F3, AKT3, and RB1.

Example 8

Molecular Activity Profiling of Endothelial Cells and Tumor Cells

In in vivo tumor-vasculature regions, tumor cell proliferation and invasion is modulated by endothelial cells in close proximity to the tumor cells. Qualitative and quantitative gene expression and cytokine secretion profiles for both the endothelial cells and the tumor cells cultured according to the methods described in Example 1 can be generated. Such assays are used to monitor the expression of angiogenic and tumorigenic factors and demonstrate that endothelial cells cultured under tumor-derived hemodynamic flow alter the molecular signature of the tumor cells, e.g., by enhancing markers of tumor molecular activity as measured using next generation mRNA sequencing and cytokine and growth factor secretion profiling.

After establishing tri-cultures as described in Example 1 above, mRNA can be collected from endothelial and tumor cells for analysis. Table 1 lists genes in both endothelial and tumor cells that are known to be regulated in the tumor microenvironment in vivo. This panel of genes serves as an initial molecular assessment of the tri-cultures described in Example 1 to demonstrate that the heterotypic cell-cell communication and hemodynamic flow and transport in the coculture systems affect the molecular activity of the tumor microenvironment. Table 1 (right) also lists a series cytokine and growth factors that are profiled using a multiplexing platform (MAGPIX), which is capable of performing qualitative and quantitative analysis of angiogenic factors such as VEGF and angiopoietins. Because of the design of the system, media can be collected in real-time from the endothelial cell and tumor cells layers separately for analysis.

TABLE 1

| Gene | Function | mRNA EC | mRNA A549 | MAGPIX EC | MAGPIX 549 |
|---|---|---|---|---|---|
| VEGFA | Angiogenesis | ✓ | ✓ | ✓ | ✓ |
| VEGFC | Angiogenesis | ✓ | ✓ | ✓ | ✓ |
| VEGFD | Angiogenesis | ✓ | ✓ | ✓ | ✓ |
| ANG1 | Angiogenesis | ✓ | ✓ | | |
| ANG2 | Angiogenesis | ✓ | ✓ | ✓ | ✓ |
| FGF-2 | Angiogenesis | | | ✓ | ✓ |
| PLGF | Angiogenesis | | | ✓ | ✓ |
| EGF | Proliferation | ✓ | ✓ | ✓ | ✓ |
| EGFR | Proliferation | | ✓ | | |
| MKI67 | Proliferation | ✓ | ✓ | | |
| PCNA | Proliferation | ✓ | ✓ | | |
| VIM | Invasion | | ✓ | | |
| CDH1 | Invasion | | ✓ | | |
| CDH2 | Invasion | | ✓ | | |
| IL-6 | Inflammation | ✓ | ✓ | | |
| IL-8 | Inflammation | ✓ | ✓ | ✓ | ✓ |
| NF-kB | Inflammation | ✓ | | | |
| eNOS | Inflammation | ✓ | | | |
| KLF2 | Inflammation | ✓ | | | |
| MCP-1 | Inflammation | ✓ | ✓ | ✓ | ✓ |

After reproducing the baseline molecular activity with a minimum of five biological replicates, next-generation sequencing-based mRNA transcriptomics (RNAseq) can be performed on the endothelial cells and tumor cells cultured as described above in Example 1, and compared to the following controls: (1) a static co-culture system, (2) endothelial cells subjected to tumor-derived shear stress in the absence of tumor cells, (3) tumor cells in monoculture; and (4) in vivo tumors. The OncoMine Research database is used to compare and contrast these results against >73,000 cancer expression profiles obtained from a large variety of human tumor samples, including clinical outcomes in >27,000 samples, pathway/drug responses in >7,800 samples and >11,000 samples from the Cancer Genome Atlas (TCGA). This provides an unbiased assessment of the coculture tumor microenvironment system.

Example 9

Testing of Anti-Cancer Drugs in In Vitro Tumor Microenvironment Tri-Cultures

The effects of anti-cancer drugs on the A549 tumor cells grown in tri-cultures generated as described above in Example 1 and depicted in FIG. 9 were assessed. The following drugs were selected: cisplatin, a front line chemotherapeutic for NSCLC (Rossi et al., 2012; National Cancer Institute, Non-Small Cell Lung Cancer Treatment (PDQ®)), and two experimental small molecule allosteric inhibitors of MEK (AZD6244/Selumetinib) and AKT (MK-2206), which are in clinical trials for NSCLC and other cancers (Leijen et al., 2011; National Cancer Institute, Randomized Phase II Study of ADZ6244; Yap et al., 2011; National Cancer Institute, MK2206 and Erlotinib Hydrochloride in Treating Patients with Advanced Non-Small Cell Lung Cancer). For each of the three drugs tested in the tri-cultures subjected to hemodynamic conditions, growth inhibition occurred at the clinically relevant human patient $C_{max}$.

The $IC_{50}$s of these three drugs for A549 tumor cells grown under static 2D conditions does not approximate the clinically relevant doses used in cancer patients. For cisplatin the in vivo $C_{max}$ is 3 µM and thus represents the clinical dose that patients with NSCLC receive (Urien et al., 2005). However, the cisplatin $IC_{50}$ for A549 cells in static 2D cultures from published results ranges from 6 µM to over 60 µM (Andriani et al., 2006; Zhang et al., 2013; Zhang et al., 2003; Barr et al., 2013). Thus, cisplatin is routinely in vitro used at 2× to 20× higher concentrations than what is achievable in vivo for NSCLC patients. Similarly, the A549 $IC_{50}$ for AZD6244/Selumetinib and MK2206 in static 2D cultures is significantly higher than the dose achieved in patients (Yeh et al., 2007; Meng et al., 2010). For AZD6244/Selumetinib the $C_{max}$ is 1.4 µM and the static 2D $IC_{50}$ is 5 µM, a 3.5-fold increase. For MK2206 the $C_{max}$ is 160 nM and the static 2D IC50 is 3 µM, nearly a 19-fold increase. These differences in $C_{max}$ and static 2D $IC_{50}$s help illustrate a major barrier that confronts work in static 2D conditions; non-physiologic drug concentrations are frequently necessary for biologic effects.

Table 2 summarizes the human and mouse in vitro $C_{max}$s and the in vitro IC50s for static cultures for cisplatin, MK2206, and AZD6422, as well the concentrations of the drugs tested tri-cultures subjected to hemodynamic conditions.

TABLE 2

| | Cisplatin | MK2206 | AZD6422 |
|---|---|---|---|
| Human $C_{max}$ | 3 µM | 160 nM | 1.4 µM |
| Mouse $C_{max}$ | >10 µM | 540 nM | 5.5 µM |

TABLE 2-continued

|  | Cisplatin | MK2206 | AZD6422 |
|---|---|---|---|
| Static 2D IC$_{50}$ | >6 µM | 3 µM | 5 µM |
| Concentration applied to tri-cultures subjected to hemodynamic conditions | 3 µM | 160 nM | 1.4 µM |

The IC$_{50}$ concentrations of cisplatin, MK2206 and AZD6244/selumetinib for the A549 cell line listed in Table 2 were taken from the literature as described above and estimated to be >6 µM, 3 µM and 5 µM, respectively. Maximal plasma concentrations (C$_{max}$) in mice were estimated using pharmacokinetic data from taken from efficacy studies in the peer-reviewed literature. For cisplatin, the steady state plasma C$_{max}$ was determined to be >10 µM (Johnsson et al., 1995). For MK2206, the steady state plasma C$_{max}$ was determined to be 540 nM (Piovan et al., 2013). For AZD6244/selumetinib, the steady state plasma C$_{max}$ was determined to be 5.5 µM (Denton and Gustafson, 2011). Maximal plasma concentrations (C$_{max}$) in humans were estimated with pharmacokinetic data from clinical trials using established therapeutic dosing paradigms. For cisplatin, the steady state plasma C$_{max}$ was determined to be 3 µM (Salas et al., 2006; Urien et al., 2005). For MK2206, the steady state plasma C$_{max}$ was determined to be 160 nM (Hudis et al., 2013; Yap et al., 2011). For AZD6244/selumetinib, the steady state plasma C$_{max}$ was determined to be 1.4 µM (Adjei et al., 2011; O'Neil et al., 2011).

The growth rate of the human lung carcinoma cell line A549 was determined in response to vehicle control ("Veh"), cisplatin, MK-2206, and AZD6244 using the human C$_{max}$ doses described above. Tri-cultures were prepared as described above in Example 1 and as depicted in FIG. 9 in the absence of exogenously added ECM and subjected to tumor capillary hemodynamics. The vehicle control or drug was added to the inflow media for the endothelial cell layer and perfused into the upper volume. Tri-cultures were maintained in the presence of absence of drugs for up to seven days under hemodynamic flow and transport. Cell number was determined at day seven using the QUANT-IT PICOGREEN dsDNA Assay Kit according to the manufacturer's instructions (Life Technologies, Grand Island, N.Y.). Data are presented in FIGS. 19A and 19B as the mean number of cells from duplicate.

Figure 19A:
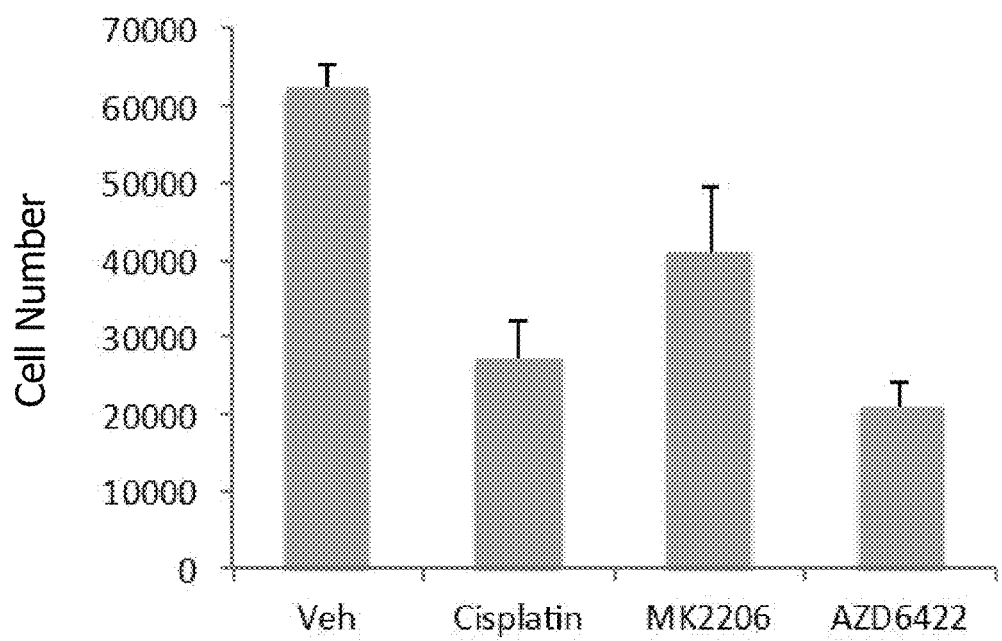
FIGS. 19A and 19B provide results showing the inhibition of the growth of A549 tumor cells in the presence of cisplatin, MK2206, or selumetinib (AZD6244).
Figure 19B:
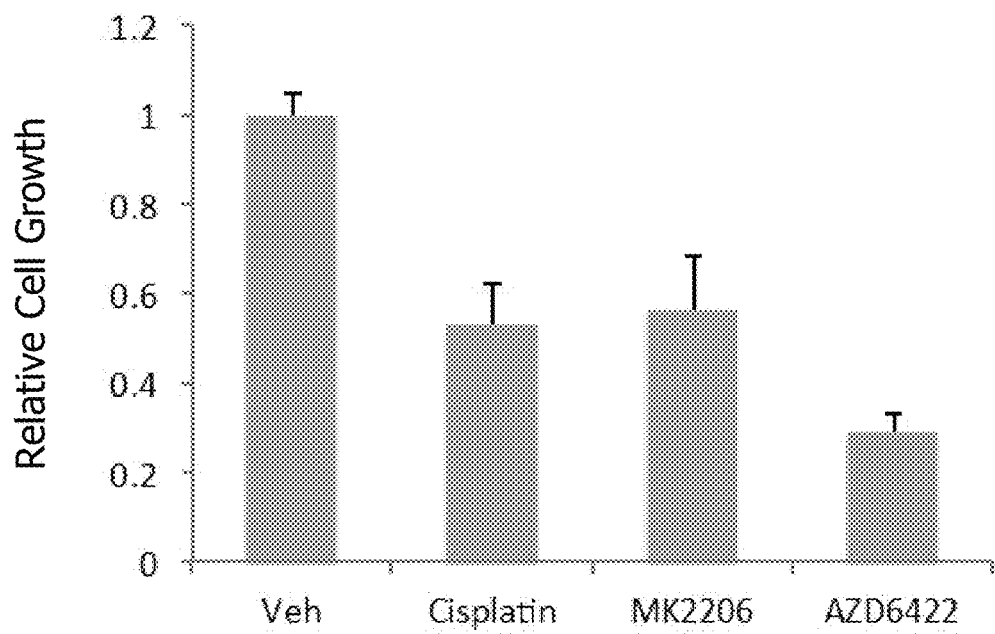

FIG. 19A shows the cell number for A549 tumor cells treated with the vehicle control ("Veh"), cisplatin, MK2206, or AZD6422. FIG. 19B shows the relative cell growth of A549 tumor cells treated with the vehicle control ("Veh"), cisplatin, MK2206, or AZD6422. Cisplatin inhibited A549 growth by 48%, MK2206 by 44%, and AZD6422/Selumetinib by 78%. These data indicate that tumor cells grown in the tri-cultures subjected to hemodynamic conditions respond to both established chemotherapeutics (cisplatin) and experimental small molecule inhibitors (MK2206, AZD6442) at therapeutically relevant concentrations.

Collectively, these data indicate that tumor cells grown in the tri-cultures and subjected to hemodynamic conditions respond to both established chemotherapeutics and experimental small molecule inhibitors at human patient physiologic doses. It is important to note that as shown in Table 2, the mouse C$_{max}$ at therapeutic doses for cisplatin, AZD6244/Selumetinib and MK2206 is higher than the human patient Cmax. In mice the C$_{max}$ of AZD6244/Selumetinib is 5.5 µM (Meng et al., 2010, Chung et al., 2009), which is equivalent to the static 2D IC$_{50}$. For MK2206 the mouse Cmax is 540 nM (Meng et al., 2010), which is 5-fold higher than the human patient C$_{max}$. Cisplatin has a mouse C$_{max}$ ranging from 10-100 µM (Andriani et al., 2006; Zhang et al., 2003; Bain et al., 2007), which exceeds the human patient C$_{max}$ and is equivalent to or higher than the static 2D IC$_{50}$. Thus, the tri-cultures subjected to hemodynamic conditions may be superior to mouse xenograft studies for testing experimental drugs at physiologic doses.

Example 10

Further Testing of Anti-Cancer Drugs in In Vitro Tumor Microenvironment Tri-Cultures Additional anti-cancer drugs can be tested in for their effects on the tumor cells, stromal fibroblasts, and/or microvascular endothelial cells grown in tri-cultures generated as described above in Example 1. The anti-cancer drug can be introduced into the tri-cultures at concentrations in the culture medium that are within the concentration range of the in vivo therapeutic C$_{max}$ in a human. For example, the antiproliferative chemotherapeutic drug carboplatin (Sigma-Aldrich), and the EGFR inhibitor erlotinib (Cayman Chemical) can be tested. These two drugs are commonly used in the treatment of lung cancer, their pharmacokinetics have been well-characterized through clinical trials, and they both have been shown to improve the survival of lung cancer patients. Carboplatin is a traditional chemotherapeutic drug that indiscriminately kills rapidly dividing cells, whereas erlotinib is a targeted therapy that is not as broadly toxic.

The drug can be added to the inflow media for the endothelial cell layer and perfused into the upper volume. Initially, the drugs can be applied to the endothelial cells at two doses, with the highest dose being the in vivo C$_{max}$ level achieved in humans (for carboplatin, 37 µg/ml; for erlotinib, 1 µg/ml), and a 10-fold lower dose, mimicking the lower degree of drug penetration observed in many solid tumors in vivo. A broader range of doses can then used to generate response profiles for each drug. As a two-dimensional control, A549 cells can be plated on tissue culture-treated dishes and cultured in conditioned media from microvascular endothelial cells in the presence of each drug, and cell counts can be performed after 3 days. As a three-dimensional control, A549 cells can be seeded in a three-dimensional collagen matrix on the bottom of a well of a 6-well dish, and endothelial cells plated on the upper surface of the porous membrane of a cell culture insert inserted into the well, similar to current in vitro three-dimensional tumor models. The endpoints described in the Examples above can be used to assess the effect of the anticancer agent, e.g. cell viability, tumor cell invasion, endothelial cell permeability, RT-PCR, mRNA sequencing, and cytokine and growth factor profiling.

Additional anti-cancer drugs can be tested in a similar manner and their dose-response curves compared with the dose-response curves for the drug in in vivo models. Such drugs include, for example, angiogenesis inhibitors such as the VEGF inhibitor bevacizumab and the VEGFR inhibitor sorafenib.

Example 11

A Model for Tumor Metastasis to the Liver

The metastasis of tumor cells through the vasculature to distal organs is the major cause of mortality in cancer. The liver is a common site for tumor metastases because if its rich blood supply. Human tumor cells (e.g., the A549 tumor cells or pancreatic tumor cells) are cultured according to the methods described above in Examples 1, under static 2D conditions, or as xeongrafts. The tumor cells are then extracted and added to an in vitro liver model system, for example, an in vitro system liver model system as described in U.S. Patent Publication No. US 2013/0309677 and PCT Publication No. 2013/158939, the contents of both of which are hereby incorporated by reference in their entirety. For example, in an in vitro liver model system described in U.S. Patent Application Publication No. US 2013/0309677 and PCT Publication No. 2013/158939, hepatocytes are sandwiched in a collagen gel and plated on a first surface of a porous membrane. Sinusoidal endothelial cells are optionally plated on the second surface of the porous membrane. Additional non-parenchymal cells (e.g., hepatic stellate cells, Kupffer cells, or a combination thereof) are optionally plated on the first or second surface of the porous membrane. A shear stress that mimics in vivo blood flow in the liver is then applied to the non-parenchymal cells on the second side of the porous membrane, and cell culture medium is perfused into and out of the upper and lower volumes. FIG. 11 provides a schematic drawing of such a system.

Tumor cells are extracted from the tri-cultures, xenografts, or 2D static cultures and added to this in vitro liver system. The tumor cells are either introduced directly into the lower volume containing the hepatocytes, or to the upper volume optionally containing the sinusoidal endothelial cells and/or other non-parenchymal cells. In the latter case, transmigration of the tumor cells into the lower volume containing the hepatocytes is assessed. Growth of the tumor cells in the in vitro liver system is also assessed.

Alternatively, a coculture system containing tumor cells, stromal fibroblasts, and microvascular endothelial cells as described above in Example 1 is linked to an in vitro liver model system by tubing that is used to transfer culture medium from the lower or upper volume of the tumor model coculture to the lower or upper volume of the in vitro liver model system as shown in FIGS. 12A-D. This creates a model of tumor metastasis mimicking the seeding of distal organs by tumor cells in vivo.

Efficacy of anticancer agents can be assessed by measuring the growth of these in vitro metastases in the in vitro liver model in the presence of an anticancer agent, as compared to the growth of the in vitro metastases in the absence of the anticancer agent.

Example 12

A Physiologic In Vitro Liver Model

Static hepatocyte cell culturing methods are associated with poor in vitro to in vivo correlations, due in part to the absence of physiological parameters which maintain metabolic phenotype over time in vivo. Restoring physiological hemodynamics and transport retains hepatocyte phenotype and function in vitro compared to the standard static hepatocyte collagen gel configuration.

To recreate a cellular hepatocyte system with fluid dynamics and transport analogous to in vivo liver circulation, a cone-and-plate device-based technology was employed that has been extensively used to re-establish in vivo blood vessel cell phenotypes by recreating the exposure of vascular endothelial cells to human-derived hemodynamic blood flow forces in vitro. This technology is described in U.S. Pat. No. 7,811,782. The technology was adapted and modified to design a rat liver monoculture system which applies hemodynamic flow and transport conditions reflective of in vivo hepatic circulatory values. The configuration of cells in the device is based on in vivo microarchitecture of hepatic lobules where cords of hepatocytes are separated from sinusoidal blood flow by a filtering layer of endothelial cells. This design uses a porous polycarbonate membrane suspended in a cell culture container, with primary rat hepatocytes sandwiched in a collagen gel on one side of the porous membrane. The porous membrane acts analogously to the filtering layer of sinusoidal endothelial cells which is present in the liver. Media is continuously perfused on both sides of the porous membrane, while hemodynamic forces, derived from a range of physiological blood flow values, are continuously applied to the non-cellular side of the porous membrane. The entire set up is housed in a controlled environment with 5% $CO_2$ and at 37° C. A flow-based culture system was effectively created whereby hepatocytes are shielded from direct effects of flow, as they would be in vivo. Recapitulating the hemodynamics and in a system designed to be analogous to the microstructure of the hepatic sinusoid results in stable retention of a differentiated hepatic and metabolic phenotype similar to that of in vivo liver.

Methods (i) Animal Surgery and Hepatocyte Isolation

All animals used for the experiments were treated according to protocols approved by HemoShear's Animal Care & Use Committee. Hepatocytes were isolated from male Fischer rats (250 g-350 g) by a modification of Seglen's two-step collagenase perfusion procedure using a 20 mL/min flow rate (Seglen, *Hepatocyte Suspensions and Cultures as Tools in Experimental Carcinogegnesis, J. Toxicology & Environmental Health*, 5(2-3): 551-560 (1979), the contents of which are hereby incorporated by reference). Briefly, the rats were anaesthetized with isoflurane, following which the abdominal cavity was incised and the inferior vena cava was canulated while making an excision was made in the portal vein for outflow. The liver was perfused in two steps, first with a $Ca^{++}$-free buffer to flush out blood and break up intercellular junctions, followed by collagenase in a $Ca^{++}$-containing buffer to digest the extracellular collagen matrix. After the liver was suitably perfused it was excised and freed of the capsule in a Petri dish under a sterile hood. An enriched hepatocyte population (~95% purity) was obtained by two sequential 65g centrifugation and washing cycles of 10 minutes each followed by a 10 minute spin with 90% PERCOLL (colloidal silica particles of 15-30 nm diameter (23% w/w in water) coated with polyvinylpyrrolidone (PVP); used to establish density gradients that can be used to isolate cells). The viability of hepatocytes was determined by trypan blue exclusion test and cells with a viability over 85% are used.

(ii) Cell Culture and Device Operating Conditions

Hepatocyte Culture Media: For the data shown in FIGS. 20-24, the rat hepatocyte culture media contained base media of DMEM/F12 containing high glucose (17.5 mM), supplemented by fetal bovine serum (10% at the time of plating and reduced to 2% for maintenance after 24 hours). The media also contained gentamycin (50 µg/ml), ITS (insulin concentration 2 µMol), 1% NEAA, 1% GLUTAMAX, and dexamethasone (1 µM at plating and 250 nM for maintenance after 24 hours).

Figure 38:
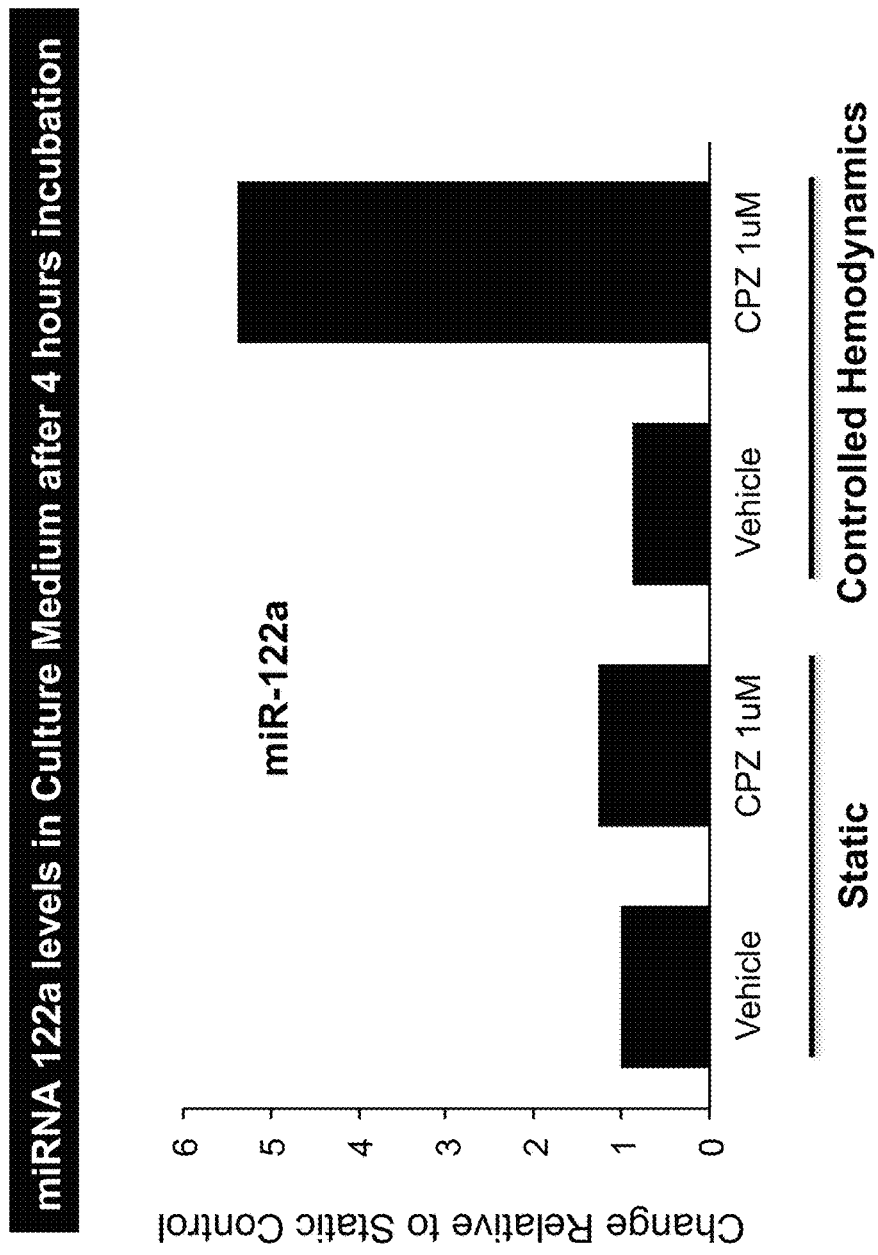
FIG. 38 provides acute toxicity data, measured by release of miRNA122, in hepatocytes cultured under controlled hemodynamic or static conditions in response to chlorpromazine.
Figure 39:
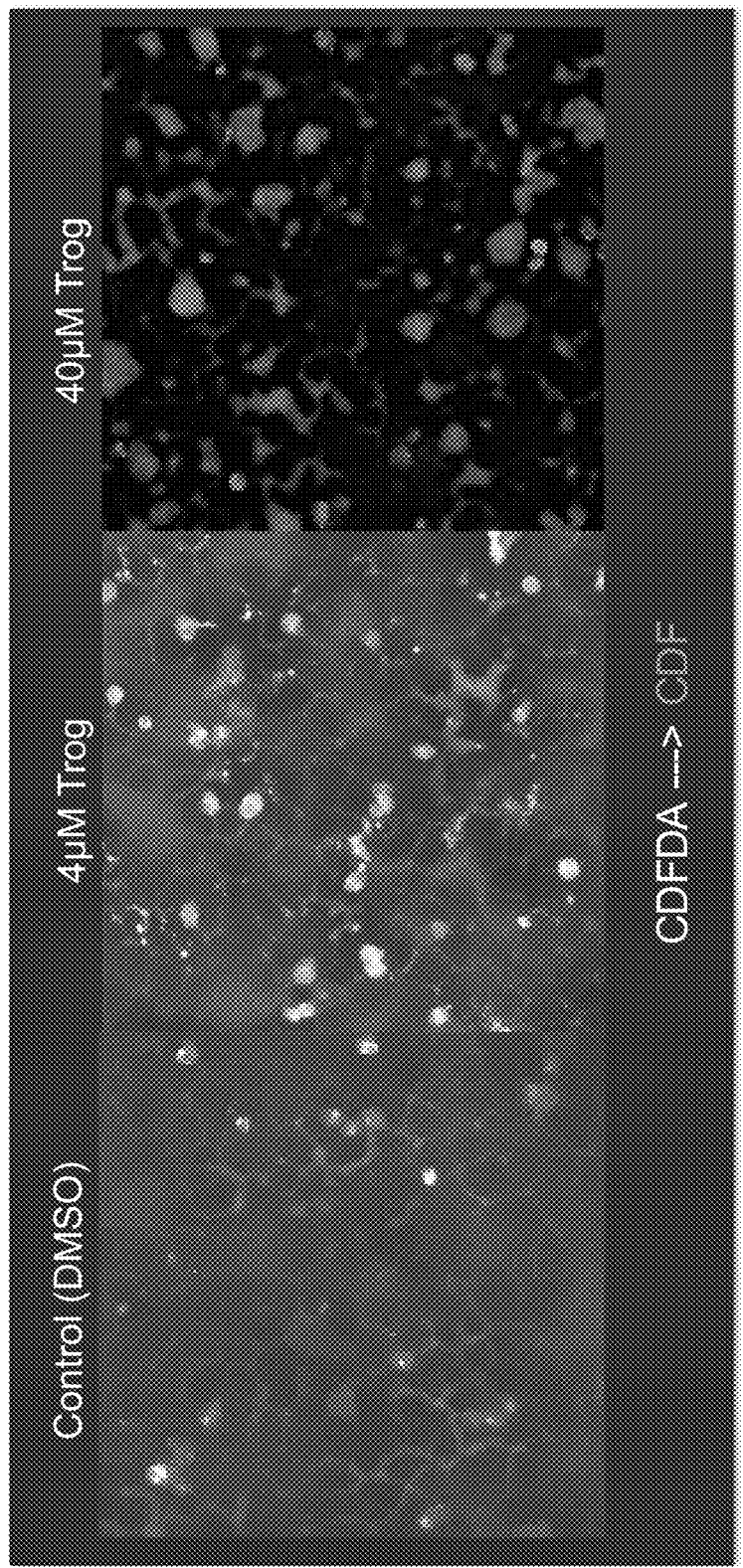
FIG. 39 provides fluorescence microscopy images showing sublethal toxicity and cholestatic changes in hepatocytes cultured under controlled hemodynamic conditions in response to treatment with troglitazone.

For the data shown in Table 6 and FIGS. 38 and 39, the rat hepatocyte culture media contained base media of DMEM/F12 containing low glucose (5.5 mM), supplemented by HEPES (3% vol/vol) and fetal bovine serum (10% vol/vol at the time of plating and reduced to 2% for maintenance after 24 hours). The media also contained gentamycin (50 µg/ml), ITS (insulin concentration 2 nMol), 1% NEAA, 1% GLUTAMAX, and dexamethasone (1 µM at plating and 100 nM for maintenance after 24 hours).

To culture human or dog hepatocytes, the culture media contained base media of DMEM/F12 containing low glucose (5.5 mM), supplemented by HEPES (3% vol/vol) and fetal bovine serum (10% vol/vol at the time of plating and reduced to 2% for maintenance after 24 hours). The media also contained gentamycin (50 µg/ml), ITS (insulin concentration 2 nMol), and dexamethasone (1 µM at plating and 100 nM for maintenance after 24 hours).

Collagen coating and plating: Collagen solution was made by mixing Type I Rat Tail Collagen in sterile distilled water, 10× phosphate buffered saline (PBS) and 0.2N sodium hydroxide in a predefined ratio (To make up 1 ml, the components were 440 µl, 375 µl, 100 µl and 85 µl respectively).

For cultures to be subjected to static conditions, 100 mm tissue culture-treated sterile cell culture dishes were coated with 7 µl/cm$^2$ of collagen solution. For cultures to be subjected to controlled hemodynamics, the lower surface of the porous membrane of 75 mm TRANSWELLS (polycarbonate, 10 µm thickness and 0.4 µm pore diameter, no. 3419, Corning) were coated with 7 µl/cm$^2$ of collagen solution. After allowing an hour for the solution to gel, the surfaces were washed with DPBS, hepatocytes were plated at a seeding density of 125,000 viable cells/cm$^2$, and a second layer of collagen gel added after 4 hours. After 1 hour, the TRANSWELLS were inverted and placed into cell culture dishes, and media was added (9 ml in the lower volume and 6 ml in the upper volume). 7 ml of media was added to the tissue culture dishes to be used for static cultures. After 24 hours, the media was switched to maintenance media (containing 2% FBS), and the cell culture dishes containing TRANSWELLS were placed into the cone-and-plate device. Controlled hemodynamics were applied to the surface of the porous membrane of the TRANSWELL in the upper volume.

Cryopreserved human hepatocytes were procured from commercial vendors (Kaly-Cell, France) and thawed as per the vendor's prescribed protocols. For plating human hepatocytes, a similar procedure to that described above for rat hepatocytes was followed, a limited cell-seeding area was used. The second layer of collagen was applied as described above.

Freshly isolated canine hepatocytes from beagle dogs were procured from commercial vendors (Triangle Research Laboratories, Research Triangle Park, N.C.) and processed as per the vendor's prescribed protocols. For plating canine hepatocytes, a similar procedure to that described above for rat hepatocytes was followed, but using a limited cell-seeding area. The second layer of collagen was applied as described above.

Operating conditions: The shear stress in dynes/cm$^2$ ($\tau$) was calculated for a typical hepatic sinusoid based on the formula for pressure driven flow of a Newtonian fluid through a cylinder, $$\tau = \frac{\Delta P \cdot r}{2l}$$

using reference values for pressure gradient across the sinusoid ($\Delta P$), radius of sinusoids (r) and length of the sinusoids (l) from the literature. As part of an initial optimization process, a range of applied shear stress conditions obtained by altering media viscosity and cone speed that resulted in rates within an order of magnitude of the value predicted from literature were seen to be correlated with different transport profiles of horse radish peroxidase dye across the membrane. These were tested for gene expression profiles of the hepatocytes 7 days into culture (data not shown). No differences were observed between static cultures and those that were simply perfused without any applied shear and based on the gene expression profiles, an operational shear rate of 0.6 dynes/cm$^2$ was selected for all the experiments described in this Example.

(iii) Assessment of Phenotypic, Functional, Metabolic, and Toxic Parameters

RT-PCR: Changes in metabolic, toxic, and insulin/glucose/lipid pathway genes were assessed by extracting RNA from hepatocytes from devices run under healthy and steatotic conditions at the end of the culture period (7 or 14 days) and performing RT-PCR on this RNA. The TRANSWELLS were removed from the devices and washed with PBS prior to scraping the cells off the porous membrane. Total RNA was isolated using a PURELINK RNA Mini Kit (a kit for purification of total RNA from cells) and reverse transcribed to cDNA using the ISCRIPT cDNA Synthesis Kit (a cDNA synthesis kit). Primers were designed for the metabolic genes CYP1A1, CYP1A2, CYP3A2, MDR, and GST as well as the insulin/glucose/lipid pathway genes GPAT, ACC1, IRS-2, PPAR-γ, SREBP, ChREBP, LXR, SCD1, CPT1. Primer sequences are shown below in Table 3:

TABLE 3

Rat Primer Sequences

| Gene | Forward (SEQ ID NO.) | Reverse (SEQ ID NO.) |
|---|---|---|
| CYP1A1 | GCTGCTCTTGGCCGTCACCA (1) | TGAAGGGCAAGCCCCAGGGT (2) |
| CYP1A2 | CCTGCGCTACCTGCCCAACC (3) | GGGCGCCTGTGATGTCCTGG (4) |
| CYP3A2 | CGGCGGGATTTTGGCCCAGT (5) | CAGGCTTGCCTGTCTCCGCC (6) |
| MDR | GCTGCTGGGAACTCTGGCGG (7) | CCGGCACCAATGCCCGTGTA (8) |
| GST (Pi subunit) | CGCAGCAGCTATGCCACCGT (9) | CTTCCAGCTCTGGCCCTGGTC (10) |
| GPAT | AGCGTTGCTCCATGGGCATATAGT (11) | TGTCAGGGATGGTGTTGGATGACA (12) |
| ACC1 | TGTCATGGTTACACCCGAAGACCT (13) | TTGTTGTTGTTTGCTCCTCCAGGC (14) |
| IRS-2 | GCGAGCTCTATGGGTATATG (15) | AGTCCTCTTCCTCAGTCCTC (16) |

TABLE 3-continued

Rat Primer Sequences

| Gene | Forward (SEQ ID NO.) | Reverse (SEQ ID NO.) |
|---|---|---|
| PPAR-g | ATATCTCCCTTTTTGTGGCTGCTA (17) | TCCGACTCCGTCTTCTYGATGA (18) |
| SREBP | GGAGCCATGGATTGCACATT (19) | AGGCCAGGGAAGTCACTGTCT (20) |
| ChREBP | CTATGTCCGGACCCGCACGC (21) | CTATGTCCGGACCCGCACGC (22) |
| LXR | ACTCTGCAACGGAGTTGTGGAAGA (23) | TCGGATGACTCCAACCCTATCCTT (24) |
| SCD1 | TGTGGAGCCACAGGACTTACAA (25) | AGCCAACCCACGTGAGAGAAGAAA (26) |
| CPT1 | ATGTGGACCTGCATTCCTTCCCAT (27) | TTGCCCATGTCCTTGTAATGTGCG (28) |
| CYP2B1 | GAGGAGTGTGGAAGAACGGATTC (29) | AGGAACTGGCGGTCTGTGTAG (30) |
| CYP2B2 | TCATCGACACTTACCTTCTGC (31) | AGTGTATGGCATTTTGGTACGA (32) |
| SORD | TCTGTGGCTCGGATGTTCACTACT (33) | CGGCCGATCTTGCAGAATTCATCT (34) |
| GSR | GGACTATGACAACATCCCTACC (35) | CCAACCACCTTCTCCTCTTT (36) |
| APEX1 | GCCTAAGGGCTTTCGTTACA (37) | ATCCACATTCCAGGAGCATATC (38) |
| MRP3 | AGGCCAGCAGGGAGTTCT (39) | AGCTCGGCTCCAAGTTCTG (40) |
| MRP4 | CAACTCCTCTCCAAGGTGCT (41) | ATCTGCTCACGCGTGTTCTT (42) |

RNA expression was analyzed by real-time RT-PCR using IQ SYBR Green Supermix (a PCR reagent mixture for RT-PCR) and a CFX96 Real-Time System with C1000 Thermal Cycler (an RT-PCR detection system and thermal cycler). RNA data were normalized to endogenous expression of β2-microglobulin and reported as a relative quantity compared to healthy cultures.

Human genes assessed for metabolism and toxicity experiments included CYP1A1. CYP2A6, CYP2B6, CYP2C9, CYP2D6, CYP3A4, CYP3A5, GSTA1, UGT1A1, GSR, SORD, TXNRD1, and APEX1. The primer sequences for these are shown in Table 4. Canine genes assessed for metabolism included CYP1A1 and CYP3A12 (primer sequences shown in Table 5).

TABLE 4

Human Primer Sequences

| Gene | Forward (SEQ ID NO.) | Reverse (SEQ ID NO.) |
|---|---|---|
| CYP1A1 | GGACCTGAATGAGAAGTTCTACAGC (43) | AGCTCCAAAGAGGTCCAAGACGAT (44) |
| CYP2A6 | TCATAGCCAAGAAGGTGGAGCACA (45) | CCCAATGAAGAGGTTCAACGTGGT (46) |
| CYP2B6 | GGGCACACAGGCAAGTTTACAA (47) | AGAGCGTGTTGAGGTTGAGGTTCT (48) |
| CYP2C9 | TGACTTGTTTGGAGCTGGGACAGA (49) | ACAGCATCTGTGTAGGGCATGT (50) |
| CYP2D6 | ACGACACTCATCACCAACCTGTCA (51) | AGGTGAAGAAGAGGAAGAGCTCCA (52) |
| CYP3A4 | CTGCATTGGCATGAGGTTTGCTCT (53) | AAATTCAGGCTCCACTTACGGTGC (54) |
| CYP3A5 | CTGCATTGGCATGAGGTTTGCTCT (55) | AGGGTTCCATCTCTTGAATCCACC (56) |
| GSTA1 | GATGCCAAGCTTGCCTTGAT (57) | AGGGAAGCTGGAGATAAAGACTGGA (58) |
| UGT1A1 | GGCCCATCATGCCCAATATGGTTT (59) | GCATCAGCAATTGCCATAGCTTTC (60) |
| SORD | TAGCGCCACCAGAAGCGACCAAA (61) | TCATTTGGGCCTGGTTCAGGGATA (62) |
| APEX1 | CCAGCCCTGTATGAGGACC (63) | GGAGCTGACCAGTATTGATGAGA (64) |
| GSR | CACTTGCGTGAATGTTGGATG (65) | TGGGATCACTCGTGAAGGCT (66) |
| TXNRD1 | ATATGGCAAGAAGGTGATGGTCC (67) | GGGCTTGTCCTAACAAAGCTG (68) |

TABLE 5

Canine Primer Sequences

| Gene | Forward (SEQ ID NO.) | Reverse (SEQ ID NO.) |
| --- | --- | --- |
| CYP1A1 | CACCATCCCCCACAGCACAACAAA (69) | GCTCTGGCCGGAATGCAAATGGAT (70) |
| CYP3A12 | GAGAGAATGAAGGAAAGTCGCC (71) | GCCACCAGCTCCAAATCAGA (72) |
| B2MG | TCCTCATCCTCCTCGCT (73) | TTCTCTGCTGGGTGTCG (74) |

Urea and Albumin Assays: Media collected from static cultures and devices at various time points was assayed for albumin using a rat-specific ELISA based kit (Bethyl Laboratories) as per the manufacturer's protocols. Urea was estimated from the media samples using a standard colorimetric assay (QUANTICHROM Urea Assay Kit, DIUR-500, Gentaur). All measurements between the systems were normalized to a per million cells/day rate for comparison based on the volume of media perfused and the number of initially plated cells.

Western Blots: Following application of controlled hemodynamics, ⅓ of the plated surface of the porous membrane of the TRANSWELL (~1.8 million cells) was harvested for protein in 150 μl 1× RIPA buffer containing fresh 150 mM DTT and protease inhibitors (HALT Protease Inhibitor Cocktail (Pierce)+1 mM PMSF+200 mM DTT). Samples were sonicated on ice with 5×1 second pulses, allowed to sit on ice for 30 minutes and centrifuged at 17,000×g for 10 minutes in a chilled microcentrifuge. Protein determination was done using A660 nm Protein Reagent (Pierce). Samples were boiled 70° C. for 10 minutes and then run on a 7.5% TGX gel (a pre-cast polyacrylamide gel, BioRad) before wet-transferring to 0.2 μm PVDF membrane and blocking in 5% non-fat milk at room temperature for 10 minutes. Membranes were incubated overnight at 4° C. in rabbit anti UGT antibody (Cell Signaling, 1:500 dilution). Secondary antibody (Santa Cruz, Goat anti Rabbit HRP, 1:5000 dilution) incubation was at room temperature for one hour. Chemiluminescent signal was developed using SUPERSIGNAL WEST PICO (a chemiluminescent substrate for horseradish peroxidase, Pierce) reagent and captured using an Innotech ALPHAEASE imaging system. For normalization, gels were probed for mouse anti β-Actin (Sigma A1978, 1:2000 dilution) followed by secondary goat anti mouse HRP (Santa Cruz sc-2005, 1:10,000 dilution).

Immunostaining and Biliary Activity Stain: Antibodies used: Hnf4a (Santa Cruz sc-8987), E-cadherin (Santa Cruz sc-71009), and anti-MRP2 (Abcam ab3373). At the chosen time points in the experimental design, the static cultures and cultures subjected to controlled hemodynamics were washed gently with 1× PBS, following which they were fixed with 4% paraformaldehyde for 30 minutes. The samples were stored in PBS at 4° C. until they were to be immunostained. For immunostaining, the samples were first permeabilized with 0.1% TRITON X (a nonionic surfactant) for 20 minutes and then washed with PBS and blocked with 5% goat serum. The incubation with primary antibodies was at a dilution of 1:100 for 1 hour. After 3 washes with PBS with 1% BSA, the secondary antibody was added at a dilution of 1:500 for another hour. The samples were then washed with PBS plus 1% BSA and then mounted for confocal imaging.

For imaging of the biliary activity at canalicular junctions, sections of the porous membrane of the TRANSWELL were washed with PBS and incubated with media containing 10 μM carboxy-2,7-dichlorofluorescein diacetate (CDFDA) for 10 minutes. Samples were then washed with PBS and placed on glass slide for confocal imaging.

Transmission Electron Microscopy: Transmission electron microscopy was performed as described below in Example 13.

Cytochrome Activity Assays: Hepatocytes were cultured in the cone-and-plate devices under static or controlled hemodynamic conditions for five days, and then treated with 0.1% dimethyl sulfoxide (DMSO) or known inducers of cytocrhome enzymes(3-methylcholanthrene and dexamethasone) for 48 hours. Porous membrane segments roughly 2cm$^2$ in area were excised and transferred to standard 24-well plates alongside corresponding static cultures. The cells were incubated with 500 μl of hepatocyte media containing substrates from commercially available P450-GLO kits (kits for luminescent cytochrome p450 assays) at the manufacturer-recommended concentrations. After 4 hours, the media was transferred to 96-well plates and assayed for luminescent metabolites to reflect cytochrome p450 activity as per the manufacturer protocol. The ATP content of the cells in the same porous membrane segments or static wells was then estimated by the CELLTITER-GLO assay (a kit for a luminescent cell viability assay) using the manufacturer's protocol, and the cytochrome values were normalized to ATP content.

To assess CYP activity and induction responses of human hepatocytes, the cells were plated and cultured in the cone-and-plate devices and subjected to controlled hemodynamics under the operating conditions described above or were cultured under static conditions (controls) for 7 days before being exposed to either 0.1% DMSO or known CYP inducer drugs phenobarbital (500 μM for static and 50 μM for devices) or rifampicin (25 μM for static and 2.5 μM for devices) for 72 hours. The hepatocytes were then incubated with medium containing a cocktail of CYP substrates [(ethoxy resorufin (10 μM), midazolam (3 μM), bufuralol hydrochloride (10 μM), (S)-mephenytoin (50 μM), bupropion hydrochloride (100 μM), and diclofenac sodium (10 μM)] for 4 hours. The culture supernatants were then collected and analyzed by HPLC for formation of metabolites to assess specific activity of specific CYP enzymes. All values were normalized to protein content of the cells.

Gluconeogenesis Assays: Primary rat hepatocytes isolated and plated as described above were cultured in the cone-and-plate devices under controlled hemodynamics for 7 days. Hepatocytes were washed with PBS and incubated in glucose free media, with addition of substrates glycerol (2 mM) or lactate (20 mM) and pyruvate (2 mM) in the presence or absence of the regulatory hormones insulin (2 nM) or glucagon (100nM). After 4 hours, the supernatants were collected and assayed for glucose content using the colorimetric AMPLEX RED kit (a glucose/glucose oxidase assay kit, Life Technologies) as per manufacturer's instructions. The glucose values were normalized to the protein content of the cellular lysates.

MTT Assay: To assess toxicity responses of human hepatocytes, the cells were plated and cultured in the cone-and-plate devices under hemodynamic conditions using the operating conditions described above or were cultured under static conditions (controls) for 7 days before being exposed to either 0.1% DMSO or known toxic drug chlorpromazine (0.1 µM, 1 µM and 10 µM) for 72 hours. Hepatocytes were then incubated with medium containing 1mg/ml of MTT reagent (thiazolyl blue tetrazolium bromide) for 1 hour, following which the cells were lysed in DMSO to release the formazan blue dye formed. The solution was transferred to a 96 well plate and the absorbance was read at 595 nm.

Live Dead Staining: To assess toxicity responses of human hepatocytes, the cells were plated and cultured in the cone-and-plate devices under hemodynamic conditions under the operating conditions described above for 7 days or were cultured under static conditions (controls) before being exposed to either 0.1% DMSO or known toxic drug chlorpromazine (0.1 µM, 1 µM and 10 µM) for 72 hours. At the end of the treatment period, the hepatocytes were washed with PBS and then incubated in LIVE/DEAD viability/cytotoxicity reagent (Invitrogen) at a concentration of 2 µM calcein AM and 4 µM ethidium homodimer-1 (EthD-1) for 30 minutes. Cells were then mounted between glass coverslips and imaged using a confocal microscope.

miRNA122 assay: Rat hepatocytes were plated and cultured in the cone-and-plate devices under controlled hemodynamic or were cultured under static conditions (controls) using the operating conditions described above for 7 days. The hepatocytes were then washed with PBS and incubated with serum free hepatocyte medium with or without known toxic drug chlorpromazine (CPZ) at two different concentrations (1 µM and 10 µM) for 4 hours. Supernatants from the cells were collected and microRNA extraction was performed using the MIRNEASY serum/plasma kit (a kit for extracting microRNA, Qiagen). The cDNA was prepared by using the MISCRIPTII RT kit (a kit for preparing cDNA, Qiagen) and samples quantified using the MISCRIPT SYBR GREEN PCR kit (a kit for quantifying cDNA, Qiagen), following the manufacturer's instructions.

Results (ii) Controlled Hemodynamics Maintain Hepatocyte Phenotype, Polarized Morphology and Transporter Localization Relative to Traditional Static Monoculture Conditions.

Figure 20A:
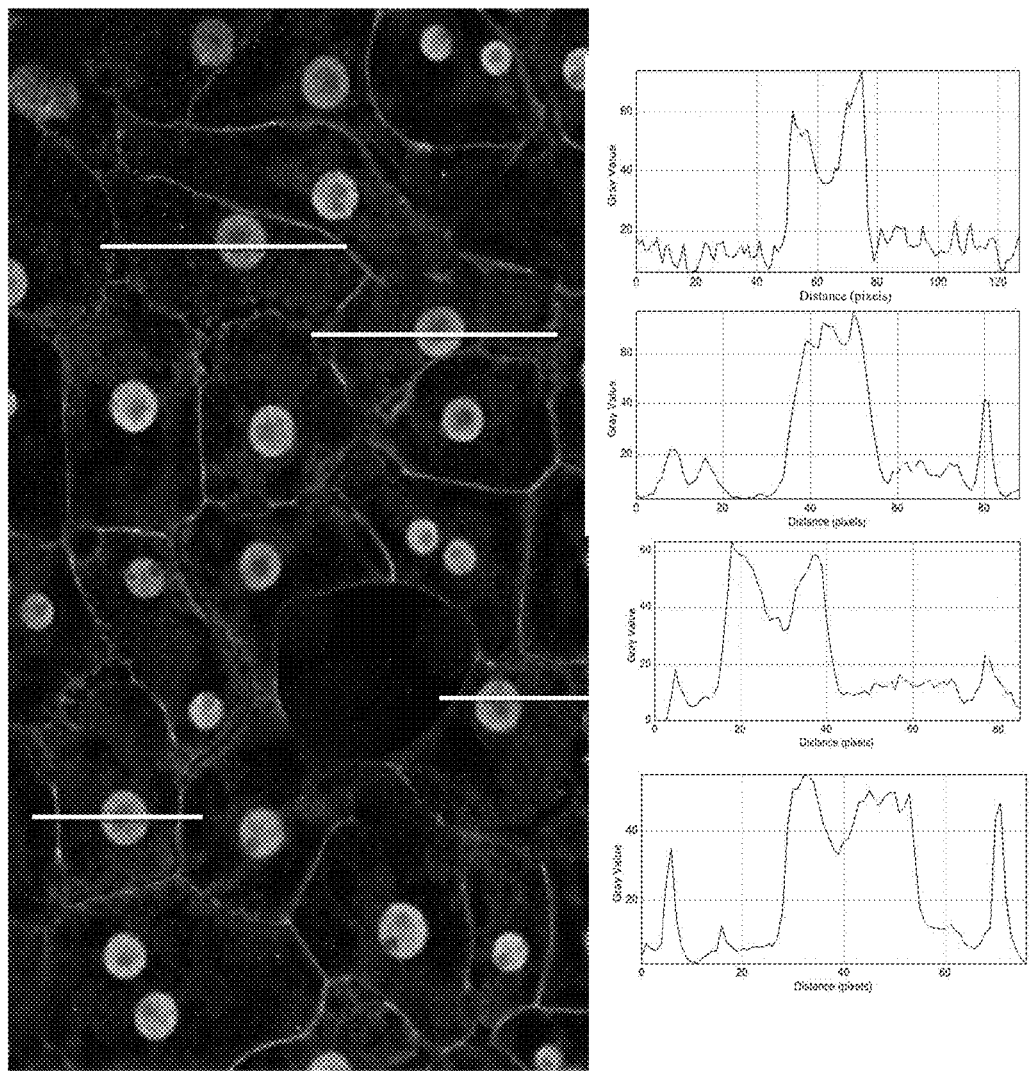
Figure 20C:
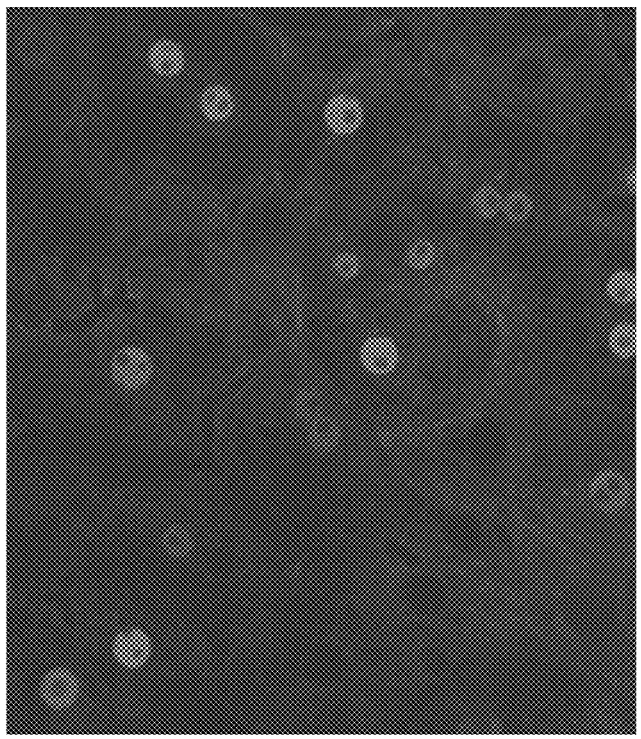
Figure 20D:
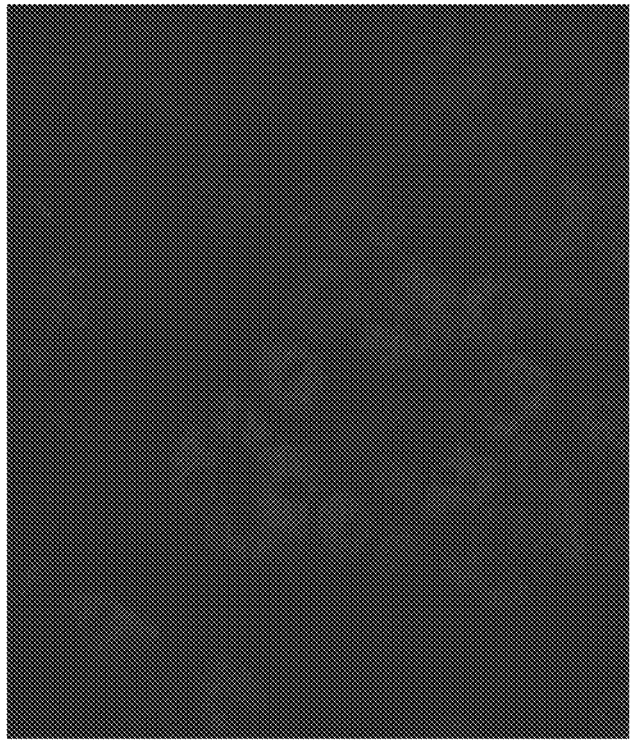
Figure 20F:
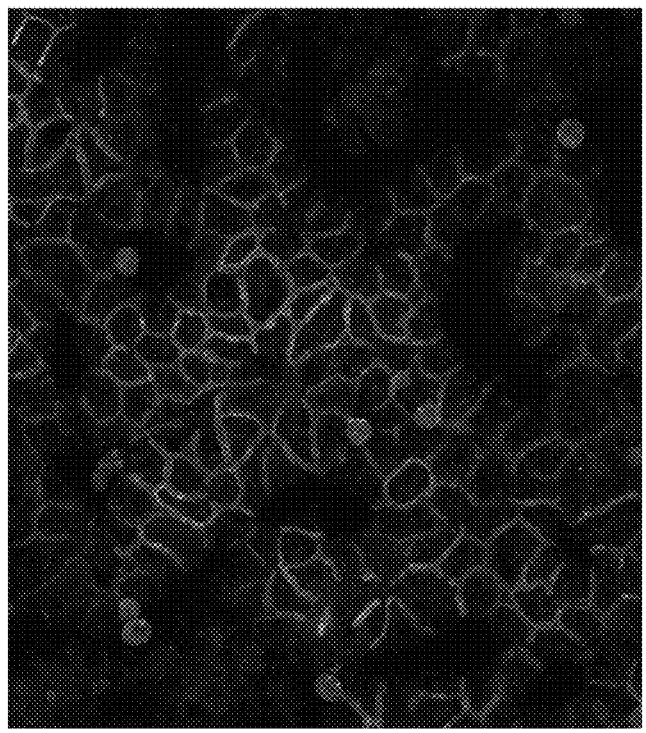
Figure 20E:
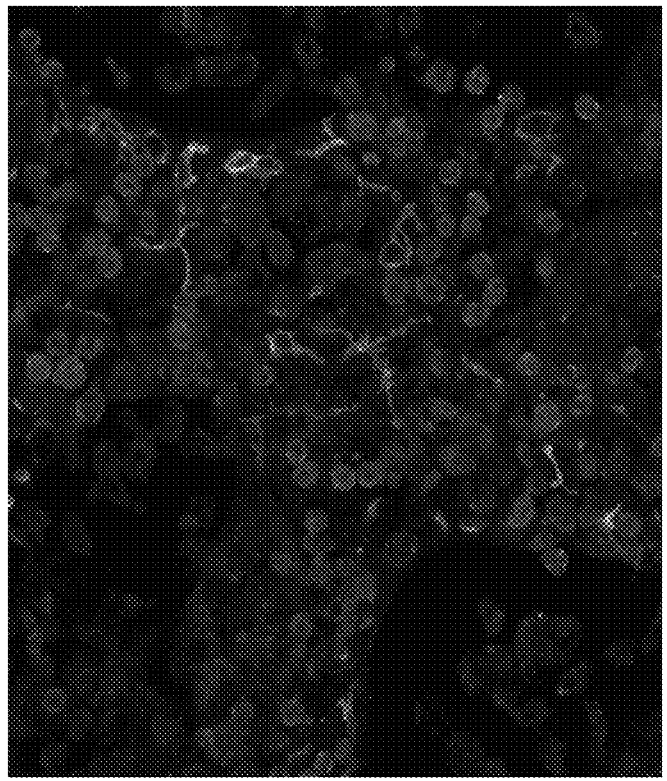
Figures 22A, 22B:
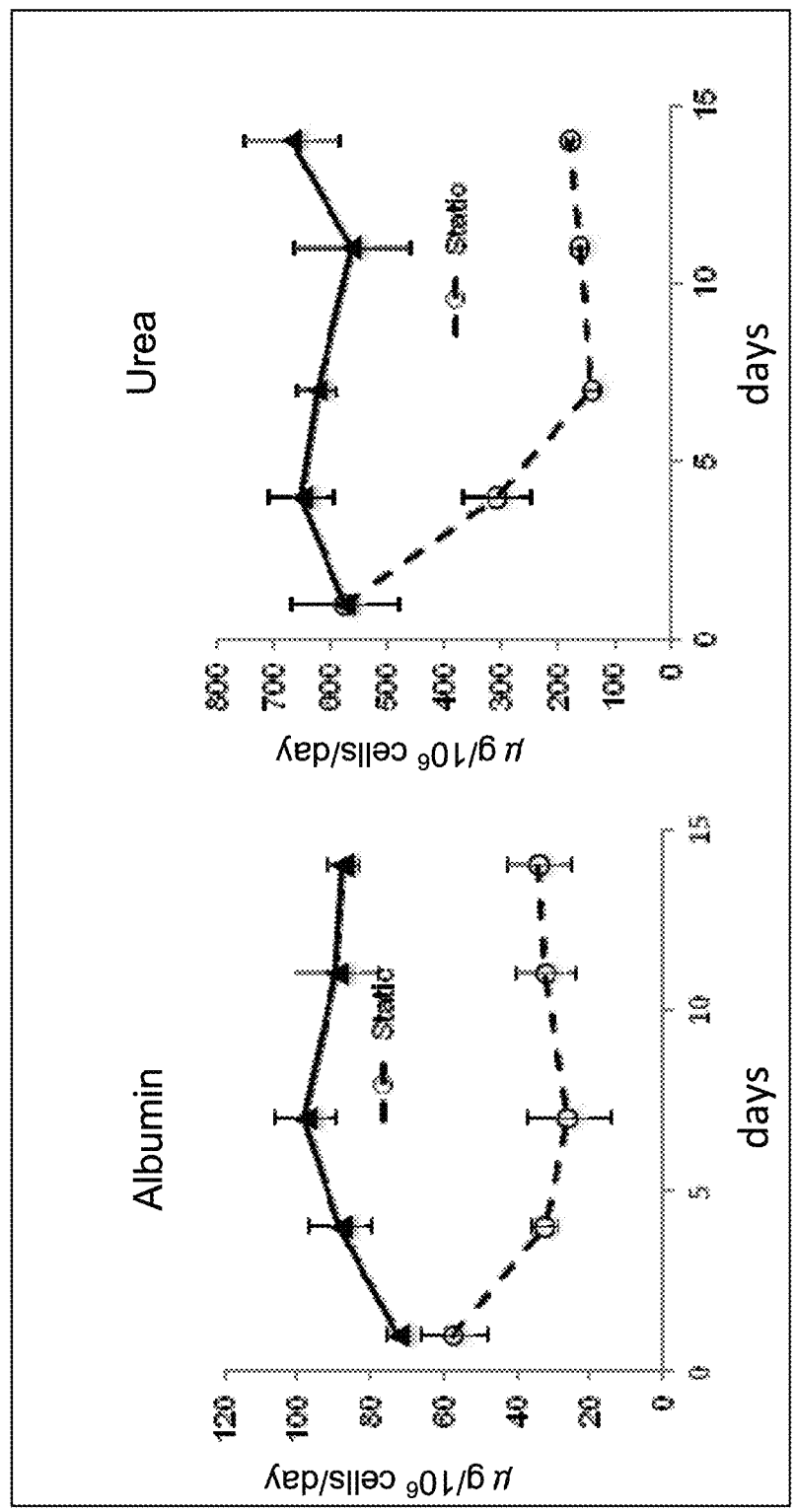
FIGS. 22A-B provide data for albumin and urea secretion in hepatocytes cultured under static conditions or controlled hemodynamics.

Freshly isolated rat primary hepatocytes were obtained and plated in collagen gel sandwiches on porous membranes. After 1 day, cultures were either continued under standard static conditions in a $CO_2$ incubator at 37° C. or introduced into the hemodynamic flow technology and maintained under controlled hemodynamics at pre-determined indirect shear rates of 0.6 dynes/cm$^2$. Media was changed every 48 hours in static cultures and the devices were continuously perfused. After 7 days, the cultures were removed and fixed with 4% paraformaldehyde before immunostaining with antibodies for the hepatocyte differentiation markers E-cadherin and HNF-4α, and visualized by confocal microscopy. E-cadherin staining patterns in static collagen gel sandwich cultures (FIG. 20A) displayed higher levels of cytoplasmic E-cadherin confirmed and quantified by morphometric analysis (adjacent graphs) and disrupted peripheral membrane distribution. Under controlled hemodynamics (FIG. 20B), hepatocytes exhibited a more differentiated morphology characterized by distinct peripheral membrane localization and lower cytoplasmic levels of E-cadherin. The staining pattern of the HNF4α showed a distinct difference in localization patterns with the cells in static cultures having a more diffuse staining pattern by 7 days (FIG. 20C) while the cells under controlled hemodynamics retained staining confined to the nucleus (FIG. 20D), similar to what is seen in vivo. Polarized morphology and canalicular localization of the transporter multi drug resistant protein-2 (MRP-2) that appears after 5-7 days of culture in collagen gel sandwiches is lost in static cultures by day 14 (FIG. 20E) but the canalicular network patterns are stable and extensive under controlled hemodynamics (FIG. 20F). Day 14 cultures maintained under controlled hemodynamics co-stained for MRP-2 and HNF-4α (FIG. 21A) alongside sections from rat in vivo liver (FIG. 21B) show very similar staining patterns. Transmission electron microscopy images of day 7 cultures under controlled hemodynamics (FIG. 21C) demonstrate the retention of subcellular components such as rough and smooth endoplasmic reticulum and mitochondria in addition to confirming the presence of bile canaliculi and tight junctions.

(ii) Controlled Hemodynamics Results in Retention of Hepatocyte-specific Function in Rat Hepatocytes in a Collagen Gel Configuration Relative to Static Cultures over 14 Days.

Hepatocytes were cultured under static or controlled hemodynamics (0.6 dynes/cm$^2$) for 2 weeks and media sampled at 4, 7, 11, and 14 days. Assays for urea and albumin were performed on the media and the values were normalized to production rates over 24 hours per million cells based on the initial number of plated cells. Hepatocyte function reflected by secreted albumin estimated from media samples at various time points over 14 days and expressed as $\mu g/10^6$ µlated hepatocytes/day (FIG. 22A), showed significantly higher levels (3-4 fold) under controlled hemodynamics (solid line) as compared to static cultures (dashed line) (Day 7: 97.96±11.34 vs. 25.84±8.22, p=0.00001; Day 14: 87.80±8.62 vs. 33.93±4.39, p=0.0001). Urea secretion (FIG. 22B) by hepatocytes expressed as $\mu g/10^6$ µlated hepatocytes/day under controlled hemodynamics (solid line) was also found to be at 4-5 fold higher levels than static cultures (dashed line) consistently over two weeks in culture (Day 7: 622.78±33.96 vs. 139.76±13.37, p=2.7×10$^{-9}$; Day 14: 667.71±84.37 vs. 178.68±6.13, p=1×10$^{-6}$).

(iii) Controlled Hemodynamics Differentially Regulates the Expression of Phase I and Phase II Metabolic Genes and Proteins Compared to Static Cultures.

Hepatocytes were cultured under static or controlled hemodynamics (0.6 dynes/cm$^2$) for 7 days. QRT-PCR was performed for select metabolic genes (Table 3) on RNA samples at day 7 from these conditions. All values were normalized to day 7 static cultures. Hepatocytes cultured under controlled hemodynamics resulted in gene expression levels that were consistently higher than in static cultures (n=11, Fold changes relative to static cultures: Cyp1A1 ~54, p=0.0003; Cyp1A2~64, p=0.005, Cyp2B1 ~15, p=0.001: FIG. 23A, Cyp2B2~2.7, p=0.09 and Cyp3A2~4, p=0.075: FIG. 23B) and closer to in vivo levels. Interestingly, the expression levels of the gene for the Pi subunit of phase II enzyme GST, known to increase in static cultures over time, was lower in both in vivo liver (−4.9 fold, p=0.152) and hepatocytes cultured under controlled hemodynamics (−2.3 fold, p=0.025) compared to static cultures (FIG. 23C).

Hepatocytes were cultured under static or controlled hemodynamics (0.6 dynes/cm$^2$). Cell cultures were taken down at 4,7, 11 and 14 days and cell lysates were obtained as described in the methods section, normalized to total protein, and equivalent samples were loaded and run on SDS page gels before probing with antibodies for the phase II enzyme UGT1 A1 and β-actin (for normalization). Western blots (FIG. 23D) demonstrate that UGT1 A1 is upregulated under controlled hemodynamics as compared to static conditions at all the time points over 2 weeks in culture. In the same experiment, part of the porous membrane of the TRANSWELL from 14 day cultures under controlled hemodynamics was fixed with 4% paraformaldehyde and stained for HNF-4a and the canalicular transporter protein MRP-2, demonstrating retention and localization of MRP-2 along the canalicular junctions between the hepatocytes (FIG. 21A). The remainder of the membrane was excised after removal from the device and immediately incubated with the substrate carboxy-2,7-dichlorofluorescein diacetate (CDFDA). The cells were imaged by confocal microscopy over a time window of 20 minutes to observe the breakdown of the substrate into carboxy-2,7-dichlorofluorescein (CDF) and its active secretion into the bile canalicular structures (seen in FIG. 21C). The pattern was very similar to that of sectioned samples of in vivo liver immunostained with antibodies to MRP-2 and HNF-4a (FIG. 21B).

(iv) Rat Hepatocytes Cultured under Controlled Hemodynamics Display a Higher Level of Basal and Inducible Cytochrome p450 Activity than Static Cultures at More In Vivo-like Concentrations.

To validate that the increase in metabolic genes and proteins translated to changes in metabolic activity, primary rat hepatocytes were cultured as described earlier in the cone-and-plate devices under controlled hemodynamics (0.6 dynes/cm$^2$) and in static collagen gel cultures. After 5 days, they were either left untreated or treated with 0.1% DMSO, 1A/1B inducer 3-Methyl Cholanthrene (3-MC, 1 μM in static and 0.1 μM under controlled hemodynamics) or 3A inducer dexamethasone (50 μM in static and 02.5 μM under controlled hemodynamics). After 48 hours, on day 7, segments of the porous membrane from the devices containing hepatocytes cultured under controlled hemodynamics that were roughly 2.0 cm$^2$ in area were excised and transferred to standard 24-well plates and treated with substrates for the Cyp p450 enzymes in parallel to corresponding static cultures treated with the different agents. Cytochrome p450 assays were done on day 7 using commercially available P450-GLO kits. After 4 hours the media was transferred to 96-well plates and assayed for luminescent metabolites to reflect cytochrome p450 activity. Values were normalized to the ATP content of the cells assessed by CELLTITER-GLO assay in order to get an accurate representation of live cells and avoid any confounding effects of the collagen gels on total protein measurements.

Basal activity level of the cytochrome p450 enzymes (FIG. 24A) in untreated cultures was upregulated by controlled hemodynamics compared to static (1A~15 fold, 1B~9 fold and 3A~5 fold). In spite of higher levels of basal activity, under controlled hemodynamics the response to classical inducers (FIG. 24B) was well maintained (1A/1B response to DMSO vs. 3-MC −4.87 vs. 133.06; 3A response to DMSO vs. Dexamethasone −11.64 vs. 57.53).

While initially measuring the Cyp activity to confirm the enhanced gene expression that was noted under controlled flow, 50 μM dexamethasone, the concentration recommended for inducing static cultures, was toxic in this system. As a result the concentration of the dexamethasone was decreased to 1 μg/ml in order to get an inductive response, a level that correlates well with plasma concentrations seen in vivo in rats. Similarly, induction responses for 3-MC were also seen at 10-fold lower levels under controlled hemodynamics.

Figure 24A:
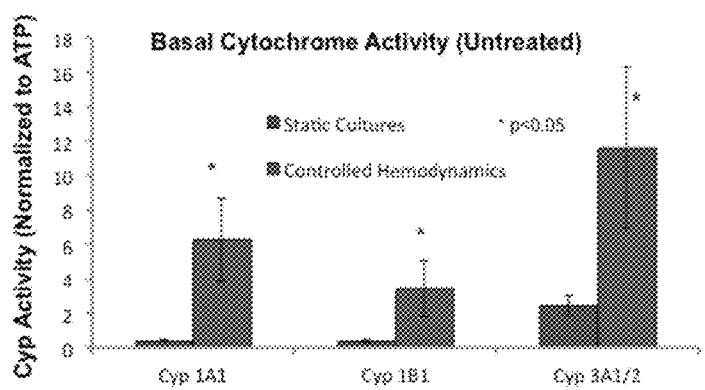
FIGS. 24A-B provide cytochrome p450 activity data for hepatocytes cultured under static conditions or controlled hemodynamics.
Figure 24B:
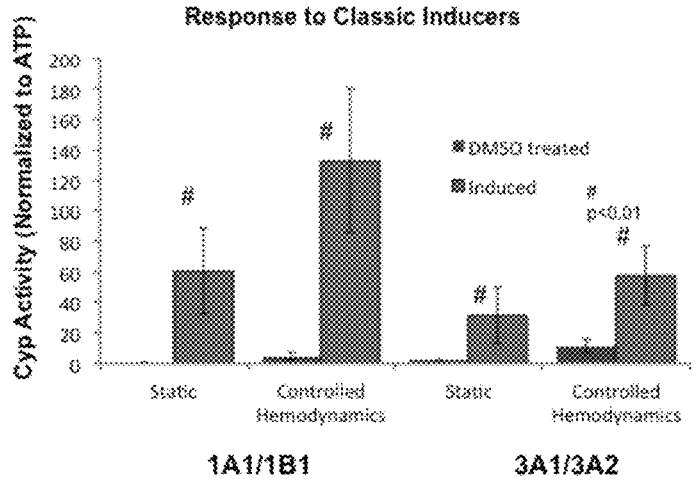
Figure 24C:
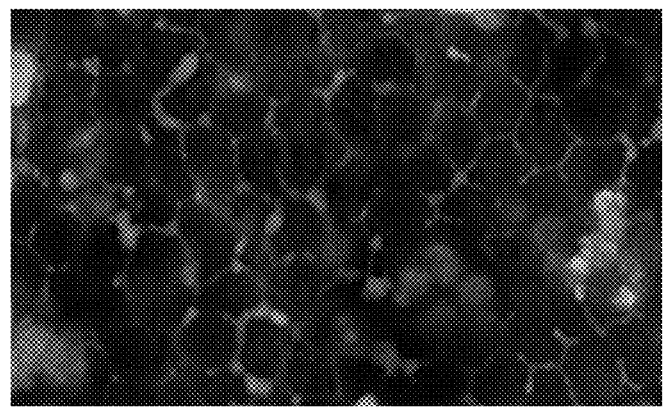
FIG. 24C is a fluorescent microscopy image from an assay for transporter activity in hepatocytes cultured under controlled hemodynamics.

To confirm the presence of transporter activity under controlled hemodynamics, TRANSWELL filter segments from the devices were incubated with the substrate carboxy-2,7-dichlorofluorescein diacetate (CDFDA). The compound was broken down to the fluorescent form CDF Carboxy-2, 7-Dichlorofluorescein which was actively secreted out into the canalicular spaces demonstrating active canalicular transport (FIG. 24C).

The data described above are the result of experiments carried out to evaluate the effect of exposing hepatocytes to controlled hemodynamics in order to restore their phenotype more similar to that observed in vivo. These experiments used standard media formulations routinely used in static culture in order to allow for side by side comparison with the static collagen gel cultures and identify the selective benefits of controlled hemodynamics. In the course of these experiments, hepatocytes cultured under these controlled hemodynamic conditions demonstrated enhanced in vivo-like phenotype and function and were more responsive to inducers such as dexamethasone and 3-MC. However, some accumulation of lipids was also observed in hepatocytes cultured with the concentrations of glucose (17.5 mM) and insulin (2 μMol) which are used routinely for assays in static systems. It was discovered that when hepatocytes are cultured under controlled hemodynamic conditions as described herein, much lower concentrations of glucose and insulin, similar to the concentrations observed in healthy individuals in vivo, can be used. The data indicate that these lower concentrations of glucose (5.5 mM) and insulin (2 nM) further enhance hepatocyte function and metabolic activity. Moreover, hepatocytes can be cultured under controlled hemodynamics in media containing the higher concentrations of glucose and insulin in order to create a model of fatty liver disease, as explained further in the following Example.

(v) Primary Rat Hepatocytes Cultured under Controlled Hemodynamics Demonstrate Responsiveness to Insulin and Glucagon.

Primary rat hepatocytes isolated and plated as described above were cultured in the cone-and-plate devices under controlled hemodynamics for 7 days prior to washing with PBS and incubation with the substrates glycerol (2 mM) or lactate (20 mM) and pyruvate (2 mM) either in the presence or absence of the regulatory hormones insulin (2 nM) or glucagon (100 nM). Glucose levels measured in the supernatant after 4 hours by the AMPLEX RED assay showed that in the absence of a substrate, insulin decreased glucose levels by 27% while glucagon increased it by 51%. In the presence of the substrate glycerol, glucose produced by the hepatocytes increased by 67%. Addition of glucagon increased glucose levels by further 15% while insulin decreased glucose levels by 38%. When lactate and pyruvate were used as substrates, glucose produced by the hepatocytes increased in the presence of glucagon by 80% while insulin decreased glucose levels by 25%. These data are summarized in Table 6.

TABLE 6

| Substrate | Effect of Insulin (% Change) | Effect of Glucagon (% Change) |
| --- | --- | --- |
| No substrate | −27% | +51% |
| Glycerol (+67%) | −38% | +15% |
| Lactate/Pyruvate | −25% | +80% |

(vi) Cryopreserved Human Hepatocytes Cultured under Controlled Hemodynamics Demonstrate Induction Responses to Phenobarbital and Rifampicin at In Vivo Level Concentrations.

Figures 35A, 35B, 35C:
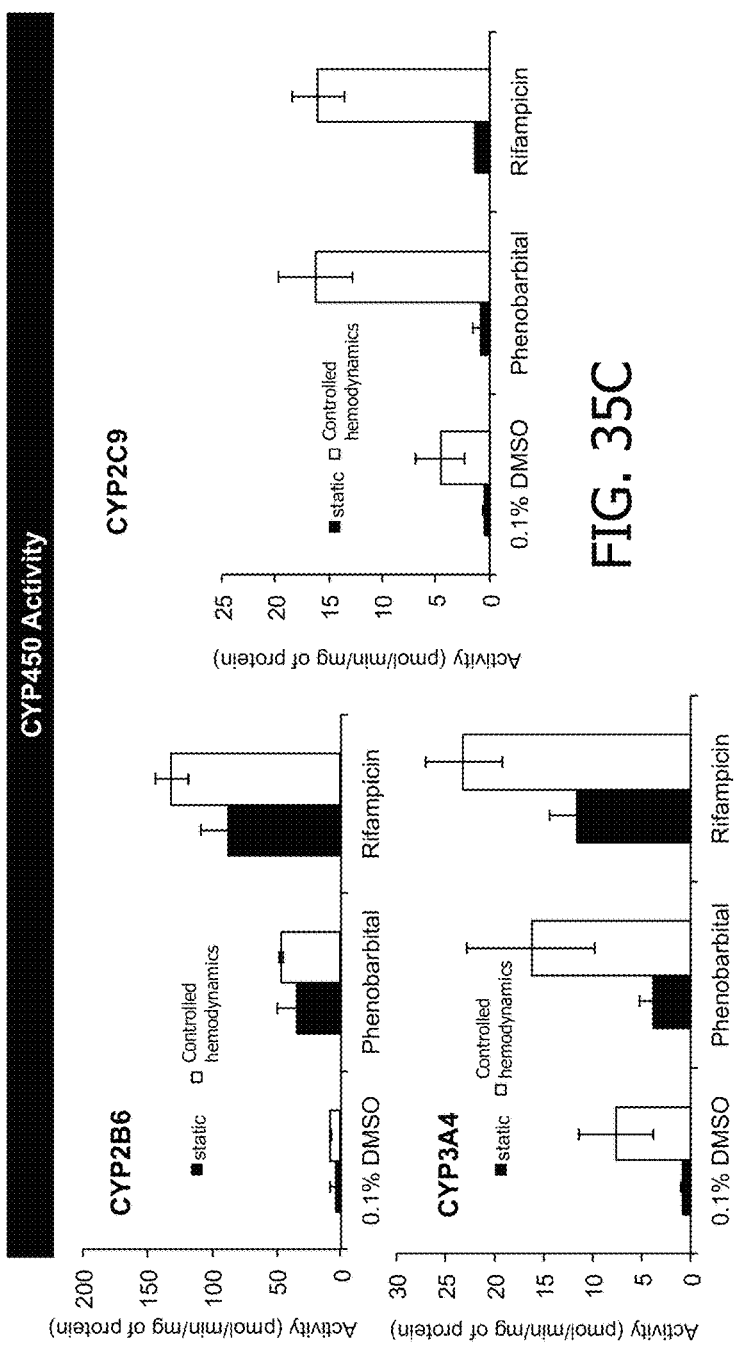
FIGS. 35A-C provide cytochrome activity data for hepatocytes cultured under controlled hemodynamic conditions or static conditions in the presence of phenobarbital or rifampicin.

Human hepatocytes were cultured in the cone-and-plate devices under controlled hemodynamics under the operating conditions described above or were cultured under static conditions (controls) for 7 days before being exposed to the known CYP inducer drugs phenobarbital (500 µM in for static conditions and 50 µM for controlled hemodynamic conditions) or rifampicin (25 µM in for static conditions and 2.5 µM for controlled hemodynamic conditions) for 72 hours. The hepatocytes were then washed with PBS and incubated with medium containing a cocktail of CYP substrates as described above for 4 hours. The culture supernatants were then collected and analyzed for formation of metabolites to assess specific activity of specific CYP enzymes. Results were normalized to protein content of the cells and expressed as pmol/min/mg of protein. Vehicle treated controls with DMSO 0.1% exhibited higher levels of CYP2B6, CYP2C9 and CYP3A4 in under controlled hemodynamic conditions as compared to static conditions (7.7 vs. 4.6, 4.6 vs. 0.5 and 7.6 vs. 0.7 µmol/min/mg of protein, respectively). Treatment with phenobarbital at the lower concentration (50 uM) under controlled hemodynamic conditions compared to higher concentration under static conditions (500 µM) also resulted in comparable or higher levels of enzyme activities of CYP2B6, CYP2C9 and CYP3A4 (45.9 vs. 34.3, 16.3 vs. 0.9 and 16.3 vs. 3.8 pmol/min/mg of protein, respectively). Similarly, treatment with rifampicin at the lower concentration (2.5 µM) under controlled hemodynamic conditions compared to the higher concentration in static conditions (25 µM) also resulted in comparable or higher levels of enzyme activities of CYP2B6, CYP2C9 and CYP3A4 (87.3 vs. 131.1, 1.4 vs. 16.0 and 11.5 vs. 23.1 µmol/min/mg of protein, respectively). These results are depicted in FIG. 35.

(vii) Cryopreserved Human Hepatocytes Cultured under Controlled Hemodynamics Demonstrate Toxicity Responses to Chlorpromazine at In Vivo Level Concentrations.

Figure 36A:
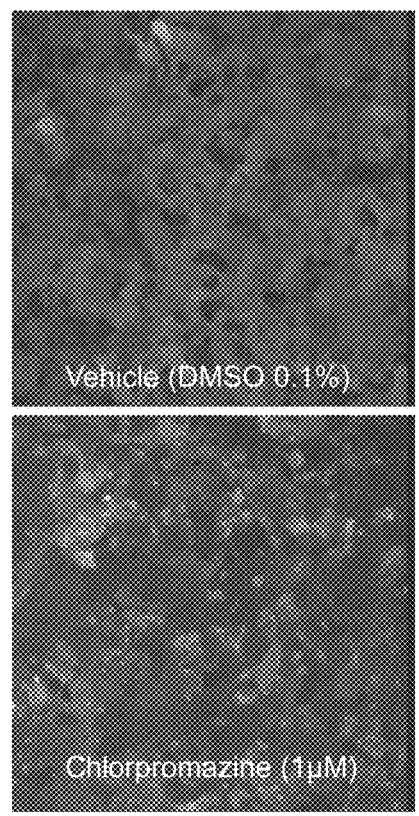
FIG. 36A provides fluorescence microscopy images showing the toxicity response of hepatocytes cultured under controlled hemodynamic conditions to chlorpromazine at an in vivo plasma $C_{max}$ concentration.
Figure 36B:
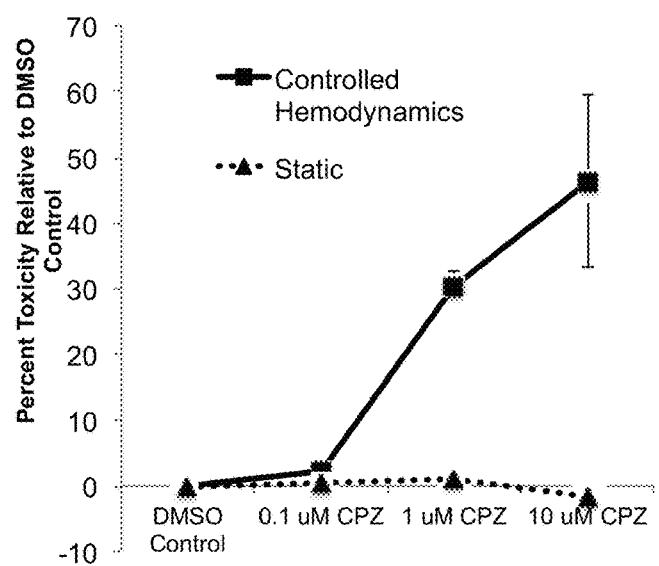
FIG. 36B provides data showing a toxicity dose-response for hepatocytes cultured under controlled hemodynamics or static conditions and exposed to varying concentrations of chlorpromazine.

Cryopreserved primary human hepatocytes thawed and plated as described above were cultured in the cone-and-plate devices under controlled hemodynamics or were cultured under static conditions (controls) for 7 days before being exposed to different concentrations of chlorpromazine (0.1 µM, 1 µM, and 10 µM) or vehicle control for 72 hours. Live-dead staining was performed on the hepatocytes with ethidium-calcein stain. Hepatocytes were also incubated with MTT reagent for 1 hour to assess viability. RNA was extracted from additional segments and RT-PCR was performed to assess selected toxicity and metabolic genes. Hepatocytes cultured under static conditions did not exhibit any toxicity at all the concentrations tested. However hepatocytes cultured under controlled hemodynamics demonstrated dose-dependent toxicity with 30.3% toxicity at 1 µM and 46.4% toxicity at 10 µuM (FIG. 36B). At 1 µM, the toxicity to the hepatocytes cultured under controlled hemodynamics devices was also detected by live-dead staining (FIG. 36A).

Figure 37A:
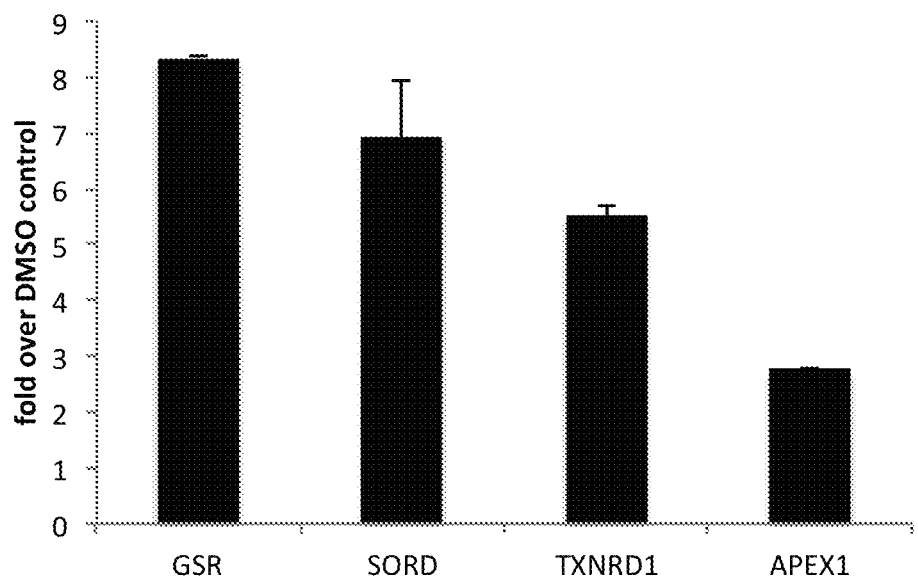
FIGS. 37A-B provides data showing upregulation of oxidative stress-related toxicity genes (FIG. 37A) and metabolic genes (FIG. 37B) in response to chlorpromazine in hepatocytes cultured under controlled hemodynamic conditions.
Figure 37B:
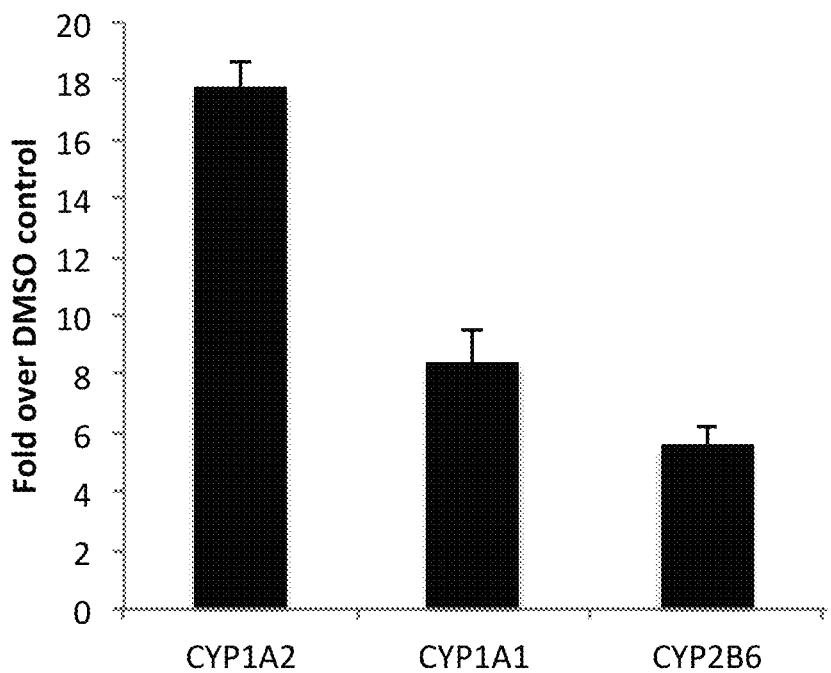

RT-PCR demonstrated upregulation of various oxidative stress related toxicity genes at 1 µM chlorpromazine under controlled hemodynamic conditions relative to static controls (8.3-fold for glutathione reductase (GSR), 5.5-fold for thioredoxin reductase 1 (TXNRD1), 6.9-fold for sorbitol dehydrogenase (SORD), and 2.8-fold for APEX nuclease (multifunctional DNA repair enzyme)). Concomitantly, certain metabolic genes were also upregulated under controlled hemodynamic conditions relative to static controls (17.8-fold for cytochrome p450 family 1 member A2 (CYP1A2), 8.4-fold for cytochrome p450 family 1 member A1 (CYP1A1), and 5.6-fold for Cytochrome p450 family 2 member B6 (CYP2B6). These results are depicted in FIG. 37. The results shown in FIG. 37 used primary human hepatocytes from KalyCell Donor #B0403VT.

These data show that primary human hepatocytes display toxic responses to chlorpromazine at clinical plasma $C_{max}$ concentrations under controlled hemodynamic conditions. These toxic responses are associated with the upregulation of oxidative stress-related genes and certain metabolic genes.

(viii) Primary Rat Hepatocytes Cultured under Controlled Hemodynamics Demonstrate Acute Toxicity and Release miRNA122 in Response to Chlorpromazine Exposure at In Vivo Level Concentrations.

Primary rat hepatocytes isolated and plated as described above were cultured in the cone-and-plate devices under controlled hemodynamic conditions or were cultured under static conditions (controls) for 7 days. The hepatocytes were washed with PBS and immediately incubated with either vehicle (distilled water) or chlorpromazine (1 µM) for 4 hours. The supernatant was collected and miRNA 122 levels were measured as described above. It was seen that under static conditions, chlorpromazine at 1 µM did not cause any change in miRNA 122 levels in the supernatants compared to vehicle controls. By contrast, hepatocytes cultured under controlled hemodynamic conditions and incubated with chlorpromazine (1 µM) for 4 hours released miRNA at significantly higher levels (6-fold over vehicle controls). These results are depicted in FIG. 38.

(ix) Primary Rat Hepatocytes Cultured under Controlled Hemodynamics Demonstrate Sublethal Toxicity and Exhibit Cholestatic Changes in Response to Troglitazone Exposure at In Vivo Level Concentrations.

Figure 40:
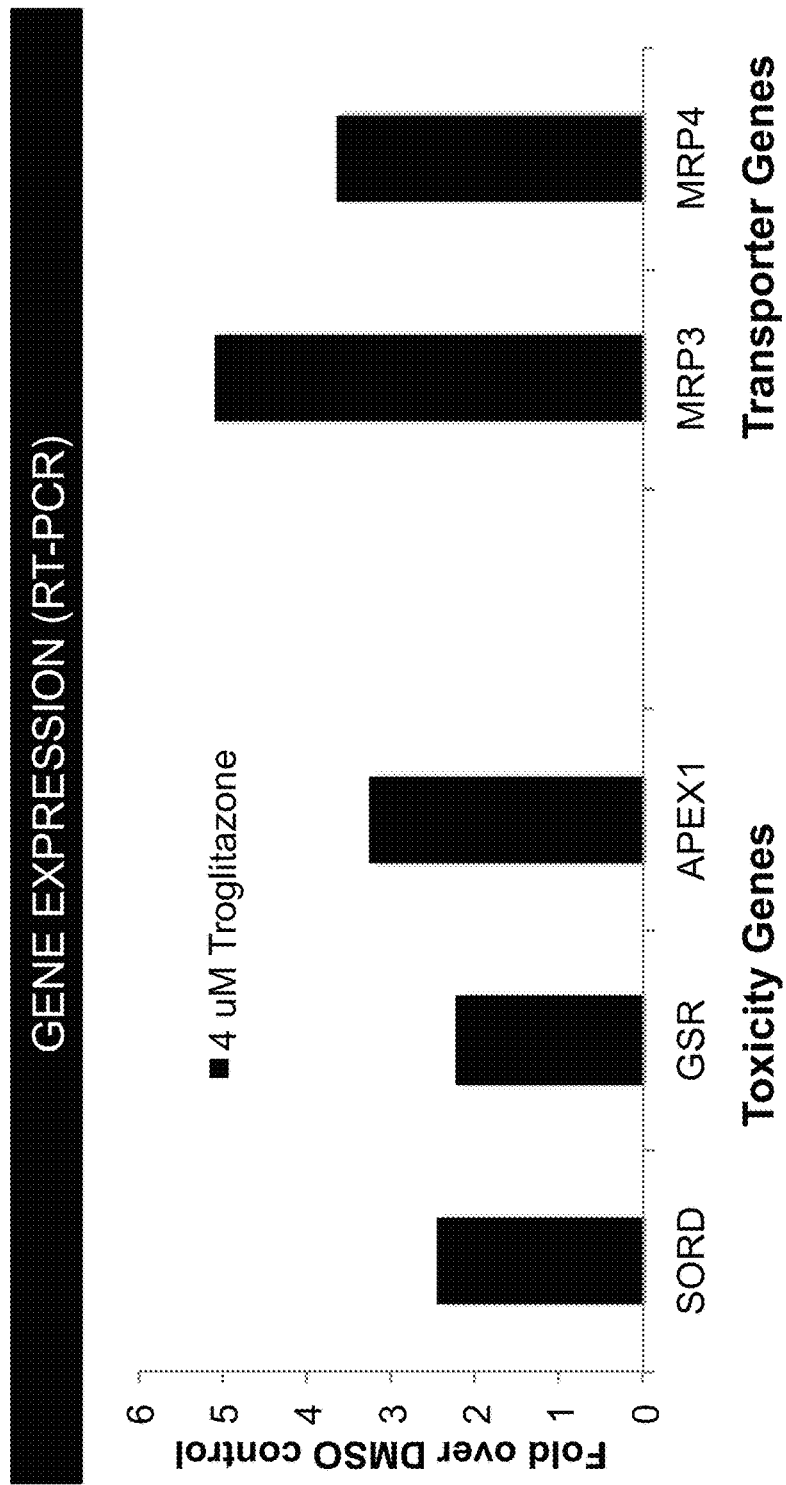
FIG. 40 provides data showing the upregulation of oxidative stress-related genes and MRP3 and MRP4 genes in hepatocytes cultured under controlled hemodynamic conditions in response to treatment with troglitazone.

Primary rat hepatocytes isolated and plated as described above were cultured in the cone-and-plate devices under controlled hyemodynamic conditions for 5 days before being exposed to 4 µM or 40 uM troglitazone for 48 hours. The hepatocytes were washed with PBS and and immediately incubated with the substrate 10 uM carboxy-2,7-dichlorofluorescein diacetate (CDFDA). The cells were imaged by confocal microscopy during a 20-min exposure to the nonfluorescent substrate CDFDA to allow for the hydrolysis of the substrate to the highly fluorescent Mrp-2 substrate carboxy-2,7-dichlorofluorescein (CDF) and its active secretion into the bile canalicular structures. At 4 uM, troglitazone was found to cause changes in the canalicular pattern with visibly dilated canalicular structures. These changes were much more prominent and extensive at 40 uM troglitazone (FIG. 39). The toxic response of rat hepatocytes to troglitazone at in vivo/clinical plasma $C_{max}$ concentrations when cultured under controlled hemodynamic conditions was associated with upregulation of oxidative stress-related genes and compensatory upregulation of MRP3 and MRP4 genes (FIG. 40).

(x) Primary Dog Hepatocytes Cultured under Controlled Hemodynamics Demonstrate Retention of Polarized Morphology and Exhibit Higher Expression of Key Metabolic Genes Relative to Static Cultures.

Figure 41A:
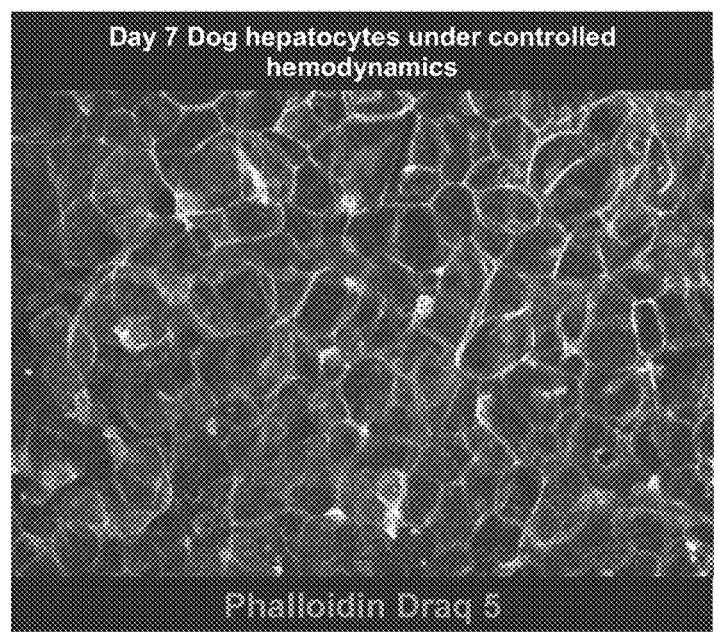
FIG. 41A provides a fluorescence microscopy image showing retention of polarized morphology in canine hepatocytes cultured under controlled hemodynamic conditions.
Figure 41B:
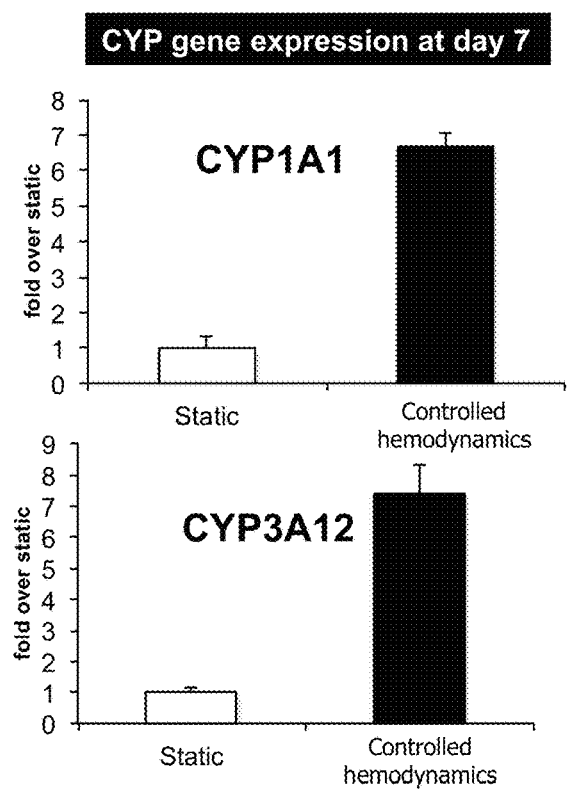
FIG. 41B provides gene expression data showing expression of CYP1A1 and CYP3A1 in canine hepatocytes cultured under controlled hemodynamic conditions or static conditions.
Figure 42:
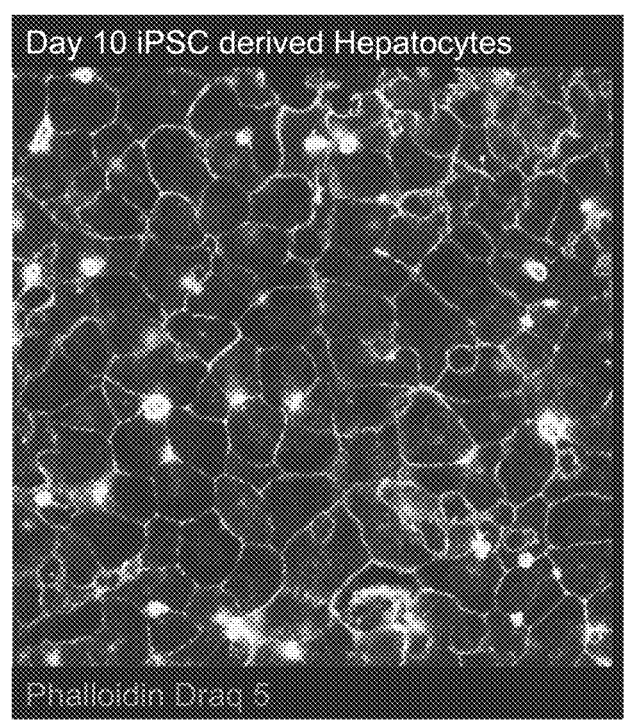
FIG. 42 provides a fluorescence microscopy image showing retention of polarized morphology in hepatocytes derived from inducible pluripotent stem cells (iPSCs) cultured under controlled hemodynamic conditions.

Freshly isolated canine hepatocytes were cultured in the cone-and-plate devices under controlled hemodynamic conditions under operating conditions similar to those described above for human hepatocytes or were cultured under static conditions (controls). After 7 days, cultures were fixed and stained with phalloidin and Draq5 for actin cytoskeleton and nucleus, respectively. RNA was collected from cells and RT-PCR was performed for specific metabolic genes. Canine hepatocytes were seen to retain polarized morphology with polygonal shape at 7 days and to express CYP1A1 and CYP3A12 at significantly higher levels than static controls (6.7- and 7.4-fold respectively). These results are depicted in FIG. 41.

Example 13

An In Vitro Model for Fatty Liver Disease

Nonalcoholic fatty liver disease (NAFLD) is the most common cause of liver dysfunction and is associated with obesity, insulin resistance, and type 2 diabetes. The changes in the fatty liver progress from early accumulation of fat vesicles within hepatocytes (hepatic steatosis) to subsequent loss of liver metabolic function and inflammatory changes, ultimately leading to fibrosis and cirrhosis. Animal in vivo models of fatty liver disease have successfully used either high fat diets or low fat, high carbohydrate diets that induce the hyperglycemia and hyperinsulinemia reflective of the diabetic milieu to induce triglyceride buildup. However in vitro models typically use only overloading with free fatty acids (oleic, palmitic or linoleic acid) to induce fatty changes and may not capture the de novo hepatocyte response to the high levels of glucose and insulin that may play a critical role in the pathogenesis of the disease. Static hepatocyte cultures are also known to have a markedly decreased insulin response and standard culture medias typically require high non-physiological levels of the hormone for basic hepatocyte survival and function. The model described herein, by contrast, preserves a more physiological hepatocyte response to drugs and hormones and allows us to maintain basic liver function at closer to in vivo concentration levels of glucose and insulin (as described above in Example 12), and furthermore allows us to elicit the pathologic response seen in fatty liver by creating a diabetic-like milieu characterized by high glucose and insulin levels.

Methods:

(i) Animal Surgery and Hepatocyte Isolation

Animal surgery and hepatocyte isolation were performed as described above in Example 12.

(ii) Cell Culture and Device Operating Conditions

Healthy hepatocyte culture media: The healthy hepatocyte culture media contained base media of DMEM/F12 containing low glucose (5.5 mM), supplemented by fetal bovine serum (10% at the time of plating and reduced to 2% for maintenance after 24 hours). Additionally, the media contained gentamycin (50 µg/ml), ITS (insulin, transferrin, and selenium; insulin concentration of 2 nM), 1% non-essential amino acids (NEAA), 1% GLUTAMAX (a media supplement containing L-alanyl-L-glutamine), and dexamethasone (1 µM at plating and 250nM for maintenance after 24 hours for the data shown in FIGS. 25 and 26; 100 nM throughout the experiment for the data shown in FIGS. 27-34).

Media to induce fatty liver changes ("fatty liver media'): The culture media used to induce fatty liver changes contained base media of DMEM/F12 containing high glucose (17.5 mM), supplemented by fetal bovine serum (10% at the time of plating and reduced to 2% for maintenance after 24 hours). The media also contained gentamycin (50 µg/ml), ITS (insulin concentration 2 µMol), 1% NEAA, 1% GLUTAMAX, and dexamethasone (1 µM at plating and 250 nM for maintenance after 24 hours for the data shown in FIGS. 25 and 26; 100 nM throughout the experiment for the data shown in FIGS. 27-34).

Collagen coating and plating: Collagen solution was made as described above in Example 12. The lower surfaces of the porous membranes of 75 mm TRANSWELLS (polycarbonate, 10 µm thickness and 0.4 µm pore diameter, no. 3419, Corning) were coated with 300 µl of the collagen solution. After allowing an hour for the solution to gel, the surfaces were washed with DPBS, hepatocytes were plated at a seeding density of 125,000 viable cells/cm$^2$, and a second layer of collagen gel added after 4 hours. After 1 hour, the TRANSWELLS were inverted and placed into cell culture dishes, and media was added (9 ml in the lower volume and 6 ml in the upper volume). After 24 hours (i.e., on day 2 of the experiments), the media was changed to maintenance media (the healthy or fatty liver media described above) and the Petri dishes were placed in the cone-and-plate hemodynamic flow device, and controlled hemodynamics were applied to the surface of the porous membrane of the TRANSWELL in the upper volume. In some experiments, the maintenance media contained 1.5 µM pioglitazone in 0.1% DMSO vehicle or the 0.1% DMSO vehicle alone. The cells were cultured under controlled hemodynamics until day 7, when hepatocytes were examined using the assays described below.

Operating conditions: The shear stress was calculated as described above in Example 12. A range of applied shear stress conditions, generated by altering media viscosity and cone speed, and resulting in rates within an order of magnitude of the value predicted from literature (0.1 to 6 dynes/cm$^2$) were used. These were correlated with different transport profiles of reference dye horse radish peroxidase dye across the membrane. Cultures were run for 7 days and assessed for fatty liver changes.

(iii) Measurement of Fatty Liver Changes:

To examine changes occurring in the fatty liver model against healthy controls the following were evaluated:
(a) Changes in metabolic and insulin/glucose/lipid pathway genes (RT-PCR);
(b) Accumulation of intracellular lipids within hepatocytes by Oil Red O assay, Nile red staining, and measurement of total triglycerides;
(c) Changes in differentiated function of hepatocytes (urea and albumin secretion);
(d) Changes in metabolic activity (Cytochrome p450 assays); and
(e) Morphological changes within hepatocytes by transmission electron microscopy (TEM).

RT-PCR and urea and albumin assays were performed as described above in Example 12.

Staining Methods: Hepatocyte TRANSWELL membrane sections were permeabilized in 0.1% Triton-X diluted in PBS for 20 minutes and washed thrice in PBS for five minutes each. Samples were then blocked in 5% goat serum, 0.2% blotting grade non-fat dry milk blocker, and 1% BSA in PBS for 45 minutes. The samples were then washed thrice in 0.1% BSA in PBS and incubated with 1:5000 dilution of Nile red (1mM stock), 1:1000 DRAQ5 (a fluorescent DNA dye; Cell Signalling), 1:500 ALEXA FLUOR 488 conjugated phalloidin (Life Technologies), and 1% BSA in PBS for thirty minutes and protected from light. The samples were washed in 0.1% BSA in PBS thrice for five minutes each and mounted on glass cover slips using PROLONG GOLD antifade mounting media (an antifade reagent; Invitrogen). The samples were imaged on a Nikon C1+ Confocal System microscope.

Transmission Imaging Microscopy (TEM): Segments of the porous membranes from TRANSWELLS containing hepatocytes cultured under healthy or steatotic conditions for 7 days were washed with PBS before fixing in a solution containing 4% paraformaldehyde and 2% glutaraldehyde for 1 hour. The samples were then sent to be processed for TEM at the University of Virginia imaging center. TEM images were evaluated for accumulation of lipid within the hepatocytes, the appearance of subcellular organelles such as mitochondria and smooth and rough endoplasmic reticulum, retention of polarized morphology, and bile canaliculi.

Oil Red O Assay: Accumulation of intracellular lipids within hepatocytes was assessed by adapting and modifying a commercially available Steatosis Colorimetric Assay Kit (Cayman Chemical). At the end of the culture period, 2 $cm^2$ sized porous membrane segments containing the hepatocytes from devices under healthy and steatotic conditions were washed with PBS and fixed in 4% paraformaldehyde for 30 minutes. These porous membrane segments were then washed with PBS, dried completely and incubated with 300 µl of Oil Red O working solution for 20 minutes in 24 well plates. The porous membrane segments were then washed repeatedly with distilled water 7-8 times followed by two five minute washes with the wash solution provided in the Steatosis Colorometric Assay Kit. Dye extraction solution (300 µl) was added to each well and the plates were incubated on an orbital shaker for 15-30 minutes under constant agitation. The solution was then transferred to clear 96-well plates and absorbance was read at 490-520 nm in a spectrophotometer.

Measurement of Total Triglycerides: Triglyceride content was assessed using a commercially available colorimetric assay kit (Cayman Triglyceride Colorimetric Assay Kit, Cat # 10010303). At the end of the treatment period, cells were collected from the porous membranes by scraping with a rubber policeman and PBS, after which they were centrifuged (2,000×g for 10 minutes at 4° C.). The cell pellets were resuspended in 100 µl of cold diluted Standard Diluent from the triglyceride assay kit and sonicated 20 times at one second bursts. The cell suspension was then centrifuged at 10,000×g for 10 minutes at 4° C. The supernatant was removed and used for the assay as per the manufacturer's protocol and normalized to protein content from the same samples.

Cytochrome Activity Assays: Hepatocytes were cultured in the cone-and-plate devices under healthy and steatotic conditions for 7 days. Porous membrane segments roughly 2$cm^2$ in area were excised and transferred to standard 24-well plates alongside corresponding static cultures. The cells were incubated with 500 µl of healthy hepatocyte media containing substrates from commercially available P450-GLO kits at the manufacturer-recommended concentrations. After 4 hours, the media was transferred to 96-well plates and assayed for luminescent metabolites to reflect cytochrome p450 activity as per the manufacturer protocol. The ATP content of the cells in the same porous membrane segments or static wells was then estimated by the CELL-TITER-GLO assay using the manufacturer's protocol, and the cytochrome values were normalized to ATP content.

Figure 27A:
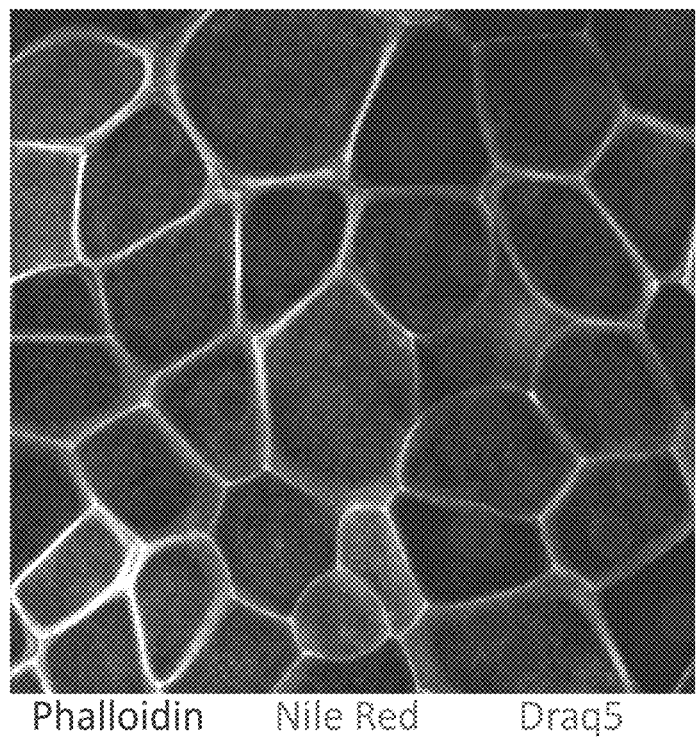
FIGS. 27A-B provide fluorescent microscopy images of hepatocytes cultured under healthy conditions or conditions that mimic fatty liver disease.
Figure 27B:
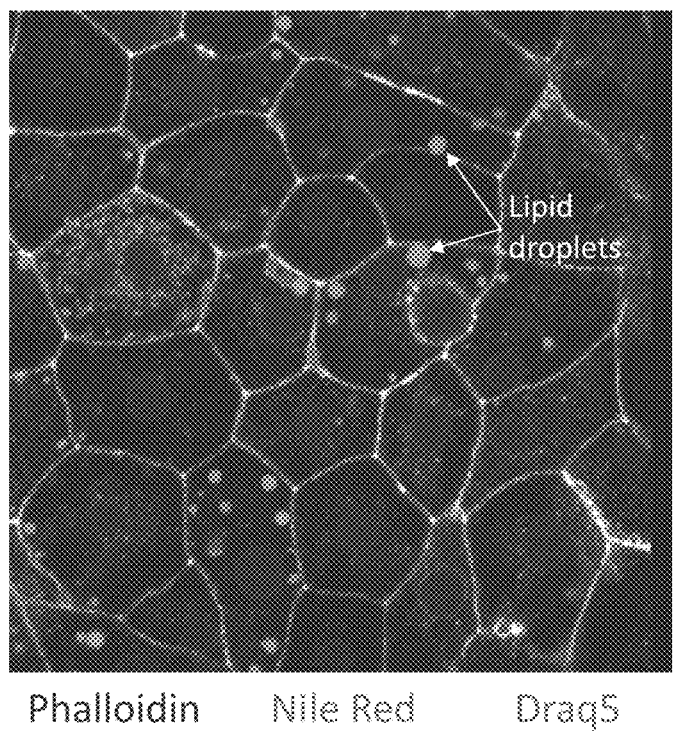

Results:

Nile red staining: FIGS. 27A and B show staining of hepatocytes cultured in the healthy (FIG. 27A) or fatty liver (FIG. 27B) media with Nile red, phalloidn, and DRAQS. As can be seen in FIG. 27B, the hepatocytes cultured in the fatty liver media (containing high concentrations of glucose and insulin) accumulate a large number of lipid droplets.

Figure 28:
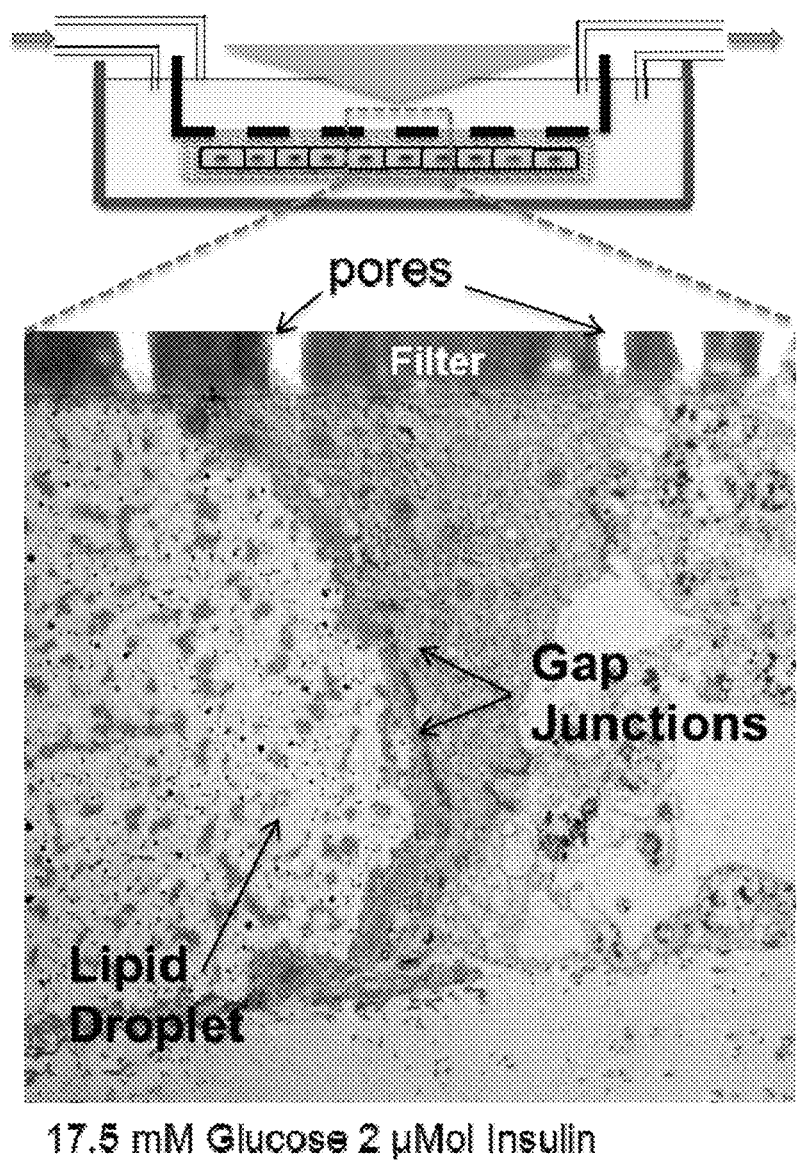
FIG. 28 shows a transmission electron microscopy image of rat hepatocytes cultured under high glucose/high insulin conditions.

Transmission electron microscopy: Hepatocytes cultured in the fatty liver media were also examined by transmission electron microscopy. As shown in FIG. 28, hepatocytes cultured under these conditions accumulate lipid. A large lipid droplet is indicated in the hepatocyte on the left side of the image. Gap junctions between two hepatocytes are also shown, demonstrating the polarized morphology.

Figure 29A:
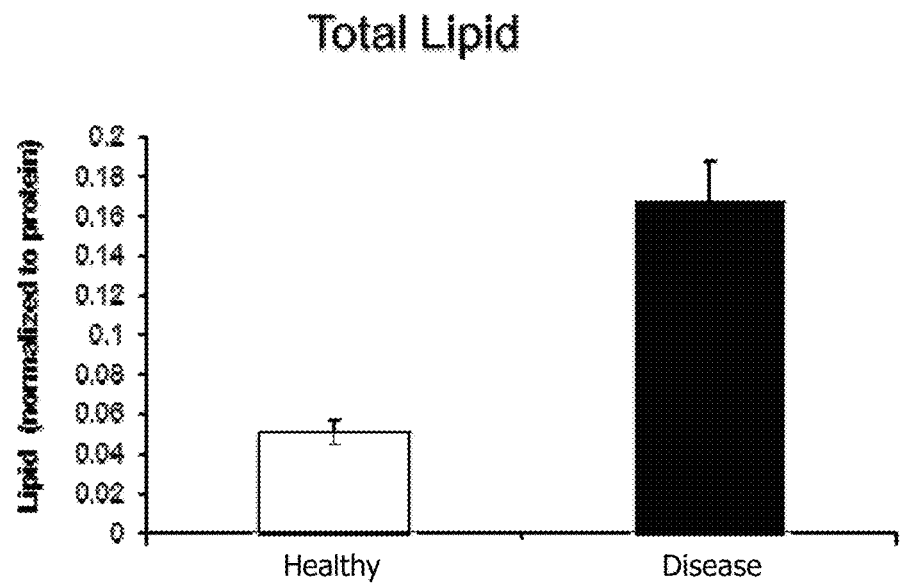
FIGS. 29A-B provide results from assays measuring total lipids and total triglycerides in hepatocytes cultured under healthy conditions or conditions that mimic fatty liver disease.
Figure 29B:
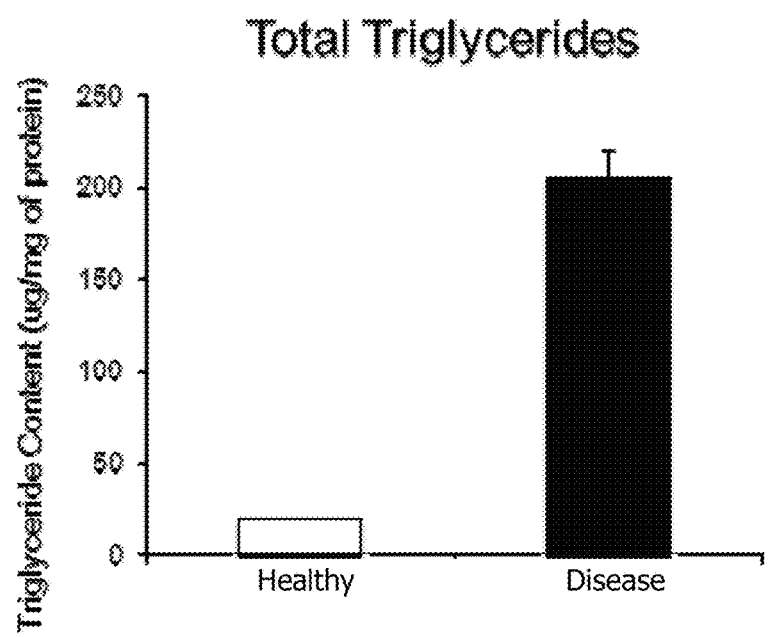

Total lipid and total triglycerides: As shown in FIG. 29, total lipid (FIG. 29A) and total triglycerides (FIG. 29B) were both significantly increased in hepatocytes cultured under the high glucose/high insulin fatty liver conditions in the presence of liver-derived hemodynamics. Oil red O quantification indicated that the total lipid was raised in the disease cultures by about 3-fold as compared to the healthy cultures.

Figure 25:
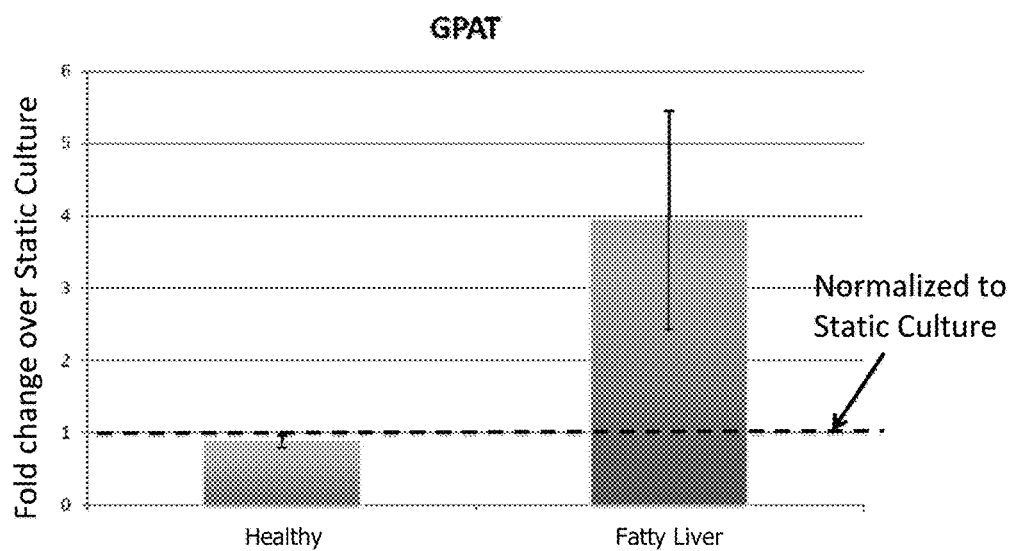
FIG. 25 shows gene expression data for an in vitro fatty liver model.

Gene expression: Glycerol 3-phosphate acyltransferase (GPAT) is a key enzyme involved in triglyceride synthesis and known to unregulated and contribute to steatosis and fatty liver. As shown in FIG. 25, primary rat hepatocytes cultured under controlled hemodynamics in the devices when exposed to pathological conditions (n=9) of high insulin (2 µMol) and high glucose (17.5 mMol) exhibit a significantly higher expression the GPAT gene (p=0.04) compared to those cultured under healthy physiological levels (n=6) of insulin (2 nMol) and glucose (5.5 mMol) in the media. The results are expressed as fold increase over standard static cultures in collagen gel sandwiches (2 µMol insulin and 17.5 mMol glucose).

Figure 30A:
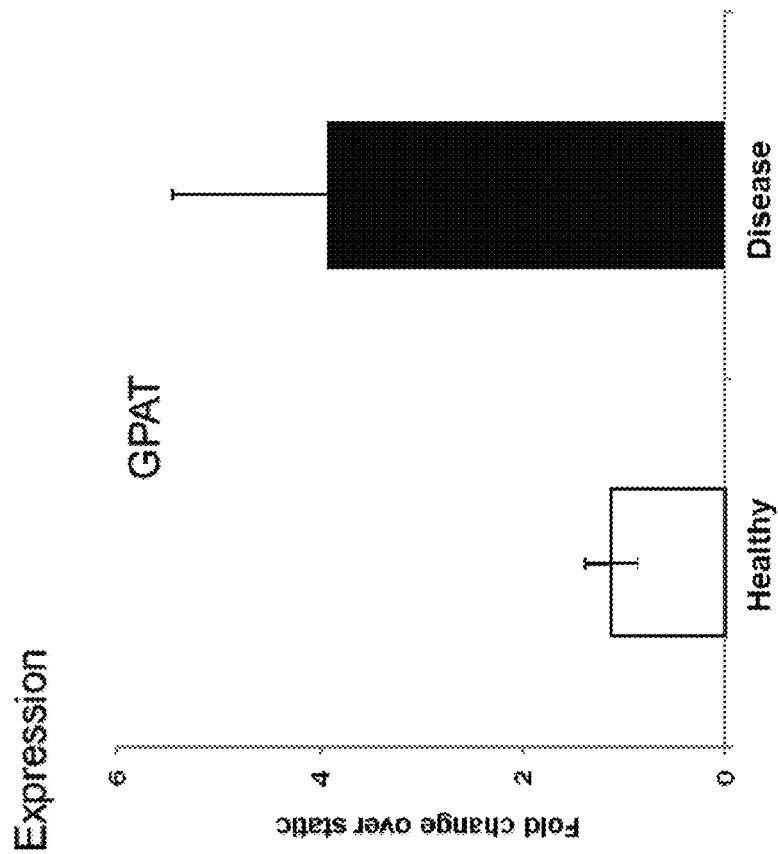
FIGS. 30A-B provide gene expression data for hepatocytes cultured under healthy conditions or conditions that mimic fatty liver disease.
Figure 30B:
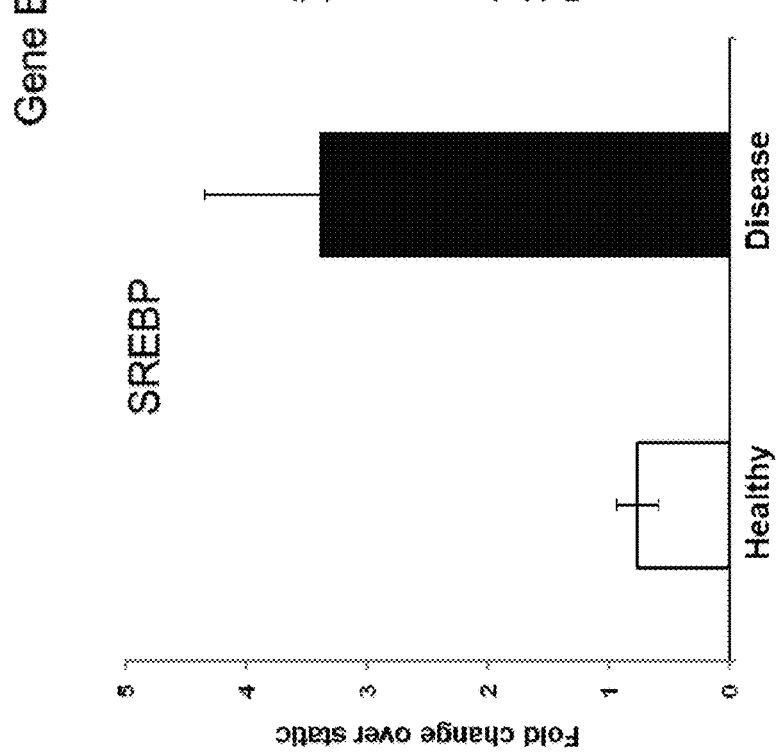

Similar results are shown in FIG. 30B for hepatocytes cultured under controlled hemodynamics in healthy or fatty liver media containing a lower concentration of dexamethasone. The hepatocytes cultured in the high insulin/high glucose (fatty liver) media exhibited significantly higher levels of GPAT expression as compared to hepatocytes cultured in the healthy media containing lower levels of insulin and glucose. As shown in FIG. 30A, hepatocytes cultured under controlled hemodynamics in the high insulin/high glucose media also exhibited significantly higher levels of expression of sterol regulatory element-binding protein (SREBP), another key gene responsible for lipogenisis, as compared to hepatocytes cultured in the healthy media.

Figure 26:
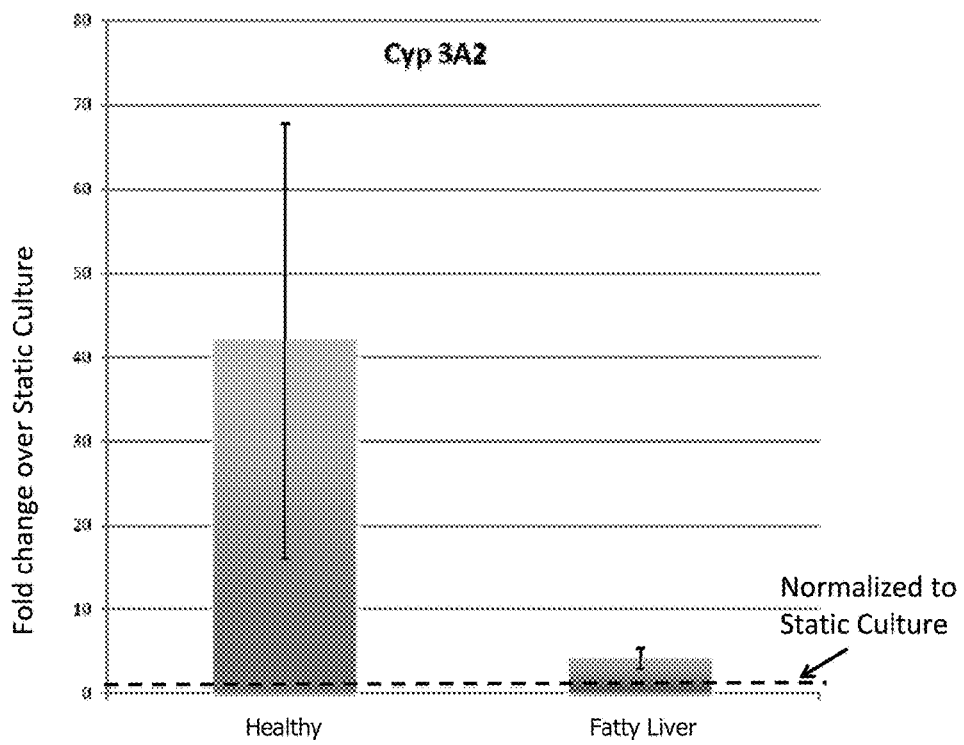
FIG. 26 shows gene expression data for an in vitro fatty liver model.

These steatotic changes were accompanied by concomitant metabolic changes. Of all the key metabolic enzymes, the cytochrome p450 3A family is responsible for the metabolism of a majority of drugs. As shown in FIG. 26, primary rat hepatocytes cultured under controlled hemodynamics in the devices with healthy physiological levels (n=6) of insulin (2 nMol) and glucose (5.5 mMol) in the media, exhibit a significantly higher expression level of the key metabolic enzyme cytochrome p450 3a2 (Cyp3A2; p=0.03), compared to those cultured under pathological conditions (n=9) with high insulin (2 µMol) and high glucose (17.5 mMol) levels. Both the healthy and pathological fatty liver levels under controlled flow are many fold higher than static cultures in collagen gel sandwiches (2 µM insulin and 17.5 mMol glucose).

Figure 31B:
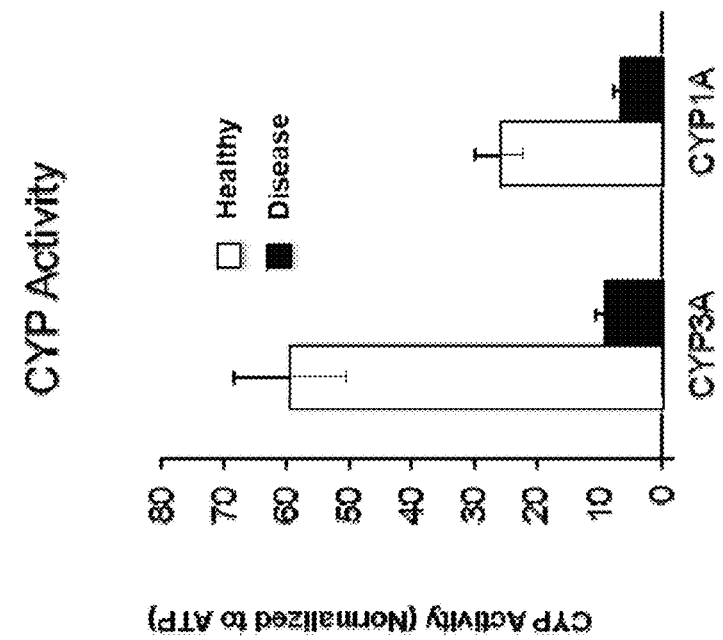
FIGS. 31A-B provide metabolic gene expression data and cytochrome p450 activity data for hepatocytes cultured under healthy conditions or conditions that mimic fatty liver disease.
Figure 31A:
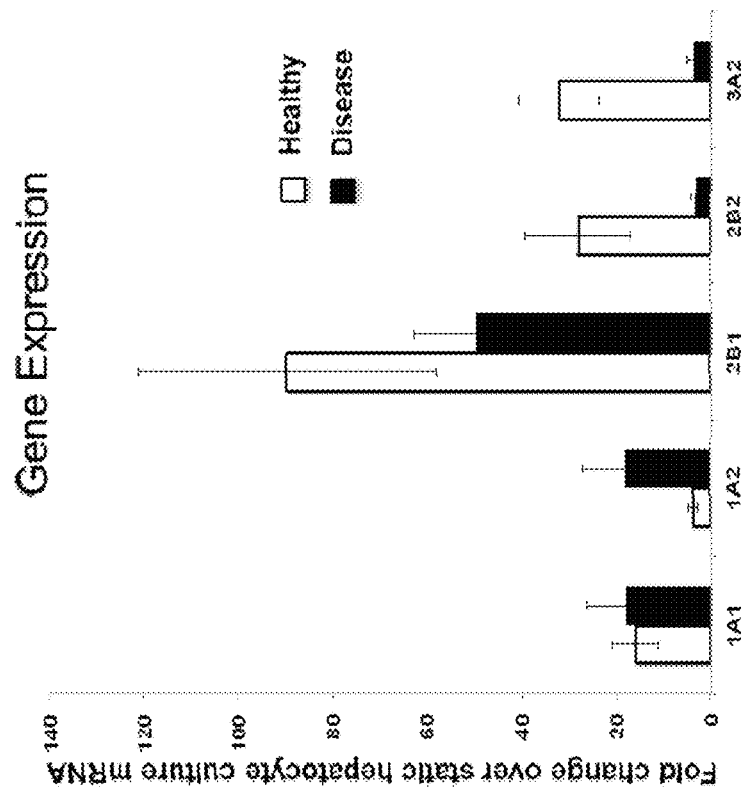

Similarly, as shown in FIG. 31A, expression of a number of phase I enzymes involved in drug metabolism are differentially regulated under low and high glucose/insulin conditions. Under hemodynamic flow, hepatocytes under healthy media conditions maintained high levels of mRNA expression of Cyp1a1, Cyp 2b1, 2b2, Cyp3a2,and (20, 90, 30 and 40-fold higher than traditional static cultures respectively), whereas Cyp 2b2 and Cyp 3a2 levels in hepatocytes cultured in the fatty liver media were decreased by 9 and 12 fold compared to healthy.

Cyp Activity: As shown in FIG. 31B, the activities of CYP3A2 and CYP1A1 were also reduced 3-6-fold under the high insulin/glucose fatty liver conditions compared to healthy, as measured by the p45glo assay.

Figure 33:
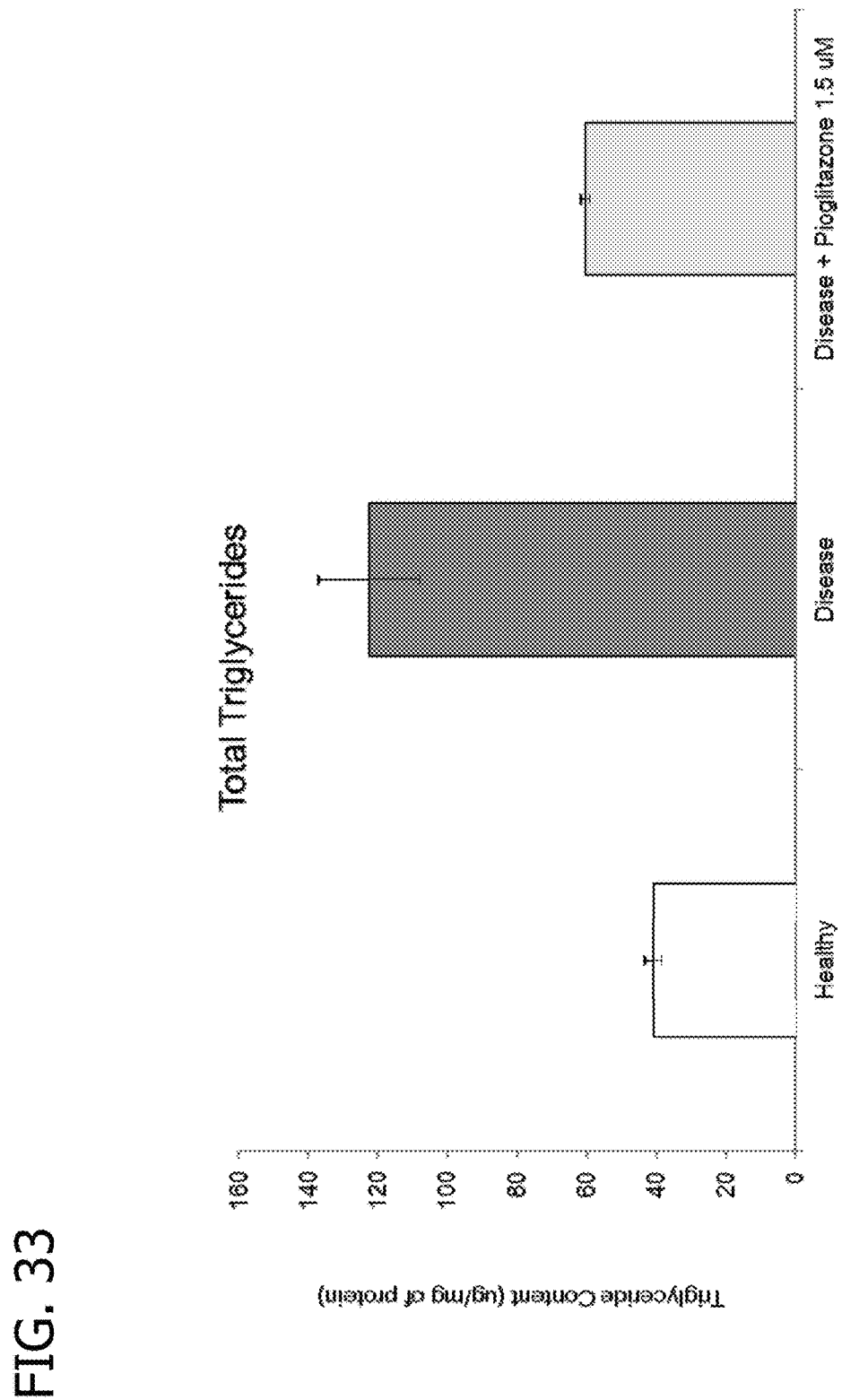
FIG. 33 provides results from an assay measuring total triglycerides in hepatocytes cultured under healthy conditions or under conditions that mimic fatty liver disease, in the presence or absence of pioglitazone.
Figure 34:
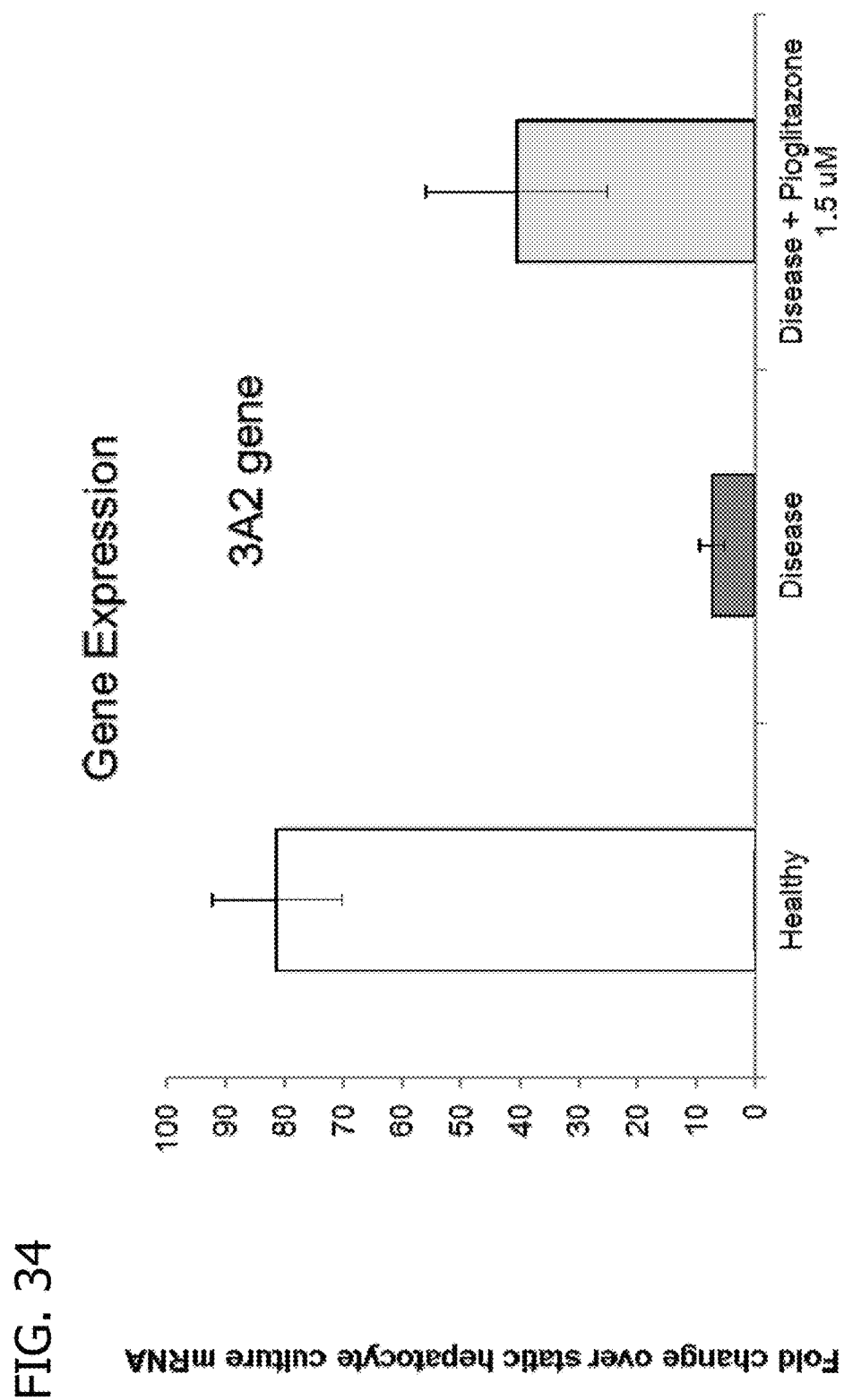
FIG. 34 provides metabolic gene expression data for hepatocytes cultured under healthy conditions or under conditions that mimic fatty liver disease, in the presence or absence of pioglitazone.

Pioglitazone treatment: Pioglitazone, a drug used to treat steatosis, was tested in the fatty liver model to determine if it could reverse the lipid accumulation and metabolic changes induced by the high insulin/glucose fatty liver media. The pioglitazone was added to the media at a concentration of 1.5 µM, a concentration selected based on the therapeutic $C_{max}$ observed for pioglitazone in vivo. Pioglitazone was effective in reducing the lipid buildup and triglyceride content while restoring metabolic gene expression under the disease conditions. As shown in FIG. 32, Nile red staining indicates that treatment with pioglitazone at in vivo therapeutic concentrations decreases lipid droplet formation under steatotic conditions. Pioglitazone also reduced total triglyceride content of hepatocytes cultured in the high insulin/glucose media to levels similar to those seem in the hepatocytes cultured under healthy conditions (FIG. 33). Moreover, as shown in FIG. 34, pioglitazone restored the expression of metabolic genes such as Cyp3A2 which are depressed by the high insulin/glucose disease conditions.

Conclusions:

In summary, a system was developed that preserves in vivo-like hepatocyte phenotype and response, to create a model of hepatic steatosis by inducing pathological steatotic changes in the presence of a high glucose/insulin milieu. Rat hepatocytes under controlled hemodynamics retain their response to insulin and glucose, and hepatocytes cultured under hemodynamic flow develop steatotic changes when cultured in high glucose and insulin (disease') conditions. The steatosis is mediated via de novo lipogenesis with upregulation of two key genes (SREBP and GPAT), and the increase in lipid accumulation and triglyceride content is accompanied by a concomitant decrease in metabolic gene expression and activity. Treatment with the PPAR-γ agonist pioglitazone helps prevent the buildup of lipid and loss of metabolic activity under the high glucose and insulin conditions. These data demonstrate a novel and important new in vitro model of diet induced non-alcoholic fatty liver disease (NAFLD) for which none currently exist.

Example 14

An Inducible Pluripotent Stem Cell (iPSC)-derived Human Hepatocyte System

Hepatocytes derived from inducible pluripotent stem cells (iPSCs) offer a potential solution for eliminating variability and studying genotypic variation in drug response but have not found widespread acceptance on account of the fetal phenotype and inadequate metabolic profile they exhibit in standard, static culture systems. The data described above in Example 12 demonstrate that primary rat and human hepatocytes, which are known to rapidly dedifferentiate under static culture conditions, stably retain a mature differentiated phenotype when cultured under controlled hemodynamic conditions, resulting in a more physiologic drug and hormone response. It was discovered that iPSCs respond similarly when physiological properties such as flow, hemodynamics and transport are maintained and exhibit the differentiated liver phenotype and response to drugs that they exhibit in vivo.

Methods (i) iPSC-derived Hepatocytes iPSC-derived Hepatocytes were purchased from Cellular Dynamics International.

(ii) iPSC-derived Hepatocyte Culture Media

The iPSC-derived hepatocyte culture media for static cultures was as per the vendors recommendations. For cells cultured under controlled hemodynamic conditions in the cone-and-plate devices, a base media of Williams E medium supplemented by fetal bovine serum (10%) and dexamethasone (1 µM) at the time of plating was used. Maintenance media was used after 24 hours that did not contain FBS but was supplemented with bovine serum albumin (0.125%). The media also contained gentamycin (25 µg/ml), ITS (insulin concentration 2 nMol), 1% NEAA, 1% GLUTAMAX, HEPES (30 mM) and dexamethasone (100 nM).

(iii) Collagen Coating and Plating

The collagen coating and plating conditions were identical to those described above in Example 12 for primary human hepatocytes. The iPSC-derived hepatocytes were dissociated and plated as per the vendor's protocols using the recommended media. iPSC-derived hepatocytes were cultured under static conditions or were transferred into the cone-and-plate devices after 24 hours for further culture under controlled hemodynamic conditions.

Figures 43A, 43B, 43C:
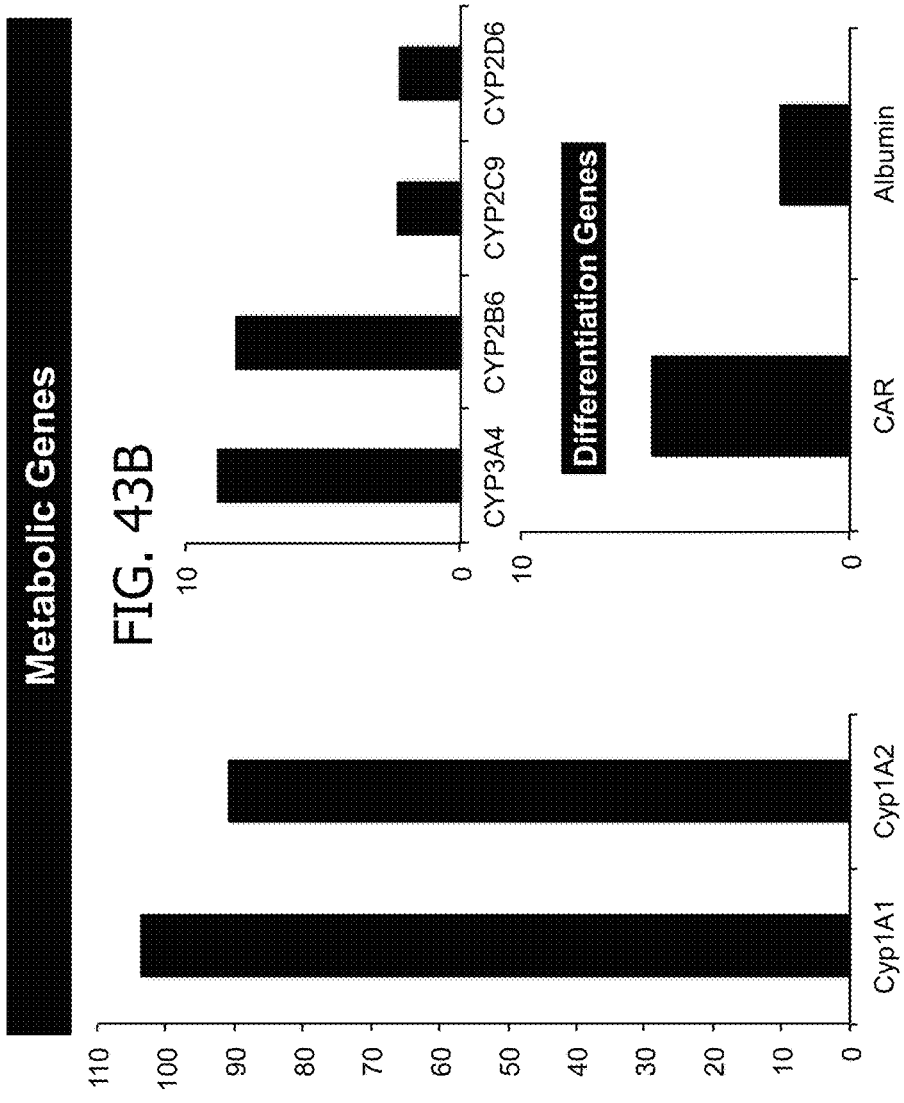
FIGS. 43A-C provide gene expression data showing the expression of metabolic genes and differentiation genes in iPSC-derived hepatocytes cultured under controlled hemodynamic conditions.

Results (i) Hepatocytes Derived from Inducible Pluripotent Stem Cells (iPSCs) Cultured under Controlled Hemodynamic Conditions Retain Polarized Morphology and Exhibit Higher Expression of Key Metabolic Genes Relative to Static Cultures.

iPSC-derived hepatocytes cultured in the cone-and-plate devices under controlled hemodynamics for 10 days retain polarized morphology (FIG. 42) and exhibit higher expression of key metabolic genes relative to static cultures (104-fold for CYP1A1, 91-fold for CYP1A2, 8.8-fold for CYP3A4, 8.2-fold for CYP2B6, 2.3-fold for CYP2C9 and 2.3-fold for CYP2D6). Expression of the constitutive androstane receptor CAR was 6.0-fold higher than cells cultured under static conditions and the liver-specific protein albumin was at 2.2-fold higher levels than in cells cultured under static conditions. These results are depicted in FIG. 43.

REFERENCES

Andriani F, Perego P, Carenini N, Sozzi G, Roz L. Increased Sensitivity to Cisplatin in Non-Small Cell Lung Cancer Cell Lines after FHIT Gene Transfer. Neoplasia N Y N. 2006 January; 8(1):9-17.

Bain J, Plater L, Elliott M, Shpiro N, Hastie C J, McLauchlan H, et al. The selectivity of protein kinase inhibitors: a further update. Biochem J. 2007; 408:297-315.

Barr M P, Gray S G, Hoffmann A C, Hilger R A, Thomale J, O'Flaherty J D, et al. Generation and Characterisation of Cisplatin-Resistant Non-Small Cell Lung Cancer Cell Lines Displaying a Stem-Like Signature. PLoS ONE. 2013 Jan. 17; 8(1):e54193.

Basu I, Locker J, Cassera M B, Belbin T J, Merino E F, Dong X, et al. Growth and Metastases of Human Lung Cancer Are Inhibited in Mouse Xenografts by a Transition State Analogue of 5'-Methylthioadenosine Phosphorylase. J Bio Chem 2011; 286:4902-11.

Bradford J R, Farren M, Powell S J, Runswick S, Weston S L, Brown H, et al. RNA-Seq Differentiates Tumour and Host mRNA Expression Changes Induced by Treatment of Human Tumour Xenografts with the VEGFR Tyrosine Kinase Inhibitor Cediranib. PLoS ONE. 2013 Jun. 19; 8(6):e66003.

Chou T-C, Zhang X, Zhong Z-Y, Li Y, Feng L, Eng S, et al. Therapeutic effect against human xenograft tumors in nude mice by the third generation microtubule stabilizing epothilones. Proc Natl Acad Sci. 2008 Sep. 2; 105(35):13157-62.

Cifone M A. In vitro growth characteristics associated with benign and metastatic variants of tumor cells. Cancer Metastasis Rev. 1982; 1(4):335-47.

Chung E J, Brown A P, Asano H, Mandler M, Burgan W E, Carter D, et al. In vitro and in vivo radiosensitization with AZD6244 (ARRY-142886), an inhibitor of mitogen-activated protein kinase/extracellular signal-regulated kinase 1/2 kinase. Clin Cancer Res Off J Am Assoc Cancer Res. 2009 May 1; 15(9):3050-7.

Denton C L, Gustafson D L. (2011) Pharmacokinetics and pharmacodynamics of AZD6244 (ARRY-142886) in tumor-bearing nude mice. Cancer Chemotherapy and Pharmacology 67(2):349-360. PMID:20407895

Görg C, Seifart U, Görg K, Zugmaier G. Color Doppler sonographic mapping of pulmonary lesions: evidence of dual arterial supply by spectral analysis. J Ultrasound Med Off J Am Inst Ultrasound Med. 2003 October; 22(10):1033-9.

Hudis C, Swanton C, Janjigian Y Y, Lee R, Sutherland S, Lehman R, Chandarlapaty S, Hamilton N, Gajria D, Knowles J, Shah J, Shannon K, Tetteh E, Sullivan D M, Moreno C, Yan L, Han H S. (2013) A phase 1 study evaluating the combination of an allosteric AKT inhibitor (MK-2206) and trastuzumab in patients with HER2-positive solid tumors. *Breast Cancer Research* 15(6):R110. PMID: 24252402.

Hsu W-H, Yu Y-H, Tu C-Y, Hsu J-Y, Chen C-Y, Chen C-L, et al. Color Doppler US pulmonary artery vessel signal: a sign for predicting the benign lesions. Ultrasound Med Biol. 2007 March; 33(3):379-88.

Hsu W H, Ikezoe J, Chen C Y, Kwan P C, Hsu C P, Hsu N Y, et al. Color Doppler ultrasound signals of thoracic lesions. Correlation with resected histologic specimens. Am J Respir Crit Care Med. 1996 June; 153(6 Pt 1):1938-51.

Johnsson A, Olsson C, Nygren O, Nilsson M, Seiving B, Cavallin-Stahl E. Pharmacokinetics and tissue distribution of cisplatin in nude mice: platinum levels and cisplatin-DNA adducts. (1995) Cancer *Chemotherapy and Pharmacology* 37(1-2):23-31. PMID: 7497593.

Langmead B, Trapnell C, Pop M, Salzberg S L. (2009) Ultrafast and memory-efficient alignment of short DNA sequences to the human genome. *Genome Biol.*, 10:R25.

Leijen S, Soetekouw PMMB, Jeffry Evans T R, Nicolson M, Schellens J H M, Learoyd M, et al. A phase I, open-label, randomized crossover study to assess the effect of dosing of the MEK 1/2 inhibitor Selumetinib (AZD6244; ARRY-142866) in the presence and absence of food in patients with advanced solid tumors. Cancer Chemother Pharmacol. 2011 December; 68(6):1619-28.

Li K, Chen B, Xu L, Feng J, Xia G, Cheng J, et al. Reversal of multidrug resistance by cisplatin-loaded magnetic Fe3O4 nanoparticles in A549/DDP lung cancer cells in vitro and in vivo. Int J Nanomedicine. 2013; 8:1867-77.

Meng J, Dai B, Fang B, Bekele B N, Bornmann W G, Sun D, et al. Combination treatment with MEK and AKT inhibitors is more effective than each drug alone in human non-small cell lung cancer in vitro and in vivo. PloS One. 2010;5(11):e14124.

Mukaida N, Baba T. Chemokines in tumor development and progression. Exp Cell Res. 2012 Jan. 15; 318(2):95-102.

National Cancer Institute, "MK2206 and Erlotinib Hydrochloride in Treating Patients With Advanced Non-Small Cell Lung Cancer Who Have Progressed After Previous Response to Erlotinib Hydrochloride Therapy" [retrieved on 2014-09-09]. Retrieved from the Internet <URL: http://clinicaltrials.gov/show/NCT01294306>.

National Cancer Institute, "Non-Small Cell Lung Cancer Treatment (PDQ®)" [retrieved 2014-07-02]. Retrieved from the Internet <URL: http://www.cancer.gov/cancertopics/pdq/treatment/non-small-celllung/healthprofessional/page11>.

National Cancer Institute, "Randomized Phase II Study of AZD6244 (Mitogen-activated Protein Kinase Inhibitor) MEK-Inhibitor With Erlotinib in KRAS Wild Type Advanced Non-Small Cell Lung Cancer (NSCLC) and a Randomized Phase II Study of AZD6244 With Erlotinib in Mutant KRAS Adva . . . ," [retrieved 2014-09-09]. Retrieved from the Internet <URL: http://clinicaltrials.gov/ct2/show/study/NCT01229150>.

Ogata H. Goto S, Sato K, Fujibuchi W, Bono H, Kanehisa M (1999) KEGG: Kyoto Encyclopedia of Genes and Genomes. *Nucleic Acids Res.* 27:29-34.

O'Neil B H, Goff L W, Kauh J S, Strosberg J R, Bekaii-Saab T S, Lee R M, Kazi A, Moore D T, Learoyd M, Lush R M, Sebti S M, Sullivan D M. (2011) Phase II study of the mitogen-activated protein kinase 1/2 inhibitor selumetinib in patients with advanced hepatocellular carcinoma. *Journal of Clinical Oncology* 29:2350-23566. PMID: 21519015.

Piovan E, Yu J, Tosello V, Herranz D, Ambesi-Impiombato A, Da Silva AC, Sanchez-Martin M, Perez-Garcia A, Rigo I, Castillo M, Indraccolo S, Cross J R, de Stanchina E, Paietta E, Racevskis J, Rowe J M, Tallman M S, Basso G, Meijerink J P, Cordon-Cardo C, Califano A, Ferrando A A. (2013) Direct reversal of glucocorticoid resistance by AKT inhibition in acute lymphoblastic leukemia. *Cancer Cell* 24(6):766-776. PMID: 24291004

Raskatov J A, Nickols N G, Hargrove A E, Marinov G K, Wold B, Dervan P B. (2012) Gene expression changes in a tumor xenograft by a pyrrole-imidazole polyamide. *Proc Natl Acad Sci.*, 109:16042-45.

Roberts A and Pachter L (2012). Streaming fragment assignment for real-time analysis of sequencing experiments. *Nature Methods,* 10:71-73.

Robinson M D and Oshlack A. (2010) A scaling normalization method for differential expression analysis of RNA-Seq data. *Genome Biol.,* 11:R25

Rossi A, Di Maio M, Chiodini P, Rudd RM, Okamoto H, Skarlos D V, et al. Carboplatin- or cisplatin-based chemotherapy in first-line treatment of small-cell lung cancer: the COCIS meta-analysis of individual patient data. J Clin Oncol Off J Am Soc Clin Oncol. 2012 May 10; 30(14):1692-8.

Salas S, Mercier C, Ciccolini J, Pourroy B, Fanciullino R, Tranchand B, Monjanel-Mouterde S, Baciuchka-Palmaro M, Dupuis C, Yang C, Balti M, Lacarelle B, Duffaud F, Durand A, Favre R. (2006) Therapeutic drug monitoring for dose individualization of Cisplatin in testicular cancer patients based upon total platinum measurement in plasma. *Therapeutic Drug Monitoring* 28(4):532-9. PMID: 16885721.

Urien S, Brain E, Bugat R, Pivot X, Lochon I, Van M-L V, et al. Pharmacokinetics of platinum after oral or intravenous cisplatin: a phase 1 study in 32 adult patients. Cancer Chemother Pharmacol. 2005 January; 55(1):55-60.

Yap T A, Yan L, Patnaik A, Fearen I, Olmos D, Papadopoulos K, et al. First-in-man clinical trial of the oral pan-AKT inhibitor MK-2206 in patients with advanced solid tumors. J Clin Oncol Off J Am Soc Clin Oncol. 2011 Dec. 10; 29(35):4688-95.

Yeh T C, Marsh V, Bernat B A, Ballard J, Colwell H, Evans R J, et al. Biological Characterization of ARRY-142886 (AZD6244), a Potent, Highly Selective Mitogen-Activated Protein Kinase Kinase 1/2 Inhibitor. Clin Cancer Res. 2007 Mar. 1; 13(5):1576-83.

Zhang Y-X, Yue Z, Wang P-Y, Li Y-J, Xin J-X, Pang M, et al. Cisplatin upregulates MSH2 expression by reducing miR-21 to inhibit A549 cell growth. Biomed Pharmacother Biomedecine Pharmacother. 2013 March; 67(2):97-102.

Zhang P, Gao W Y, Turner S, Ducatman B S. Gleevec (STI-571) inhibits lung cancer cell growth (A549) and potentiates the cisplatin effect in vitro. Mol Cancer. 2003 Jan. 3; 2(1):1.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above methods without departing from the scope of the invention, it is intended that all matter contained in the above description and shown in the accompanying drawings shall be interpreted as illustrative and not in a limiting sense.

What is claimed is:

1. An in vitro method of testing a drug or a compound for an effect on a tumor, the method comprising:
   (a) mimicking a tumor microenvironment in vitro, wherein mimicking the tumor microenvironment in vitro comprises:
      (i) adding a culture medium to a cell culture container;
      (ii) plating at least one tumor cell type on a first surface of a porous membrane within the cell culture container;
      (iii) indirectly applying a shear stress upon the at least one tumor cell type by applying a shear stress upon a second surface of the porous membrane, the shear stress resulting from flow of the culture medium induced by a flow device, the flow mimicking flow to which the tumor cells are indirectly exposed in vivo in the tumor microenvironment; and
   (b) adding a drug or a compound to the culture medium; wherein a change in the at least one tumor cell type, in the presence of the drug or the compound, indicates that the drug or the compound has an effect on the tumor.

2. The method of claim 1, wherein the porous membrane is suspended in the cell culture container such that the first surface is proximal and in spaced relation to a bottom surface of the cell culture container, thereby defining within the cell culture container a lower volume comprising the at least one tumor cell type and an upper volume comprising a second surface of the porous membrane, wherein the shear stress is applied upon the second surface of the porous membrane in the upper volume of the container.

3. The method of claim 1, further comprising:
   (i) depositing at least one extracellular matrix component on the first surface of the porous membrane and plating the at least one tumor cell type on the at least one extracellular matrix component; or
   (ii) suspending the at least one tumor cell type in a solution comprising at least one extracellular matrix component to create a suspension comprising the at least one tumor cell type and the at least one extracellular matrix component, and depositing the suspension on the first surface of the porous membrane;
   the porous membrane being suspended in the cell culture container such that the first surface is proximal and in spaced relation to a bottom surface of the cell culture container, thereby defining within the cell culture container a lower volume comprising the at least one extracellular matrix component and the at least one tumor cell type, and an upper volume comprising a second surface of the porous membrane, wherein the shear stress is applied upon the second surface of the porous membrane in the upper volume of the container.

4. The method of claim 1, further comprising plating endothelial cells on the second surface of the porous membrane and applying the shear stress upon the plated endothelial cells.

5. The method of claim 1, further comprising plating at least one stromal cell type on the second surface of the porous membrane and applying the shear stress upon the plated stromal cell type.

6. The method of claim 1, wherein upon application of the shear stress:
   (i) a change in the level of a marker of the tumor microenvironment in the at least one tumor cell type, as compared to the level of the marker in the at least one tumor cell type in the absence of the shear stress, confirms mimicking of the tumor microenvironment; or
   (ii) a change in the localization of a marker of the tumor microenvironment in the at least one tumor cell type, as compared to the localization of the marker in the at least one tumor cell type in the absence of the shear stress, confirms mimicking of the tumor microenvironment; or
   (iii) a change in the level of a marker of the tumor microenvironment in the culture medium, as compared to the level of the marker in the culture medium in the absence of application of the shear stress, confirms mimicking of the tumor microenvironment.

7. The method of claim 2, wherein the cell culture container further comprises inlets and outlets within the portions of the cell culture container defining the upper and lower volumes.

8. The method of claim 2, further comprising perfusing culture medium into and out of the upper volume and into and out of the lower volume.

9. The method of claim 1, further comprising plating at least one stromal cell type on the first surface of the porous membrane.

10. The method of claim 1, wherein the at least one tumor cell type comprises cells derived from a carcinoma, a sarcoma, a lymphoma, an adenosquamous carcinoma, a mixed mesodermal tumor, carcinosarcoma, a teratocarcinoma, or a combination thereof.

11. The method of claim 1, wherein the at least one tumor cell type is derived from a tumor of connective tissue, a tumor of endothelium or mesothelium, a tumor of lymphoid tissue, a tumor of muscle, a tumor of an epithelial tissue, a tumor of a neural tissue, a tumor of the amine precursor uptake and decarboxylation (APUD) system, a tumor of a neural crest-derived cell, a gonadal tumor, or a combination thereof.

12. The method of claim 1, wherein the at least one tumor cell type comprises cells derived from a tumor of the lung, breast, colon, rectum, prostate, bladder, bone, pancreas, liver, bile duct, ovary, testis, uterus, placenta, brain, cartilage, smooth muscle, striated muscle, membranous lining of a body cavity, fibrous tissue, blood vessel, lymph vessel, lymph node, adipose tissue, neurogenic connective tissue of the brain, kidney, pituitary gland, parathyroid, thyroid, bronchial lining, adrenalmedulla, stomach, large intestine, small intestine, carotid body, chemoreceptor system, skin, gall bladder, or a combination thereof.

13. The method of claim 1, wherein the at least one tumor cell type comprises primary tumor cells obtained from a subject by biopsy, tumor resection, blood draw, or a combination thereof.

14. The method of claim 1, wherein the at least one tumor cell type comprises tumor cells derived from a humanized mouse bearing a tumor derived from a human subject.

15. The method of claim 14, wherein the humanized mouse comprises a non-obese diabetic severe combined immunodeficiency (NOD SCID) mouse, a NOD/Shi-scid/IL-2Rγnull (NOG) mouse, or a NOD SCID IL-2Rγknockout (NSG) mouse.

16. The method of claim 4, wherein the endothelial cells comprise:
   microvascular endothelial cells, macrovascular endothelial cells, endothelial progenitor cells, or a combination thereof;
   endothelial cells derived from a tumor;
   endothelial cells derived from an organ or tissue in which a tumor resides;
   endothelial cells derived from lung, breast, colon, rectum, prostate, bladder, bone, pancreas, liver, bile duct, ovary, testis, uterus, placenta, brain, cartilage, smooth muscle, striated muscle, a membranous lining of a body cavity, fibrous tissue, blood vessel, lymph vessel, lymph node, adipose tissue, neurogenic connective tissue of the brain, kidney, pituitary gland, parathyroid, thyroid, bronchial lining, adrenal medulla, stomach, large intestine, small intestine, carotid body, chemoreceptor system, skin, gall bladder, or a combination thereof;
   cells derived from inducible pluripotent stem cells (iPSC); or a combination of any thereof.

17. The method of claim 9, wherein the at least one stromal cell type comprises fibroblasts, immune cells, pericytes, inflammatory cells, or a combination thereof.

18. The method of claim 9, further comprising mixing the at least one stromal cell type with the at least one tumor cell type prior to plating.

19. The method of claim 9, wherein the method comprises sequentially plating the at least one tumor cell type and the at least one stromal cell type.

20. The method of claim 19, comprising plating the at least one stromal cell type and subsequently plating the at least one tumor cell type on the plated stromal cell type.

21. The method of claim 17, wherein at least one stromal cell type comprises the fibroblasts, the fibroblasts comprising human lung fibroblast cell line Hs888Lu.

22. The method of claim 1, wherein the method comprises culturing the cell type or cell types in the substantial absence of exogenously added extracellular matrix.

23. The method of claim 3, wherein the at least one extracellular matrix component comprises a collagen, heparan sulfate, chondroitin sulfate, keratan sulfate, hyaluronic acid, an elastin, a fibronectin, a laminin, a vitronectin, decellularized extracellular matrix purified from a biological source, or a combination thereof.

24. The method of claim 1, wherein the culture medium comprises sera, blood, blood cells, a blood component, immune cells, conditioned culture medium, or a combination thereof.

25. The method of claim 24, wherein the sera, blood, blood cells, blood component, or immune cells are derived from a human or other animal.

26. The method of claim 25, wherein the sera, blood, blood cells, blood component, or immune cells comprise sera, blood, blood cells, a blood component, or immune cells derived from a mouse, rat, guinea pig, hamster, rabbit, cat, dog, monkey, cow, pig, horse, goat, sheep, bird, or fish.

27. The method of claim 24, wherein the immune cells comprise B cells, dendritic cells, granulocytes, innate lymphoid cells, megakaryocytes, monocytes, macrophages, natural killer cells, T cells, thymocytes, or a combination thereof.

28. The method of claim 24, wherein the blood cells comprise platelets, red blood cells, or a combination thereof.

29. The method of claim 24, wherein the blood component comprises a clotting factor, a lipoprotein, a triglyceride, or a combination thereof.

30. The method of claim 24, wherein the conditioned culture medium comprises conditioned culture medium from a culture comprising tumor cells, a culture comprising endothelial cells, a culture comprising a stromal cell type, or a combination thereof.

31. The method of claim 1, wherein the at least one tumor cell type comprises tumor cells derived from a subject's tumor and the method further comprises determining whether to administer the drug or the compound to the subject based on the results of the in vitro testing.

32. The method of claim 1, wherein the concentration of the drug or compound in the culture medium is within the concentration range of the drug or the compound that achieves the effect in vivo.

33. The method of claim 1, wherein the concentration of the drug or the compound in the culture medium is within the concentration range of the in vivo therapeutic $C_{max}$ for the drug or the compound.

34. The method of claim 33, wherein the concentration of the drug or the compound in the culture medium is approximately the same as the in vivo therapeutic $C_{max}$ for the drug or the compound.

35. The method of claim 1, wherein the concentration of the drug or the compound in the culture medium is about 2-fold to about 20-fold lower than the concentration range of the in vivo therapeutic $C_{max}$ for the drug or the compound.

36. The method of claim 35, wherein the concentration of the drug or the compound in the culture medium is about 5-fold to about 15-fold lower than the concentration range of the in vivo therapeutic $C_{max}$ for the drug or the compound.

37. The method of claim 35, wherein the concentration of the drug or the compound in the culture medium is about 10-fold lower than the concentration range of the in vivo therapeutic $C_{max}$ for the drug or the compound.

38. The method of claim 1, wherein the effect comprises a toxic effect, a protective effect, a pathologic effect, a disease-promoting effect, an inflammatory effect, an oxidative effect, an endoplasmic reticulum stress effect, a mitochondrial stress effect, an apoptotic effect, a necrotic effect, an autophagic effect, an immunogenic cell death effect, a ferroptotic effect, a remodeling effect, a proliferative effect, an effect on angiogenesis, an effect on the activity of a protein, or an effect on the expression of a gene.

39. The method of claim 1, wherein the drug comprises an anti-cancer agent.

40. The method of claim 39, wherein the anti-cancer agent comprises an alkylating agent, an anti-metabolite, an anti-tumor antibiotic, a topoisomerase inhibitor, a corticosteroid, an anti-microtubule agent, a kinase inhibitor, a pathway inhibitor, a differentiating agent, a hormone therapy, an immunotherapy, L-asparaginase, a chelating agent, an ATP mimetic, a biologic medical product, or a combination thereof.

41. The method of claim 1, wherein the method further comprises perfusing the drug or the compound into at least one of the upper volume and the lower volume.

42. The method of claim 1, wherein the shear stress applied upon the at least one tumor cell type is about 0.1 dynes/cm$^2$ to about 200 dynes/cm$^2$.

43. The method of claim 42, wherein the shear stress applied upon the at least one tumor cell type is about 0.1 dynes/cm$^2$ to about 100 dynes/cm$^2$.

44. The method of claim 1, wherein the shear stress is applied at a rate of about 1 sec$^{-1}$ to about 1000 sec$^{-1}$.

45. The method of claim 1, wherein the method comprises directly exposing the at least one tumor cell type to the drug or the compound.

46. The method of claim 1, wherein the method comprises indirectly exposing the at least one tumor cell type to the drug or the compound.

47. The method of claim 4, wherein upon application of the shear stress, a change in the level or localization of a marker of the tumor microenvironment in the endothelial cells, as compared to the level or localization of the marker in the endothelial cells in the absence of application of the shear stress, confirms mimicking of the tumor microenvironment.

48. The method of claim 9, wherein upon application of the shear stress, a change in the level or localization of a marker of the tumor microenvironment in the at least one stromal cell type, as compared to the level or localization of the marker in the at least one stromal cell type in the absence of application of the shear stress, confirms mimicking of the tumor microenvironment.

* * * * *

SEQUENCE LISTING

```
<160> NUMBER OF SEQ ID NOS: 74

<210> SEQ ID NO 1
<211> LENGTH: 20
<212> TYPE: DNA
<213> ORGANISM: Rattus norvegicus

<400> SEQUENCE: 1
gctgctcttg gccgtcacca                                              20

<210> SEQ ID NO 2
<211> LENGTH: 20
<212> TYPE: DNA
<213> ORGANISM: Rattus norvegicus

<400> SEQUENCE: 2
tgaagggcaa gccccagggt                                              20

<210> SEQ ID NO 3
<211> LENGTH: 20
<212> TYPE: DNA
<213> ORGANISM: Rattus norvegicus

<400> SEQUENCE: 3
cctgcgctac ctgcccaacc                                              20

<210> SEQ ID NO 4
<211> LENGTH: 20
<212> TYPE: DNA
<213> ORGANISM: Rattus norvegicus

<400> SEQUENCE: 4
gggcgcctgt gatgtcctgg                                              20

<210> SEQ ID NO 5
<211> LENGTH: 20
<212> TYPE: DNA
<213> ORGANISM: Rattus norvegicus

<400> SEQUENCE: 5
cggcgggatt ttggcccagt                                              20

<210> SEQ ID NO 6
<211> LENGTH: 20
<212> TYPE: DNA
<213> ORGANISM: Rattus norvegicus

<400> SEQUENCE: 6
```
caggcttgcc tgtctccgcc                                              20

<210> SEQ ID NO 7
<211> LENGTH: 20
<212> TYPE: DNA
<213> ORGANISM: Rattus norvegicus

<400> SEQUENCE: 7
gctgctggga actctggcgg                                              20

<210> SEQ ID NO 8
<211> LENGTH: 20
<212> TYPE: DNA
<213> ORGANISM: Rattus norvegicus

<400> SEQUENCE: 8
ccggcaccaa tgcccgtgta                                              20

<210> SEQ ID NO 9
<211> LENGTH: 20
<212> TYPE: DNA
<213> ORGANISM: Rattus norvegicus

<400> SEQUENCE: 9
cgcagcagct atgccaccgt                                              20

<210> SEQ ID NO 10
<211> LENGTH: 21
<212> TYPE: DNA
<213> ORGANISM: Rattus norvegicus

<400> SEQUENCE: 10
cttccagctc tggccctggt c                                            21

<210> SEQ ID NO 11
<211> LENGTH: 24
<212> TYPE: DNA
<213> ORGANISM: Rattus norvegicus

<400> SEQUENCE: 11
agcgttgctc catgggcata tagt                                         24

<210> SEQ ID NO 12
<211> LENGTH: 24
<212> TYPE: DNA
<213> ORGANISM: Rattus norvegicus

<400> SEQUENCE: 12
tgtcagggat ggtgttggat gaca                                         24

<210> SEQ ID NO 13
<211> LENGTH: 24
<212> TYPE: DNA
<213> ORGANISM: Rattus norvegicus

<400> SEQUENCE: 13
tgtcatggtt acacccgaag acct                                         24

<210> SEQ ID NO 14
<211> LENGTH: 24
<212> TYPE: DNA
<213> ORGANISM: Rattus norvegicus

<400> SEQUENCE: 14
ttgttgttgt ttgctcctcc aggc                                          24

<210> SEQ ID NO 15
<211> LENGTH: 20
<212> TYPE: DNA
<213> ORGANISM: Rattus norvegicus

<400> SEQUENCE: 15
gcgagctcta tgggtatatg                                               20

<210> SEQ ID NO 16
<211> LENGTH: 20
<212> TYPE: DNA
<213> ORGANISM: Rattus norvegicus

<400> SEQUENCE: 16
agtcctcttc ctcagtcctc                                               20

<210> SEQ ID NO 17
<211> LENGTH: 24
<212> TYPE: DNA
<213> ORGANISM: Rattus norvegicus

<400> SEQUENCE: 17
atatctccct ttttgtggct gcta                                          24

<210> SEQ ID NO 18
<211> LENGTH: 22
<212> TYPE: DNA
<213> ORGANISM: Rattus norvegicus

<400> SEQUENCE: 18
tccgactccg tcttctygat ga                                            22

<210> SEQ ID NO 19
<211> LENGTH: 20
<212> TYPE: DNA
<213> ORGANISM: Rattus norvegicus

<400> SEQUENCE: 19
ggagccatgg attgcacatt                                               20

<210> SEQ ID NO 20
<211> LENGTH: 21
<212> TYPE: DNA
<213> ORGANISM: Rattus norvegicus

<400> SEQUENCE: 20
aggccaggga agtcactgtc t                                             21

<210> SEQ ID NO 21
<211> LENGTH: 20
<212> TYPE: DNA
<213> ORGANISM: Rattus norvegicus

<400> SEQUENCE: 21
ctatgtccgg acccgcacgc                                               20

<210> SEQ ID NO 22
<211> LENGTH: 20
<212> TYPE: DNA
<213> ORGANISM: Rattus norvegicus

<400> SEQUENCE: 22
ctatgtccgg acccgcacgc                                               20

<210> SEQ ID NO 23
<211> LENGTH: 24
<212> TYPE: DNA
<213> ORGANISM: Rattus norvegicus

<400> SEQUENCE: 23
actctgcaac ggagttgtgg aaga                                          24

<210> SEQ ID NO 24
<211> LENGTH: 24
<212> TYPE: DNA
<213> ORGANISM: Rattus norvegicus

<400> SEQUENCE: 24
tcggatgact ccaaccctat cctt                                          24

<210> SEQ ID NO 25
<211> LENGTH: 22
<212> TYPE: DNA
<213> ORGANISM: Rattus norvegicus

<400> SEQUENCE: 25
tgtggagcca caggacttac aa                                            22

<210> SEQ ID NO 26
<211> LENGTH: 24
<212> TYPE: DNA
<213> ORGANISM: Rattus norvegicus

<400> SEQUENCE: 26
agccaaccca cgtgagagaa gaaa                                          24

<210> SEQ ID NO 27
<211> LENGTH: 24
<212> TYPE: DNA
<213> ORGANISM: Rattus norvegicus

<400> SEQUENCE: 27
atgtggacct gcattccttc ccat                                          24

<210> SEQ ID NO 28
<211> LENGTH: 24
<212> TYPE: DNA
<213> ORGANISM: Rattus norvegicus

<400> SEQUENCE: 28
ttgcccatgt ccttgtaatg tgcg                                          24

<210> SEQ ID NO 29
<211> LENGTH: 23
<212> TYPE: DNA
<213> ORGANISM: Rattus norvegicus

<400> SEQUENCE: 29
gaggagtgtg gaagaacgga ttc                                           23

<210> SEQ ID NO 30
<211> LENGTH: 21
<212> TYPE: DNA
<213> ORGANISM: Rattus norvegicus

```
<400> SEQUENCE: 30
aggaactggc ggtctgtgta g                                           21

<210> SEQ ID NO 31
<211> LENGTH: 21
<212> TYPE: DNA
<213> ORGANISM: Rattus norvegicus

<400> SEQUENCE: 31
tcatcgacac ttaccttctg c                                           21

<210> SEQ ID NO 32
<211> LENGTH: 22
<212> TYPE: DNA
<213> ORGANISM: Rattus norvegicus

<400> SEQUENCE: 32
agtgtatggc attttggtac ga                                          22

<210> SEQ ID NO 33
<211> LENGTH: 24
<212> TYPE: DNA
<213> ORGANISM: Rattus norvegicus

<400> SEQUENCE: 33
tctgtggctc ggatgttcac tact                                        24

<210> SEQ ID NO 34
<211> LENGTH: 24
<212> TYPE: DNA
<213> ORGANISM: Rattus norvegicus

<400> SEQUENCE: 34
cggccgatct tgcagaattc atct                                        24

<210> SEQ ID NO 35
<211> LENGTH: 22
<212> TYPE: DNA
<213> ORGANISM: Rattus norvegicus

<400> SEQUENCE: 35
ggactatgac aacatcccta cc                                          22

<210> SEQ ID NO 36
<211> LENGTH: 20
<212> TYPE: DNA
<213> ORGANISM: Rattus norvegicus

<400> SEQUENCE: 36
ccaaccacct tctcctcttt                                             20

<210> SEQ ID NO 37
<211> LENGTH: 20
<212> TYPE: DNA
<213> ORGANISM: Rattus norvegicus

<400> SEQUENCE: 37
gcctaagggc tttcgttaca                                             20

<210> SEQ ID NO 38
<211> LENGTH: 22
<212> TYPE: DNA
```

<213> ORGANISM: Rattus norvegicus

<400> SEQUENCE: 38
atccacattc caggagcata tc                                          22

<210> SEQ ID NO 39
<211> LENGTH: 18
<212> TYPE: DNA
<213> ORGANISM: Rattus norvegicus

<400> SEQUENCE: 39
aggccagcag ggagttct                                               18

<210> SEQ ID NO 40
<211> LENGTH: 19
<212> TYPE: DNA
<213> ORGANISM: Rattus norvegicus

<400> SEQUENCE: 40
agctcggctc caagttctg                                              19

<210> SEQ ID NO 41
<211> LENGTH: 20
<212> TYPE: DNA
<213> ORGANISM: Rattus norvegicus

<400> SEQUENCE: 41
caactcctct ccaaggtgct                                             20

<210> SEQ ID NO 42
<211> LENGTH: 20
<212> TYPE: DNA
<213> ORGANISM: Rattus norvegicus

<400> SEQUENCE: 42
atctgctcac gcgtgttctt                                             20

<210> SEQ ID NO 43
<211> LENGTH: 25
<212> TYPE: DNA
<213> ORGANISM: Homo sapiens

<400> SEQUENCE: 43
ggacctgaat gagaagttct acagc                                       25

<210> SEQ ID NO 44
<211> LENGTH: 24
<212> TYPE: DNA
<213> ORGANISM: Homo sapiens

<400> SEQUENCE: 44
agctccaaag aggtccaaga cgat                                        24

<210> SEQ ID NO 45
<211> LENGTH: 24
<212> TYPE: DNA
<213> ORGANISM: Homo sapiens

<400> SEQUENCE: 45
tcatagccaa gaaggtggag caca                                        24

<210> SEQ ID NO 46
<211> LENGTH: 24

<212> TYPE: DNA
<213> ORGANISM: Homo sapiens

<400> SEQUENCE: 46
cccaatgaag aggttcaacg tggt                                              24

<210> SEQ ID NO 47
<211> LENGTH: 22
<212> TYPE: DNA
<213> ORGANISM: Homo sapiens

<400> SEQUENCE: 47
gggcacacag gcaagtttac aa                                                22

<210> SEQ ID NO 48
<211> LENGTH: 24
<212> TYPE: DNA
<213> ORGANISM: Homo sapiens

<400> SEQUENCE: 48
agagcgtgtt gaggttgagg ttct                                              24

<210> SEQ ID NO 49
<211> LENGTH: 24
<212> TYPE: DNA
<213> ORGANISM: Homo sapiens

<400> SEQUENCE: 49
tgacttgttt ggagctggga caga                                              24

<210> SEQ ID NO 50
<211> LENGTH: 22
<212> TYPE: DNA
<213> ORGANISM: Homo sapiens

<400> SEQUENCE: 50
acagcatctg tgtagggcat gt                                                22

<210> SEQ ID NO 51
<211> LENGTH: 24
<212> TYPE: DNA
<213> ORGANISM: Homo sapiens

<400> SEQUENCE: 51
acgacactca tcaccaacct gtca                                              24

<210> SEQ ID NO 52
<211> LENGTH: 24
<212> TYPE: DNA
<213> ORGANISM: Homo sapiens

<400> SEQUENCE: 52
aggtgaagaa gaggaagagc tcca                                              24

<210> SEQ ID NO 53
<211> LENGTH: 24
<212> TYPE: DNA
<213> ORGANISM: Homo sapiens

<400> SEQUENCE: 53
ctgcattggc atgaggtttg ctct                                              24

<210> SEQ ID NO 54

```
<211> LENGTH: 24
<212> TYPE: DNA
<213> ORGANISM: Homo sapiens

<400> SEQUENCE: 54
aaattcaggc tccacttacg gtgc                                          24

<210> SEQ ID NO 55
<211> LENGTH: 24
<212> TYPE: DNA
<213> ORGANISM: Homo sapiens

<400> SEQUENCE: 55
ctgcattggc atgaggtttg ctct                                          24

<210> SEQ ID NO 56
<211> LENGTH: 24
<212> TYPE: DNA
<213> ORGANISM: Homo sapiens

<400> SEQUENCE: 56
agggttccat ctcttgaatc cacc                                          24

<210> SEQ ID NO 57
<211> LENGTH: 20
<212> TYPE: DNA
<213> ORGANISM: Homo sapiens

<400> SEQUENCE: 57
gatgccaagc ttgccttgat                                               20

<210> SEQ ID NO 58
<211> LENGTH: 25
<212> TYPE: DNA
<213> ORGANISM: Homo sapiens

<400> SEQUENCE: 58
agggaagctg gagataaaga ctgga                                         25

<210> SEQ ID NO 59
<211> LENGTH: 24
<212> TYPE: DNA
<213> ORGANISM: Homo sapiens

<400> SEQUENCE: 59
ggcccatcat gcccaatatg gttt                                          24

<210> SEQ ID NO 60
<211> LENGTH: 24
<212> TYPE: DNA
<213> ORGANISM: Homo sapiens

<400> SEQUENCE: 60
gcatcagcaa ttgccatagc tttc                                          24

<210> SEQ ID NO 61
<211> LENGTH: 23
<212> TYPE: DNA
<213> ORGANISM: Homo sapiens

<400> SEQUENCE: 61
tagcgccacc agaagcgacc aaa                                           23
```

```
<210> SEQ ID NO 62
<211> LENGTH: 24
<212> TYPE: DNA
<213> ORGANISM: Homo sapiens

<400> SEQUENCE: 62
tcatttgggc ctggttcagg gata                                            24

<210> SEQ ID NO 63
<211> LENGTH: 19
<212> TYPE: DNA
<213> ORGANISM: Homo sapiens

<400> SEQUENCE: 63
ccagccctgt atgaggacc                                                  19

<210> SEQ ID NO 64
<211> LENGTH: 23
<212> TYPE: DNA
<213> ORGANISM: Homo sapiens

<400> SEQUENCE: 64
ggagctgacc agtattgatg aga                                             23

<210> SEQ ID NO 65
<211> LENGTH: 21
<212> TYPE: DNA
<213> ORGANISM: Homo sapiens

<400> SEQUENCE: 65
cacttgcgtg aatgttggat g                                               21

<210> SEQ ID NO 66
<211> LENGTH: 20
<212> TYPE: DNA
<213> ORGANISM: Homo sapiens

<400> SEQUENCE: 66
tgggatcact cgtgaaggct                                                 20

<210> SEQ ID NO 67
<211> LENGTH: 23
<212> TYPE: DNA
<213> ORGANISM: Homo sapiens

<400> SEQUENCE: 67
atatggcaag aaggtgatgg tcc                                             23

<210> SEQ ID NO 68
<211> LENGTH: 21
<212> TYPE: DNA
<213> ORGANISM: Homo sapiens

<400> SEQUENCE: 68
gggcttgtcc taacaaagct g                                               21

<210> SEQ ID NO 69
<211> LENGTH: 24
<212> TYPE: DNA
<213> ORGANISM: Canis familiaris

<400> SEQUENCE: 69
caccatcccc cacagcacaa caaa                                            24
```

-continued

```
<210> SEQ ID NO 70
<211> LENGTH: 24
<212> TYPE: DNA
<213> ORGANISM: Canis familiaris

<400> SEQUENCE: 70
gctctggccg gaatgcaaat ggat                                              24

<210> SEQ ID NO 71
<211> LENGTH: 22
<212> TYPE: DNA
<213> ORGANISM: Canis familiaris

<400> SEQUENCE: 71
gagagaatga aggaaagtcg cc                                                22

<210> SEQ ID NO 72
<211> LENGTH: 20
<212> TYPE: DNA
<213> ORGANISM: Canis familiaris

<400> SEQUENCE: 72
gccaccagct ccaaatcaga                                                   20

<210> SEQ ID NO 73
<211> LENGTH: 17
<212> TYPE: DNA
<213> ORGANISM: Canis familiaris

<400> SEQUENCE: 73
tcctcatcct cctcgct                                                      17

<210> SEQ ID NO 74
<211> LENGTH: 17
<212> TYPE: DNA
<213> ORGANISM: Canis familiaris

<400> SEQUENCE: 74
ttctctgctg ggtgtcg                                                      17
```